(12) United States Patent
Kuzuyama et al.

(10) Patent No.: US 7,361,483 B2
(45) Date of Patent: Apr. 22, 2008

(54) AROMATIC PRENYLTRANSFERASES, NUCLEIC ACIDS ENCODING SAME AND USES THEREFOR

(75) Inventors: Tomohisa Kuzuyama, Tokyo (JP); Joseph P. Noel, San Diego, CA (US); Stephane B. Richard, Del Mar, CA (US)

(73) Assignees: The Salk Institute for Biological Studies, La Jolla, CA (US); Toudai TLO, Ltd., Tokyo (JP)

( * ) Notice: Subject to any disclaimer, the term of this patent is extended or adjusted under 35 U.S.C. 154(b) by 47 days.

(21) Appl. No.: 11/342,328

(22) Filed: Jan. 27, 2006

(65) Prior Publication Data

US 2006/0183211 A1 Aug. 17, 2006

Related U.S. Application Data

(60) Provisional application No. 60/648,046, filed on Jan. 28, 2005.

(51) Int. Cl.
*C12N 9/10* (2006.01)
*C12Q 1/48* (2006.01)

(52) U.S. Cl. .......................... 435/15; 435/193
(58) Field of Classification Search ...................... None
See application file for complete search history.

(56) References Cited

OTHER PUBLICATIONS

Wiencek et al. New strategies for protein crystal growth. Ann. Rev. Biomed. Eng. 1999, 1, 505-534.*
Ke et al. Crystallization of RNA and RNA-protein complexes. Methods 34, 2004, 408-414.*
Gilliland et al. Crystallization of biological molecules for X-ray diffraction studies. Current Opinion in Structure Biology 1996, 6, 595-603.*

Altschul et al., Gapped BLAST and PSI-BLAST: A New Generation of Protein Database Search Programs, *J. Mol. Biol.* 215:403-410 (1990).

(Continued)

*Primary Examiner*—Nashaat T. Nashed
(74) *Attorney, Agent, or Firm*—Foley & Lardner LLP; Stephen E. Reiter

(57) ABSTRACT

In accordance with the present invention, a novel aromatic prenyltransferase, Orf2 from *Streptomyces* sp. strain CL190, involved in naphterpin biosynthesis has been identified and the structure thereof elucidated. This prenyltransferase catalyzes the formation of a C—C bond between a prenyl group and a compound containing an aromatic nucleus, and also displays C—O bond formation activity. Numerous crystallographic structures of the prenyltransferase have been solved and refined, e.g., (1) prenyltransferase complexed with a buffer molecule (TAPS), (2) prenyltransferase as a binary complex with geranyl diphosphate (GPP) and $Mg^{2+}$, and prenyltransferase as ternary complexes with a non-hydrolyzable substrate analogue, geranyl S-thiolodiphosphate (GSPP) and either (3) 1,6-dihydroxynaphthalene (1,6-DHN), or (4) flaviolin (i.e., 2,5,7-trihydroxy-1,4-naphthoquinone, which is the oxidized product of 1,3,6,8-tetrahydroxynaphthalene (THN)). These structures have been solved and refined to 1.5 Å, 2.25 Å, 1.95 Å and 2.02 Å, respectively. This first structure of an aromatic prenyltransferase displays an unexpected and non-canonical (β/α)-barrel architecture. The complexes with both aromatic substrates and prenyl containing substrates and analogs delineate the active site and are consistent with a proposed electrophilic mechanism of prenyl group transfer. These structures also provide a mechanistic basis for understanding prenyl chain length determination and aromatic co-substrate recognition in this structurally unique family of aromatic prenyltransferases. This structural information is useful for predicting the aromatic prenyltransferase activity of proteins.

7 Claims, 13 Drawing Sheets

OTHER PUBLICATIONS

Altschul et al., Basic Local Alignment Search Tool, *Nucl. Acids Res.* 25:3389-3402 (1977).

Austin and Noel, The Chalcone Synthase Superfamily of Type III Polyketide Synthases, Nat Prod Rep 20(1):79-110 (2003).

Funa et al., A New Pathway For Polyketide Synthesis in Microorganisms, Nature 400(6747):897-9 (1999).

Gerlt and Raushel, Evolution of function in $(\beta/\alpha)_8$-Barrel Enzymes, Curr Opin Chem Biol 7(2):252-64 (2003).

Henikoff & Henikoff, Amino Acid Substitution Matrices From Protein Blocks, *Proc. Natl. Acad. Sci. USA* 89:10915 (1989).

Jez et al., Dissection of Malonyl-Coenzyme A Decarboxylation From Polyketide Formation in the Reaction Mechanism of a Plant Polyketide Synthase, Biochemistry 39(5):890-902 (2000).

Lattman, Use of the Rotation and Translation Functions, *Meth. Enzymol.* 115:55-77 (1985).

Liang, Structure, Mechanism and Function of Prenyltransferases, Eur J Biochem 269(14):3339-54 (2002).

Long et al., Reaction Path of Protein Farnesyltransferase at Atomic Resolution, Biochemistry 37(27):9612-8 (1998).

Long et al., Cocrystal Structure of Protein Farnesyltransferase Complexed with a Farnesyl Diphosphate Substrate, Nature 419(6907):645-50 (2002).

Milligan et al., Identification of a Potent Phytoestrogen in Hops (*Humulus lupulus* L.) and Beer, J Clin Endocrinol Metab 84:2249-52 (1999).

Needleman & Wunsch, A General Method Applicable to the Search for Similarities in the Amino Acid Sequence of Two Proteins, *J. Mol. Biol.* 48:443 (1970).

Park et al., Crystal Structure of Protein Farnesyltransferase at 2.25 Angstrom Resolution, Science 275(5307):1800-4 (1997).

Person & Lipman, Improved Tools for Biological Sequence Comparison, *Proc. Natl. Acad. Sci. USA* 85:2444 (1988).

Pojer et al., CloQ, a Prenyltransferase Involved in Clorobiocin Biosynthesis, Proc Natl Acad Sci USA 100:2316-2321 (2003).

Sacchettini et al., Crystal Structure of Rat Intestinal Fatty-acid-binding Protein, J Mol Biol 208(2):327-39 (1989).

Shin-ya, et al., Isolation and Structural Elucidation of an Antioxidative Agent, Naphterpin, in J. Antibiot. (Tokyo) 43, 444-447 (1990).

Smith & Waterman, Comparison of Biosequences, *Adv. Appl. Math.* 2:482 (1981).

Takagi et al., A Gene Cluster for the Mevalonate Pathway from Streptomyces sp. Strain CL190, J Bacteriol 182:41534157 (2000).

Tarshis et al., Crystal Structure of Recombinant Farnesyl Diphosphate Synthase at 2.6-Å Resolution, Biochemistry 33(36):10871-7 (1994).

Xu et al., The Adipocyte Lipid-binding Protein at 1.6-Å Resolution, J Mol Biol 268(11):7874-84 (1993).

\* cited by examiner

AROMATIC PRENYLTRANSFERASES, NUCLEIC ACIDS ENCODING SAME AND USES THEREFOR

ACKNOWLEDGMENT

This invention was made with government support under Grant No. AI-051438 by the National Institutes of Health. The government has certain rights in the invention.

FIELD OF THE INVENTION

The present invention relates to aromatic prenyltransferases, nucleic acids encoding same, crystalline forms of aromatic prenyltransferases, and various uses therefor. In one embodiment, methods are provided for predicting the activity and/or substrate specificity of putative aromatic prenyltransferases. In another embodiment, methods of screening compounds to identify compounds which bind aromatic prenyltransferases and/or modulate the activity thereof, are provided. In yet another embodiment, methods of screening compounds to identify potential substrates of aromatic prenyltransferases are provided. In still another embodiment, methods are provided for prenylating aromatic structures, as well as controlling and/or modifying the degree of prenylation promoted by aromatic prenyltransferases. In a further embodiment, methods are provided for identifying proteins having the newly discovered beta/alpha barrel structure. In a still further embodiment, methods are provided for controlling and/or modifying the substrate specificity of aromatic prenyltransferases.

BACKGROUND OF THE INVENTION

Nature is a prolific producer of small molecules that have evolved to interact with diverse biological targets. From a human health perspective, natural products have dramatically altered our lives by providing many front-line drugs as well as chemical probes to unravel basic molecular pathways germane to health and disease. Although natural products continue to provide about half of all new chemical entities approved as drugs by the US Food and Drug Administration, drug discovery during the latter part of the $20^{th}$ century shifted away from natural products towards synthetic libraries. This paradigm shift reflected the complexity of small, natural libraries against the simplicity of large, combinatorial synthetic libraries and was rationalized in order to keep pace with the enormous capacity of industrial high-throughput screening programs. New drugs from combinatorial chemical libraries, however, did not materialize during this time period, while natural products continued as an important source. Natural products, like drugs, cover a chemical space that is much more diverse than combinatorial compounds, thereby reflecting the rich chemical diversity of this resource.

Recent technological advances in natural product research involving isolation, characterization, synthesis, and biosynthesis have rekindled an interest in their investigation in academia and industry. With the advent of modern molecular biology, the field of biosynthesis has blossomed over the past decade with new approaches to generate biosynthetic libraries that further extend natural product structural diversity into new chemical space. In vivo approaches involving combinatorial biosynthesis, mutasynthesis, and precursor-directed biosynthesis and complementary in vitro approaches that combine chemical synthesis and enzymology (chemoenzymatic synthesis) have led to impressive libraries of novel molecules never encountered in nature. Natural product structural classes that have been biosynthetically manipulated in this fashion include the polyketides, nonribosomal peptides, terpenoids, and alkaloids. Most progress in this burgeoning field has resided with the actinomycetes (soil bacteria), which offer impressive arrays of natural products whose biosynthetic genes are typically clustered and are thus readily amenable to genetic manipulation. One notable exception that is absent from the biosynthetic diversification platform, however, is the hybrid isoprenoid class of natural products.

Natural products, such as the isoprenoid (terpenoid) family of diverse chemical scaffolds have held significant interest for the synthetic organic chemistry community because they are both challenging synthetic projects and possess varied biological activities and medicinal properties. Within the terpenoid family, the total synthesis of sesquiterpene natural products and related analogs continue to dominate the chemical literature. The demand for a reliable production platform for structurally complex terpenes has increased dramatically over the last 10 years and is of growing interest. Elegant synthetic schemes for terpenoids have been developed, but suffer from low yields and low regio- and enantio-selectivity. Although engineered E. coli has the potential to make mg/L levels of sesquiterpene hydrocarbons, the more biologically active terpenes are highly functionalized with hydroxyl, methyl, acetyl, halide, carbohydrate, and peroxide functional groups that require multi-step biosynthetic mechanisms often tethered to endo-membrane systems conducive for metabolic coupling. By integrating biosynthetic complexity with synthetic diversification, it may be possible for many of these hurdles to the technological development of terpenoids to be overcome.

Moreover, hybrid compounds containing terpene-derived residues comprise a large and diverse group of natural products that command an important role in human health (see Table 1). Historically this class of compounds has provided important drugs (e.g., the anticancer agent vincristine, the antimalarial quinine and the immunosuppressant mycophenolate mofetil) as well as challenging synthetic targets (e.g., strychnine and reserpine). In addition to natural products, many important coenzymes (ubiquinone and plastoquinone) and vitamins (tocopherols, phylloquinones, and menaquinones), which function in electron transport systems, contain isoprenoid residues.

TABLE 1

Representative hybrid isoprenoids, their sources and biological significance

| Natural Product | Source | Isoprenoid Hybrid | Biological Activity |
|---|---|---|---|
| mycophenolic acid | fungus | polyketide | immunosuppressant |
| khellin | plant | polyketide | bronchial asthma |
| tetrahydro-cannabinol | plant | polyketide | narcotic, antiemetic |
| rotenone | plant | isoflavonoid | insecticide |
| psoralen | plant | coumarin | skin pigment and irritant |
| novobiocin | bacterium | coumarin | antibiotic |
| lucidin | plant | quinine | mutagen |
| emetine | plant | tetrahydro-isoquinoline | alkaloid emetic (ipecac) |
| ergometrine | fungus | ergot | alkaloidoxytocic |
| reserpine | plant | indole | alkaloidantihypertensive |
| vincristine | plant | indole alkaloid | anticancer |
| strychnine | plant | indole alkaloid | toxin |
| lyngbyatoxin | cyano-bacterium | indole alkaloid | inflammatory agent |
| quinine | plant | quinoline alkaloid | antimalarial |
| camptothecin | plant | quinoline alkaloid | topoisomerase/inhibitor |

Nature has assembled a myriad of scaffolds to which isoprenoids have been attached, and these include polyketides (the so-called meroterpenoids), flavonoids, coumarins, quinones, alkaloids, phenazines, and the like. Often the terpenoid unit is further elaborated by electrophilic cyclization and oxidative chemistry upon attachment to its building block, thereby leading to the great structural diversity observed within this group. While most of these natural products contain a single isoprenoid unit of varying chain length, others harbor multiple isoprene units such as in the tetraprenylated benzoylphloroglucinol derivatives sampsoniones A-I.

The vast majority of hybrid isoprenoids are derived from eukaryotes, particularly plants. For instance, over a thousand monoterpenoid indole alkaloids have been characterized, making this a major class of plant alkaloids. On the other hand, terpenoids, and in particular hybrid isoprenoids, appear to have a limited distribution in prokaryotes. While actinomycetes are metabolically very rich bacteria and produce many important biosynthetic classes of natural products that include polyketides, nonribosomal peptides, aminoglycosides, and the like, the terpenoids are notably scarce. As a consequence, while other natural product structural classes have been biosynthetically exploited in the drug discovery arena, the hybrid isoprenoids are noticeably absent due to our limited understanding of their biosynthesis at the biochemical and genetic levels.

The majority of the basic understanding of how hybrid isoprenoids are biosynthesized in plants, fungi and bacteria is based on feeding experiments with labeled precursors. Enzymes and their encoding genes associated with interfacing isoprenyl diphosphates with their small molecule building blocks are very few and are mostly associated with plant natural products such as shikonin and with coenzymes and vitamins such as the ubiquinones, plastoquinones, menaquinones, and tocopherols. Very recently, two prokaryotic prenyltransferases (PTases) involved in the biosynthesis of the streptomycete antibiotics clorobiocin and novobiocin and the cyanobacterial toxin lyngbyatoxin were discovered. These soluble, monomeric PTases contrast with the membrane-associated PTases previously identified from eukaryotes.

Actinomycetes produce a limited set of pure and hybrid terpenoids. The antibiotic novobiocin was the first streptomycete natural product discovered with a terpenoid side chain; this group has since grown to include other members bearing naphthoquinones (naphterpin, furaquinocin, napyradiomycins), phenazines (lavanducyanin, aestivophoenin), shikimate-derived quinones, and other aromatic substrates (see FIG. 1B). Feeding experiments delineated a number of biosynthetic pathways, including those to novobiocin, naphterpin, and furaquinocin, and revealed that actinomycetes utilize both the mevalonate and nonmevalonate (methyl-D-erythritol 4-phosphate (MEP)) pathways to synthesize their isoprene building blocks.

The development of novel methodologies related to natural products chemistry and biosynthesis is of growing interest. Prenylated aromatic natural products appear to be a very promising class of therapeutically compounds. The prenylation of aromatic compounds often leads to significant alteration in the bioactivity profile of a compound, by both the creation of a novel C—C bond and also the introduction of one or more double bonds in the framework of the final product. Such compounds can affect a wide variety of biological systems in mammals and include roles as antioxidants, anti-inflammatories, anti-virals, anti-proliferatives, and anti-cancers.

Prenyltransferases (PTases) are ubiquituous enzymes that catalyze the alkylation of electron rich prenyl acceptors by the alkyl moieties of allylic isoprene diphosphates. Prenyltransferases utilize isoprenoid diphosphates as substrates, and catalyze the addition of the acyclic prenyl moiety to isopentenyl diphosphate (IPP), higher order prenyl diphosphates, aromatic rich molecules and proteins. Until now, only a few "aromatic" prenyltransferases have been isolated, each of which has been shown to interact with only a limited range of substrate(s) and/or prenyl donors. Such prenyltransferases have otherwise only been nominally characterized; and none of such prenyltransferases have been characterized at the structural level.

Accordingly, there is a need in the art for the identification of novel enzymes capable of promoting the prenylation of aromatic compounds, as well as compounds which can modulate the prenylation of aromatic compounds. These and other needs are addressed by the present invention, as described in greater detail in the specification and claims which follow.

SUMMARY OF THE INVENTION

In accordance with the present invention, a novel aromatic prenyltransferase, Orf2 from *Streptomyces* sp. strain CL190, involved in naphterpin biosynthesis (Shin-ya, et al., in J. Antibiot. (Tokyo) 43, 444-447 (1990)) has been identified and the structure thereof elucidated. This prenyltransferase catalyzes the formation of a C—C bond between a prenyl group and a compound containing an aromatic nucleus, and also displays C—O bond formation activity. Numerous crystallographic structures of the prenyltransferase have been solved and refined, e.g., (1) prenyltransferase complexed with a buffer molecule (TAPS), (2) prenyltransferase as a binary complex with geranyl diphosphate (GPP) and $Mg^{2+}$, and prenyltransferase as ternary complexes with a non-hydrolyzable substrate analogue, geranyl S-thiolodiphosphate (GSPP) and either (3) 1,6-dihydroxynaphthalene (1,6-DHN), or (4) flaviolin (i.e., 2,5,7-trihydroxy-1,4-naphthoquinone, which is the oxidized product of 1,3,6,8-tetrahydroxynaphthalene (THN)). These structures have been solved and refined to 1.5 Å, 2.25 Å, 1.95 Å and 2.02 Å, respectively. This first structure of an aromatic prenyltransferase displays an unexpected and non-canonical (β/α)-barrel architecture.

The complexes with both aromatic substrates and geranyl containing substrates and analogs delineate the active site and are consistent with a proposed electrophilic mechanism of prenyl group transfer. These structures also provide a mechanistic basis for understanding prenyl chain length determination and substrate recognition in this structurally unique family of aromatic prenyltransferases. This structural information is useful for predicting the aromatic prenyltransferase activity of proteins.

Specifically, the present disclosure describes the identification of two novel aromatic prenyltransferases with promiscuous activity: Orf2 from *Streptomyces* CL.190 and HypSc from *Streptomyces coelicolor*. The present disclosure also describes a high resolution structure of a new type of β/α-barrel which provides a useful structural template for understanding the mechanistic features accompanying Orf2's promiscuous activity with respect to a number of aromatic prenyl acceptors and its means of regulating prenyl chain length specificity through a well ordered prenyl chain binding surface. The β/α-barrel catalyzes the prenylation of aromatic compounds, accepts a wide range of aromatic substrates and uses hydrophobic interactions to bind the hydrocarbon moiety of an allylic diphosphate substrate (GPP or FPP).

It is demonstrated herein that this "biosynthetic barrel" can be used as starting point for engineering the prenylation of natural products of both microbial and plant origin. The structural details involved in substrate specificity in this newly characterized small molecule prenyltransferase enables the biosynthetic diversification of numerous aromatic compounds foind in nature, and of synthetic origin by providing a structurally guided process of enzyme design and evolution, leading to the production and metabolic engineering of novel prenylated natural products through in vivo transgenic approaches, or ultimately, for in vitro combinatorial chemistry.

BRIEF DESCRIPTION OF THE FIGURES

FIG. 3 collectively presents a comparison of the different types of protein barrel topologies. Two-dimensional topology diagrams and three dimensional views of protein barrels are displayed from top to bottom. Each secondary structure element (helices represented as circles (or spiral ribbons) and β-strands as triangles (or flat ribbons)) maintains directionality (N to C) which is either "up" (out of the plane of the diagram) or 'down' (into the plane of the diagram). The direction of elements can be deduced from the connecting lines, and also from the orientation of the strands.

FIG. 4 collectively presents close-up views of the active site of Orf2 of SEQ ID NO:2 in different complexes.

DETAILED DESCRIPTION OF THE INVENTION

Figure 1A:
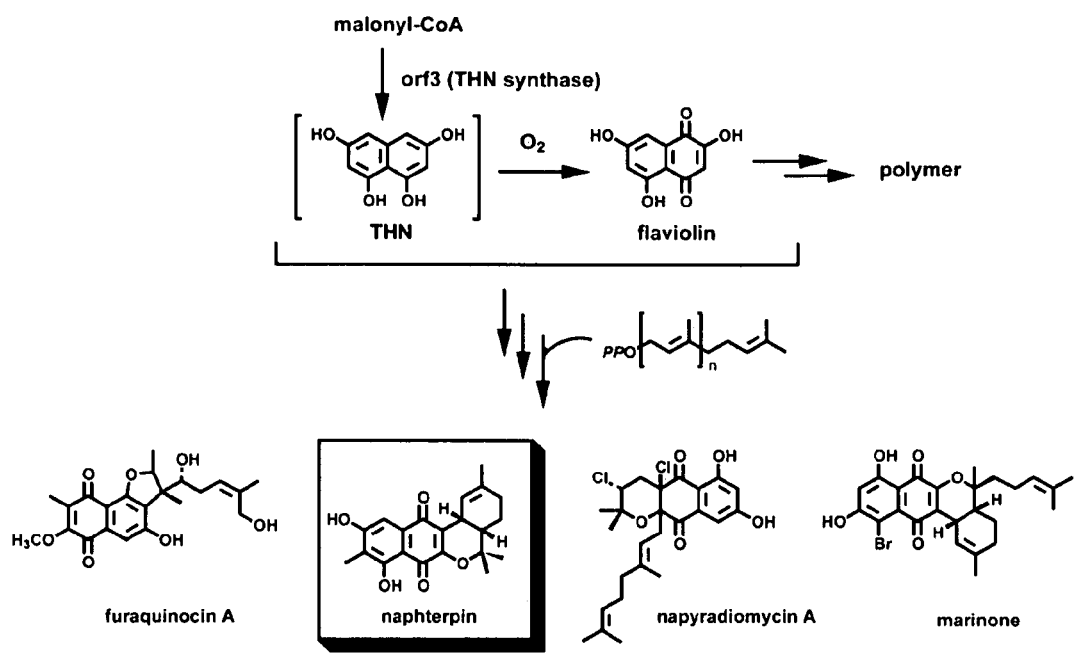
FIG. 1A presents the structures of hybrid terpenoid-polyketide compounds produced by Actinomycetes. The synthesis of naphterpin involves the prenylation of THN, flaviolin or a derived metabolite using a GPP co-substrate. THN is produced from malonyl-CoA by the action of THN synthase encoded by orf3. THN is readily oxidized to give a hydroquinone derivative, 2,5,7-trihydroxy-1,4-naphthoquinone (flaviolin). The THN skeleton is further modified, prenylated and incorporated into hybrid terpenoid-polyketide compounds such as naphterpin, furaquinocin A, napyradiomycin A and marinone.

Naphterpin is a bioactive natural product (hemiterpenoidal anti-oxidant agent) produced by *Streptomyces* sp. strain CL190 via both the mevalonate (MVA) isoprenoid biosynthetic pathway as well as a polyketide biosynthetic pathway (see, for example, Shin-ya, et al., in Tetrahedron Lett. 31, 6025-6026 (1990); Shin-ya, et al., in J. Antibiot. (Tokyo) 43, 444-447 (1990); and Seto, et al, in Tetrahedron Letters 37(44):7979 (1996), see also FIG. 1A). The compound is composed of a tetrahydroxynaphthalene (THN) derivative and a geranyl moiety. THN is known in the art to be biosynthesized from 5 molecules of malonyl coenzyme A (CoA) by the action of type III polyketide synthase (THN synthase) cloned from *Streptomyces griseus* (see Funa, et al., in Nature 400, 897-899 (1999)) and *Streptomyces coelicolor* (see Izumikawa et al., in J. Ind. Microbiol. Biotechnol. 30:510-515 (2003)). Compounds with naphthoquinone rings, including naphterpin, furaquinocin, napyradiomycin and marinone, are biosynthesized via the symmetric polyketide intermediate 1,3,6,8-tetrahydroxynaphthalene (THN; see Shin-ya, et al., in J. Antibiot. (Tokyo) 43, 444-447 (1990)) (FIG. 1A). In *Streptomyces griseus* and *Streptomyces coelicolor* A3(2), THN is the product of a chalcone synthase-like type III polyketide synthase (PKS), known as THN synthase (THNS) (Austin and Noel, Nat Prod Rep 20(1):79-110 (2003)). THN readily (or enzymaticaly) oxidizes forming a hydroquinone derivative, 2,5,7-trihydroxy-1,4-naphthoquinone (flaviolin), part of which subsequently undergoes polymerization to form a variety of colored polymeric compounds (Funa et al., Nature 400(6747):897-9 (1999)).

In addition to its role in pigment production, the THN skeleton is further modified and incorporated into naphterpin in *Streptomyces* sp. strain CL190 (Shin-ya et al., J. Antibiot (Tokyo) 45(1):124-5 (1992)).

In actinomycetes, three mevalonate gene clusters have been cloned to date, i.e., from CL190, *Kitasatospora griseola* (terpentecin producer) (see Hamano, et al., in Biosci. Biotechnol. Biochem. 65:1627-1635 (2001)), and *Actinoplanes* sp. strain A40644 (BE-40644 producer) (see Kawasaki, et al., in J. Antibiot. 56:957-966 (2003)). All of these clusters encode mevalonate kinase, diphosphomevalonate decarboxylase, phosphomevalonate kinase, isopentenyl diphosphate isomerase, 3-hydroxy-3-methylglutaryl (HMG)-CoA reductase, and HMG-CoA synthase. The order of each of the genes is also the same and respective homologous genes have 50 to 80% amino acid identity with each other.

In contrast to the high conservation of the mevalonate pathway gene clusters, a diversity of genes is distributed in their flanking regions. For example, the geranylgeranyl diphosphate synthase, a key enzyme of the terpentecin biosynthesis, is encoded in the region just upstream of the mevalonate kinase gene, with the terpentecin biosynthetic gene cluster located further upstream. In addition, farnesyl diphosphate synthase, a key enzyme of the BE40644 biosynthesis, is located just upstream of the mevalonate kinase gene, with the BE-40644 biosynthetic gene cluster located in the region downstream of the mevalonate pathway gene cluster.

These facts, taken together, gave rise to the hypothesis that the mevalonate pathway genes cluster, that terpenoid biosynthetic genes are usually clustered in a terpenoid-producing actinomycetes, and that the mevalonate pathway gene cluster could be a good marker to clone the terpenoid biosynthetic genes from the terpenoid-producing actinomycetes. Based on this hypothesis, in order to clone a naphterpin biosynthetic genes cluster, the flanking regions of the mevalonate pathway genes cluster which was cloned from CL190 were sequenced.

Figure 1B:
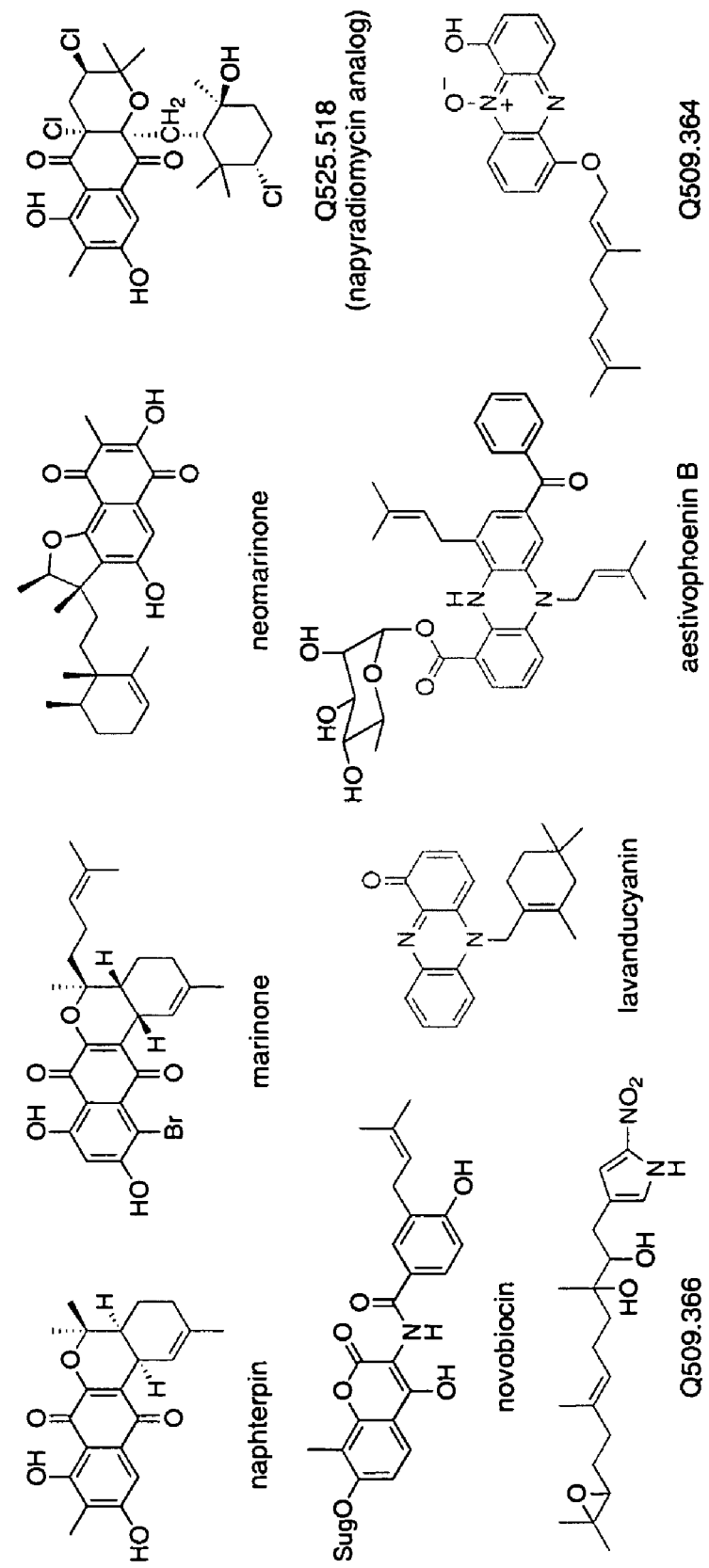
FIG. 1B provides structures of representative hybrid isoprenoids from actinomycetes. Isoprenoid units are appended to naphthoquinone (see naphterpin, marinone, neomarinone, and Q525.518), phenol (see novobiocin), phenazine (see lavanducyanin and aestivophoenin B), and nitropyrrole (see Q509.364) residues via C-, N-, and O-linkages, as appropriate.
Figure 1C:
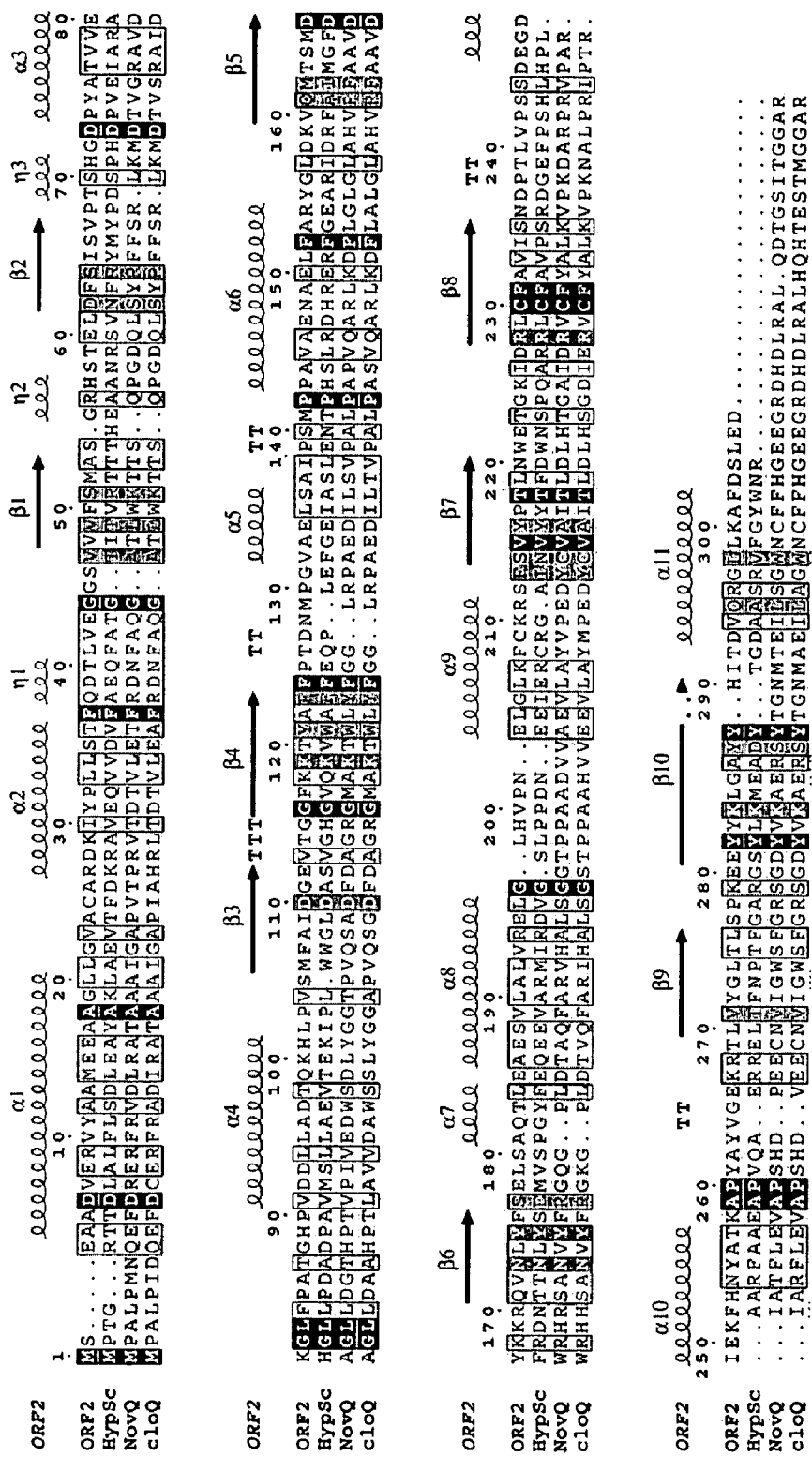
FIG. 1C presents a structure based multiple sequence alignment. The orf2 gene product of SEQ ID NO:2 from Streptomyces sp. strain CL190, Orf2, is a 33kDa soluble, monomeric protein comprising 307 residues. PSI-BLAST searches revealed strong homologies between Orf2 and three other bacterial proteins: a protein from Streptomyces coelicolor A3(2)(HypSc, accession number AL939130) (SEQ II) NO: 5) and the previously described 4-hydroxyphenylpyruvate: dimthyallyl transferase genes, cloQ (accession number AF329398) (SEQ ID NO: 7) and novQ (accession number AF170880) (SEQ ID NO: 6), from Streptomyces roseochromogenes and Streptomyces spheroids NCIMB 11891, respectively. Residues (one-letter amino acid code) are numbered according to Orf2's sequence. Dashes represent insertions and deletions. This alignment has been linked with the known Orf2 secondary structure and rendered with ESPript (accessible via the internet on the world wide web at the URL "prodes.toulouse.inra.fr/ESPript"). The coding is as follows: grey on grey for residues located in the active site, white on black for residues strictly conserved, and white on grey overlay for residues both strictly conserved and located in the active site. Residues bounded by grey frames represent similar residues in the aligned sequences.

To understand the biosynthetic pathway of this mixed terpene/polyketide derived natural product, the gene cluster responsible for naphterpin production was identified based upon proximity to genes encoding the MVA pathway biosynthetic enzymes. An upstream region of the gene cluster containing the MVA pathway genes revealed three new open reading frames or orfs designated orf1, orf2, and orf3. The comparative analysis of these orfs with genes encoding functionally characterized proteins is summarized in Table 2. PSI-BLAST searches revealed homologies between Orf2 and three other bacterial proteins: a protein from *Streptomyces coelicolor* A3(2) (HypSc, accession number AL939130) and the previously described 4-hydroxyphenylpyruvate:dimethylallyl transferase genes, cloQ (accession number AF329398) and novQ (accession number AF170880), from *Streptomyces roseochromogenes* and *Streptomyces spheroides* NCIMB 11891, respectively (FIG. 1B).

To further understand the function of the genes referred to above, a mutant *Streptomyces* sp. (strain CL190) was prepared by disrupting the Orf2 gene of SEQ ID NO:1. This mutant exhibited no naphterpin production. The high degree of homology between Orf2 and the functionally characterized prenyltransferases CloQ/NovQ (Pojer et al., Proc Natl Acad Sci USA 100:2316-2321 (2003)) (FIG. 1B), and the fact that Orf3 encodes a type III polyketide synthase with amino acid similarity to THNS, establishes that off2 encodes a prenyltransferase involved in geranyl group transfer to THN or a THN derivative produced through the action of orf3 (and possibly other tailoring enzymes).

When expressed in *E. coli*, Orf2 of SEQ ID NO:2 is as a 33kDa soluble, monomeric protein having 307 residues. To assess enzyme activity, the purified recombinant Orf2 protein was incubated with one of the following prenyl (geranyl) donors, i.e., dimethylallyl diphosphate (DMAPP, C05), geranyl diphosphate (GPP, C 10) or farnesyl diphosphate (FPP, C 15) along with several possible substrates (i.e., prenyl acceptors) possessing one or more aromatic groups. A variety of THN analogues (e.g.,1,3-dihydroxynaphtalene (1,3-DHN), 1,6-DHN, 2,7-DHN, and flaviolin) are observed to function as substrates for Orf2 of SEQ ID NO:2, i.e., are converted by Orf2 into prenylated derivatives thereof (see FIGS. 2A and 2B). The 4-hydroxyphenylpyruvate (4-HPP) substrate of CloQ/NovQ (Pojer et al, supra) was also converted by Orf2 of SEQ ID NO:2 into a prenylated derivative thereof. In contrast, the related molecules, phenylalanine or tyrosine, did not serve as substrates (see FIG. 2B). No activity was observed with DMAPP, the highest relative activity was observed with GPP, and weak activity was observed with FPP. In summary, Orf2 of SEQ ID NO:2 recognizes a variety of substrates.

Figure 2A:
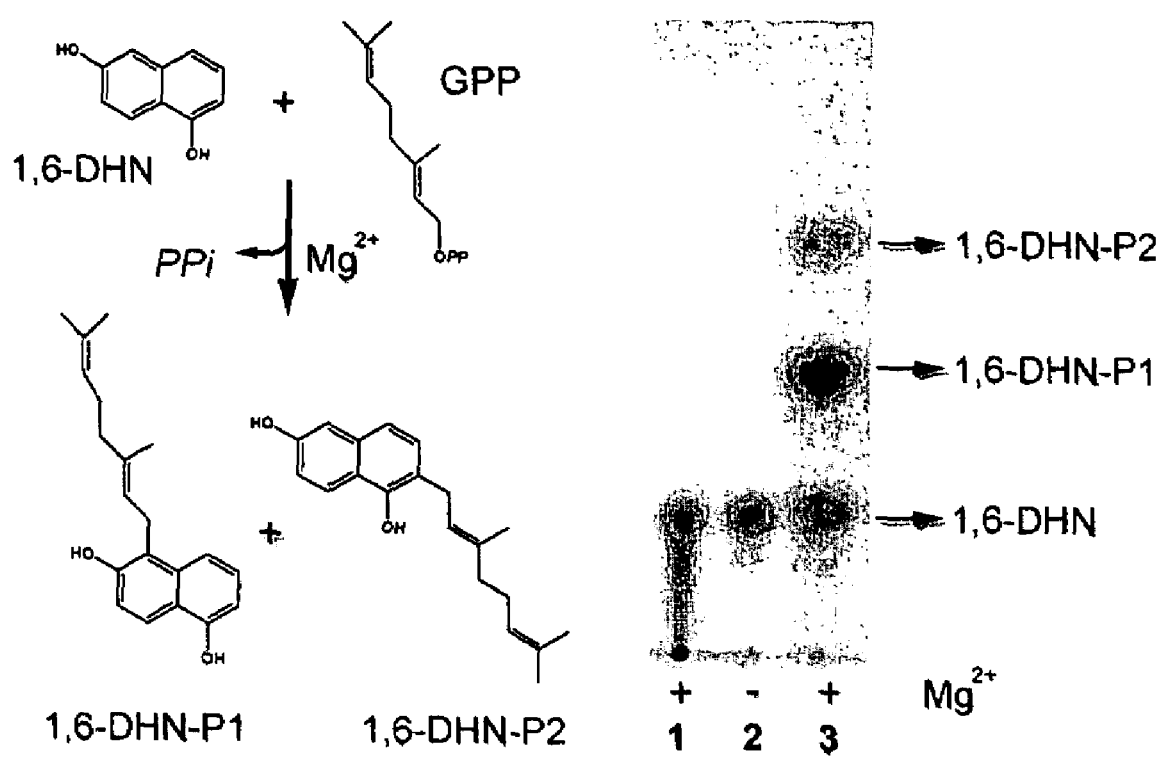
FIG. 2A illustrates the $Mg^{2+}$ dependent prenylation of 1,6-DHN. The reaction buffer consisted of 50 mM HEPES (pH 7.5), 5 mM 1,6-DHN, and 5 mM GPP in a final volume of 20 μl. The reaction was initiated by adding 20 μg of Orf2 to the assay mixture. After incubation at 25° C. for 4 hours, the mixture was dried, and spotted on a silica gel TLC plate. The TLC plate was developed with a chloroform/methanol (20:1) solvent mixture. 1,6-DHN and reaction products were detected at 254 nm. The chemical analyses of the two HPLC purified products were accomplished by both MS and $^1$H NMR analyses. In lane 1 (control), Orf2 was boiled prior to adding. The reaction mixture in lane 2 contained no $MgCl_2$, while 5 mM $MgCl_2$ was added in lane 3.
Figure 2B:
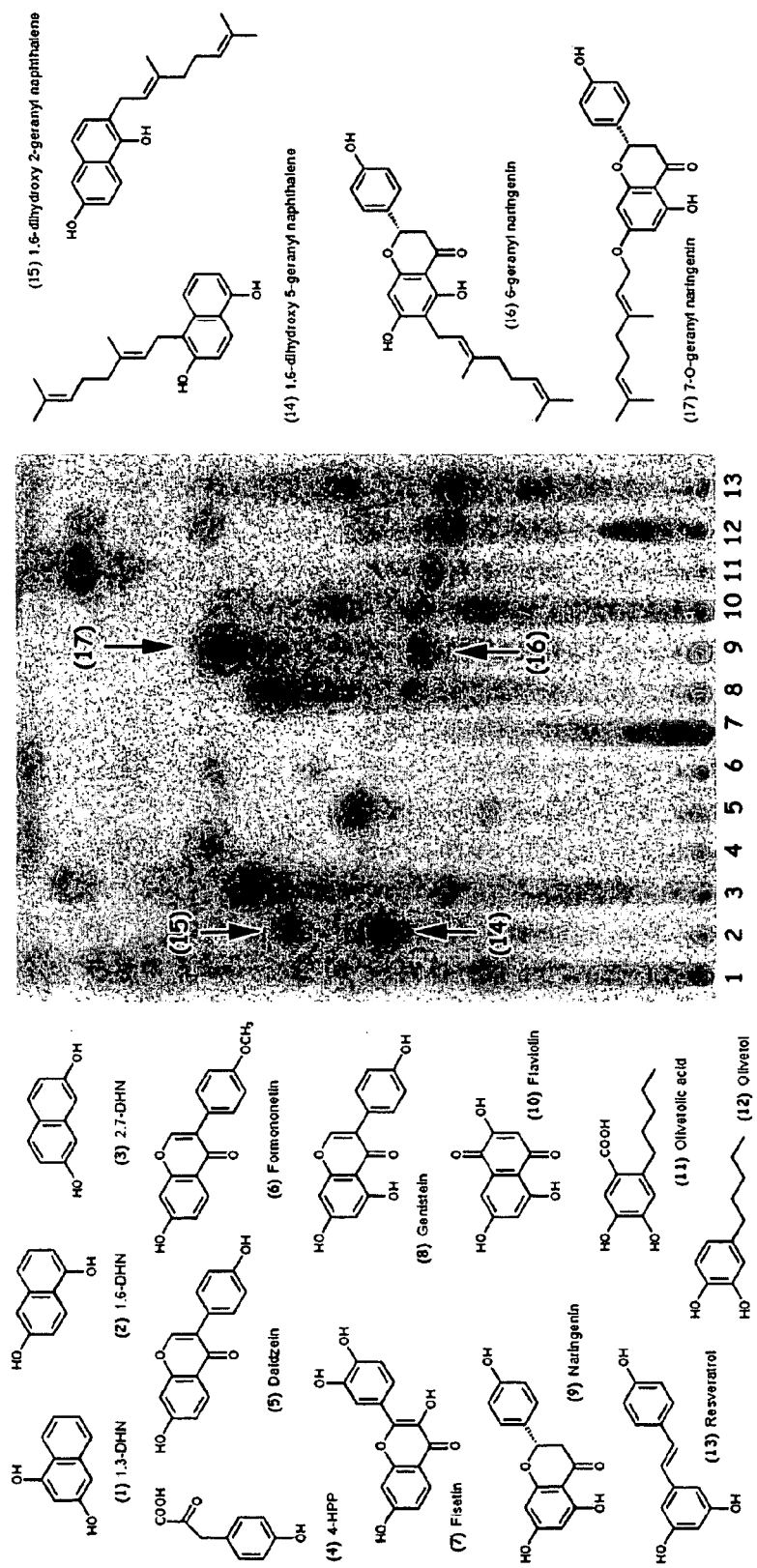
FIG. 2B illustrates the promiscuous activity of Orf2. Several assays were conducted, employing a variety of potential substrates, i.e., 1,3-DHN (1), 1,6-DHN (2), 2,7-DHN (3), 4-HPP (4) and several isoflavonoids and polyketide derivatives, including daidzein (7,4'-dihydroxy-isoflavonone, 5), formononetin (7-hydroxy, 4'-methoxy-isoflavonone, 6), fisetin (3,3',4',7-tetrahydroxyflavone, 7), genistein (5,7,4'-trihydroxyisoflavone, 8), naringenin (5,7, 4'-trihydroxyflavonone, 9), flaviolin (10), olivetol (11), olivetolic acid (12), and resveratrol (3,4',5-trihydroxystilbene, 13). The chemical structures of four reaction products (i.e., 1,6-dihydroxy 2-geranyl naphthalene (14), 1,6-dihydroxy 5-geranyl naphthalene (15), 6-geranyl naringenin (16) and 7-O-geranyl naringenin (17)) were determined by both MS and 1H NMR analyses. The reaction buffer consisted of 50 mM HEPES (pH 7.5), 5 mM $MgCl_2$, and 0.1 mM GPP, 0.009 mM [$^{14}$C]GPP, and 0.1 mM of each substrate, in a final volume of 20 μl. The reaction was initiated by adding 30 μg of Orf2 to the assay mixture. After incubation at 25° C. for 6 hours, the mixture was dried, and spotted on a silica gel TLC plate. The TLC plate was developed with a chloroform/methanol (15:1) solvent mixture. Reaction products were detected with a [$^{14}$C] imaging plate (Fuji Photo Film).

Moreover, significant $Mg^{2+}$ dependent, in vitro activity is observed with the dihydroxy containing THN analogs (FIGS. 2A and 2B). Thus, two prenylated products, 1,6-DHN-P1 and 1,6-DHN-P2, were readily detected by thin layer chromatography when Orf2 was incubated with 1,6-DHN and GPP (TLC, FIGS. 2A and 2B). Large scale incubations with GPP and 1,6-DHN produced a sufficient amount of both products (in an approximate ratio of 10:1) to permit their structure elucidation by both MS and $^1$H NMR analyses: these compounds, trans-5-geranyl 1,6-DHN and trans-2-geranyl 1,6-DHN, are believed to be novel natural products (see FIG. 2A).

Orf2's potential to serve as a template for the diversification of novel aromatic natural products was demonstrated by assaying the ability of Orf2 to interact with various flavonoids, isoflavonoids and related compounds (e.g., resveratrol; see FIG. 2B). While Orf2 showed prenyltransferase activity in the presence of daidzein (7,4'-dihydroxyisoflavanone), formononetin (7-hydroxy, 4'-methoxyisoflavanone), genistein (5,7,4'-trihydroxyisoflavone), and resveratrol (3,4',5-trihydroxystilbene), little or no activity was observed in the same test conditions with fisetin (3,3',4',7-tetrahydroxyflavone). In the presence of naringenin (5,7,4'-trihydroxyflavanone) and GPP, two reaction products, 6-geranyl naringenin, and 7-O-geranyl naringenin, were identified (by both MS and $^1$H NMR analyses; see FIG. 2B). 6-geranyl naringenin (also known as bonannione A; see Bruno, Heterocycles 23(5):1147-1153 (1985)), is a prenylated flavanone displaying significant antibacterial activity (Schutz, Phytochemistry 40:1273-1277 (1995)). 7-O-geranyl naringenin, which harbors a prenyl unit in the form of an ether moiety, which is only occasionally found in isoflavones, is a novel prenylated flavonoid.

Only a trace component in hops, 6-geranyl naringenin is formed by the isomerization (cyclization) of the more abundant hop flavonoid, 2',4',6',4-tetrahydroxy-3'-geranylchalcone. Interestingly, the antifungal activity of various yellow lupin constituents has been reported, using *Cladosporium herbarum* as the test fungus. It was found that for isoflavones, the 6-prenyl and 3'-prenyl compounds were more fungitoxic than the 8-prenyl analogues and that transformation of the prenyl group to a cyclized derivative greatly reduced or eliminated the fungitoxic effects.

Orf2 was also active in the presence of both olivetol and olivetolic acid (see FIG. 2B). These compounds are intermediates in the biosynthesis of the therapeutic plant derived polyketide-terpene natural product $\Delta^9$-tetrahydrocannabinol ($\Delta^9$-THC). $\Delta^9$-THC is the primary psychoactive component found in *Cannabis sativa*. A synthetic analogue thereof, i.e., dronabinol, is currently used to alleviate nausea/vomiting and to stimulate appetite in order to counter weight loss in cancer and AIDS patients. The primary psychoactive component in cannabis, $\Delta^9$-THC affects the brain mainly by activating two specific cannabinoid receptors (CB1 and CB2). These receptors also bind to 'endogenous' cannabinoids, which are produced naturally by the human body. Recent studies of the cannabinoid signaling system shows its involvement in an ever-increasing number of pathological conditions. As the geranyl prenyltransferase activity involved in $\Delta^9$-THC biosynthesis in *Cannabis sativa* has until now only been detected in cell extracts, it was decided to test Orf2's activity in the presence of both olivetol and olivetolic acid, two supposed intermediates of $\Delta^9$-THC biosynthesis: Orf2's reaction products were detected on TLC with both $\Delta^9$-THC precursors, differing from the *C. sativa* endogenous enzyme for which activity was only observed in the presence of olivetolate molecule. These results are very promising for the opening of new therapeutic avenues based on the ability to modulate the endocannabinoid system.

Thus, in accordance with the present invention, there are provided aromatic prenyltransferases having a beta/alpha barrel structure.

As used herein, the phrase "beta/alpha barrel structure" refers to a closed β-sheet comprising antiparallel β-strands arranged around a central β-barrel core, itself surrounded by a ring of α-helices forming the outer, solvent exposed surface of the beta/alpha barrel, as described in greater detail herein. Thus, aromatic prenyltransferases are seen to have the unique beta/alpha barrel secondary structure.

This protein is the first identified and structurally characterized enzyme involved in a mixed polyketide-isoprenoid biosynthetic pathway, namely naphterpin biosynthesis. While this protein family has been identified and characterized from *Streptomyces* bacteria, numerous prenylated aromatic natural products are found in plants. For example, the therapeutically important natural product, tetrahydrocannabinol (THC) is a mixed polyketide-isoprenoid. Biosynthetic logic would dictate that plants are likely to contain enzymes similar in structure and function to Orf2, but such enzymes have thus far not been identified. Given this likelihood, Orf2/CloQ/NovQ/HypSc are believed to be the first identified members of a widespread and catalytically interesting family of enzymes.

Exemplary aromatic prenyltransferases according to the present invention have the amino acid sequence set forth in SEQ ID NO:2, or conservative variations thereof, provided that the variant polypeptide retains prenyltransferase activity. As used herein, "conservative variations" refer to the replacement of an amino acid residue by another, biologically similar residue. Examples of conservative variations include the substitution of one hydrophobic residue such as isoleucine, valine, leucine or methionine for another; or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine, and the like. The term "conservative variation" also includes the use of a substituted amino acid in place of an unsubstituted amino acid.

Modifications and substitutions contemplated herein are not limited to replacement of amino acids. For a variety of purposes, such as increased stability, solubility, or configuration concerns, one skilled in the art will recognize the need to introduce other modifications (e.g., by deletion, replacement, or addition). Examples of such other modifications include incorporation of rare amino acids, dextra-amino acids, glycosylation sites, cytosine for specific disulfide bridge formation. The modified peptides can be chemically synthesized, or the isolated gene can be site-directed mutagenized, or a synthetic gene can be synthesized and expressed in bacteria, yeast, baculovirus, tissue culture, and the like.

Aromatic prenyltransferases having sequence substantially identical to the amino acid sequence set forth in SEQ ID NO:2 are also contemplated herein. By "substantially identical" is meant a polypeptide or nucleic acid exhibiting at least 50%, preferably 60%, more preferably 70%, more preferably 80%, more preferably 85%, more preferably 90%, and most preferably 95% homology to a reference amino acid or nucleic acid sequence, provided that the "substantially identical" polypeptide retains prenyltransferase activity.

Alternatively, aromatic prenyltransferases according to the present invention have at least 80% sequence identity with the amino acid sequence set forth in SEQ ID NO:2. Sequence homology and identity are often measured using sequence analysis software (e.g., Sequence Analysis Software Package of the Genetics Computer Group, University of Wisconsin Biotechnology Center, 1710 University Avenue, Madison, Wis. 53705). The term "identity" in the context of two or more nucleic acids or polypeptide sequences, refers to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. The term "homology" in the context of two or more nucleic acids or polypeptide sequences, refers to two or more sequences or subsequences that are homologous or have a specified percentage of amino acid residues or nucleotides that are homologous when compared and aligned for maximum correspondence over a comparison window or designated region as measured using any number of sequence comparison algorithms or by manual alignment and visual inspection. Programs as mentioned above allow for substitution of an amino acid with a similar amino acid by determining a degree of homology between the sequences being compared.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment (typically having from about 20 up to about 600 contiguous residues) in which a sequence may be compared to a reference sequence of the same number of contiguous residues after the two sequences are optimally aligned. Methods of alignment of sequence for comparison are well known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Person & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, accessible on the world wide web (www) at the URL "weber.u-.Washington.edu/~roach/human_genome_progress 2.html") (Gibbs, 1995). Several databases containing genomic information annotated with some functional information are maintained by different organization, and are accessible via the internet on the world wide web (www), for example, at the URL "tigr.org/tdb"; "genetics.wisc.edu"; "genome-www.stanford.edu/~ball"; "hiv-web.lanl.gov"; "ncbi.nlm.nih-.gov"; "ebi.ac.uk"; "Pasteur.fr/other/biology"; and "genome.wi.mit.edu".

One example of a useful algorithm is BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. Software for performing BLAST analyses is publicly available through the National Center for Biotechnology Information on the world wide web (www) at the URL "ncbi.nlm.nih.gov". This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Natl. Acad. Sci. USA* 90:5873 (1993)). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445 (1992); Henikoff and Henikoff, Proteins 17:49-61 (1993)). Less preferably, the PAM or PAM250 matrices may also be used (see, e.g., Schwartz and Dayhoff, eds., *Matrices for Detecting Distance Relationships: Atlas of Protein Sequence and Structure*, Washington: National Biomedical Research Foundation (1978)). BLAST programs are accessible through the U.S. National Library of Medicine, e.g., accessible on the world wide web (www) at ncbi.nlm-.nih.gov.

The parameters used with the above algorithms may be adapted depending on the sequence length and degree of homology studied. In some embodiments, the parameters may be the default parameters used by the algorithms in the absence of instructions from the user.

In accordance with another aspect of the present invention, there are provided nucleic acids encoding any of the above-described prenyltransferases, including all variations embraced by the degeneracy of the genetic code. Exemplary nucleic acids according to the present invention include nucleic acids which specifically hybridize to the nucleotide sequence set forth in SEQ ID NO:1 (or the complement thereof) under stringent hybridization conditions, wherein said nucleic acid encodes an aromatic prenyltransferase.

Hybridization methods are well known to those skilled in the art of molecular biology. "Specifically hybridizable" and "specifically complementary" are terms that indicate a sufficient degree of complementarity such that stable and specific binding occurs between a first nucleic acid and a DNA or RNA target. The first nucleic acid need not be 100% complementary to its target sequence to be specifically hybridizable. A first nucleic acid is specifically hybridizable when there is a sufficient degree of complementarity to avoid non-specific binding of the first nucleic acid to non-target sequences under conditions where specific binding is desired. Such binding is referred to as specific hybridization.

An alternative indication that two nucleic acid molecules are closely related is that the two molecules hybridize to each other. In certain embodiments, orf2 nucleic acid variants hybridize to a disclosed orf2 nucleic acid sequence (or fragments thereof), for example, under low stringency, moderate stringency, or high stringency conditions. Hybridization conditions resulting in particular degrees of stringency will vary depending upon the nature of the hybridization method of choice and the composition and length of the hybridizing nucleic acid sequences. Generally, the temperature of hybridization and the ionic strength (for example, the $Na^+$ concentration) of the hybridization buffer will determine the stringency of hybridization, although wash times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11.

The following exemplary sets of hybridization conditions are not meant to be limiting. High stringency conditions include hybridization in 5×SSC at 65° C. for 16 hours, two washes in 2×SSC at room temperature (RT) for 15 minutes each and two washes in 0.5×SSC at 65° C. for 20 minutes each. Moderate stringency conditions include hybridization in 5×-6×SSC at 65° C.-70° C. for 16-20 hours, two washes in 2×SSC at RT for 5-20 minutes each and two washes in 1×SSC at 55° C.-70° C. for 30 minutes each. Low stringency conditions include hybridization in 6×SSC at RT to 55° C. for 16-20 hours and two washes in 2×-3×SSC at RT to 55° C. for 20-30 minutes each.

Alternatively, nucleic acids according to the present invention include nucleic acids having at least 80% sequence identity with the nucleotide sequence set forth in SEQ ID NO:1, wherein said nucleic acid encodes an aromatic prenyltransferase.

To investigate the structural features accompanying prenyl chain length determination, aromatic substrate selectivity and the mechanism of prenyl group transfer, X-ray crystal structures of four Orf2 substrate/substrate analogue complexes were determined, namely Orf2 complexed with a TAPS buffer molecule, a binary Orf2 complex containing GPP and $Mg^{2+}$, a ternary Orf2 complex with a non-hydrolyzable GPP analogue (GSPP), $Mg^{2+}$ and 1,6-DHN, and a ternary Orf2 complex with GSPP, $Mg^{2+}$ and flaviolin (results are summarized in Table 3).

The three dimensional structure of Orf2 consists of a single domain that forms a novel barrel type of structure (FIG. 3). This new barrel, here termed a $\beta/\alpha$-barrel, is a closed $\beta$-sheet comprising sufficient antiparallel $\beta$-strands to form a central $\beta$-barrel core (typically in the range of about 6 up to 12 $\beta$-strands), with the central $\beta$-barrel core surrounded by a ring of $\alpha$-helices forming the outer, solvent exposed surface of the barrel (FIG. 3B). In the specific example when a $\beta/\alpha$-barrel structure comprises 10 $\beta$-strands, the secondary connectivity nearly conforms to a $(\alpha\alpha\beta\beta)_5$ classification, but is more specifically described using the $(\alpha\alpha\beta\beta)_4$-$(\alpha\beta\beta)$-$\alpha$ nomenclature, where helices 6 and 8, both involved in inter-protein contacts in the crystal lattice, display a helical "kink".

The most hydrophobic section of the $\beta/\alpha$-barrel is the region residing between the outer surface of the cylindrical $\beta$-barrel and the belt of surrounding $\alpha$-helices. Additionally, a number of hydrophobic residues located inside the barrel accommodate the prenyl tail of the GPP and GSPP molecules, while the diphosphate or the thio-diphosphate head groups of substrate and substrate analogs, respectively, point toward the "upper", more polar end of the barrel where a $Mg^{2+}$ ion is coordinated. Typically, the bottom of the barrel is capped by a short C-terminal helix. In the specific example when a $\beta/\alpha$-barrel structure comprises 10 $\beta$-strands, the C-terminal helix would be $\alpha_{11}$.

Structurally related proteins belonging to either the TIM barrel or the $\beta$-barrel structural families, both of which display barrel folds with connectivity patterns that are distinctively different from the $\beta/\alpha$-barrel are illustrated herein (see FIG. 3). TIM barrel proteins (ie. the aldo-keto reductase family represented by pdb entry code 2ACQ) consist of a repeated $\beta$-strand-loop-$\alpha$-helix-loop motif, most often containing eight repeats, with the parallel $\beta$-strands forming the interior of an open barrel, and the helices forming the outer belt of the complete protein (Gerlt and Raushel, Curr Opin Chem Biol 7(2):252-64 (2003)) (FIG. 3A).

$\beta$-barrel proteins including human fatty acid-binding proteins (FABP, pdb entry code 1HMT), consist of ten antiparallel $\beta$-strands arranged as an elliptical barrel capped at the bottom by two short $\alpha$-helices (Sacchettini et al., J Mol Biol 208(2):327-39 (1989); Xu et al., J Mol Biol 268(11): 7874-84 (1993) (FIG. 3D).

Figure 3A:
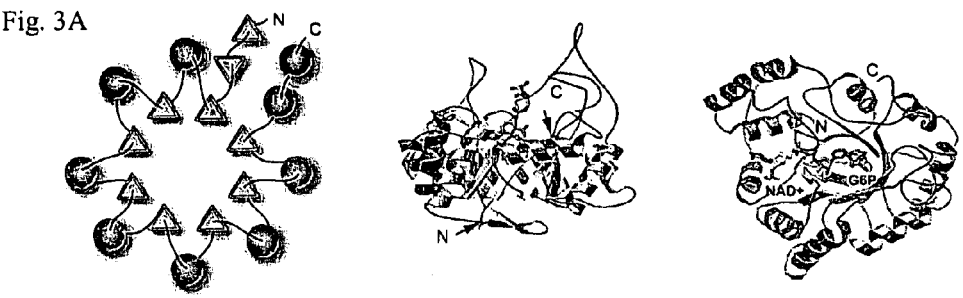
FIG. 3A illustrates an α/β-barrel (e.g., an human aldoketo reductase complexed with $NADP^+$ and glucose 6-phosphate (pdb entry 2ACQ)).
Figure 3B:
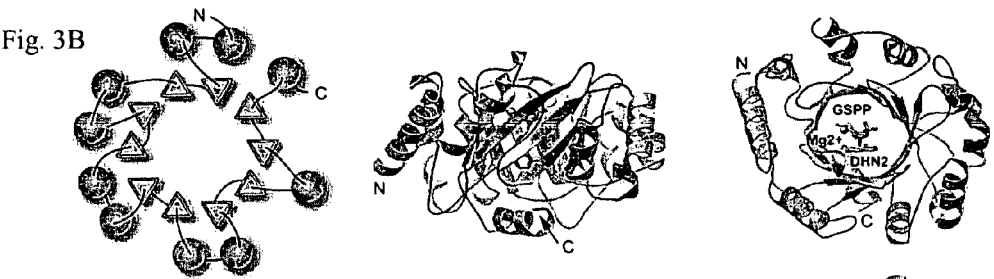
FIG. 3B illustrates a β/α-barrel (e.g., Streptomyces sp. strain CL190 Orf2 aromatic prenyltransferase of SEQ ID NO:2 complexed with GSPP, DHN2 and $Mg_{+2}$).
Figure 3C:
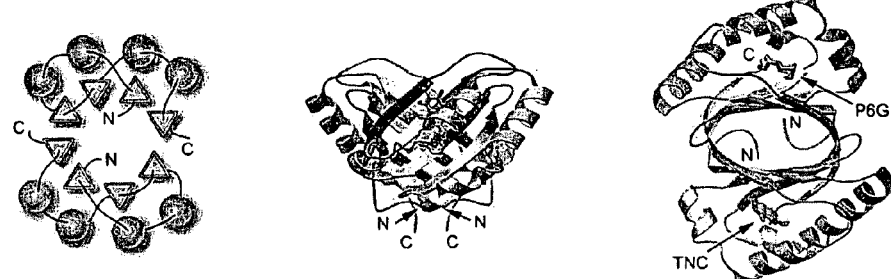
FIG. 3C illustrates an α+β-barrel (e.g., a dimeric ferrodoxin-like α+β sandwich fold of the ActVA-Orf6 monooxygenase (pdb entry 1LQ9) from S. coelicolor A3).

Another class of protein displaying an elliptical $\beta$-barrel surrounded by helices is the dimeric ferredoxin-like $\alpha+\beta$ sandwich fold: the ActVA-Orf6 monooxygenase (pdb entry code 1LQ9) from S. coelicolor A3 belongs to the latter class, and is a small enzyme that oxidizes a relatively large three ringed aromatic substrate at two active sites located between $\beta$-sheets and $\alpha$-helices (FIG. 3C).

$\alpha/\beta$-barrels have been defined as large structures (at least 200 amino acids), predominantly composed of alternating $\alpha$-helices and $\beta$-strands, with parallel $\beta$-strands forming a "hub" surrounded by a "tire" of $\alpha$-helices (see Branden and Tooze, Introduction to protein structure. Second edn. (1999), New York: Garland), while $\alpha+\beta$ class encompasses proteins with mainly antiparallel $\beta$-sheets but with segregated $\alpha$-helical and $\beta$-sheet regions. In this regard, it is proposed that the $\alpha/\beta$ class definition, including protein domains exclusively composed of parallel $\beta$-strands, connected by $\alpha$-helices, should be enlarged to include Orf2's novel architecture, the $\beta/\alpha$-barrel. The $\beta/\alpha$-barrel would introduce a novel $\beta/\alpha$-barrel category comprising antiparallel $\beta$-strands connected and surrounded by $\alpha$-helices as a subcategory of the $\alpha/\beta$-class, but distinct from the $\alpha/\beta$-barrel subcategory.

Figure 3D:
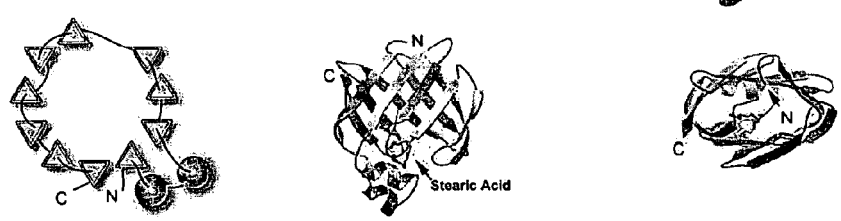
FIG. 3D illustrates a β-barrel (e.g., human fatty acid binding protein, M-FABP, complexed with one molecule of stearic acid (pdb entry 1HMT).
Figure 3E:
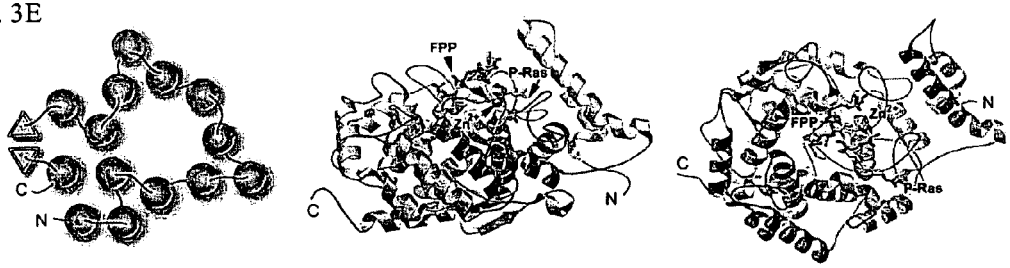
FIG. 3E illustrates an α-α barrel (e.g., the β-subunit of the Rattus norvegicus protein farnesyltransferase complexed with farnesylated Ras4B peptide product and farnesyl diphosphate substrate bound simultaneously (pdb entry 1KZO)).

Interestingly, a last type of barrel, an $\alpha$-$\alpha$ barrel domain, can be found in the $\beta$-subunit of the heterodimeric human protein farnesyltransferase, which catalyzes the carboxyl-terminal prenylation of Ras and several other signaling proteins (Park et al., Science 275(5307):1800-4 (1997) (FIG. 3D). This domain displays a very different overall fold but presents a similar aromatic rich substrate binding pocket and active site topology as described herein for Orf2 (Park et al., supra; Long et al., Nature 419(6907):645-50 (2002)).

It seems, indeed, that isoprenyl diphosphate synthases, protein prenyltransferases, and prenyltransferases (PTases), all involved in the binding of prenyl compounds, use a similar strategy regarding the active site environment. In most cases, prenyl chain bonding occurs within a large hydrophobic tunnel with highly conserved residues. Structures of the trans-type farnesyl diphosphate synthase display two identical subunits associated as a homodimer, forming a four layer helix-bundle; eight of these helices are assembled in a domain similarly to the $\alpha$-$\alpha$ domain previously described for the protein prenyl transferase. The structures of the cis-type dimeric enzymes, undecaprenyl pyrophosphate synthase (UPPS) from E. coli and M. luteus, reveal two hydrophobic tunnels each surrounded by two $\alpha$-helices and four $\beta$-strands. Both UPPS enzymes require $Mg^{2+}$ for activity even though both lack the classical prenyl diphosphate $Mg^{2+}$ binding motif (i.e., the (N/D)DXXD motif) found in most other trans-prenyltransferases and terpene synthases. The structures of terpenoid cyclases such as pentalene synthase, 5-epi-aristolochene synthase and trichodiene synthase harbor the similar structural feature referred to as "terpenoid synthase fold" with 10-12 mostly anti-parallel $\alpha$-helices, as also observed in isoprenyl pyrophosphate synthases and protein prenyltransferases (see Liang, Eur J Biochem 269(14):3339-54 (2002)). All of the above cited structures differ greatly from the $\beta/\alpha$-barrel fold described herein.

Figure 4A:
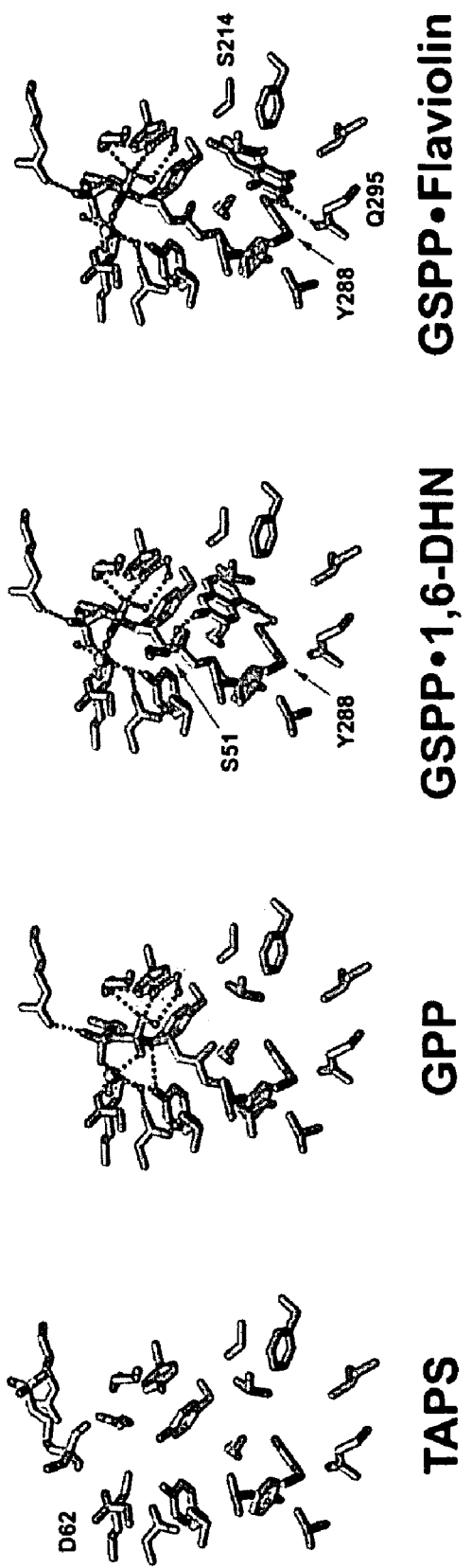
FIG. 4A illustrates the following complexes: the TAPS molecule, bound GPP, and GSPP with either 1,6-DHN or flaviolin.
Figure 4B:
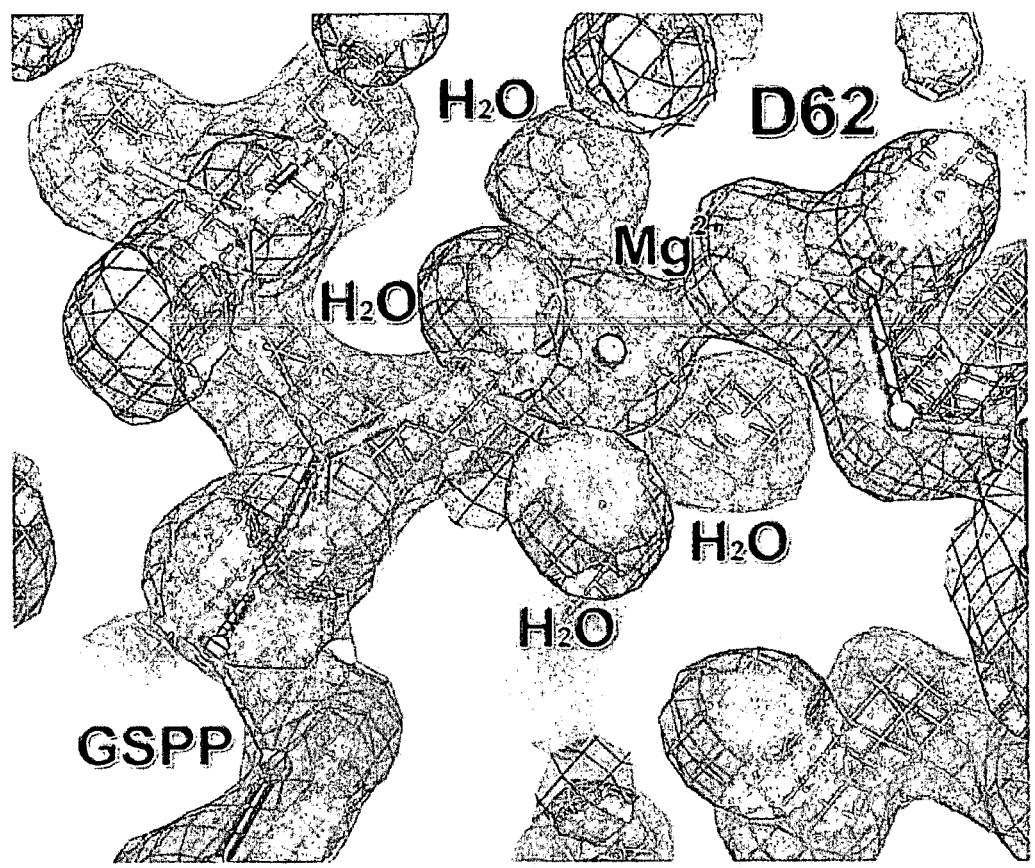
FIG. 4B illustrates the structure of the divalent metal binding site. A representative $2f_o$-$f_c$ electron density map (rendered from a normalized map at 1.0σ level) displays octahedral coordination of the $Mg^{2+}$ ion, where two oxygen atoms, one from Asp 62, and one from the diphosphate moiety of the GSPP molecule contribute together with four water molecules to the octahedral coordination geometry.
Figure 4C:
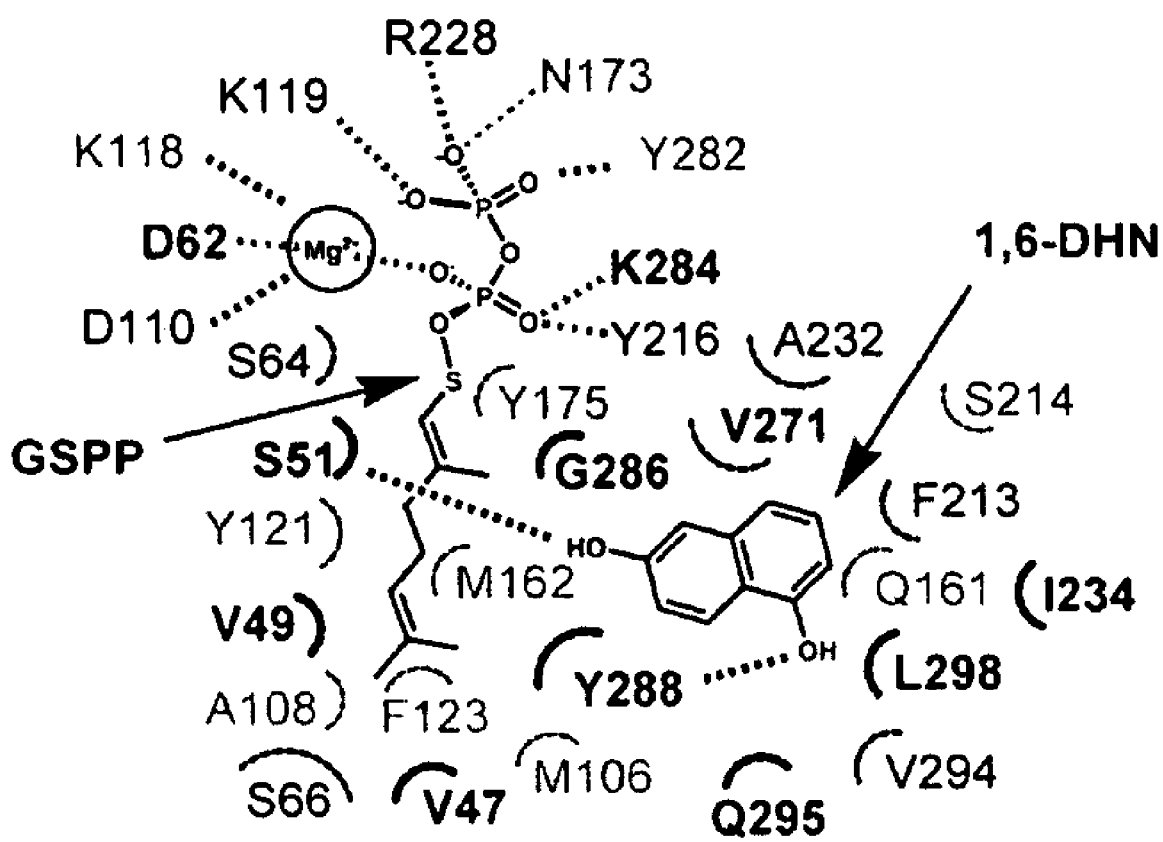
FIG. 4C provides a schematic representation of the active site of Orf2 of SEQ ID NO:2 . The side chain involved in $Mg^{2+}$, GSPP and 1,6-DHN binding is depicted with hydrogen and coordination bonds as grey dashed lines. Black dashed lines represent indirect hydrogen bonds via a water molecule. This close-up view, shown in an identical orientation to that in FIG. 4A, is rotated by 180 degrees along the vertical axis compared to that depicted in FIG. 4B. The half circles depict van der Waals contacts with the two substrates. Tentative depth queuing coding is as follows: grey for residues in the back of the GSPP-1,6-DHN plane, black in the same plane, and thick black for residues in the front.

While a bound TAPS molecule in the first Orf2 structure tentatively indicated the approximate location of the diphosphate binding site near Asp 62 (FIG. 4A), structures complexed with GPP or a non-hydrolyzable analogue, GSPP, precisely define the residues involved in recognition and binding of the complete GPP substrate (FIGS. 4B and 4C). Lys 119, Asn 173 and Arg 228, located near the polar open end of the barrel, are hydrogen bonded to the terminal $\beta$-phosphate of the GSPP molecule (FIG. 4C). The $\alpha$-phosphate linked to the geranyl chain hydrogen bonds with Tyr 216 and Lys 284, and also coordinates a $Mg^{2+}$ ion. The complete coordination geometry of this $Mg^{2+}$ ion exhibits perfect octahedral symmetry, with four equatorially arranged water molecules and two axially located oxygen atoms contributed by the side chain carboxylate of Asp 62 and an α-phosphate non-bridging oxygen of the GSPP molecule (FIGS. 4B and 4C). Despite the absence of a (N/D)DXXD motif, a second well conserved residue, Asp 110, proximal to Asp 62 in the tertiary structure, indirectly coordinates the $Mg^{2+}$ ion via one of the four equatorially arranged water molecules. Tyr 121 resides within hydrogen bonding distance of the bridging atom (sulfur in GSPP and oxygen in GPP) linking the diphosphate moiety to the C10 geranyl chain. Finally, the hydrophobic geranyl chain of the GPP or GSPP molecules rest against the side chains of Val 49, Phe 123, Met 162, Tyr 175 and Tyr 216 (FIG. 4C).

The ternary complexes with $Mg^{2+}$, GSPP and either 1,6-DHN or flaviolin delineate the chemical nature of the aromatic substrate binding site (FIGS. 4A, 4B and 4C). 1,6-DHN rests against the GSPP prenyl tail and is sequestered between the side chains of Met 162 and Phe 213. The Gln 295 and Leu 298 side chains provided by the short C-terminal helix line the wall of the substrate binding pocket with additional contacts made through the side chains of Phe 213, Ser 214 and Tyr 288. Flaviolin binds in a slightly different position than 1,6-DHN with extra pairs of hydrogen bonds formed with Ser 214, Tyr 288 and Gln 295, while the aromatic planes of both 1,6-DHN and flaviolin reside in the same active site orientation (FIG. 4A).

While not wishing to be bound by any theory, the structures of the substrates and products are consistent with an electrophilic aromatic substitution for the alkylation. Theoretically, two catalytic mechanisms can be considered for prenylation of aromatic substrates. One invokes a carbon mediated nucleophilic attack on the C1 carbon of GPP with the diphosphate moiety serving as a leaving group stabilized by $Mg^{2+}$ coordination and the basic character of the diphosphate binding site. This Sn2-like mechanism has been described for protein farnesyltransferase (Park et al., supra; Long et al., supra). A second mechanism is reminiscent of terpene synthases involved in allylic diphosphate biosynthesis and prenyl group cyclization and invokes carbocation mediated electrophilic capture as proposed for the trans-prenyltransferase reaction of FPP synthase (Tarshis et al., Biochemistry 33(36):10871-7 (1994)) and numerous terpene synthases (cyclases) of secondary metabolism (Cane, in *Comprehensive Naturals Products Chemistry: Isoprenoids*, D. E. Cane, Editor, 1998, Elsevier Science: Oxford, UK).

The distance between the C5 atom of 1,6-DHN, which is the identified site for prenylation, or the C3 atom of flaviolin, and the C1 atom of GSPP are 4 Å and 7 Å, respectively. Notably, these distances are similar to the 7.3 Å separation recently described in human protein farnesyltransferase between the C1 atom of a bound farnesyl diphosphate (FPP) molecule and a Cys residue on a peptide substrate (Long, 2002 supra). Even though an Sn2-like mechanism has been proposed for prenyltransferases, these distances, combined with the structures of substrates and products, and the apparent requirement for a conformational change of the cleaved prenyl chain are consistent with an electrophilic aromatic substitution mechanism for Orf2-mediated alkylation of aromatic substrates (see FIG. 5).

Figure 5:
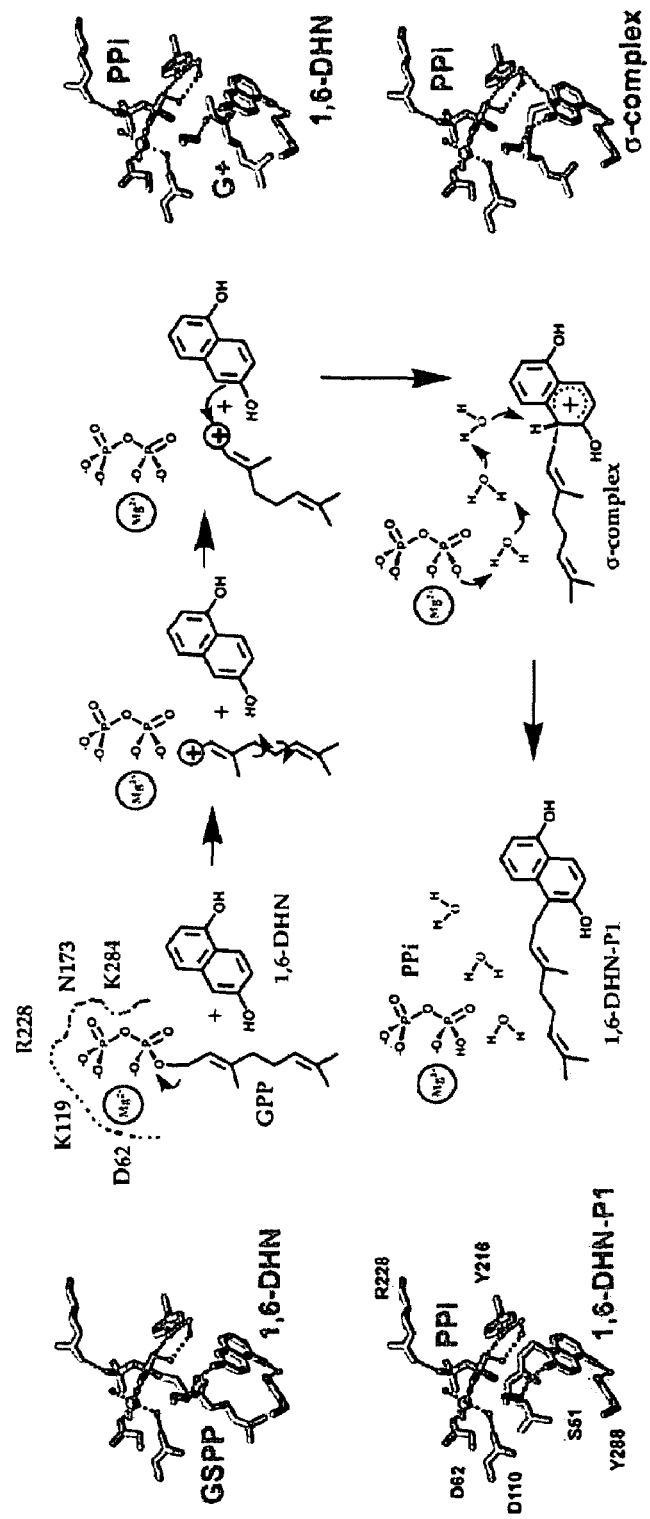
FIG. 5 presents a schematic and structural representation of the proposed mechanism for aromatic prenylation in the active site of Or2 of SEQ ID NO:2. This panel depicts the binding of the aromatic substrate next to the GPP molecule, formation of a geranyl carbocation (noted G+), rotation of the prenyl chain into a productive conformation, electrophilic attack of the carbocation on the aromatic ring of 1,6-DHN, formation of a a-complex, and final proton removal by a water molecule.

A model for the overall reaction catalyzed by Orf2 with 1,6-DHN serving as the prenyl accepting group is depicted in FIG. 5. Firstly, a carbocation intermediate is proposed to result from the ionization of the diphosphate moiety, triggered by $Mg^{2+}$ coordination, electrostatic hydrogen bonds with Lys 119, Arg 228, Asn 173 and Lys 284, and co-substrate binding. The positively charged C1 atom of the geranyl carbocation rotates toward the target double bond located 7 Å away on the prenyl acceptor (as previously described for human protein farnesyltransferase; see also Long, 2002, supra). A "tyrosine belt" including Tyr 121, Tyr 175 and Tyr 216, surrounding the 10 carbons of GPP, and similar to the one observed in the human protein farnesyltransferase (Park et al., supra; Long et al., Biochemistry 37(27):9612-8 (1998), may help stabilize and position the carbocationic intermediates via cation-π interactions (Wise and Croteau, in *Comprehensive Naturals Products Chemistry: Isoprenoids*, D. E. Cane, Editor, 1998, Elsevier Science: Oxford, UK).

This step involves the attachment of the reactive electrophile to the C5 atom of the 1,6-DHN molecule to form a resonance stabilized carbocation or σ-complex (Olah and Mo, J. Am. Chem. Soc. 94:9241 (1972)) (FIG. 5). Finally, Tyr 216, which interacts with the diphosphate moiety of the GPP molecule, is also hydrogen bonded to a conserved and well ordered network of water molecules linked to the diphosphate moiety and located just above the co-substrate binding location. One of these water molecules, highlighted in FIG. 5, is ideally positioned to abstract an acidic proton from the prenylated C5 atom of the cationic σ-complex allowing for the restoration of the neutral aromatic now containing a covalently tethered geranyl chain.

To confirm the enzymatic importance of certain active site residues, preliminary mutational studies of Orf2 were carried out, and residual activities were monitored using cell extracts containing mutant enzymes. The D62S and D62N single mutants, as well as D62S/S51R and D62N/S51K double mutants, displayed only residual activity in the presence of GPP (in the presence or absence of $Mg^{2+}$), while no detectable activity was observed for the D62A single mutant with either GPP or DMAPP as a prenyl donor, indicative of the importance of D62 in catalytic processes.

Figure 6:
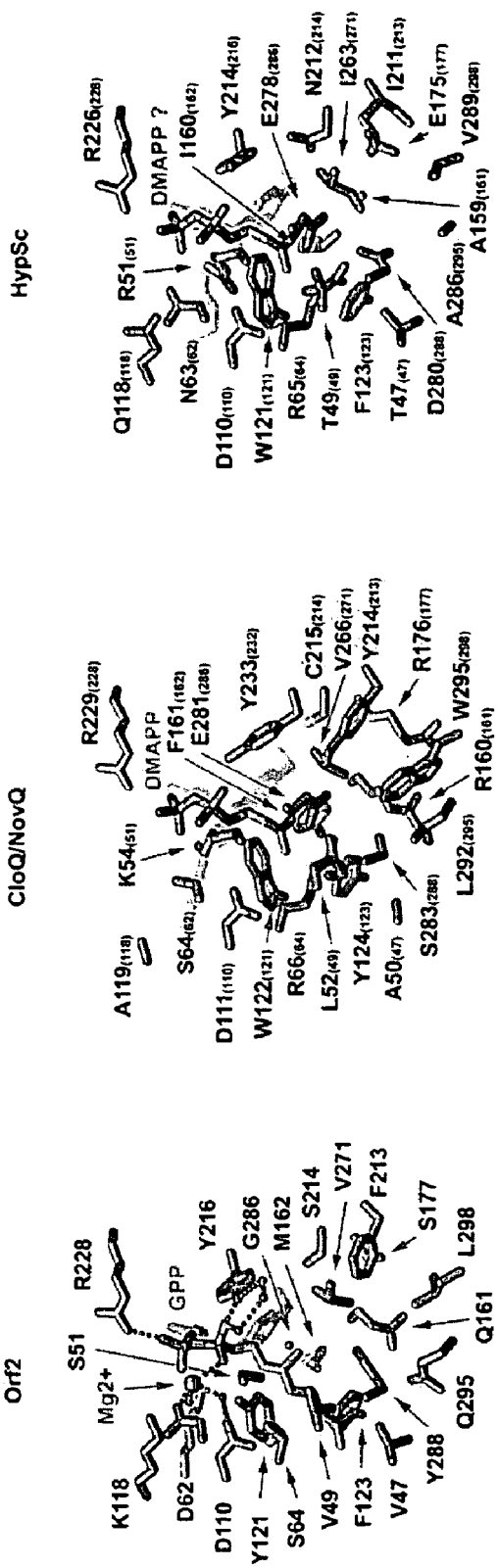
FIG. 6 presents active site models for Orf2 homologs. Modeling of CloQ/NovQ and HypSc were performed using Orf2 as a structural template. Side chains presenting potentially significant variation between the different active sites are displayed and labeled. Conserved residues in the different models include Asp 110, Lys 119, Asn 173, Tyr 175, Tyr 216, and Arg 228, of which only Asp 110 and Arg 228 are displayed for clarity.

In order to decipher the prenyl diphosphate chain length selectivity, molecular determinants of aromatic substrate recognition and divalent cation dependence, homology modeling of CloQ (*Streptomyces roseochromogenes*, accession number AF329398), NovQ (*Streptomyces spheroides* NCIMB 11891, accession number AF170880) and HypSc (*Streptomyces coelicolor* A3(2), accession number AL939130) sequences were carried out using the three dimensional architecture of Orf2 as a structural template (FIG. 6). The large degree of overall sequence similarity between these sequences as well as the considerable degree of active site conservation between Orf2 and CloQ/NovQ/HypSc is indicative of the conservation of the β/α-barrel fold for this family of aromatic prenyltransferases.

In the HypSc model, Asp 62 is replaced by an Asn residue and is complemented by the replacement of Ser 52 by an Arg residue. Also, as observed in the CloQ/NovQ model, the presence of a salt bridge between Arg 65 and Glu 278 appears from modeling to prevent the binding of a prenyl donor with an alkyl chain longer thatn C5 (i.e., C10 or C15). From this modeling analysis, the deduced protein from *Streptomyces coelicolor* would be predicted to show a DMAPP specificity and $Mg^{2+}$ independent prenyltransferase activity.

In order to validate this model, HypSc was subcloned from genomic DNA, and over-expressed in *E. coli* as an octa-histidine tagged protein and purified for $Ni^{2+}$-chelation chromatography. The purified enzyme was then assayed for prenyltransferase activity using DMAPP and GPP as prenyl donors. Notable prenyltransferase activity was detected when using DMAPP and 1,6-DHN as substrates in the absence of $Mg^{2+}$, consistent with the model based hypothesis set forth herein regarding the chain length selectivity and $Mg^{2+}$ independence of invention enzymes.

In accordance with yet another aspect of the present invention, there are provided compositions comprising an aromatic prenyltransferase as described herein in crystalline form. Optionally, such compositions further comprise one or more substrates for the aromatic prenyltransferase. As used herein, "substrates" refer to compounds susceptible to the action of invention prenyltransferases, e.g., such reactive aromatic compounds as tetrahydroxynaphthalene, analogs, homologs and metabolites thereof.

As used herein, "analogs" refer to compounds which are related to the above-described aromatic substrates and retain a biological activity thereof, but have one or more substitutions and/or modifications thereof relative to the parent compound, e.g., substitution of —O— for —$CH_2$—. Alternatively, analogs may have relatively little primary structure similarity, but may still display a biological activity of a substrate as a result of similar secondary and/or tertiary structural features, electronic properties, and the like.

As used herein, "homolog" refers to compounds which are related to the above-described aromatic substrates by the presence or absence of a simple unit, such as a methylene unit, or some multiple of such units, e.g., —$(CH_2)_x$—.

As used herein, "metabolite" refers to compounds which are related to the above-described substrates as a form of such compound obtained in a human or animal body by action of the body on the administered form of the compound, for example a de-methylated analogue of a compound bearing a methyl group which is obtained in the body after administration of the methylated compound as a result of action by the body on the methylated compound.

X-ray crystallography can elucidate the three-dimensional structure of crystalline forms according to the invention. Typically, the first characterization of crystalline forms by X-ray crystallography can determine the unit cell shape and its orientation in the crystal. The term "unit cell" refers to the smallest and simplest volume element of a crystal that is completely representative of the unit of pattern of the crystal. The dimensions of the unit cell are defined by six numbers: dimensions a, b and c and angles $\alpha$, $\beta$ and $\gamma$. A crystal can be viewed as an efficiently packed array of multiple unit cells. Detailed descriptions of crystallographic terms are provided in Hahn, THE INTERNATIONAL TABLES FOR CRYSTALLOGRAPHY, VOLUME A, $4^{th}$ Ed., Kluwer Academic Publishers (1996); and Shmueli, THE INTERNATIONAL TABLES FOR CRYSTALLOGRAPHY, VOLUME B, $1^{st}$ Ed., Kluwer Academic Publishers. The term "space group" refers to the symmetry of a unit cell. In a space group designation (e.g., P2) the capital letter indicates the lattice type and the other symbols represent symmetry operations that can be carried out on the unit cell without changing its appearance.

The term "selenomethionine substitution" refers to the method of producing a chemically modified form of a protein crystal. The protein is expressed by bacteria in media that is depleted in methionine and supplemented with selenomethionine. Selenium is thereby incorporated into the crystal in place of methionine sul furs. The location(s) of selenium is(are) determined by X-ray diffraction analysis of the crystal. This information is used to generate the phase information used to construct a three-dimensional structure of the protein.

"Heavy atom derivatization" refers to a method of producing a chemically modified form of a protein crystal. In practice, a crystal is soaked in a solution containing heavy atom salts or organometallic compounds, e.g., lead chloride, gold thiomalate, thimerosal, uranyl acetate, and the like, which can diffuse through the crystal and bind to the protein's surface. Locations of the bound heavy atoms can be determined by X-ray diffraction analysis of the soaked crystal. This information is then used to construct phase information which can then be used to construct three-dimensional structures of the enzyme as described in Blundel and Johnson, PROTEIN CRYSTALLOGRAPHY, Academic Press (1976), which is incorporated by reference herein.

The knowledge obtained from X-ray diffraction patterns can be used in the determination of the three-dimensional structure of the binding sites of other homologous polypeptides. This is achieved through the use of commercially available software known in the art that is capable of generating three-dimensional graphical representations of molecules or portions thereof from a set of structure coordinates. The binding domain can also be predicted by various computer models. Based on the structural X-ray coordinates of the solved structure, mutations and variants of the solved structure can also be designed.

An exemplary isolated aromatic prenyltransferase according to the present invention has been further characterized by the structural coordinates set forth in Appendix 1.

In accordance with still another aspect of the present invention, there are provided methods of predicting the activity and/or substrate specificity of a putative aromatic prenyltransferase, the methods comprising:

comparing a three-dimensional representation of a known aromatic prenyltransferase and a three-dimensional representation of a putative aromatic prenyltransferase, wherein differences between the two representations are predictive of aromatic prenyltransferase activity and/or substrate specificity.

In accordance with yet another aspect of the present invention, there are provided methods of screening for compounds which bind aromatic prenyltransferase(s), said methods comprising:

modeling a potential binding agent that interacts with one or more domains of an aromatic prenyltransferase or fragment thereof, defined by a plurality of atomic coordinates of the aromatic prenyltransferase or fragment thereof, and determining the ability of said potential binding agent to compete with said aromatic prenyltransferase substrate for binding to said aromatic prenyltransferase.

As used herein, "molecular replacement" refers to generating a preliminary model of a polypeptide whose structure coordinates are unknown, by orienting and positioning a molecule whose structure coordinates are known within the unit cell of the unknown crystal so as to best account for the observed diffraction pattern of the unknown crystal. Phases can then be calculated from this model and combined with the observed amplitudes to give an approximate Fourier synthesis of the structure whose coordinates are unknown. This in turn can be subject to any of the several forms of refinement to provide a final, accurate structure of the unknown crystal (Lattman, *Meth. Enzymol.* 115:55-77 (1985); Rossmann, M G., ed., THE MOLECULAR REPLACEMENT METHOD (1972), Int. Sci. Rev. Ser. No. 13, Gordon & Breach, New York). Using structure coordinates of the aromatic prenyltransferase provided herein, molecular replacement may be used to determine the structure coordinates of a crystalline mutant, homologue, or a different crystal form of an aromatic prenyltransferase.

In accordance with this invention, an aromatic prenyltransferase, or a portion thereof, may be crystallized in association or complex with any known or putative substrate and/or binding agent. The crystal structures of a series of such complexes may then be solved by molecular replacement and compared with that of a native aromatic prenyltransferase molecule. Potential sites for modification within the aromatic prenyltransferase molecule or a corresponding substrate and/or binding agent therefor may thus be identified based on the points of interaction between the aromatic prenyltransferase and substrate and/or binding agent therefor. This information provides an additional tool for determining the most efficient binding interactions, for example, increased hydrophobic interactions, between an aromatic prenyltransferase and a putative chemical entity or compound, even before any synthesis or modifications are performed.

All of the complexes referred to above may be studied using well-known X-ray diffraction techniques as described herein, and may be refined versus 2-3 Å resolution X-ray data to an R value of about 0.20 or less using computer software, such as X-PLOR (Yale University, 1992, distributed by Molecular Simulations, Inc.). See, e.g., Blundel & Johnson, supra; Methods in Enzymology, vol. 114 and 115, H. W. Wyckoffet al., eds., Academic Press (1985). This information may thus be used to optimize known classes of aromatic prenyltransferase substrate and/or binding agent therefor, such as natural THN, and to design, modify and/or synthesize novel classes of aromatic prenyltransferase substrate and/or binding agents.

The modeling or design of substrates and/or binding agents for aromatic prenyltransferases, i.e., compounds that bind to and/or modulate an aromatic prenyltransferase polypeptide according to the invention generally involves consideration of two factors. First, the compound or molecule must be capable of physically and structurally associating with an aromatic prenyltransferase molecule. Non-covalent molecular interactions important in the association of an aromatic prenyltransferase with a putative substrate and/or binding agent include hydrogen bonding, van der Waals and hydrophobic interactions, and the like.

Second, the compound or molecule must be able to assume a conformation that allows it to associate with an aromatic prenyltransferase molecule. Although certain portions of the compound or molecule will not directly participate in this association, those portions may still influence the overall conformation of the molecule. This, in turn, may have a significant impact on affinity with the receptor. Such conformational requirements include the overall three-dimensional structure and orientation of the compound or molecule in relation to all or a portion of the binding site, or the spacing between functional groups of a compound or molecule comprising several chemical entities that directly interact with an aromatic prenyltransferase.

The term "modeling" as used herein, refers to analysis of the interaction of an aromatic prenyltransferase and a known or test compound or molecule by utilizing a computer generated representation of the molecules, as opposed to physical molecules.

The potential binding of a test compound with an aromatic prenyltransferase may be analyzed prior to its actual synthesis and testing by the use of computer modeling techniques. If the theoretical structure of the given compound is indicative of insufficient interaction and association between it and an aromatic prenyltransferase, synthesis and testing of the compound may be obviated. However, if computer modeling indicates a strong interaction, the molecule may then be tested for its ability to bind to an aromatic prenyltransferase. Methods of assaying for aromatic prenyltransferase activity are known in the art (as identified and discussed herein). Methods for assaying the effect of a potential binding agent can be performed in the presence of a known binding agent of an aromatic prenyltransferase. For example, the effect of the potential binding agent can be assayed by measuring the ability of the potential binding agent to compete with a known binding agent.

A test compound may be computationally evaluated and designed by means of a series of steps in which chemical entities or fragments are screened and selected for their ability to associate with the individual binding pockets or other areas of an aromatic prenyltransferase associated with a substrate and/or binding agent therefor.

One skilled in the art may use one of several methods to predict a molecule capable of binding to an aromatic prenyltransferase and to screen test compounds for their ability to associate with an aromatic prenyltransferase and more particularly with the individual active site (e.g., binding pockets and/or specific points of interaction) of an aromatic prenyltransferase polypeptide. This process may begin by visual inspection of, for example, the binding pocket of an aromatic prenyltransferase on the computer screen based on structure coordinates obtained derived from X-ray diffraction data obtained from crystals of an aromatic prenyltransferase, such as those provided in Appendix 1. Selected fragments or chemical entities may then be positioned in a variety of orientations, or docked, within an individual binding pocket of the aromatic prenyltransferase. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities at this stage. These include:

1. GRID (Goodford, P. J., "A Computational Procedure for Determining Energetically Favorable Binding Sites on Biologically Important Macromolecules", J. Med. Chem., 28, pp. 849-857 (1985)). GRID is available from Oxford University, Oxford, UK.

2. MCSS (Miranker, A. and M. Karplus, "Functionality Maps of Binding Sites: A Multiple Copy Simultaneous Search Method." Proteins: Structure. Function and Genetics, 11, pp. 29-34 (1991)). MCSS is available from Molecular Simulations, Burlington, Mass.

3. AUTODOCK (Goodsell, D. S. and A. J. Olsen, "Automated Docking of Substrates to Proteins by Simulated Annealing", Proteins: Structure. Function, and Genetics, 8, pp. 195-202 (1990)). AUTODOCK is available from Scripps Research Institute, La Jolla, Calif.

4. DOCK (Kuntz, I. D. et al., "A Geometric Approach to Macromolecule-Ligand Interactions", J. Mol. Biol., 161, pp. 269-288 (1982)). DOCK is available from University of California, San Francisco, Calif.

Once suitable chemical entities or fragments have been selected, they can be assembled into a single compound that is a candidate substrate and/or binding agent. Assembly may be performed by visual inspection of the relationship of the fragments to each other on the three-dimensional image displayed on a computer screen in relation to the structure coordinates of the aromatic prenyltransferase molecule as set forth in Appendix 1. This would be followed by manual model building using software such as Quanta or Sybyl.

Useful programs to aid one of skill in the art in connecting the individual chemical entities or fragments include:

1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., Royal Chem. Soc., 78, pp. 182-196 (1989)). CAVEAT is available from the University of California, Berkeley, Calif.

2. 3D Database systems such as MACCS-3D (MDL Information Systems, San Leandro, Calif.). This area is reviewed in Martin, Y. C., "3D Database Searching in Drug Design", J. Med. Chem., 35, pp. 2145-2154 (1992)).

3. HOOK (available from Molecular Simulations, Burlington, Mass.).

In addition to the method of building or identifying a substrate and/or binding agent in a step-wise fashion one fragment or chemical entity at a time as described above, aromatic prenyltransferase substrates and/or binding agents may be designed as a whole or "de novo" using either an empty binding pocket or optionally including some portion(s) of a known substrate(s) and/or binding agent(s). These methods include:

1. LUDI (Bohm, H.-J., "The Computer Program LUDI: A New Method for the De Novo Design of Enzyme Inhibitors", J. Comp. Aid. Molec. Design, 6, pp. 61-78 (1992)). LUDI is available from Biosym Technologies, San Diego, Calif.

2. LEGEND (Nishibata, Y. and A. Itai, Tetrahedron, 47, p. 8985 (1991)). LEGEND is available from Molecular Simulations, Burlington, Mass.

3. LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry", J. Med. Chem., 33, pp. 883-894 (1990). See also, Navia, M. A. and M. A. Murcko, "The Use of Structural Information in Drug Design", Current Opinions in Structural Biology, 2, pp. 202-210 (1992).

Once a test compound or binding agent has been designed or selected by the above methods, the efficiency with which that compound may bind to an aromatic prenyltransferase may be tested and optimized by computational evaluation.

A compound designed or selected as a putative substrate and/or binding agent may be further computationally optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the binding agent and an aromatic prenyltransferase when the substrate and/or binding agent is bound to the aromatic prenyltransferase, preferably make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa., 1992); AMBER, version 4.0 (P. A. Kollman, University of California at San Francisco, 1994); QUANTA/CHARMM (Molecular Simulations, Inc., Burlington, Mass. 1994); and Insight II/Discover (Biosym Technologies Inc., San Diego, Calif., 1994). These programs may be implemented, for example, using a Silicon Graphics workstation, IRIS 4D/35 or IBM RISC/6000 workstation model 550. Other hardware systems and software packages will be known to those skilled in the art of which the speed and capacity are continually modified.

Other molecular modeling techniques may also be employed in accordance with this invention. For exemplary reviews and techniques, see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)]

In accordance with still another aspect of the present invention, there are provided alternate methods of screening for compounds which bind aromatic prenyltransferase(s), said methods comprising:

defining an interaction site of an aromatic prenyltransferase based on a plurality of atomic coordinates of said aromatic prenyltransferase;

modeling a potential binding agent that fits spatially into said interaction site;

contacting said potential binding agent with said aromatic prenyltransferase in the presence of an aromatic prenyltransferase substrate; and determining the ability of said potential binding agent to compete with said aromatic prenyltransferase substrate for binding to said aromatic prenyltransferase.

In accordance with a further aspect of the present invention, there are provided additional methods of screening for compounds which bind aromatic prenyltransferase(s), said methods comprising:

defining an interaction site of an aromatic prenyltransferase based on a plurality of atomic coordinates of said aromatic prenyltransferase;

modeling a potential binding agent that fits spatially into said interaction site; and determining the ability of said potential binding agent to compete with an aromatic prenyltransferase substrate for said interaction site by contacting said potential binding agent with said aromatic prenyltransferase in the presence of said aromatic prenyltransferase substrate.

In accordance with a still further aspect of the present invention, there are provided additional methods of screening for compounds which bind aromatic prenyltransferase(s), said methods comprising:

modeling a potential binding agent that fits spatially into an interaction site of an aromatic prenyltransferase defined by a plurality of atomic coordinates of said aromatic prenyltransferase;

contacting said potential binding agent with said aromatic prenyltransferase in the presence of an aromatic prenyltransferase substrate; and determining the ability of said potential binding agent to compete with said aromatic prenyltransferase substrate for binding to said aromatic prenyltransferase.

In accordance with another aspect of the present invention, there are provided additional methods of screening for compounds which bind aromatic prenyltransferase(s), said methods comprising:

modeling a potential binding agent that fits spatially into an interaction site of an aromatic prenyltransferase defined by a plurality of atomic coordinates of said aromatic prenyltransferase; and determining the ability of said potential binding agent to compete with an aromatic prenyltransferase substrate for said interaction site by contacting said potential binding agent with said aromatic prenyltransferase in the presence of said aromatic prenyltransferase substrate.

In accordance with yet another aspect of the present invention, there are provided additional methods of screening for compounds which bind aromatic prenyltransferase(s), said methods comprising:

determining the ability of a potential binding agent to compete with an aromatic prenyltransferase substrate for binding to an aromatic prenyltransferase, wherein the potential binding agent is modeled to fit spatially into an aromatic prenyltransferase interaction site defined by a plurality of atomic coordinates.

In accordance with still another aspect of the present invention, there are provided methods of identifying potential substrate(s) of an aromatic prenyltransferase, said methods comprising:

defining an active site of said aromatic prenyltransferase based on a plurality of atomic coordinates of said aromatic prenyltransferase;

identifying a potential substrate that fits said active site; and contacting the aromatic prenyltransferase with the potential substrate and determining its activity thereon.

In accordance with a further aspect of the present invention, there are provided methods of screening compounds to determine whether such compounds are aromatic prenyltransferase substrates, said methods comprising:

determining the points of interaction between an aromatic prenyltransferase and a substrate or product therefor;

selecting compound(s) having similar interaction with said aromatic prenyltransferase; and testing the selected compound for the ability to be converted by said aromatic prenyltransferase.

In accordance with still another aspect of the present invention, there are provided alternate methods of screening compounds to determine whether such compounds are aromatic prenyltransferase substrates, said methods comprising:

selecting compound(s) having points of interaction with said aromatic prenyltransferase, wherein similar points of interaction have been determined between said aromatic prenyltransferase and a substrate or product therefor; and testing the selected compound for the ability to be converted by said aromatic prenyltransferase.

In accordance with a still further aspect of the present invention, there are provided additional methods of screening compounds to determine whether such compounds are aromatic prenyltransferase substrates, said methods comprising:

testing a compound for the ability to be converted by said aromatic prenyltransferase, wherein said compound has been selected as having points of interaction with said aromatic prenyltransferase, and wherein similar points of interaction have been determined between said aromatic prenyltransferase and a substrate or product therefor.

In accordance with yet another aspect of the present invention there are provided methods for stimulating the activity of an aromatic prenyltransferase, said methods comprising contacting said aromatic prenyltransferase with an effective amount of a compound identified by any of the above-described methods.

Such compounds are typically administered as part of formulations comprising at least one of the above-described compounds in a pharmaceutically acceptable carrier therefor. Exemplary pharmaceutically acceptable carriers include solids, solutions, emulsions, dispersions, micelles, liposomes, and the like. Optionally, the pharmaceutically acceptable carrier employed herein further comprises an enteric coating.

Pharmaceutically acceptable carriers contemplated for use in the practice of the present invention are those which render invention compounds amenable to oral delivery, transdermal delivery, intravenous delivery, intramuscular delivery, topical delivery, nasal delivery, and the like.

Thus, formulations contemplated for use in the practice of the present invention can be used in the form of a solid, a solution, an emulsion, a dispersion, a micelle, a liposome, and the like, wherein the resulting formulation contains one or more of the compounds of the present invention, as an active ingredient, in admixture with an organic or inorganic carrier or excipient suitable for enterable or parenteral applications. The active ingredient may be compounded, for example, with the usual non-toxic, pharmaceutically acceptable carriers for tablets, pellets, capsules, suppositories, solutions, emulsions, suspensions and any other suitable for use. The carriers which can be used include glucose, lactose, gum acacia, gelatin, manitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening, and coloring agents and perfumes may be used. The active compound(s) is (are) included in the formulation in an amount sufficient to produce the desired effect upon the process or disease condition.

Formulations contemplated for use in the practice of the present invention containing the active ingredient may be in a form suitable for oral use, for example, as tablets, troches, lozenges, aqueous or oily suspensions, dispersible powders or granules, emulsions, hard or soft capsules, or syrups or elixirs. Formulations intended for oral use may be prepared according to any method known to the art for the manufacture of pharmaceutical compositions and such formulations may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients used may be, for example (1) inert diluents such as calcium carbonate, lactose, calcium phosphate or sodium phosphate; (2) granulating and disintegrating agents such corn starch, potato starch or alginic acid; (3) binding agents such as gum tragacanth, corn starch, gelatin or acacia, and (4) lubricating agents such as magnesium stearate, steric acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by such techniques as those described in U.S. Pat. Nos. 4,256, 108; 4,160,452; and 4,265,874, to form osmotic therapeutic tablets for controlled release.

In some cases, formulations contemplated for oral use may be in the form of hard gelatin capsules wherein the active ingredient is mixed with inert solid diluent(s), for example, calcium carbonate, calcium phosphate or kaolin.

They may also be in the form of soft gelatin capsules wherein the active ingredient is mixed with water or an oil medium, for example, peanut oil, liquid paraffin, or olive oil.

Formulations contemplated for use in the practice of the present invention may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids, naturally occurring vegetable oils like sesame oil, coconut oil, peanut oil, cottonseed oil, etc. or synthetic fatty vehicles like ethyl oleate or the like. Buffers, preservatives, antioxidants, and the like can be incorporated as required.

Formulations contemplated for use in the practice of the present invention may also be administered in the form of suppositories for rectal administration of the drug. These formulations may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug. Since individual subjects may present a wide variation in severity of symptoms and each drug has its unique therapeutic characteristics, the precise mode of administration and dosage employed for each subject is left to the discretion of the practitioner.

Amounts effective for the particular therapeutic goal sought will, of course, depend on the severity of the condition being treated, and the weight and general state of the subject. Various general considerations taken into account in determining the "effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990, each of which is herein incorporated by reference.

The term "effective amount" as applied to compounds contemplated for use in the practice of the present invenion, means the quantity necessary to effect the desired therapeutic result, for example, a level effective to treat, cure, or alleviate the symptoms of a disease state for which the therapeutic compound is being administered, or to establish homeostasis. Since individual subjects may present a wide variation in severity of symptoms and each drug or active agent has its unique therapeutic characteristics, the precise mode of administration, dosage employed and treatment protocol for each subject is left to the discretion of the practitioner.

The above-described methods for stimulating activity of aromatic prenyltransferases can be applied in many situations. For example, cancer cell resistance to chemotherapy is often mediated by overexpression of P-glycoprotein, a plasma membrane ABC (ATP-binding cassette) transporter which extrudes cytotoxic drugs at the expense of ATP hydrolysis. Prenylated flavoinoids have recently been reported as potential inhibitor of human multidrug resistant protein (MRP1) which belong to the ABC transporter superfamily. Some of these prenylated compounds have also shown HIV-inhibitory effects. Recently, common forms of the prenylated flavonoids have been identified in beer: 6- and 8-prenylnaringenin, xanthohumol and isoxanthohumol are present in high concentrations in hops (*Humulus lupulus* L.) and their oestrogenic potency has been determined in in vitro and animal model systems, with data indicating that they are more potent oestrogens than the isoflavones class (see Milligan et al., J Clin Endocrinol Metab 84:2249-52 (1999).

In accordance with a still further aspect of the present invention, there are provided methods of identifying potential modulator(s) of aromatic prenyltransferase(s), said methods comprising:
    defining an aromatic prenyltransferase polypeptide or fragment thereof based on a plurality of atomic coordinates of the aromatic prenyltransferase polypeptide;
    modeling a potential binding agent that interacts with one or more domains of the aromatic prenyltransferase polypeptide;
    contacting the potential binding agent with the aromatic prenyltransferase polypeptide; and
    determining the ability of said potential binding agent to modulate an aromatic prenyltransferase biological function, thereby identifying a potential modulator of an aromatic prenyltransferase polypeptide.

As employed herein, "modulators" refers to compound(s) which, either directly (by binding to a prenyltransferase) or indirectly (as a precursor for a compound which binds to a prenyltransferase, or an inducer which promotes production of a compound which binds to a prenyltransferase from a precursor) induce the activity of prenyltransferase, or to repress the activity of prenyltransferase. Exemplary modulators contemplated in the practice of the present invention include flavonoids, isoflavonoids, and the like.

In accordance with yet another aspect of the present invention, there are provided alternate methods of identifying potential modulator(s) of the activity of aromatic prenyltransferase(s), said methods comprising:
    defining the active site of said aromatic prenyltransferase based on a plurality of atomic coordinates of said aromatic prenyltransferase,
    contacting a potential compound that fits the active site of (a) with the aromatic prenyltransferase in the presence of a substrate, and
    determining the ability of said compound to modulate the activity of said aromatic prenyltransferase with respect to said substrate.

In accordance with still another aspect of the present invention, there are provided additional methods of identifying potential modulator(s) of the activity of aromatic prenyltransferase(s), said methods comprising:
    contacting a potential compound that fits an active site based on a plurality of atomic coordinates of said aromatic prenyltransferase; and
    determining the ability of said compound to modulate the activity of said aromatic prenyltransferase.

In accordance with a further aspect of the present invention, there are provided methods of screening for compounds that modulate the activity of aromatic prenyltransferase(s), said methods comprising:
    determining the points of interaction between an aromatic prenyltransferase, and substrate or substrate mimic therefor;
    selecting compound(s) having similar interaction with said aromatic prenyltransferase; and
    testing the selected compound for the ability to modulate the activity of an aromatic prenyltransferase.

As employed herein, "modulating" refers to the ability of a modulator for a prenyltransferase to either directly or indirectly induce prenyltransferase activity, or to repress prenyltransferase activity. Exemplary processes contemplated for modulation according to the invention include cholesterol metabolism, regulation of lipid homeostasis, stimulation of bile transport and absorption, regulation of the expression of genes involved in the excretion and transportation of bile acids (including intestinal bile acid-binding protein (IBABP)), bile salt export pump (BSEP) and canalicular multi-specific organic anion transporter (cMOAT), and the like.

In accordance with still another aspect of the present invention, there are provided alternate methods of screening for compounds that modulate the activity of aromatic prenyltransferase(s), said methods comprising:
  selecting compound(s) having points of interaction with an aromatic prenyltransferase, wherein similar points of interaction have been determined between said aromatic prenyltransferase and a substrate or substrate mimic therefor; and
  testing the selected compound for the ability to modulate the activity of said aromatic prenyltransferase.

In accordance with yet another aspect of the present invention, there are provided additional methods of screening for compounds that modulate the activity of aromatic prenyltransferase(s), said methods comprising:
  testing a compound for the ability to modulate the activity of an aromatic prenyltransferase,
  wherein said compound has been selected as having points of interaction with said aromatic prenyltransferase, and
  wherein similar points of interaction have been determined between said aromatic prenyltransferase and a substrate or substrate mimic therefor.

In accordance with yet another aspect of the present invention, there are provided methods for prenylating aromatic substrates, said methods comprising:
  contacting an aromatic substrate with an aromatic prenyltransferase as described herein, under prenylating conditions.

In accordance with still another aspect of the present invention, there are provided methods of identifying proteins having a beta/alpha barrel structure, said methods comprising:
  comparing a three-dimensional representation of an aromatic prenyltransferase as described herein with a three-dimensional representation of a putative protein having a beta/alpha barrel structure, wherein similarities between the two representations are predictive of aromatic prenyltransferase proteins having a beta/alpha barrel structure.

In accordance with a further aspect of the present invention, there are provided methods for controlling the degree of prenylation promoted by an aromatic prenyltransferase, said methods comprising:
  altering one or more active site residues of said aromatic prenyltransferase so as to change the dimensions of the active site sufficiently to control the degree of prenylation promoted by said aromatic prenyltransferase.

As used herein, "degree of prenylation" refers to the number of isoprenoid units added to a substrate. This embraces prenylation at multiple sites, as well as introduction of one or more isoprenoid units at a single site.

In accordance with a still further aspect of the present invention, there are provided methods for modifying the degree of prenylation promoted by an aromatic prenyltransferase, said methods comprising:
  modifying one or more active site residues of said aromatic prenyltransferase so as to change the dimensions of the active site sufficiently to modify the degree of prenylation promoted by said aromatic prenyltransferase.

In accordance with yet another aspect of the present invention, there are provided methods for controlling the substrate specificity of an aromatic prenyltransferase, said methods comprising:
  altering one or more active site residues of said aromatic prenyltransferase so as to change the dimensions of the active site sufficiently to control the selectivity of said aromatic prenyltransferase with respect to aromatic substrates which are prenylated by said aromatic prenyltransferase.

As used herein, "substrate specificity" refers to the selectivity with which an enzyme recognizes a substrate. A selective prenyltransferase will recognize only a single, or a limited number of substrates, whereas a non-selective (promiscuous) prenyltransferase will recognize a plurality of substrates.

In accordance with a further aspect of the present invention, there are provided methods for modifying the substrate specificity of an aromatic prenyltransferase, said methods comprising:
  modifying one or more active site residues of said aromatic prenyltransferase so as to change the dimensions of the active site sufficiently to modify the selectivity of said aromatic prenyltransferase with respect to aromatic substrates which are prenylated by said aromatic prenyltransferase.

In accordance with still another aspect of the present invention, there are provided methods for controlling the donor specificity of an aromatic prenyltransferase, said methods comprising:
  altering one or more active site residues of said aromatic prenyltransferase so as to change the dimensions of the active site sufficiently to control the selectivity of said aromatic prenyltransferase with respect to prenyl donors which are employed to prenylate an aromatic substrate.

As used herein, "donor specificity" refers to the selectivity with which an enzyme recognizes a prenyl donor. A selective prenyltransferase will recognize only a single, or a limited number of prenyl donors, whereas a non-selective (promiscuous) prenyltransferase will recognize a plurality of prenyl donors. Exemplary prenyl donors include dimethylallyl diphosphate (DMAPP, C5), isopentenyl diphosphate (IPP, C5), geranyl diphosphate (GPP, C10), farnesyl diphosphate (FPP, C15), and the like.

In accordance with a further aspect of the present invention, there are provided methods for modifying the donor specificity of an aromatic prenyltransferase, said methods comprising:
  modifying one or more active site residues of said aromatic prenyltransferase so as to change the dimensions of the active site sufficiently to modify the selectivity of said aromatic prenyltransferase with respect to prenyl donors employed to prenylate an aromatic substrate.

In accordance with still another aspect of the present invention, there are provided computer programs on a computer readable medium, said computer programs comprising instructions to cause a computer to define an aromatic prenyltransferase or fragment thereof based on a plurality of atomic coordinates of the aromatic prenyltransferase.

According to another aspect of the present invention, there is provided a computer for determining at least a portion of the structure coordinates corresponding to X-ray diffraction data obtained from an aromatic prenyl transferase molecule or molecular complex or a homologue of said aromatic prenyl transferase molecule or molecular complex, said computer comprising:

(i) a computer-readable data storage medium comprising a data storage material encoded with machine-readable data, wherein said data comprises at least a portion of the structure coordinates of Appendix 1;

(ii) a computer-readable data storage medium comprising a data storage material encoded with computer-readable data, wherein said data comprises X-ray diffraction data obtained from said aromatic prenyl transferase molecule or molecular complex or a homologue of said aromatic prenyl transferase molecule or molecular complex;

(iii) a working memory for storing instructions for processing said computer-readable data of (i) and (ii);

(iv) a central-processing unit coupled to said working memory and to said computer-readable data storage medium of (i) and (ii) for performing a Fourier transform of the machine readable data of (i) and for processing said computer-readable data of (ii) into structure coordinates; and (v) a display coupled to said central-processing unit for displaying said structure coordinates of said molecule or molecular complex.

The term "computer" as used herein can be composed of a central processing unit (for example, the Pentium III from Intel Corporation, or similar processor from Sun, Motorola, Compaq, AMD or International Business Machines, and the like), a working memory which may be random-access memory or core memory, mass storage memory (for example, one or more floppy disk drives, compact disk drives or magnetic tape containing data recorded thereon), at least one display terminal, at least one keyboard and accompanying input and output devices and connections therefor. The computer typically includes a mechanism for processing, accessing and manipulating input data. A skilled artisan can readily appreciate that any one of the currently available computer systems are suitable. It should also be noted that the computer can be linked to other computer systems in a network or wide area network to provide centralized access to the information contained within the computer.

Contemplated input devices for entering machine readable data include, for example, telephone modem lines, cable modems, CD-ROMs, a keyboard or disk drives. The computer may advantageously include or be programmed with appropriate software for reading the data from the data storage component or input device, for example computational programs for use in rational drug design that are described in detail below. Contemplated output devices include conventional systems known in the art, for example, display terminals, printers, or disk drives for further storage of output.

Figure 8:
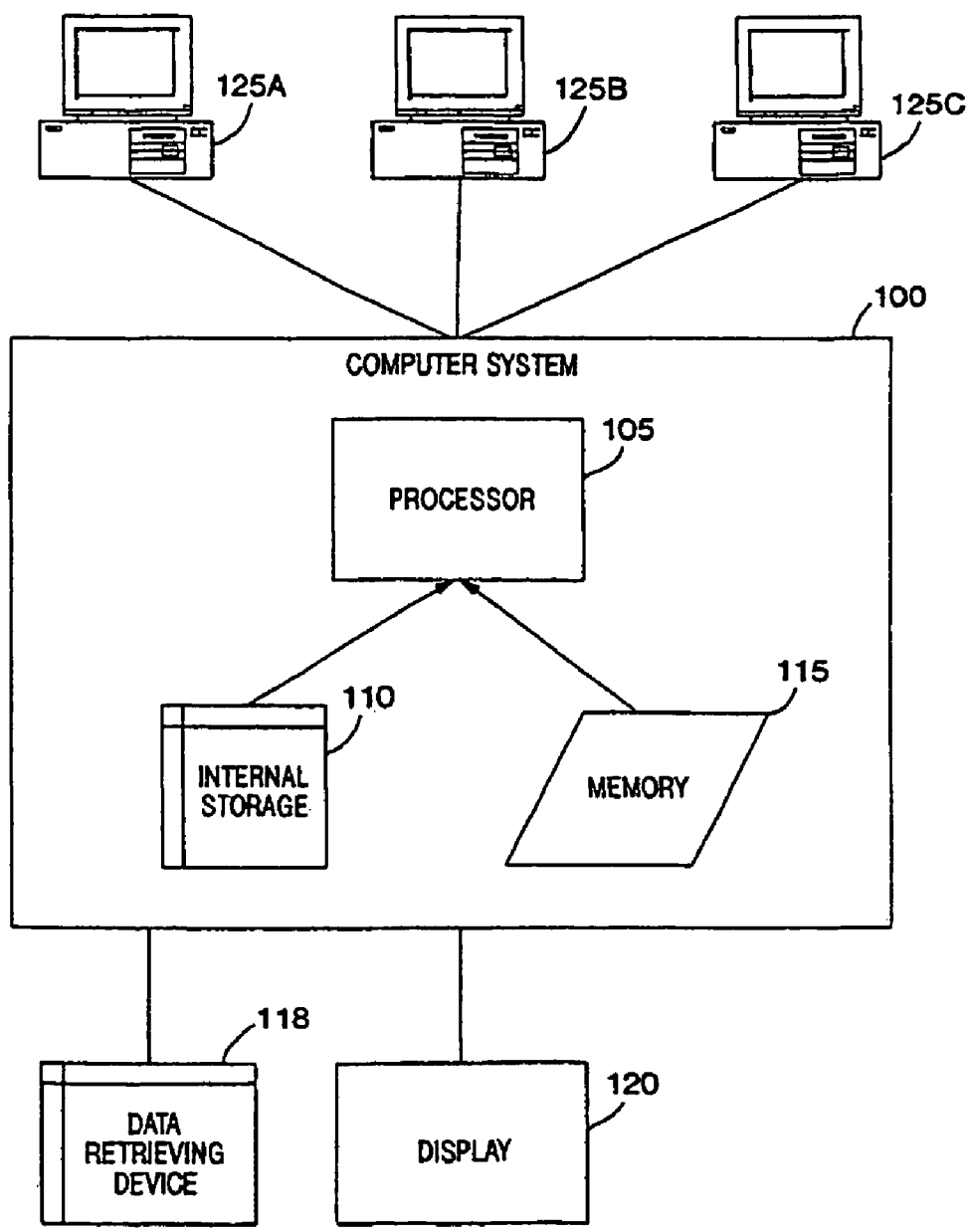
FIG. 8 is a block diagram of a computer system contemplated for use in the practice of the present invention.

Embodiments of the invention include systems (e.g., internet based systems), particularly computer systems which store and manipulate the coordinate and sequence information described herein. One example of a computer system 100 is illustrated in block diagram form in FIG. 8. As used herein, "a computer system" refers to the hardware components, software components, and data storage components used to analyze the coordinates and sequences such as those set forth in Appendix 1. The computer system 100 typically includes a processor for processing, accessing and manipulating the sequence data. The processor 105 can be any well-known type of central processing unit, such as, for example, the Pentium III from Intel Corporation, or similar processor from other suppliers such as Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device(s) 118 for reading the data stored on the internal data storage devices 110.

The data retrieving device 118 may represent, for example, a floppy disk drive, a compact disk drive, a magnetic tape drive, a modem capable of connection to a remote data storage system (e.g., via the internet), and the like. In some embodiments, the internal data storage device 110 is a removable computer readable medium such as a floppy disk, a compact disk, a magnetic tape, and the like, containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the coordinate and sequences of Appendix 1, (such as search tools, compare tools, and modeling tools etc.) may reside in main memory 115 during execution (Appendix 1, discloses residues 3-303 of SEQ ID NO: 2).

Computer programs are widely available that are capable of carrying out the activities necessary to model structures and substrates using the crystal structure information provided herein. Examples include, but are not limited to, the computer programs listed below:

CATALYST DATABASE™—an information retrieval program accessing chemical databases such as BioByte Master File, Derwent WDI and ACD;

CATALYST/HYPO™—generates models of compounds and hypotheses to explain variations of activity with the structure of drug candidates;

LUDI™—fits molecules into the active site of a protein by identifying and matching complementary polar and hydrophobic groups;

LEAPFROG™—"grows" new ligands using an algorithm with parameters under the control of the user.

In addition, various general purpose machines may be used with programs written in accordance with the teachings herein, or it may be more convenient to construct more specialized apparatus to perform the operations. However, preferably this is implemented in one or more computer programs executing on programmable systems each comprising at least one processor, at least one data storage system (including volatile and non-volatile memory and/or storage elements), at least one input device, and at least one output device. The program is executed on the processor to perform the functions described herein.

The following examples are provided to further illustrate aspects of the invention. These examples are non-limiting and should not be construed as limiting any aspect of the invention.

EXAMPLES

All solvents and reagents were obtained from the Aldrich Chemical Company (Milwaukee, Wis.) unless otherwise indicated.

Example 1

Cloning of ORF2

A cosmid pCLC7 (see Takagi et al., J Bacteriol 182: 41534157 (2000)), which contains the mevalonate pathway gene cluster and the flanking regions cloned from CL190, was sequenced. The DNA sequence of Orf2 was determined by standard techniques, and is set forth as SEQ ID NO:1. The amino acid sequence of Orf2 was deduced from the DNA sequence and is set forth as SEQ ID NO:2.

This sequencing revealed 3 new complete orfs, orf1, orf2, and orf3 and a partial orf4 in a 9.0 kb-BamHI-BamHI DNA fragment which contains mevalonate kinase and diphospho-mevalonate decarboxylase (see pCL3301 in FIG. 6). To deduce function of each orf, a database search was done. The results are summarized in Table 2.

TABLE 2

| ORFs | Amino acids | Most homologous proteins and their accession numbers |
|---|---|---|
| ORF1 | 319 aa | *S. avermitilis* RNA polymerase ECF-subfamily σ factor, AP005050 |
| ORF2 | 307 aa | *S. coelicolor* A3(2) protein, AL391041 |
| ORF3 | 410 aa | *S. antibioticus* type III polyketide synthase, AB084489 |
| ORF4 | 177 aa | *S. erythraeus* protein, AY078067 |

ORF2 also showed sequence similarity to the previously described 4-hydroxyphenylpyruvate:dimethylallytransferase, cloQ (accession number AF329398) and novQ (accession number AF 170880), from *Steptomyces roseochromogenes* and *Streptomyces spheroides* NCIMB 11891, respectively (Pojer et al., supra). ORF3 is most likely to encode type III polyketide synthase which produces THN. These data confirm that ORF2 encodes geranyltransferase which catalyzes geranyl transfer to THN or a THN derivative produced by the action of ORF3.

Example 2

Cloning, expression and purification of the ORF2 of SEQ ID NO:1 gene

The orf2 gene of SEQ ID NO:1 from *Streptomyces* sp. strain CL190 (GenBank accession number AB187169) was cloned by PCR amplification of total genomic DNA from CL190 using oligonucleotides designed for ligation into the *E. coli* expression vector pQE30 (QIAGEN), to generate the expression plasmid pQEORF2. PCR amplification of pQE-ORF2, using oligonucleotides designed for ligation into the *E. coli* expression vector pHlS8 (Jez et al., Biochemistry 39(5): 890-902 (2000)) was carried out using the forward primer sequence:

5'- GGG GGG GGATCC TCC GAA GCC GCT GAT GTC G-3' (SEQ ID NO:3; BamHI site underlined), and the reverse primer sequence:
5'-GGG GGG GAATTC TCA GTC CTC CAG CGA GTC G-3' (SEQ ID NO:4; EcoRI site underlined) to generate the expression vector pHIS8ORF2. Constructs of pHIS8ORF2 were transformed into *E. coli* BL21 (DE3) from NOVOGEN. Recombinant Orf2 protein of SEQ ID NO:2 was obtained and purified using a standard protocol described before Jez et al., supra. Selenomethionine (Se-Met)-subsituted protein was obtained from *E. coli* grown in M9 minimal medium using the methionine pathway inhibition approach (Doublir, 1997), and purified as described for the native protein.

Example 3

Crystallization of Orf2 of SEQ ID NO:2 were obtained by the vapor diffusion method at 40C. 2 μl hanging drops containing a 1:1 mixture of a 15 mg/ml protein with crystallization buffer (28% [w/v] PEG 4000, 0.3 M magnesium nitrate, 2 mM DL-dithiothreitol (DTT), 0.1 M PIPES pH 8.5) equilibrated over a 500 μl reservoir of the same solution produced small diffracting crystals overnight. Larger crystals were obtained by the macro-seeding technique in the same conditions. Crystals were stabilized by soaking briefly in a cryoprotectant solution (30% (w/v) PEG 4000, 15% (v/v) glycerol, 0.3 M magnesium nitrate, 2 mM DTT, 0.1 M TAPS, pH 8.5), and flash frozen in liquid nitrogen prior to data collection. Orf2 of SEQ ID NO:2 crystals belong to the $P2_12_12$ space group with average unit cell dimensions of a=71, b=92 Å, c=48 Å, $\alpha=\beta=\gamma=90°$., and contain one monomer per asymmetric unit and a solvent content of 45%. Se-Met substituted crystals were obtained as described (Doublie, Methods Enzymol 276:523-30 (1997)). Various complexes were obtained by soaking wild type Orf2 of SEQ ID NO:2 crystals in stabilization solution containing 5 mM GPP, 10 mM GSPP and 40 mM 1,6-DHN, and 10 mM GSPP and 10 mM flaviolin (GPP and GSPP were purchased from Echelon Biosciences Inc.).

Example 4

Structure Determination and Refinement

A multi-wavelength anomalous dispersion (MAD) data set was collected at the selenium edge on a Se-Met incorporated protein crystal at the Brookhaven National Laboratory (BNL) on beam line X8C. Data were processed with HKL2000 (Otwinowski and Minor, Methods Enzymol 307-326 (1997)), and reduced to a unique set of indexed intensities to a resolution of 1.6 Å. Single wavelength data sets were collected in house, at Brookhaven National Laboratory (BNL), the European Synchrotron Facility (ESRF), and at the Stanford Synchrotron Radiation Laboratory (SSRL) on the various complexes (Table 1). Phasing, density modification and automatic model building were carried out with the program suite Solve/Resolve (Terwilliger, Acta Crystallogr D Biol Crystallogr 58(Pt 11): 1937-40 (2002); Terwilliger and Berendzen, Acta Crystallogr D Biol Crystallogr 55(Pt 4):849-61 (1999)) providing a high quality initial electron density map, using 7 identified Se sites. Additional rounds of building and refinement were carried out with the programs O (Jones, The O Manual, 1993, Upsalla, Sweden) and CNS (Brünger, Acta Crystallogr D Biol Crystallogr 54(Pt 5):905-21 (1998)), respectively. This first model was used to solve the various complexes by molecular replacement with AMoRe (Navaza, Acta Crystallogr D Biol Crystallogr 57(Pt 10):1367-72 (2001)).

Example 5

Detection of prenyltransferase activity of ORF2 ofSEQ ID NO:2

The basal reaction buffer employed contained 50 mM HEPES (pH 7.5), 5 mM MgCl2, 5 mM DTT (as needed), 5 mM prenyl acceptor (DHN1, DHN2 and DHN3; see FIG. 2B), and optionally 5 mM FPP or GPP, in a final volume of 20 µl. The reaction (except for control) was initiated by adding 20 µg of ORF2 protein of SEQ ID NO:2 to the basal assay mixture. After incubation at room temperature for 4 hrs., the reaction mixture was dried using SPEEDVAC and the dried residue was spotted on a silica gel TLC plate. The plate was developed with chloroform:methanol (15-30:1). Reaction products were detected at 254 nm UV.

With prenyl acceptors DHN1 and DHN2, and either prenyl donor, FPP or GPP, prenyltransferase activity was observed. With prenyl acceptor DHN3, prenyltransferase activity was observed with GPP.

Additional studies were carried out with ORF2 and (a) 1,6-DHN (2), (b) 2,7-DHN (3), (c) daidzein (7,4'-dihydroxy-isoflavonone, 5), (d) genistein (5,7,4'-trihydroxyisoflavone, 8), (e) naringenin (5,7,4'-trihydroxyflavonone, 9), (f) olivetol (12), and (g) resveratrol (3,4',5-trihydroxystilbene, 13). These prenyl acceptors gave the following reaction products:
(a) 5-geranyl-1,6-DHN and 2-geranyl-1,6-DHN;
(b) 1-geranyl-2,7-DHN and 1,6-digeranyl-2,7-DHN;
(c) 7-O-geranyl-daidzein;
(d) 7-O-geranyl-genistein;
(e) 6-geranyl-naringenin and 7-O-geranyl-naringenin;
(f) 2-geranyl-olivetol and 4-geranyl-olivetol, and
(g) 4-geranyl-resveratrol.

Example 6

$Mg^{2+}$ Dependent Prenyltransferase Activity of ORF2

The basal reaction buffer employed contained 50 mM HEPES (pH 7.5), 5 mM DTT (as needed), 5 mM prenyl acceptor, DHN2, and 5 mM GPP, in a final volume of 20 µl. The magnesium-containing reaction mixture contained 5 mM $MgCl_2$. The reaction was initiated by adding 20 µg of ORF2 protein to the basal assay mixture. After incubation at room temperature for 4 hrs., the reaction mixture was dried using SpeedVac and the dried residue was spotted on a silica gel TLC plate. The plate was developed with chloroform: methanol (15-30:1). Reaction products were detected at 254 nm UV.

In the presence of magnesium in the reaction mixture, prenylated products were readily observed, while in the absence of magnesium in the reaction mixture, no prenylated products were observed.

Example 7

Promiscuous Activity of ORF2 with Different Flavonoids and Other Compounds

The reaction buffer employed contained 50 mM HEPES (pH 7.5), 5 mM DTT (as needed), 5 mM $MgCl_2$, 0.1 mM of each prenyl acceptor, 0.1 mM GPP, and 0.01 mM [$^{14}$C]GPP in a final volume of 20 µl. The reaction was initiated by adding 20 µg of ORF2 protein to the assay mixture. After incubation at room temperature for 4 hrs., the reaction mixture was dried using SpeedVac and the dried residue was spotted on a silica gel TLC plate. The plate was developed with chloroform:methanol (15-30:1). Reaction products were detected with a phosphoimager. The compounds tested were daidzein, fisetin, formononetin, genistein, naringenin, 4-HPP and DHN2.

With each of the prenyl acceptors tested, prenylated products were readily observed.

Example 8

Knock Out ORF2 Mutant in *Streptomyces* sp. Strain CL190

To gain insight into the function of ORF2, an ORF2 knock out mutant was constructed by frame-shift mutation into orf2. Thus, the 9.0 kb-BamHI-BamHI DNA fragment containing orf2 was cloned into BamHI site of pUC118 (Takara, Kyoto, Japan), a vector of *E. coli*. The resulting plasmid, pCL3301, was digested with EcoRI and then a 3.5-kb EcoRI-EcoRI DNA fragment was cloned into EcoRI site of pUC118 to give pCL3301E3. In addition, a 2.0-kb BamHI-EcoRI DNA fragment in pCL3301 was cloned into BamHI-EcoRI site of pBluescript (Toyobo, Tsuruga, Japan) to give pCL3301BE2. pCL3301E3 was digested with BglII, the recognition site of which is in the targeted orf2, and then blunt-ended with T4 DNA polymerase (Takara). Next, this blunt-ended DNA fragment was self-ligated to give pCL3301E3Bg, which contains orf2 having a frame shift mutation. A 3.5-kb EcoRI-EcoRI DNA fragment cut from pCL3301E3Bg was cloned into the EcoRI site of pCL3301BE2 to give pBluedORF2. Finally, a 5.0-kb XbaI-KpnI fragment, both the recognition sites of which are in the vector pBluescript, was ligated into the same sites of pSE101 (see Dairi et al., Biosci Biotechnol Biochem 59:1835-1841 (1995)), a *Streptomyces-E. coli* shuttle vector, to give pSEdORF2.

Figure 7:
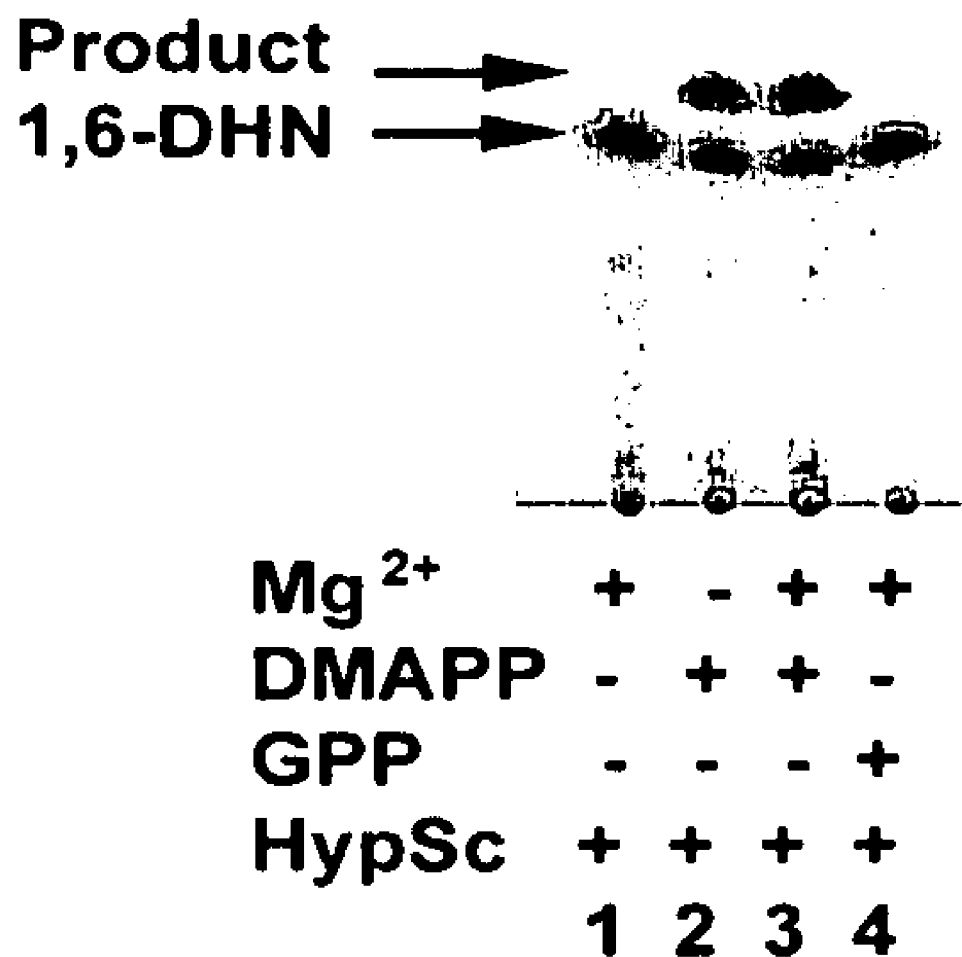
FIG. 7 relates to the functional evaluation of HypSc. Thus, HypSc prenyltransferase activity was assayed as described above with respect to FIG. 2A, using 1,6-DHN as a prenyl acceptor (in each of lanes 1-4), with no prenyl acceptor in lane 1, DMAPP in lanes 2 and 3, and GPP in lane 4. No $Mg^{2+}$ was used in lane 2. The samples were incubated overnight at room temperature.

*Streptomyces* sp. strain CL190 was transformed with pSEdORF2 (as described by Kieser, et al., in "Practical *Streptomyces* Genetics", eds. The John Innes Foundation, Norwich (2000). General considerations about gene cloning in *Streptomyces*. pp. 211-228) and a desired transformant was selected on R2YE plates containing 20 µg thiostrepton/ml. Next, the transformant was cultivated in SK2 liquid medium containing 20 µg thiostrepton/ml at 30° C. for 3 days. As described by Kieser et al., supra, protoplast was prepared from the transformant mycelium and regenerated on R2YE medium without thiostrepton. Each regenerated colony was simultaneously inoculated on Bennet plates with and without thiostrepton and a thiostrepton sensitive colony was selected to obtain the ORF2 knocking out mutant, *Streptomyces* sp. strain CL190 dORF2-8. It was confirmed by PCR that the mutant actually had frame-shift mutation in orf2 (FIG. 7).

The constructed mutant and CL190 were cultivated as reported by Shin-ya, et al., in J. Antibiot. (Tokyo) 43, 444-447 (1990). Myceria were harvested by centrifuge and then naphterpin produced by CL190 was extracted from the CL190 mycerium by the same method previously reported (Shin-ya et al., supra). The mycerium of the mutant was also extracted by the same method. Both the extracts were analyzed on silica gel-thin layer chromatography (TLC) as described. As a result, naphterpin was detected in the extract from CL190, but not in the extract from the mutant (FIG. 7). This result unequivocally indicates that ORF2 is essential for the naphterpin biosynthesis.

Example 9

Database Searches

Data base searches for sequence and structural homologues were performed with PSI-BLAST and VAST (accessible via the internet on the world wide web at the URL "ncbi.nlm.nih.gov"), SSM and DALI (accessible via the internet on the world wide web at the URL "ebi.ac.uk/msd-srv/ssm"), CE (accessible via the internet on the world wide web at the URL "cl.sdsc.edu/ce.html") and DEJAVU (accessible via the internet on the world wide web at the URL "portray.bmc.uu.se/") respectively, through the Protein Data Bank (accessible via the internet on the world wide web at the URL "rcsb.org/pdb/"), the Structural Classification of Proteins (SCOP, accessible via the internet on the world wide web at the URL "scop.mrc-lmb.cam.ac.uk/scop"), and the CATH Protein structure classification (accessible via the internet on the world wide web at the URL "biochem.ucl.ac.uk/bsm/cath").

Example 10

Modeling

Models of CloQ/NovQ and HypSc were performed with the Modeller-4 package (Sali et al., Proteins 23(3):318-26 (1995)) using Orf2 as a structural template (see FIG. 6). For each sequence, five different models were calculated and evaluated. The multiple sequence alignment was then hand modified based on the superposition of the Orf2 structure with the different models. Modeller was then re-run and the iteratively generated models visually inspected and adjusted if necessary. Model quality was assessed with PROCHECK (see Laskowski, et al., J Appl Cryst 26:283-291 (1993)). Side chains presenting potentially significant variation between the different active sites are displayed and labeled. Conserved residues in the different models include Asp 110, Lys 119, Asn 173, Tyr 175, Tyr 216, and Arg 228, of which only Asp 110 and Arg 228 are displayed for clarity.

Example 11

Comparative Modeling of CloQ/NovQ and hypSc

While a significant degree of active site residue correspondence is consistent with the validity of the homology models, small but critical differences in key active site residues provide reasons for the shorter prenyl chain length specificity of CloQ/NovQ and for differences in aromatic substrate selectivity (Pojer et al., supra). In addition, the homology model of HypSc is consistent with the hypothesis for prenyl chain length specificity in this predicted protein. Tyr 121, involved in GPP binding in Orf2, is replaced in all other sequences by a Trp (115 in CloQ/NovQ, and 117 in HypSc): the modeled ring orientation is identical to Tyr 121 while the increased bulkiness may better sequester the shorter C5 prenyl chain of DMAPP. Ser 64 and Gly 286, replaced by Arg (59 in CloQ/NovQ, 61 in HypSc) and Glu (274 in CloQ/NovQ/HypSC), respectively, appear poised to form an internal salt-bridge precisely over the location of the second C5 isoprene unit of the GPP molecule experimentally positioned in the Orf2 active site. Identical changes observed in the HypSc prenyltransferase model predict that this enzyme will also use DMAPP as a prenyl donor. Notably, in Orf2, the geranyl chain of the GPP molecule ends next to the barrel opening, thus providing a probable reason for Orf2's ability to accommodate the C15 prenyl chain of the FPP unit.

Moreover, structural alignment of Orf2 with the CloQ/NovQ and HypSc models reveals the molecular determinants for Orf2's requirement for divalent cations. Asp 62, directly involved in Orf2's diphosphate binding via a coordinated $Mg^{2+}$ ion, is conservatively replaced in HypSc by Asn 59 but changes to a Ser 57 in CloQ/NovQ. In a complementary manner, Ser 51 in Orf2 is replaced by a positively charged Lys 47 in CloQ/NovQ and a positively charged Arg 47 in HypSc that, with little rotamer rearrangement, can be positioned over the $Mg^{2+}$ ion observed in Orf2. Furthermore, these basic side chains are ideally positioned for electrostatic binding to the negatively charged α-phosphate of the GPP molecule. However, Asp 110, involved indirectly in binding $Mg^{2+}$ via a water molecule, is conserved in all the sequences examined (FIG. 1B); thus providing an explanation as to why CloQ and NovQ are active in the absence of $Mg^{2+}$ but display maximum activity in the presence of 2.5 mM $Mg^{2+}$ (Pojer et al, supra). Regarding CloQ's specificity for 4-HPP, Orf2's Gln 161 and Ser 177 are replaced by Arg, 153 and 169 in CloQ, and are positioned to possibly bind the negatively charged tail of the 4-HPP substrate.

This analysis allows one to predict that the HypSc enzyme is a prenyltransferase, accepting only DMAPP as a substrate, while not requiring $Mg^{2+}$ for its activity; this homology modeling based hypothesis has been confirmed by the cloning, protein expression and enzymatic assays of HypSc (see FIG. 7).

TABLE 3

Crystallographic data, phasing, and refinement statistics

| Data Set | SeMet-Orf2 | | | Wt + TAPS | Wt + GPP | Wt + GSPP + 1,6-DHN | wt + GSPP + Flaviolin |
| --- | --- | --- | --- | --- | --- | --- | --- |
| | λ1 (inf, max f') | λ 2 (peak, min f') | λ 3 (remote) | | | | |
| Beam line | BNL-X8C | BNL-X8C | BNL-X8C | BNL-X6A | Salk Inst. | ESRF-BM30A | SSRL-9.1 |
| Wavelength (Å) | 0.9793 | 0.97915 | 0.9641 | 0.934 | 1.54178 | 0.9797 | |
| Space Group | $P2_12_12$ | $P2_12_12$ | $P2_12_12$ | $P2_12_12$ | $P2_12_12$ | $P2_12_12$ | $P2_12_12$ |
| Unit cell a, b, c (Å) | 71.3, 91.2, 48.3 | 71.4, 91.2, 48.4 | 71.3, 91.1, 48.3 | 71.3, 91.2, 48.3 | 74.6, 91.9, 48.8 | 71.3, 90.2, 47.5 | 73.6, 91.6, 48.6 |
| Resolution (Å) | 50-1.55 | 50-1.55 | 50-1.50 | 50-1.45 | 99-2.25 | 99-1.95 | 50-2.02 |
| last shell (Å) | 1.61-1.55 | 1.57-1.52 | 1.55-1.50 | 1.42-1.40 | 2.29-2.25 | 2.00-1.95 | 2.09-2.02 |

TABLE 3-continued

Crystallographic data, phasing, and refinement statistics

| Data Set | SeMet-Orf2 | | | Wt + TAPS | Wt + GPP | Wt + GSPP + 1,6-DHN | wt + GSPP + Flaviolin |
|---|---|---|---|---|---|---|---|
| | λ1 (inf, max f') | λ 2 (peak, min f') | λ 3 (remote) | | | | |
| Observations | | | | | | | |
| Overall[a] | 156510 | 162052 | 170494 | 139582 | 70572 | 115225 | 110252 |
| Unique[a] | 86828 | 91336 | 95274 | 49390 | 16155 | 22960 | 21790 |
| Redundancy[a,b] | 1.8 (1.9) | 1.8 (1.5) | 1.8 (1.5) | 2.84 (1.94) | 4.4 (4.2) | 5.0 (5.1) | 4.5 (5.0) |
| Completeness[a,b](%) | 98.2 (98.2) | 97.5 (91.1) | 98 (94.8) | 78.3 (50.4) | 98 (99.9) | 99.5 (99.6) | 99.1 (99.5) |
| I/σ I[b] | 15.3 (2.2) | 14.7 (1.7) | 14.3 (1.7) | 37.34 (38.9) | 13.5 (2.5) | 32.3 (35.5) | 31.9 (38.0) |
| Rsym[b,c](%) | 7.4 (49.9) | 6.6 (48.3) | 7.2 (55.7) | 9.7 (51.5) | 8.6 (54.8) | 8.6 (51.2) | 9.0 (57.2) |
| No. of Se sites | | 7 | | | | | |
| FOM[d] | | | | | | | |
| centric | 0.57 | | | | | | |
| acentric | 0.55 | | | | | | |
| $R_{cryst}^{e}/R_{free}^{f}$(%) | | 21.42 (24.22) | | | 23.0 (25.8) | 22.25 (25.1) | 24.1 (27.1) | 23.0 (26.8) |
| Missing residues | | 5 | | | 6 | 5 | 6 | 6 |
| Protein atoms | | 2322 | | | 2332 | 2338 | 2332 | 2332 |
| Water molecules | | 254 | | | 429 | 205 | 346 | 320 |
| Ions bound[g] | | 0 | | | 0 | 3 | 2 | 3 |
| Substrate and/or binding agent atoms[h] | | 0 | | | 15 | 19 | 31 | 32 |
| R.m.s.d. bond length (Å) | | 0.005 | | | 0.005 | 0.006 | 0.006 | 0.007 |
| R.m.s.d. bond angles (°) | | 1.2 | | | 1.2 | 1.2 | 1.2 | 1.1 |
| average B-factor(Å$^2$) | | | | | | | | |
| protein | | 13.6 | | | 16.2 | 28.2 | 43.5 | 29.4 |
| water | | 22.8 | | | 27.7 | 35.3 | 42.5 | 42.6 |
| substrate and/or binding agent | | 0 | | | 20.5 | 67.4 | 52.5 | 41.0 |

[a]For the SeMet data sets, F$^+$and F$^-$ were considered non-equivalent when calculating the number of unique reflections and completeness.
[b]Number in parenthesis is for highest resolution shell.
[c]Rsym = $\Sigma_h|I_h - <I_h>|/\Sigma_h(I_h)$, where $<I_h>$ is the average intensity over symmetry equivalent reflections.
[d]FOM is the Figure of Merit
[e]$R_{cryst} = \Sigma | F_{obs} - F_{calc}|/\Sigma|F_{obs}|$, where summation is over the data used for refinement.
[f]$R_{free}$ factor is $R_{cryst}$ calculated using 5% of data (test set) excluded from refinement.
[g]Ion bounds refers to Mg$^{2+}$, (NO$_3$)$^{2-}$ ions.
[h]Substrate and/or binding agent atoms refers to TAPS, GPP, GSPP and 1,6-DHN, GSPP and flaviolin molecules.

Thus, Table 3 summarizes the structural features accompanying prenyl chain length determination, aromatic substrate selectivity and the mechanism of prenyl group transfer, as determined by obtaining X-ray crystal structures of four Orf2 substrate/substrate analogue complexes, namely Orf2 complexed with a TAPS buffer molecule, a binary Orf2 complex containing GPP and Mg$^{2+}$, a ternary Orf2 complex with a non-hydrolyzable GPP analogue, GSPP, Mg$^{2+}$ and 1,6-DHN, and a ternary Orf2 complex with GSPP, Mg$^{2+}$ and flaviolin.

Example 12

Detection of Prenyltransferase Activity of hypSc

The assay described in Example 5 was repeated with hypSc and (a) 1,6-DHN (2), (b) 2,7-DHN (3), (c) daidzein (7,4'-dihydroxyisoflavonone, 5), (d) genistein (5,7,4'-trihydroxyisoflavone, 8), (e) naringenin (5,7,4'-trihydroxyflavonone, 9), (f) olivetol (12), and (g) resveratrol (3,4',5-trihydroxystilbene, 13). These prenyl acceptors gave the following reaction products:
  (a) 5-dimethylallyl-1,6-DHN;
  (b) 1-dimethylallyl-2,7-DHN;
  (c) no reaction products detected;
  (d) no reaction products detected;
  (e) 6-dimethylallyl-naringenin;
  (f) 2-dimethylallyl-olivetol and 4-dimethylallyl-olivetol, and
  (g) 4-dimethylallyl-resveratrol.

Example 13

Biosynthesis of Hybrid Isoprenoids from Marine Actinomycetes

With the PTases Orf2 and HypSc in hand, additional actinomycete PTases with different substrate specificities can be identified. To this end, a group of marine actinomycetes that produce assorted hybrid isoprenoid natural products was compiled (see FIG. 1B, Table 4).

TABLE 4

Hybrid isoprenoid-producing actinomycetes

| Strain | natural product | attachment | isoprene | arom. substrate |
|---|---|---|---|---|
| S. sp. CL190 | naphterpin | C | GPP | hydroxy-naphthalene |

TABLE 4-continued

Hybrid isoprenoid-producing actinomycetes

| Strain | natural product | attachment | isoprene | arom. substrate |
|---|---|---|---|---|
| CNB632 | marinone + analogs | C | FPP | hydroxy-naphthalene |
| CNH099 | marinone | C | FPP | hydroxy-naphthalene |
|  | neomarinone | C | FPP | hydroxy-naphthalene |
|  | lavanducyanin | N | GPP | phenazine |
| CNQ525 | Q525.518 | C × 2 | DMAPP/GPP | hydroxy-naphthalene |
| CNQ509 | Q509.364 | O | GPP | phenazine |
|  | Q509.366 | C | FPP | nitropyrrole |
| S. purpeofuscus | aestivophoenins | N and C | DMAPP | phenazine |

Strain CNH099 produces three isoprenoid chemotypes, namely the farnesylated naphterpin analog marinone, the rearranged derivative neomarinone and the phenazine lavanducyanin. Feeding experiments with labeled precursors delineated the biosynthetic course for these metabolites. The biosynthesis of the naphthoquinone core common amongst the marinones must proceed through a symmetrical pentaketide intermediate such as THN to satisfy the observed labeling patterns. Flaviolin, a known auto-oxidation product of THN, either directly or methylated at C10 via S-adenosyl methionine may serve as an intermediate in neomarinone biosynthesis. FPP, derived from the MEP pathway, provides the sesquiterpenoid side chain. Prenylation may occur directly via C-prenylation though attachment of C3 of FPP or indirectly via O-prenylation of the C5 or C7-hydroxy groups of flaviolin followed by Claisen rearrangement to yield the same furan intermediate. Proton assisted cyclization of the linear diene following Wagner-Meerwein rearrangements yields neomarinone.

A preliminary search for the respective biosynthetic gene clusters allows the generation of a cosmid library in the E. coli-Streptomyces shuttle cosmid pOJ446, the development of a genetics system in this strain for homologous recombination involving the E. coli to CNH099 conjugal transfer of pKC1139-based temperature-sensitive plasmids, and the sequence analysis of genes encoding THN and phenazine biosynthesis. Additionally a pOJ446 cosmid library of the aestivophoenin producer Streptomyces purpeofuscus has been prepared. This information is useful for the identification and cloning of novel aromatic PTases.

Example 14

X-Ray Crystallographic Structures of Orf2 Complexed to Geranylated Products

The reaction products of Orf2 incubated with GPP and 1,6-DHN and naringenin, respectively, have been identified as trans-5-geranyl 1,6-DHN/trans-2-geranyl 1,6-DHN and 6-geranyl naringenin/7-O-geranyl naringenin, respectively (see FIG. 2B). Large scale production of these compounds can be carried out in vitro using 500 uL reaction volumes in the assay buffer described herein and incorporating 20-50 mM GPP and 20-50 mM 1,6-DHN or (2S)-naringenin. Incubations can be carried out overnight and a sample of the resultant solution analyzed by HPLC-MS to assess the product yield and extent of reaction. Multiple reactions can be combined (approximately 5-10 individual reactions), extracted two times with equal volumes of ethyl acetate each time, the combined organic extracts dried down, then dissolved in a minimal amount of methanol followed by injection on an HPLC and purified on a preparative reverse phase column. Purified products can then be characterized. Purified trans-5-geranyl 1,6-DHN, trans-2-geranyl 1,6-DHN, 6-geranyl naringenin, and 7-O-geranyl naringenin can be dissolved in 100% ethanol or methanol to near saturation (approximately 100-200 mM). Each of the four Orf2 product complexes can be prepared employing co-crystallization and soaking strategies. To ensure the maximal occupancy of the product in Orf2 crystals, both co-crystallization and soaking approaches employ a grid whereby the concentrations of the respective products is varied between 5 and 25 mM.

Example 15

Creating an Orf2 Mutant Capable of Efficient Use of DMAPP and Elucidate Its Three Dimensional Structure in the Presence of DMASPP and 1,6-DHN In order to further define prenyl diphosphate chain length selectivity, molecular determinants of aromatic substrate recognition and divalent cation dependence, homology modeling of CloQ, NovQ and HypSc sequences were carried out using the three dimensional coordinates of Orf2 as a structural template (FIG. 6). While the degree of active site residue correspondence is consistent with the homology models discussed above, small differences in key active site residues may explain the shorter prenyl chain length specificity of CloQ/NovQ and the differences in aromatic substrate selectivity. In addition, the homology model of a newly identified PTase from Streptomyces coelicolor, HypSc, lead to the biochemical characterization of HypSc as a DMAPP-specific, $Mg^{2+}$-independent PTase. Prenyl chain length dependence in Orf2 can be evaluated in a variety of ways. One approach involves the generation of a limited set of site directed mutants based upon the initial homology models of CloQ/NovQ and HypSc shown in FIG. 6. An alternate approach involves the generation of several 1024 member mutant libraries of all possible amino acid permutations derived from the comparative analysis of Orf2 with either HypSc or CloQ/NovQ and centered around the geranyl binding site mapped previously.

The first set of Orf2 mutants can be constructed using a traditional QuickChange protocol. Specifically, a Trp residue (residue 115 in CloQ/NovQ and residue 117 in HypSc) replaces Tyr 121 in Orf2. The increased bulkiness of the indole ring in HypSc/CloQ/NovQ compared to the phenolic ring in Orf2 may better accommodate the shorter C5 prenyl chain of DMAPP. In addition, in HypSc/CloQ/NovQ, Arg and Glu residues replace Ser 64 and Gly 286, respectively in Orf2 (residues 59 and 274 in CloQ/NovQ and residues 61 and 274 in HypSc). This apparent salt bridge in the DMAPP-specific PTases sits poised over the location of the second C5 isoprene unit of the GPP molecule. Notably, this change in the homology model of HypSc lead to the biochemical characterization of this newly discovered S. coelicolor enzyme as a DMAPP specific PTase. This rather directed approach towards enzyme engineering minimizes the potential influence of neighboring residues towards prenyl chain length determination. If this mutagenic strategy fails to significantly alter Orf2's prenyl chain length specificity, a larger library of mutant Orf2s can be prepared employing the SCOPE approach described in Example 17.

Comparative homology modeling used to initially select residues for further functional examination is performed with the package Modeller-4 using Orf2 as a structural template. As new sequences are identified, additional models can be constructed. For each sequence, five different models are calculated and evaluated. The multiple sequence alignment is then modified by hand based on the superposition of the Orf2 structure with the individual models. Modeller-4 is then re-run and the iteratively generated models visually inspected and adjusted again if necessary. Model quality is assessed with PROCHECK.

Example 16

Development of a Quantitative PTase Kinetic Assay

To determine the steady state kinetic parameters for PTases, a radiometric TLC assay can be employed. The typical reaction buffer contemplated for use consists of 50 mM HEPES (pH 7.5), 0.1-10 mM aromatic acceptor, 0.1-5 mM [$^{14}$C]-DMAPP, [$^{14}$C]-GPP or [$^{14}$C]-FPP (New England Nuclear), 5 mM MgCl$_2$ in a final volume of 20 μl. The reaction is initiated by adding 10 ng-5 μg of PTase to the assay mixture. Enzyme concentration ranges can be selected to achieve the optimal PTase concentration obeying Michaelis-Menten kinetics. Incubations can be carried out and 4-6 time points collected in triplicate over an initial time range of 1-120 minutes. Reactions can be quenched with ethyl acetate. Extracts can be evaporated to dryness, re-dissolved in methanol, and applied to Whatman LK6D silica TLC plates. The TLC plate can be developed with a chloroform/methanol (20:1) solvent mixture. Aromatic reaction products can be detected at 254 nm or by autoradiography using imaging plates. Products can be quantified by scraping sections of the TLC plate into Ecolume scintillation fluid, detecting [$^{14}$C]-radioactivity with a scintillation counter, and converting the corrected cpm into nmoles of product using the final specific radioactivity of [$^{14}$C]-DMAPP, [$^{14}$C]-GPP or [$^{14}$C]-FPP. Kinetic constants can be determined from initial velocity measurements, in which product formation is linear over the time periods monitored (up to two hours for low activity PTases or mutants thereof). Given the fact that two substrates are employed, $K_M$ values for the prenyl donor are established using saturating concentrations of aromatic acceptor (typically 50 mM) and $K_M$ values for the aromatic acceptors are established using saturating concentrations of prenyl donors, typically 50 mM. In order to reach 50 mM prenyl donor, the radioactive sample is diluted to 50 mM using cold DMAPP, GPP or FPP and corrections for dilution applied as appropriate.

Example 17

A Rapid UPLC-MS-Based Qualitative Assay to Monitor Prenyl Group Transfer

An efficient analysis technique is desirable to serve as a qualitative (or semi-quantitative) assay for prenylation reactions. Specifically, biosynthetic transformations to be monitored include the prenylation (via IPP, GPP and FPP) of both natural and unnatural substrates for wild-type as well as mutant PTase. Efficiency for such an assay is defined in terms of speed, resolution and sensitivity. The assay must accommodate large numbers of samples (high-throughput) for evaluating the several 1024 mutant libraries and must provide analysis on low volume (sub milliliter) reaction volumes (given the number of reactions and the associated costs for reagents). In addition to screening these enzymes and enzyme libraries against natural substrates with a selection of isoprenoid diphosphates, screening may also be desirable with respect to various unnatural substrates designed to probe the structure-to-reactivity relationships governing regio-specific prenylation of chemical building blocks. Finally, given the established promiscuity of Orf2 and its ability to generate multiple products, the assay must also resolve and identify multiple prenylated species per reaction.

Given these requirements, Ultra Performance Liquid Chromatography coupled with ESCi Mass Spectroscopy (UPLC-MS) has been identified as a suitable technique to satisfy the above described assay needs. Briefly, UPLC is a recent advancement in separations technology. The new 1.7 μm particle technology coupled with operating pressures approaching 15,000 psi results in gains of 1.7× in resolution, 3× in speed and 1.7× in sensitivity versus standard HPLC using 5 μm particles when column lengths are normalized. However, the greatest benefit of this technology is realized when normalizing resolution (L/dp); here the gains are 1× in resolution, 9× in speed and 3× in sensitivity versus traditional HPLC 5 μm particles. These significant gains in speed and sensitivity are very beneficial for achieving a qualitative assay.

An additional benefit of this platform stems from the 500% reduction in time for methods development. Preferably, the experiments are carried out using micro-well plates (96 or 384-well format) where the PTases, isoprenoid diphosphate, and aromatic substrate are sequentially added from stock solutions and mixed. Libraries of mutant enzymes are conveniently purified in parallel using small scale (5-10 ml) cultures and an automated Qiagen robot for the parallel purification of histidine-tagged proteins. Following the optimal reaction time, the reactions are quenched and loaded into the UPLC sample organizer/manager for assay. The target operating parameters include LC run times <5 min. (run times as short as 1 min. may be attainable) and direct injection of the quenched reaction mixtures to eliminate sample loss issues. If direct injection is not feasible for high-throughput, an extraction step using a less polar organic solvent can be included, and then sample can be taken directly from the top layer of the reaction well, even while covered to address any evaporation and subsequent sample concentration issues.

Finally, product detection can be achieved via diode array UV detection triggering MS acquisition. Because injection volumes as low as 0.1 μl are possible, and retention times are so short, total volumes of <5 ml/sample are run directly through the ESCi MS assuring all peaks are detected. With the parent ion information, the identification of prenylated products will be facile. The Mass Lynx data management system permits the automation of data analysis, quickly identifying peaks of interest by predefining product mass tables.

Example 18

Structure Elucidation

Large scale in vitro reactions and whole cell fermentations can be directly analyzed on a Waters 600 HPLC or a Agilent 1100 HPLC equipped with photodiode array detection (PDA), auto-sampling and fraction collection. Separations are achieved using a YMC ODS-AQ 4.6×150 mm reversed-phase column with a linear solvent gradient of 0.15% TFA in water to methanol over 30 min at a flow rate of 0.5 ml/min. Alternatively, the samples are first extracted with ethyl acetate, dried over MgSO$_4$, filtered, dried, and redissolved in methanol for analysis. When possible, chromatographic peaks are identified by co-injection with authentic standards. Automated screening will be carried out on a Waters Acquity UPLC equipped with PDA detection and an in-line MicroMass ZQ ESCi (combination APCI-ESI) Mass Spectrometer for low resolution mass analysis. Isolation of pure constituents are carried out with pre-fractionated samples a 20×250 mm YMC pack ODS-A HPLC column that can operate at a flow rate of up to 10 ml/min.

Structures of pure metabolites can be elucidated by 1D and 2D-NMR spectroscopy on Bruker DRX-300 and DRX-600 spectrometers, or on a Varian Unity Inova 500 Spectrometer. Proton and carbon assignments can be obtained from COSY, HSQC, HMBC, and nOe spectral data. Homonuclear $^1$H connectivities can be determined by the phase-sensitive, double-quantum filtered COSY experiment. One-bond heteronuclear $^1$H-$^{13}$C connectivities can be determined by gradient-enhanced proton-detected HSQC experiments. Two- and three-bond $^1$H-$^{13}$C connectivities can be determined by gradient-enhanced proton-detected HMBC experiments. Homonuclear $^1$H nOe's can be obtained by difference nOe experiments and by two-dimensional ROESY experiments to generate relative stereochemistry while the absolute stereochemistry of new compounds can often be achieved through the modified Mosher analytical method or single crystal X-ray analysis. When appropriate, biosynthetic intermediates labeled with stable isotopes (such as sodium [1,2-$^{13}$C$_2$]acetate or [U-$^{13}$C$_6$]glucose) can be administered to the cultures to aid in analog identification through the $^{13}$C INADEQUATE or related experiment. High-resolution mass determination can be performed by TOF-ESI (TSRI Mass Spectroscopy Laboratory) or FAB. Additional characterization techniques include Polarimetry (Perkin-Elmer 341 Polarimeter) and Fourier-Transform Infrared Spectroscopy (Nicolet 4700 FT-IR).

While the invention has been described in detail with reference to certain preferred embodiments thereof, it will be understood that modifications and variations are within the spirit and scope of that which is described and claimed.

APPENDIX 1

Atomic coordinates of aromatic prenyltransferase residues 3-302 of SEQ ID NO: 2.

PROGRAM: CNS 1.1
AUTHORS: BRUNGER, ADAMS, CLORE, DELANO, GROS, GROSSE-KUNSTLEVE, JIANG, KUSZEWSKI, NILGES, PANNU, READ, RICE, SIMONSON, WARREN
DATA USED IN REFINEMENT.
    RESOLUTION RANGE HIGH (ANGSTROMS): 1.95
    RESOLUTION RANGE LOW (ANGSTROMS): 29.74
    DATA CUTOFF (SIGMA(F)): 0.0
    DATA CUTOFF HIGH (ABS(F)): 1386159.12
    DATA CUTOFF LOW (ABS(F)): 0.000000
    COMPLETENESS (WORKING + TEST) (%): 99.4
    NUMBER OF REFLECTIONS: 22923
FIT TO DATA USED IN REFINEMENT.
    CROSS-VALIDATION METHOD: THROUGHOUT
    FREE R VALUE TEST SET SELECTION: RANDOM
    R VALUE (WORKING SET): 0.241
    FREE R VALUE: 0.271
    FREE R VALUE TEST SET SIZE (%): 5.0
    FREE R VALUE TEST SET COUNT: 1154
    ESTIMATED ERROR OF FREE R VALUE: 0.008
FIT IN THE HIGHEST RESOLUTION BIN.
    TOTAL NUMBER OF BINS USED: 6
    BIN RESOLUTION RANGE HIGH (A): 1.95
    BIN RESOLUTION RANGE LOW (A): 2.07
    BIN COMPLETENESS (WORKING + TEST) (%): 99.7
    REFLECTIONS IN BIN (WORKING SET): 3569
    BIN R VALUE (WORKING SET): 0.352
    BIN FREE R VALUE: 0.386
    BIN FREE R VALUE TEST SET SIZE (%): 4.9
    BIN FREE R VALUE TEST SET COUNT: 184
    ESTIMATED ERROR OF BIN FREE R VALUE: 0.028
NUMBER OF NON-HYDROGEN ATOMS USED IN REFINEMENT.
    PROTEIN ATOMS: 0
    NUCLEIC ACID ATOMS: 0
    HETEROGEN ATOMS: 0
    SOLVENT ATOMS: 0
B VALUES.
    FROM WILSON PLOT (A**2): 25.5
    MEAN B VALUE (OVERALL, A**2): 43.5
    OVERALL ANISOTROPIC B VALUE.
    B11 (A**2): −3.35
    B22 (A**2): −13.96
    B33 (A**2): 17.30
    B12 (A**2): 0.00
    B13 (A**2): 0.00
    B23 (A**2): 0.00
BULK SOLVENT MODELING.
    METHOD USED: FLAT MODEL
    KSOL: 0.355809
    BSOL: 42.5443 (A**2)

APPENDIX 1-continued

Atomic coordinates of aromatic prenyltransferase residues 3-302 of SEQ ID NO: 2.

| | | | | | | | | | | | | | | |
|---|---|---|---|---|---|---|---|---|---|---|---|---|---|---|
| ESTIMATED COORDINATE ERROR. | | | | | | | | | | | | | | |
| ESD FROM LUZZATI PLOT (A): | | | | 0.30 | | | | | | | | | | |
| ESD FROM SIGMAA (A): | | | | 0.35 | | | | | | | | | | |
| LOW RESOLUTION CUTOFF (A): | | | | 5.00 | | | | | | | | | | |
| CROSS-VALIDATED ESTIMATED COORDINATE ERROR. | | | | | | | | | | | | | | |
| ESD FROM C-V LUZZATI PLOT (A): | | | | 0.35 | | | | | | | | | | |
| ESD FROM C-V SIGMAA (A): | | | | 0.36 | | | | | | | | | | |
| RMS DEVIATIONS FROM IDEAL VALUES. | | | | | | | | | | | | | | |
| BOND LENGTHS (A): | | | | 0.006 | | | | | | | | | | |
| BOND ANGLES (DEGREES): | | | | 1.2 | | | | | | | | | | |
| DIHEDRAL ANGLES (DEGREES): | | | | 24.4 | | | | | | | | | | |
| IMPROPER ANGLES (DEGREES): | | | | 0.89 | | | | | | | | | | |
| ISOTROPIC THERMAL MODEL: | | | | RESTRAINED | | | | | | | | | | |
| ISOTROPIC THERMAL FACTOR RESTRAINTS. | | | | RMS SIGMA | | | | | | | | | | |
| MAIN-CHAIN BOND (A**2): | | | | NULL; NULL | | | | | | | | | | |
| MAIN-CHAIN ANGLE (A**2): | | | | NULL; NULL | | | | | | | | | | |
| SIDE-CHAIN BOND (A**2): | | | | NULL; NULL | | | | | | | | | | |
| SIDE-CHAIN ANGLE (A**2): | | | | NULL; NULL | | | | | | | | | | |
| NCS MODEL: | | | | NONE | | | | | | | | | | |
| NCS RESTRAINTS. | | | | RMS SIGMA/WEIGHT | | | | | | | | | | |
| GROUP 1 POSITIONAL (A): | | | | NULL; NULL | | | | | | | | | | |
| GROUP 1 B-FACTOR (A*2): | | | | NULL; NULL | | | | | | | | | | |
| PARAMETER FILE 1: | | | | CNS_TOPPAR/protein_rep.param | | | | | | | | | | |
| PARAMETER FILE 2: | | | | CNS_TOPPAR/dna-rna_rep.param | | | | | | | | | | |
| PARAMETER FILE 3: | | | | CNS_TOPPAR/water_rep.param | | | | | | | | | | |
| PARAMETER FILE 4: | | | | CNS_TOPPAR/ion.param | | | | | | | | | | |
| PARAMETER FILE 5: | | | | CNSPAR:gspp_dhn2_no3.param | | | | | | | | | | |
| TOPOLOGY FILE 1: | | | | CNS_TOPPAR/protein.top | | | | | | | | | | |
| TOPOLOGY FILE 2: | | | | CNS_TOPPAR/dna-rna.top | | | | | | | | | | |
| TOPOLOGY FILE 3: | | | | CNS_TOPPAR/water.top | | | | | | | | | | |
| TOPOLOGY FILE 4: | | | | CNS_TOPPAR/ion.top | | | | | | | | | | |
| TOPOLOGY FILE 5: | | | | CNSPAR:gspp_dhn2_no3.top | | | | | | | | | | |
| OTHER REFINEMENT REMARKS: NULL | | | | | | | | | | | | | | |
| SEQRES | 1 | A | 514 | GLU | ALA | ALA | ASP | VAL | GLU | ARG | VAL | TYR | ALA | ALA | MET | GLU |
| SEQRES | 2 | A | 514 | GLU | ALA | ALA | GLY | LEU | LEU | GLY | VAL | ALA | CYS | ALA | ARG | ASP |
| SEQRES | 3 | A | 514 | LYS | ILE | TYR | PRO | LEU | LEU | SER | THR | PHE | GLN | ASP | THR | LEU |
| SEQRES | 4 | A | 514 | VAL | GLU | GLY | GLY | SER | VAL | VAL | VAL | PHE | SER | MET | ALA | SER |
| SEQRES | 5 | A | 514 | GLY | ARG | HIS | SER | THR | GLU | LEU | ASP | PHE | SER | ILE | SER | VAL |
| SEQRES | 6 | A | 514 | PRO | THR | SER | HIS | GLY | ASP | PRO | TYR | ALA | THR | VAL | VAL | GLU |
| SEQRES | 7 | A | 514 | LYS | GLY | LEU | PHE | PRO | ALA | THR | GLY | HIS | PRO | VAL | ASP | ASP |
| SEQRES | 8 | A | 514 | LEU | LEU | ALA | ASP | THR | GLN | LYS | HIS | LEU | PRO | VAL | SER | MET |
| SEQRES | 9 | A | 514 | PHE | ALA | ILE | ASP | GLY | GLU | VAL | THR | GLY | GLY | PHE | LYS | LYS |
| SEQRES | 10 | A | 514 | THR | TYR | ALA | PHE | PHE | PRO | THR | ASP | ASN | MET | PRO | GLY | VAL |
| SEQRES | 11 | A | 514 | ALA | GLU | LEU | SER | ALA | ILE | PRO | SER | MET | PRO | PRO | ALA | VAL |
| SEQRES | 12 | A | 514 | ALA | GLU | ASN | ALA | GLU | LEU | PHE | ALA | ARG | TYR | GLY | LEU | ASP |
| SEQRES | 13 | A | 514 | LYS | VAL | GLN | MET | THR | SER | MET | ASP | TYR | LYS | LYS | ARG | GLN |
| SEQRES | 14 | A | 514 | VAL | ASN | LEU | TYR | PHE | SER | GLU | LEU | SER | ALA | GLN | THR | LEU |
| SEQRES | 15 | A | 514 | GLU | ALA | GLU | SER | VAL | LEU | ALA | LEU | VAL | ARG | GLU | LEU | GLY |
| SEQRES | 16 | A | 514 | LEU | HIS | VAL | PRO | ASN | GLU | LEU | GLY | LEU | LYS | PHE | CYS | LYS |
| SEQRES | 17 | A | 514 | ARG | SER | PHE | SER | VAL | TYR | PRO | THR | LEU | ASN | TRP | GLU | THR |
| SEQRES | 18 | A | 514 | GLY | LYS | ILE | ASP | ARG | LEU | CYS | PHE | ALA | VAL | ILE | SER | ASN |
| SEQRES | 19 | A | 514 | ASP | PRO | THR | LEU | VAL | PRO | SER | SER | GLU | GLY | ASP | ILE |
| SEQRES | 20 | A | 514 | GLU | LYS | PHE | HIS | ASN | TYR | ALA | THR | LYS | ALA | PRO | TYR | ALA |
| SEQRES | 21 | A | 514 | TYR | VAL | GLY | GLU | LYS | ARG | THR | LEU | VAL | TYR | GLY | LEU | THR |
| SEQRES | 22 | A | 514 | LEU | SER | PRO | LYS | GLU | GLU | TYR | TYR | LYS | LEU | GLY | ALA | TYR |
| SEQRES | 23 | A | 514 | TYR | HIS | ILE | THR | ASP | VAL | GLN | ARG | GLY | LEU | LEU | LYS | ALA |
| SEQRES | 24 | A | 514 | PHE | ASP | MG2 | GSP | DH2 | NO3 | TIP | TIP | TIP | TIP | TIP | TIP | TIP |
| SEQRES | 25 | A | 514 | TIP | TIP | TIP | TIP | TIP | TIP | TIP | TIP | TIP | TIP | TIP | TIP | TIP |
| SEQRES | 26 | A | 514 | TIP | TIP | TIP | TIP | TIP | TIP | TIP | TIP | TIP | TIP | TIP | TIP | TIP |
| SEQRES | 27 | A | 514 | TIP | TIP | TIP | TIP | TIP | TIP | TIP | TIP | TIP | TIP | TIP | TIP | TIP |
| SEQRES | 28 | A | 514 | TIP | TIP | TIP | TIP | TIP | TIP | TIP | TIP | TIP | TIP | TIP | TIP | TIP |
| SEQRES | 29 | A | 514 | TIP | TIP | TIP | TIP | TIP | TIP | TIP | TIP | TIP | TIP | TIP | TIP | TIP |
| SEQRES | 30 | A | 514 | TIP | TIP | TIP | TIP | TIP | TIP | TIP | TIP | TIP | TIP | TIP | TIP | TIP |
| SEQRES | 31 | A | 514 | TIP | TIP | TIP | TIP | TIP | TIP | TIP | TIP | TIP | TIP | TIP | TIP | TIP |
| SEQRES | 32 | A | 514 | TIP | TIP | TIP | TIP | TIP | TIP | TIP | TIP | TIP | TIP | TIP | TIP | TIP |
| SEQRES | 33 | A | 514 | TIP | TIP | TIP | TIP | TIP | TIP | TIP | TIP | TIP | TIP | TIP | TIP | TIP |
| SEQRES | 34 | A | 514 | TIP | TIP | TIP | TIP | TIP | TIP | TIP | TIP | TIP | TIP | TIP | TIP | TIP |
| SEQRES | 35 | A | 514 | TIP | TIP | TIP | TIP | TIP | TIP | TIP | TIP | TIP | TIP | TIP | TIP | TIP |
| SEQRES | 36 | A | 514 | TIP | TIP | TIP | TIP | TIP | TIP | TIP | TIP | TIP | TIP | TIP | TIP | TIP |
| SEQRES | 37 | A | 514 | TIP | TIP | TIP | TIP | TIP | TIP | TIP | TIP | TIP | TIP | TIP | TIP | TIP |
| SEQRES | 38 | A | 514 | TIP | TIP | TIP | TIP | TIP | TIP | TIP | TIP | TIP | TIP | TIP | TIP | TIP |
| SEQRES | 39 | A | 514 | TIP | TIP | TIP | TIP | TIP | TIP | TIP | TIP | TIP | TIP | TIP | TIP | TIP |
| SEQRES | 40 | A | 514 | TIP | TIP | TIP | TIP | TIP | TIP | | | | | | | |
| CRYST1 | 71.319 | 90.243 | 47.513 | 90.00 | 90.00 | 90.00 | P 21 21 2 | 4 | | | | | | | |
| ORIGX1 | 1.000000 | 0.000000 | 0.000000 | 0.00000 | | | | | | | | | | | |
| ORIGX2 | 0.000000 | 1.000000 | 0.000000 | 0.00000 | | | | | | | | | | | |
| ORIGX3 | 0.000000 | 0.000000 | 1.000000 | 0.00000 | | | | | | | | | | | |

APPENDIX 1-continued

Atomic coordinates of aromatic prenyltransferase residues 3-302 of SEQ ID NO: 2.

| | | | | | | | | | | |
|---|---|---|---|---|---|---|---|---|---|---|
| SCALE1 | | 0.014022 | 0.000000 | | 0.000000 | 0.00000 | | | | |
| SCALE2 | | 0.000000 | 0.011081 | | 0.000000 | 0.00000 | | | | |
| SCALE3 | | 0.000000 | 0.000000 | | 0.021047 | 0.00000 | | | | |
| ATOM | 1 | CB | GLU | A | 3 | 34.602 | 9.738 | 21.871 | 1.00 | 67.30 A |
| ATOM | 2 | CG | GLU | A | 3 | 34.388 | 9.619 | 23.371 | 1.00 | 67.06 A |
| ATOM | 3 | CD | GLU | A | 3 | 35.148 | 8.453 | 23.975 | 1.00 | 66.81 A |
| ATOM | 4 | OE1 | GLU | A | 3 | 36.396 | 8.490 | 23.969 | 1.00 | 66.45 A |
| ATOM | 5 | OE2 | GLU | A | 3 | 34.497 | 7.497 | 24.449 | 1.00 | 66.55 A |
| ATOM | 6 | C | GLU | A | 3 | 32.569 | 8.406 | 21.275 | 1.00 | 68.45 A |
| ATOM | 7 | O | GLU | A | 3 | 31.776 | 9.074 | 20.608 | 1.00 | 68.75 A |
| ATOM | 8 | N | GLU | A | 3 | 34.407 | 8.713 | 19.628 | 1.00 | 67.62 A |
| ATOM | 9 | CA | GLU | A | 3 | 34.078 | 8.542 | 21.070 | 1.00 | 67.93 A |
| ATOM | 10 | N | ALA | A | 4 | 32.177 | 7.535 | 22.198 | 1.00 | 68.54 A |
| ATOM | 11 | CA | ALA | A | 4 | 30.768 | 7.318 | 22.493 | 1.00 | 68.73 A |
| ATOM | 12 | CB | ALA | A | 4 | 30.598 | 6.047 | 23.317 | 1.00 | 68.94 A |
| ATOM | 13 | C | ALA | A | 4 | 30.212 | 8.517 | 23.257 | 1.00 | 69.02 A |
| ATOM | 14 | O | ALA | A | 4 | 29.070 | 8.927 | 23.045 | 1.00 | 69.08 A |
| ATOM | 15 | N | ALA | A | 5 | 31.036 | 9.076 | 24.139 | 1.00 | 68.87 A |
| ATOM | 16 | CA | ALA | A | 5 | 30.649 | 10.222 | 24.953 | 1.00 | 67.96 A |
| ATOM | 17 | CB | ALA | A | 5 | 31.752 | 10.542 | 25.956 | 1.00 | 67.47 A |
| ATOM | 18 | C | ALA | A | 5 | 30.332 | 11.458 | 24.117 | 1.00 | 67.32 A |
| ATOM | 19 | O | ALA | A | 5 | 29.330 | 12.131 | 24.356 | 1.00 | 67.46 A |
| ATOM | 20 | N | ASP | A | 6 | 31.186 | 11.762 | 23.144 | 1.00 | 66.37 A |
| ATOM | 21 | CA | ASP | A | 6 | 30.967 | 12.927 | 22.291 | 1.00 | 65.49 A |
| ATOM | 22 | CB | ASP | A | 6 | 32.130 | 13.117 | 21.310 | 1.00 | 65.78 A |
| ATOM | 23 | CG | ASP | A | 6 | 33.432 | 13.479 | 22.002 | 1.00 | 65.79 A |
| ATOM | 24 | OD1 | ASP | A | 6 | 33.412 | 14.365 | 22.887 | 1.00 | 65.52 A |
| ATOM | 25 | OD2 | ASP | A | 6 | 34.477 | 12.887 | 21.648 | 1.00 | 65.81 A |
| ATOM | 26 | C | ASP | A | 6 | 29.667 | 12.802 | 21.506 | 1.00 | 64.46 A |
| ATOM | 27 | O | ASP | A | 6 | 28.836 | 13.710 | 21.519 | 1.00 | 65.11 A |
| ATOM | 28 | N | VAL | A | 7 | 29.493 | 11.675 | 20.824 | 1.00 | 63.25 A |
| ATOM | 29 | CA | VAL | A | 7 | 28.292 | 11.442 | 20.031 | 1.00 | 61.69 A |
| ATOM | 30 | CB | VAL | A | 7 | 28.331 | 10.054 | 19.351 | 1.00 | 60.95 A |
| ATOM | 31 | CG1 | VAL | A | 7 | 27.042 | 9.815 | 18.575 | 1.00 | 60.38 A |
| ATOM | 32 | CG2 | VAL | A | 7 | 29.530 | 9.968 | 18.423 | 1.00 | 60.39 A |
| ATOM | 33 | C | VAL | A | 7 | 27.023 | 11.547 | 20.871 | 1.00 | 61.64 A |
| ATOM | 34 | O | VAL | A | 7 | 26.055 | 12.185 | 20.458 | 1.00 | 61.60 A |
| ATOM | 35 | N | GLU | A | 8 | 27.028 | 10.919 | 22.045 | 1.00 | 61.47 A |
| ATOM | 36 | CA | GLU | A | 8 | 25.871 | 10.953 | 22.936 | 1.00 | 61.38 A |
| ATOM | 37 | CB | GLU | A | 8 | 26.031 | 9.939 | 24.076 | 1.00 | 63.51 A |
| ATOM | 38 | CG | GLU | A | 8 | 25.959 | 8.480 | 23.639 | 1.00 | 67.51 A |
| ATOM | 39 | CD | GLU | A | 8 | 26.050 | 7.504 | 24.805 | 1.00 | 70.62 A |
| ATOM | 40 | OE1 | GLU | A | 8 | 25.181 | 7.560 | 25.706 | 1.00 | 71.88 A |
| ATOM | 41 | OE2 | GLU | A | 8 | 26.990 | 6.678 | 24.819 | 1.00 | 72.29 A |
| ATOM | 42 | C | GLU | A | 8 | 25.662 | 12.345 | 23.523 | 1.00 | 59.87 A |
| ATOM | 43 | O | GLU | A | 8 | 24.531 | 12.748 | 23.787 | 1.00 | 59.59 A |
| ATOM | 44 | N | ARG | A | 9 | 26.755 | 13.072 | 23.729 | 1.00 | 58.71 A |
| ATOM | 45 | CA | ARG | A | 9 | 26.681 | 14.418 | 24.285 | 1.00 | 57.97 A |
| ATOM | 46 | CB | ARG | A | 9 | 28.077 | 14.907 | 24.679 | 1.00 | 57.94 A |
| ATOM | 47 | CG | ARG | A | 9 | 28.108 | 16.329 | 25.214 | 1.00 | 58.66 A |
| ATOM | 48 | CD | ARG | A | 9 | 29.481 | 16.687 | 25.761 | 1.00 | 59.63 A |
| ATOM | 49 | NE | ARG | A | 9 | 30.534 | 16.601 | 24.752 | 1.00 | 60.75 A |
| ATOM | 50 | CZ | ARG | A | 9 | 30.662 | 17.435 | 23.724 | 1.00 | 60.72 A |
| ATOM | 51 | NH1 | ARG | A | 9 | 29.798 | 18.430 | 23.561 | 1.00 | 59.60 A |
| ATOM | 52 | NH2 | ARG | A | 9 | 31.659 | 17.277 | 22.861 | 1.00 | 60.10 A |
| ATOM | 53 | C | ARG | A | 9 | 26.054 | 15.381 | 23.281 | 1.00 | 57.24 A |
| ATOM | 54 | O | ARG | A | 9 | 25.192 | 16.184 | 23.634 | 1.00 | 56.91 A |
| ATOM | 55 | N | VAL | A | 10 | 26.488 | 15.298 | 22.029 | 1.00 | 56.17 A |
| ATOM | 56 | CA | VAL | A | 10 | 25.948 | 16.163 | 20.989 | 1.00 | 54.31 A |
| ATOM | 57 | CB | VAL | A | 10 | 26.769 | 16.052 | 19.688 | 1.00 | 54.27 A |
| ATOM | 58 | CG1 | VAL | A | 10 | 26.041 | 16.741 | 18.542 | 1.00 | 54.08 A |
| ATOM | 59 | CG2 | VAL | A | 10 | 28.130 | 16.691 | 19.891 | 1.00 | 53.91 A |
| ATOM | 60 | C | VAL | A | 10 | 24.488 | 15.828 | 20.700 | 1.00 | 53.68 A |
| ATOM | 61 | O | VAL | A | 10 | 23.661 | 16.725 | 20.541 | 1.00 | 53.84 A |
| ATOM | 62 | N | TYR | A | 11 | 24.163 | 14.542 | 20.636 | 1.00 | 52.98 A |
| ATOM | 63 | CA | TYR | A | 11 | 22.786 | 14.147 | 20.370 | 1.00 | 52.80 A |
| ATOM | 64 | CB | TYR | A | 11 | 22.683 | 12.631 | 20.169 | 1.00 | 52.32 A |
| ATOM | 65 | CG | TYR | A | 11 | 21.290 | 12.169 | 19.791 | 1.00 | 51.40 A |
| ATOM | 66 | CD1 | TYR | A | 11 | 20.788 | 12.376 | 18.506 | 1.00 | 51.32 A |
| ATOM | 67 | CE1 | TYR | A | 11 | 19.488 | 11.996 | 18.169 | 1.00 | 51.46 A |
| ATOM | 68 | CD2 | TYR | A | 11 | 20.457 | 11.567 | 20.732 | 1.00 | 50.53 A |
| ATOM | 69 | CE2 | TYR | A | 11 | 19.158 | 11.186 | 20.408 | 1.00 | 50.55 A |
| ATOM | 70 | CZ | TYR | A | 11 | 18.678 | 11.403 | 19.128 | 1.00 | 51.02 A |
| ATOM | 71 | OH | TYR | A | 11 | 17.387 | 11.042 | 18.814 | 1.00 | 51.32 A |
| ATOM | 72 | C | TYR | A | 11 | 21.882 | 14.570 | 21.528 | 1.00 | 53.23 A |
| ATOM | 73 | O | TYR | A | 11 | 20.705 | 14.869 | 21.332 | 1.00 | 52.82 A |
| ATOM | 74 | N | ALA | A | 12 | 22.440 | 14.592 | 22.735 | 1.00 | 53.71 A |

APPENDIX 1-continued

Atomic coordinates of aromatic prenyltransferase residues 3-302 of SEQ ID NO: 2.

| ATOM | 75 | CA | ALA | A | 12 | 21.681 | 14.979 | 23.923 | 1.00 | 53.92 | A |
|---|---|---|---|---|---|---|---|---|---|---|---|
| ATOM | 76 | CB | ALA | A | 12 | 22.515 | 14.745 | 25.179 | 1.00 | 54.54 | A |
| ATOM | 77 | C | ALA | A | 12 | 21.297 | 16.447 | 23.822 | 1.00 | 53.28 | A |
| ATOM | 78 | O | ALA | A | 12 | 20.151 | 16.826 | 24.073 | 1.00 | 53.07 | A |
| ATOM | 79 | N | ALA | A | 13 | 22.273 | 17.267 | 23.454 | 1.00 | 53.23 | A |
| ATOM | 80 | CA | ALA | A | 13 | 22.062 | 18.697 | 23.305 | 1.00 | 52.67 | A |
| ATOM | 81 | CB | ALA | A | 13 | 23.382 | 19.385 | 23.012 | 1.00 | 52.66 | A |
| ATOM | 82 | C | ALA | A | 13 | 21.083 | 18.947 | 22.170 | 1.00 | 52.84 | A |
| ATOM | 83 | O | ALA | A | 13 | 20.266 | 19.865 | 22.239 | 1.00 | 53.13 | A |
| ATOM | 84 | N | MET | A | 14 | 21.164 | 18.115 | 21.134 | 1.00 | 52.38 | A |
| ATOM | 85 | CA | MET | A | 14 | 20.295 | 18.248 | 19.973 | 1.00 | 53.03 | A |
| ATOM | 86 | CB | MET | A | 14 | 20.715 | 17.257 | 18.882 | 1.00 | 51.89 | A |
| ATOM | 87 | CG | MET | A | 14 | 20.349 | 17.708 | 17.474 | 1.00 | 51.33 | A |
| ATOM | 88 | SD | MET | A | 14 | 20.752 | 16.499 | 16.197 | 1.00 | 51.22 | A |
| ATOM | 89 | CE | MET | A | 14 | 22.491 | 16.786 | 15.974 | 1.00 | 49.08 | A |
| ATOM | 90 | C | MET | A | 14 | 18.824 | 18.042 | 20.333 | 1.00 | 53.97 | A |
| ATOM | 91 | O | MET | A | 14 | 17.975 | 18.844 | 19.960 | 1.00 | 54.01 | A |
| ATOM | 92 | N | GLU | A | 15 | 18.517 | 16.967 | 21.053 | 1.00 | 55.62 | A |
| ATOM | 93 | CA | GLU | A | 15 | 17.135 | 16.710 | 21.450 | 1.00 | 57.23 | A |
| ATOM | 94 | CB | GLU | A | 15 | 17.037 | 15.420 | 22.257 | 1.00 | 58.42 | A |
| ATOM | 95 | CG | GLU | A | 15 | 17.273 | 14.154 | 21.472 | 1.00 | 59.79 | A |
| ATOM | 96 | CD | GLU | A | 15 | 17.036 | 12.922 | 22.317 | 1.00 | 60.46 | A |
| ATOM | 97 | OE1 | GLU | A | 15 | 17.775 | 12.731 | 23.307 | 1.00 | 60.40 | A |
| ATOM | 98 | OE2 | GLU | A | 15 | 16.106 | 12.152 | 21.995 | 1.00 | 61.48 | A |
| ATOM | 99 | C | GLU | A | 15 | 16.621 | 17.862 | 22.307 | 1.00 | 57.68 | A |
| ATOM | 100 | O | GLU | A | 15 | 15.477 | 18.298 | 22.171 | 1.00 | 57.72 | A |
| ATOM | 101 | N | GLU | A | 16 | 17.482 | 18.340 | 23.201 | 1.00 | 58.40 | A |
| ATOM | 102 | CA | GLU | A | 16 | 17.151 | 19.442 | 24.094 | 1.00 | 59.28 | A |
| ATOM | 103 | CB | GLU | A | 16 | 18.354 | 19.746 | 24.993 | 1.00 | 60.79 | A |
| ATOM | 104 | CG | GLU | A | 16 | 18.104 | 20.769 | 26.090 | 1.00 | 63.28 | A |
| ATOM | 105 | CD | GLU | A | 16 | 19.295 | 20.904 | 27.027 | 1.00 | 65.30 | A |
| ATOM | 106 | OE1 | GLU | A | 16 | 19.675 | 19.886 | 27.644 | 1.00 | 66.30 | A |
| ATOM | 107 | OE2 | GLU | A | 16 | 19.853 | 22.019 | 27.143 | 1.00 | 66.14 | A |
| ATOM | 108 | C | GLU | A | 16 | 16.780 | 20.673 | 23.268 | 1.00 | 58.94 | A |
| ATOM | 109 | O | GLU | A | 16 | 15.718 | 21.272 | 23.461 | 1.00 | 58.58 | A |
| ATOM | 110 | N | ALA | A | 17 | 17.661 | 21.041 | 22.342 | 1.00 | 58.27 | A |
| ATOM | 111 | CA | ALA | A | 17 | 17.422 | 22.188 | 21.480 | 1.00 | 56.94 | A |
| ATOM | 112 | CB | ALA | A | 17 | 18.559 | 22.336 | 20.484 | 1.00 | 57.55 | A |
| ATOM | 113 | C | ALA | A | 17 | 16.105 | 21.985 | 20.748 | 1.00 | 56.33 | A |
| ATOM | 114 | O | ALA | A | 17 | 15.275 | 22.888 | 20.676 | 1.00 | 56.73 | A |
| ATOM | 115 | N | ALA | A | 18 | 15.917 | 20.787 | 20.208 | 1.00 | 55.47 | A |
| ATOM | 116 | CA | ALA | A | 18 | 14.697 | 20.466 | 19.486 | 1.00 | 54.97 | A |
| ATOM | 117 | CB | ALA | A | 18 | 14.796 | 19.072 | 18.885 | 1.00 | 54.31 | A |
| ATOM | 118 | C | ALA | A | 18 | 13.511 | 20.545 | 20.439 | 1.00 | 55.41 | A |
| ATOM | 119 | O | ALA | A | 18 | 12.408 | 20.920 | 20.041 | 1.00 | 54.89 | A |
| ATOM | 120 | N | GLY | A | 19 | 13.749 | 20.186 | 21.698 | 1.00 | 55.81 | A |
| ATOM | 121 | CA | GLY | A | 19 | 12.693 | 20.225 | 22.690 | 1.00 | 56.15 | A |
| ATOM | 122 | C | GLY | A | 19 | 12.109 | 21.617 | 22.812 | 1.00 | 56.43 | A |
| ATOM | 123 | O | GLY | A | 19 | 10.896 | 21.800 | 22.726 | 1.00 | 57.40 | A |
| ATOM | 124 | N | LEU | A | 20 | 12.976 | 22.603 | 23.011 | 1.00 | 56.49 | A |
| ATOM | 125 | CA | LEU | A | 20 | 12.538 | 23.985 | 23.139 | 1.00 | 57.06 | A |
| ATOM | 126 | CB | LEU | A | 20 | 13.747 | 24.925 | 23.087 | 1.00 | 57.40 | A |
| ATOM | 127 | CG | LEU | A | 20 | 14.770 | 24.808 | 24.223 | 1.00 | 56.87 | A |
| ATOM | 128 | CD1 | LEU | A | 20 | 15.963 | 25.704 | 23.942 | 1.00 | 57.07 | A |
| ATOM | 129 | CD2 | LEU | A | 20 | 14.116 | 25.196 | 25.538 | 1.00 | 57.91 | A |
| ATOM | 130 | C | LEU | A | 20 | 11.546 | 24.355 | 22.038 | 1.00 | 57.57 | A |
| ATOM | 131 | O | LEU | A | 20 | 10.574 | 25.069 | 22.281 | 1.00 | 58.18 | A |
| ATOM | 132 | N | LEU | A | 21 | 11.786 | 23.853 | 20.829 | 1.00 | 58.02 | A |
| ATOM | 133 | CA | LEU | A | 21 | 10.916 | 24.145 | 19.694 | 1.00 | 57.66 | A |
| ATOM | 134 | CB | LEU | A | 21 | 11.729 | 24.134 | 18.399 | 1.00 | 58.07 | A |
| ATOM | 135 | CG | LEU | A | 21 | 12.849 | 25.173 | 18.313 | 1.00 | 58.73 | A |
| ATOM | 136 | CD1 | LEU | A | 21 | 13.711 | 24.888 | 17.097 | 1.00 | 59.17 | A |
| ATOM | 137 | CD2 | LEU | A | 21 | 12.252 | 26.572 | 18.245 | 1.00 | 59.02 | A |
| ATOM | 138 | C | LEU | A | 21 | 9.749 | 23.172 | 19.565 | 1.00 | 57.77 | A |
| ATOM | 139 | O | LEU | A | 21 | 8.904 | 23.320 | 18.681 | 1.00 | 57.50 | A |
| ATOM | 140 | N | GLY | A | 22 | 9.702 | 22.177 | 20.443 | 1.00 | 57.54 | A |
| ATOM | 141 | CA | GLY | A | 22 | 8.628 | 21.206 | 20.386 | 1.00 | 56.71 | A |
| ATOM | 142 | C | GLY | A | 22 | 8.716 | 20.353 | 19.136 | 1.00 | 56.49 | A |
| ATOM | 143 | O | GLY | A | 22 | 7.701 | 19.951 | 18.564 | 1.00 | 55.99 | A |
| ATOM | 144 | N | VAL | A | 23 | 9.943 | 20.081 | 18.707 | 1.00 | 56.46 | A |
| ATOM | 145 | CA | VAL | A | 23 | 10.177 | 19.267 | 17.525 | 1.00 | 56.41 | A |
| ATOM | 146 | CB | VAL | A | 23 | 11.229 | 19.921 | 16.603 | 1.00 | 56.91 | A |
| ATOM | 147 | CG1 | VAL | A | 23 | 11.383 | 19.104 | 15.325 | 1.00 | 57.54 | A |
| ATOM | 148 | CG2 | VAL | A | 23 | 10.819 | 21.353 | 16.279 | 1.00 | 56.70 | A |
| ATOM | 149 | C | VAL | A | 23 | 10.682 | 17.897 | 17.967 | 1.00 | 56.54 | A |
| ATOM | 150 | O | VAL | A | 23 | 11.404 | 17.785 | 18.958 | 1.00 | 56.02 | A |
| ATOM | 151 | N | ALA | A | 24 | 10.300 | 16.859 | 17.231 | 1.00 | 56.63 | A |

APPENDIX 1-continued

Atomic coordinates of aromatic prenyltransferase residues 3-302 of SEQ ID NO: 2.

| ATOM | 152 | CA | ALA | A | 24 | 10.708 | 15.498 | 17.557 | 1.00 | 56.80 | A |
|------|-----|-----|-----|---|----|--------|--------|--------|------|-------|---|
| ATOM | 153 | CB | ALA | A | 24 | 9.568 | 14.535 | 17.267 | 1.00 | 55.99 | A |
| ATOM | 154 | C | ALA | A | 24 | 11.949 | 15.079 | 16.780 | 1.00 | 57.61 | A |
| ATOM | 155 | O | ALA | A | 24 | 12.082 | 15.386 | 15.593 | 1.00 | 58.66 | A |
| ATOM | 156 | N | CYS | A | 25 | 12.857 | 14.380 | 17.453 | 1.00 | 57.65 | A |
| ATOM | 157 | CA | CYS | A | 25 | 14.081 | 13.911 | 16.817 | 1.00 | 58.14 | A |
| ATOM | 158 | CB | CYS | A | 25 | 15.257 | 14.002 | 17.783 | 1.00 | 57.35 | A |
| ATOM | 159 | SG | CYS | A | 25 | 15.899 | 15.659 | 17.971 | 1.00 | 61.13 | A |
| ATOM | 160 | C | CYS | A | 25 | 13.949 | 12.480 | 16.323 | 1.00 | 57.86 | A |
| ATOM | 161 | O | CYS | A | 25 | 13.127 | 11.714 | 16.824 | 1.00 | 58.16 | A |
| ATOM | 162 | N | ALA | A | 26 | 14.768 | 12.131 | 15.336 | 1.00 | 57.41 | A |
| ATOM | 163 | CA | ALA | A | 26 | 14.765 | 10.793 | 14.759 | 1.00 | 57.03 | A |
| ATOM | 164 | CB | ALA | A | 26 | 14.318 | 10.854 | 13.301 | 1.00 | 58.04 | A |
| ATOM | 165 | C | ALA | A | 26 | 16.166 | 10.208 | 14.854 | 1.00 | 56.71 | A |
| ATOM | 166 | O | ALA | A | 26 | 17.007 | 10.454 | 13.994 | 1.00 | 55.93 | A |
| ATOM | 167 | N | ARG | A | 27 | 16.404 | 9.431 | 15.905 | 1.00 | 57.35 | A |
| ATOM | 168 | CA | ARG | A | 27 | 17.703 | 8.811 | 16.139 | 1.00 | 57.63 | A |
| ATOM | 169 | CB | ARG | A | 27 | 17.622 | 7.860 | 17.332 | 1.00 | 58.97 | A |
| ATOM | 170 | CG | ARG | A | 27 | 18.978 | 7.432 | 17.852 | 1.00 | 60.53 | A |
| ATOM | 171 | CD | ARG | A | 27 | 19.022 | 7.413 | 19.371 | 1.00 | 61.60 | A |
| ATOM | 172 | NE | ARG | A | 27 | 20.387 | 7.220 | 19.851 | 1.00 | 62.55 | A |
| ATOM | 173 | CZ | ARG | A | 27 | 21.098 | 6.119 | 19.629 | 1.00 | 62.39 | A |
| ATOM | 174 | NH1 | ARG | A | 27 | 20.571 | 5.121 | 18.934 | 1.00 | 63.03 | A |
| ATOM | 175 | NH2 | ARG | A | 27 | 22.330 | 6.013 | 20.106 | 1.00 | 63.44 | A |
| ATOM | 176 | C | ARG | A | 27 | 18.215 | 8.045 | 14.926 | 1.00 | 57.62 | A |
| ATOM | 177 | O | ARG | A | 27 | 19.418 | 8.009 | 14.667 | 1.00 | 57.59 | A |
| ATOM | 178 | N | ASP | A | 28 | 17.293 | 7.427 | 14.193 | 1.00 | 57.67 | A |
| ATOM | 179 | CA | ASP | A | 28 | 17.634 | 6.653 | 13.004 | 1.00 | 58.11 | A |
| ATOM | 180 | CB | ASP | A | 28 | 16.369 | 6.065 | 12.381 | 1.00 | 60.19 | A |
| ATOM | 181 | CG | ASP | A | 28 | 15.645 | 5.131 | 13.316 | 1.00 | 62.69 | A |
| ATOM | 182 | OD1 | ASP | A | 28 | 16.187 | 4.040 | 13.602 | 1.00 | 65.01 | A |
| ATOM | 183 | OD2 | ASP | A | 28 | 14.535 | 5.492 | 13.769 | 1.00 | 63.34 | A |
| ATOM | 184 | C | ASP | A | 28 | 18.342 | 7.495 | 11.953 | 1.00 | 57.11 | A |
| ATOM | 185 | O | ASP | A | 28 | 19.248 | 7.019 | 11.269 | 1.00 | 56.40 | A |
| ATOM | 186 | N | LYS | A | 29 | 17.922 | 8.750 | 11.830 | 1.00 | 56.47 | A |
| ATOM | 187 | CA | LYS | A | 29 | 18.494 | 9.654 | 10.843 | 1.00 | 55.04 | A |
| ATOM | 188 | CB | LYS | A | 29 | 17.375 | 10.451 | 10.172 | 1.00 | 55.10 | A |
| ATOM | 189 | CG | LYS | A | 29 | 16.244 | 9.581 | 9.662 | 1.00 | 56.13 | A |
| ATOM | 190 | CD | LYS | A | 29 | 15.225 | 10.386 | 8.886 | 1.00 | 57.94 | A |
| ATOM | 191 | CE | LYS | A | 29 | 14.082 | 9.498 | 8.434 | 1.00 | 58.81 | A |
| ATOM | 192 | NZ | LYS | A | 29 | 14.581 | 8.276 | 7.733 | 1.00 | 60.48 | A |
| ATOM | 193 | C | LYS | A | 29 | 19.531 | 10.614 | 11.411 | 1.00 | 54.01 | A |
| ATOM | 194 | O | LYS | A | 29 | 20.078 | 11.439 | 10.684 | 1.00 | 54.19 | A |
| ATOM | 195 | N | ILE | A | 30 | 19.809 | 10.507 | 12.704 | 1.00 | 52.40 | A |
| ATOM | 196 | CA | ILE | A | 30 | 20.782 | 11.392 | 13.323 | 1.00 | 51.39 | A |
| ATOM | 197 | CB | ILE | A | 30 | 20.170 | 12.124 | 14.533 | 1.00 | 51.07 | A |
| ATOM | 198 | CG2 | ILE | A | 30 | 21.168 | 13.122 | 15.096 | 1.00 | 51.54 | A |
| ATOM | 199 | CG1 | ILE | A | 30 | 18.887 | 12.841 | 14.115 | 1.00 | 49.68 | A |
| ATOM | 200 | CD1 | ILE | A | 30 | 19.077 | 13.829 | 12.993 | 1.00 | 49.27 | A |
| ATOM | 201 | C | ILE | A | 30 | 22.048 | 10.676 | 13.781 | 1.00 | 51.27 | A |
| ATOM | 202 | O | ILE | A | 30 | 23.159 | 11.111 | 13.473 | 1.00 | 50.40 | A |
| ATOM | 203 | N | TYR | A | 31 | 21.878 | 9.573 | 14.507 | 1.00 | 51.61 | A |
| ATOM | 204 | CA | TYR | A | 31 | 23.018 | 8.827 | 15.030 | 1.00 | 52.03 | A |
| ATOM | 205 | CB | TYR | A | 31 | 22.544 | 7.673 | 15.918 | 1.00 | 54.81 | A |
| ATOM | 206 | CG | TYR | A | 31 | 23.178 | 7.688 | 17.296 | 1.00 | 58.36 | A |
| ATOM | 207 | CD1 | TYR | A | 31 | 22.785 | 8.624 | 18.253 | 1.00 | 60.03 | A |
| ATOM | 208 | CE1 | TYR | A | 31 | 23.381 | 8.666 | 19.514 | 1.00 | 61.40 | A |
| ATOM | 209 | CD2 | TYR | A | 31 | 24.189 | 6.788 | 17.632 | 1.00 | 59.71 | A |
| ATOM | 210 | CE2 | TYR | A | 31 | 24.795 | 6.821 | 18.891 | 1.00 | 61.71 | A |
| ATOM | 211 | CZ | TYR | A | 31 | 24.384 | 7.762 | 19.826 | 1.00 | 62.61 | A |
| ATOM | 212 | OH | TYR | A | 31 | 24.966 | 7.797 | 21.074 | 1.00 | 63.90 | A |
| ATOM | 213 | C | TYR | A | 31 | 23.995 | 8.295 | 13.989 | 1.00 | 50.42 | A |
| ATOM | 214 | O | TYR | A | 31 | 25.206 | 8.452 | 14.141 | 1.00 | 50.96 | A |
| ATOM | 215 | N | PRO | A | 32 | 23.490 | 7.651 | 12.921 | 1.00 | 49.99 | A |
| ATOM | 216 | CD | PRO | A | 32 | 22.091 | 7.335 | 12.584 | 1.00 | 49.46 | A |
| ATOM | 217 | CA | PRO | A | 32 | 24.401 | 7.123 | 11.898 | 1.00 | 49.18 | A |
| ATOM | 218 | CB | PRO | A | 32 | 23.449 | 6.566 | 10.841 | 1.00 | 48.74 | A |
| ATOM | 219 | CG | PRO | A | 32 | 22.256 | 6.163 | 11.646 | 1.00 | 49.30 | A |
| ATOM | 220 | C | PRO | A | 32 | 25.297 | 8.222 | 11.339 | 1.00 | 48.53 | A |
| ATOM | 221 | O | PRO | A | 32 | 26.458 | 7.984 | 10.993 | 1.00 | 48.53 | A |
| ATOM | 222 | N | LEU | A | 33 | 24.750 | 9.430 | 11.267 | 1.00 | 47.26 | A |
| ATOM | 223 | CA | LEU | A | 33 | 25.486 | 10.570 | 10.745 | 1.00 | 47.08 | A |
| ATOM | 224 | CB | LEU | A | 33 | 24.505 | 11.679 | 10.356 | 1.00 | 46.08 | A |
| ATOM | 225 | CG | LEU | A | 33 | 25.021 | 12.774 | 9.422 | 1.00 | 45.61 | A |
| ATOM | 226 | CD1 | LEU | A | 33 | 25.592 | 12.152 | 8.156 | 1.00 | 44.68 | A |
| ATOM | 227 | CD2 | LEU | A | 33 | 23.875 | 13.720 | 9.080 | 1.00 | 45.94 | A |
| ATOM | 228 | C | LEU | A | 33 | 26.517 | 11.095 | 11.745 | 1.00 | 46.98 | A |

APPENDIX 1-continued

Atomic coordinates of aromatic prenyltransferase residues 3-302 of SEQ ID NO: 2.

| ATOM | 229 | O | LEU | A | 33 | 27.673 | 11.314 | 11.392 | 1.00 | 46.18 | A |
| --- | --- | --- | --- | --- | --- | --- | --- | --- | --- | --- | --- |
| ATOM | 230 | N | LEU | A | 34 | 26.104 | 11.290 | 12.993 | 1.00 | 47.69 | A |
| ATOM | 231 | CA | LEU | A | 34 | 27.019 | 11.780 | 14.021 | 1.00 | 49.32 | A |
| ATOM | 232 | CB | LEU | A | 34 | 26.276 | 11.978 | 15.348 | 1.00 | 49.84 | A |
| ATOM | 233 | CG | LEU | A | 34 | 25.193 | 13.061 | 15.415 | 1.00 | 50.05 | A |
| ATOM | 234 | CD1 | LEU | A | 34 | 24.545 | 13.051 | 16.786 | 1.00 | 49.62 | A |
| ATOM | 235 | CD2 | LEU | A | 34 | 25.806 | 14.420 | 15.136 | 1.00 | 50.80 | A |
| ATOM | 236 | C | LEU | A | 34 | 28.202 | 10.825 | 14.229 | 1.00 | 49.93 | A |
| ATOM | 237 | O | LEU | A | 34 | 29.333 | 11.262 | 14.445 | 1.00 | 50.30 | A |
| ATOM | 238 | N | SER | A | 35 | 27.936 | 9.524 | 14.167 | 1.00 | 50.31 | A |
| ATOM | 239 | CA | SER | A | 35 | 28.984 | 8.525 | 14.344 | 1.00 | 50.96 | A |
| ATOM | 240 | CB | SER | A | 35 | 28.395 | 7.114 | 14.318 | 1.00 | 51.84 | A |
| ATOM | 241 | OG | SER | A | 35 | 27.562 | 6.890 | 15.442 | 1.00 | 54.71 | A |
| ATOM | 242 | C | SER | A | 35 | 30.022 | 8.652 | 13.243 | 1.00 | 51.29 | A |
| ATOM | 243 | O | SER | A | 35 | 31.220 | 8.738 | 13.512 | 1.00 | 51.44 | A |
| ATOM | 244 | N | THR | A | 36 | 29.554 | 8.669 | 12.000 | 1.00 | 50.28 | A |
| ATOM | 245 | CA | THR | A | 36 | 30.444 | 8.782 | 10.855 | 1.00 | 49.52 | A |
| ATOM | 246 | CB | THR | A | 36 | 29.645 | 8.980 | 9.559 | 1.00 | 49.26 | A |
| ATOM | 247 | OG1 | THR | A | 36 | 28.690 | 7.923 | 9.425 | 1.00 | 49.50 | A |
| ATOM | 248 | CG2 | THR | A | 36 | 30.568 | 8.968 | 8.358 | 1.00 | 49.15 | A |
| ATOM | 249 | C | THR | A | 36 | 31.410 | 9.950 | 11.025 | 1.00 | 49.71 | A |
| ATOM | 250 | O | THR | A | 36 | 32.552 | 9.893 | 10.571 | 1.00 | 50.28 | A |
| ATOM | 251 | N | PHE | A | 37 | 30.956 | 11.009 | 11.689 | 1.00 | 49.29 | A |
| ATOM | 252 | CA | PHE | A | 37 | 31.807 | 12.174 | 11.891 | 1.00 | 48.84 | A |
| ATOM | 253 | CB | PHE | A | 37 | 31.146 | 13.416 | 11.284 | 1.00 | 46.61 | A |
| ATOM | 254 | CG | PHE | A | 37 | 30.934 | 13.323 | 9.799 | 1.00 | 43.07 | A |
| ATOM | 255 | CD1 | PHE | A | 37 | 29.729 | 12.873 | 9.283 | 1.00 | 41.56 | A |
| ATOM | 256 | CD2 | PHE | A | 37 | 31.957 | 13.656 | 8.920 | 1.00 | 39.81 | A |
| ATOM | 257 | CE1 | PHE | A | 37 | 29.543 | 12.754 | 7.908 | 1.00 | 42.57 | A |
| ATOM | 258 | CE2 | PHE | A | 37 | 31.785 | 13.542 | 7.549 | 1.00 | 41.01 | A |
| ATOM | 259 | CZ | PHE | A | 37 | 30.576 | 13.090 | 7.039 | 1.00 | 40.00 | A |
| ATOM | 260 | C | PHE | A | 37 | 32.136 | 12.423 | 13.359 | 1.00 | 50.82 | A |
| ATOM | 261 | O | PHE | A | 37 | 32.304 | 13.568 | 13.781 | 1.00 | 50.54 | A |
| ATOM | 262 | N | GLN | A | 38 | 32.246 | 11.343 | 14.128 | 1.00 | 52.93 | A |
| ATOM | 263 | CA | GLN | A | 38 | 32.543 | 11.433 | 15.557 | 1.00 | 54.33 | A |
| ATOM | 264 | CB | GLN | A | 38 | 32.543 | 10.036 | 16.180 | 1.00 | 55.97 | A |
| ATOM | 265 | CG | GLN | A | 38 | 33.536 | 9.088 | 15.535 | 1.00 | 58.11 | A |
| ATOM | 266 | CD | GLN | A | 38 | 33.584 | 7.741 | 16.221 | 1.00 | 59.72 | A |
| ATOM | 267 | OE1 | GLN | A | 38 | 32.549 | 7.124 | 16.483 | 1.00 | 60.66 | A |
| ATOM | 268 | NE2 | GLN | A | 38 | 34.790 | 7.271 | 16.510 | 1.00 | 60.33 | A |
| ATOM | 269 | C | GLN | A | 38 | 33.871 | 12.113 | 15.870 | 1.00 | 53.93 | A |
| ATOM | 270 | O | GLN | A | 38 | 33.990 | 12.818 | 16.868 | 1.00 | 53.58 | A |
| ATOM | 271 | N | ASP | A | 39 | 34.868 | 11.901 | 15.022 | 1.00 | 53.91 | A |
| ATOM | 272 | CA | ASP | A | 39 | 36.178 | 12.495 | 15.252 | 1.00 | 54.34 | A |
| ATOM | 273 | CB | ASP | A | 39 | 37.199 | 11.935 | 14.259 | 1.00 | 55.58 | A |
| ATOM | 274 | CG | ASP | A | 39 | 37.421 | 10.443 | 14.431 | 1.00 | 57.29 | A |
| ATOM | 275 | OD1 | ASP | A | 39 | 37.553 | 9.990 | 15.587 | 1.00 | 57.11 | A |
| ATOM | 276 | OD2 | ASP | A | 39 | 37.475 | 9.724 | 13.409 | 1.00 | 58.78 | A |
| ATOM | 277 | C | ASP | A | 39 | 36.188 | 14.019 | 15.186 | 1.00 | 54.75 | A |
| ATOM | 278 | O | ASP | A | 39 | 37.163 | 14.653 | 15.594 | 1.00 | 53.65 | A |
| ATOM | 279 | N | THR | A | 40 | 35.104 | 14.608 | 14.686 | 1.00 | 54.95 | A |
| ATOM | 280 | CA | THR | A | 40 | 35.019 | 16.061 | 14.569 | 1.00 | 55.03 | A |
| ATOM | 281 | CB | THR | A | 40 | 34.192 | 16.487 | 13.336 | 1.00 | 53.61 | A |
| ATOM | 282 | OG1 | THR | A | 40 | 32.825 | 16.109 | 13.526 | 1.00 | 51.16 | A |
| ATOM | 283 | CG2 | THR | A | 40 | 34.720 | 15.833 | 12.080 | 1.00 | 52.82 | A |
| ATOM | 284 | C | THR | A | 40 | 34.366 | 16.707 | 15.783 | 1.00 | 56.50 | A |
| ATOM | 285 | O | THR | A | 40 | 34.613 | 17.876 | 16.082 | 1.00 | 57.15 | A |
| ATOM | 286 | N | LEU | A | 41 | 33.536 | 15.937 | 16.478 | 1.00 | 57.42 | A |
| ATOM | 287 | CA | LEU | A | 41 | 32.803 | 16.432 | 17.639 | 1.00 | 58.80 | A |
| ATOM | 288 | CB | LEU | A | 41 | 31.702 | 15.430 | 18.004 | 1.00 | 57.63 | A |
| ATOM | 289 | CG | LEU | A | 41 | 30.761 | 15.083 | 16.844 | 1.00 | 56.86 | A |
| ATOM | 290 | CD1 | LEU | A | 41 | 29.770 | 14.018 | 17.277 | 1.00 | 55.61 | A |
| ATOM | 291 | CD2 | LEU | A | 41 | 30.039 | 16.341 | 16.378 | 1.00 | 56.19 | A |
| ATOM | 292 | C | LEU | A | 41 | 33.647 | 16.751 | 18.871 | 1.00 | 60.36 | A |
| ATOM | 293 | O | LEU | A | 41 | 33.108 | 17.030 | 19.942 | 1.00 | 60.30 | A |
| ATOM | 294 | N | VAL | A | 42 | 34.967 | 16.725 | 18.719 | 1.00 | 62.05 | A |
| ATOM | 295 | CA | VAL | A | 42 | 35.859 | 17.015 | 19.834 | 1.00 | 63.74 | A |
| ATOM | 296 | CB | VAL | A | 42 | 37.280 | 16.494 | 19.562 | 1.00 | 64.26 | A |
| ATOM | 297 | CG1 | VAL | A | 42 | 38.190 | 16.837 | 20.733 | 1.00 | 65.42 | A |
| ATOM | 298 | CG2 | VAL | A | 42 | 37.243 | 14.990 | 19.333 | 1.00 | 64.88 | A |
| ATOM | 299 | C | VAL | A | 42 | 35.942 | 18.510 | 20.126 | 1.00 | 64.12 | A |
| ATOM | 300 | O | VAL | A | 42 | 36.493 | 19.277 | 19.332 | 1.00 | 64.30 | A |
| ATOM | 301 | N | GLU | A | 43 | 35.398 | 18.910 | 21.273 | 1.00 | 64.21 | A |
| ATOM | 302 | CA | GLU | A | 43 | 35.403 | 20.308 | 21.694 | 1.00 | 64.09 | A |
| ATOM | 303 | CB | GLU | A | 43 | 35.025 | 20.410 | 23.175 | 1.00 | 65.49 | A |
| ATOM | 304 | CG | GLU | A | 43 | 33.621 | 19.924 | 23.503 | 1.00 | 68.00 | A |
| ATOM | 305 | CD | GLU | A | 43 | 33.338 | 19.927 | 24.997 | 1.00 | 69.13 | A |

APPENDIX 1-continued

Atomic coordinates of aromatic prenyltransferase residues 3-302 of SEQ ID NO: 2.

| ATOM | 306 | OE1 | GLU | A | 43 | 34.017 | 19.180 | 25.733 | 1.00 | 68.77 | A |
|---|---|---|---|---|---|---|---|---|---|---|---|
| ATOM | 307 | OE2 | GLU | A | 43 | 32.440 | 20.677 | 25.436 | 1.00 | 70.84 | A |
| ATOM | 308 | C | GLU | A | 43 | 36.770 | 20.955 | 21.473 | 1.00 | 63.27 | A |
| ATOM | 309 | O | GLU | A | 43 | 37.795 | 20.424 | 21.901 | 1.00 | 63.43 | A |
| ATOM | 310 | N | GLY | A | 44 | 36.778 | 22.102 | 20.802 | 1.00 | 61.60 | A |
| ATOM | 311 | CA | GLY | A | 44 | 38.027 | 22.792 | 20.543 | 1.00 | 59.61 | A |
| ATOM | 312 | C | GLY | A | 44 | 38.003 | 23.516 | 19.215 | 1.00 | 58.39 | A |
| ATOM | 313 | O | GLY | A | 44 | 37.805 | 24.730 | 19.161 | 1.00 | 59.02 | A |
| ATOM | 314 | N | GLY | A | 45 | 38.219 | 22.770 | 18.138 | 1.00 | 56.07 | A |
| ATOM | 315 | CA | GLY | A | 45 | 38.201 | 23.362 | 16.816 | 1.00 | 54.08 | A |
| ATOM | 316 | C | GLY | A | 45 | 36.946 | 22.906 | 16.101 | 1.00 | 52.48 | A |
| ATOM | 317 | O | GLY | A | 45 | 36.914 | 22.817 | 14.879 | 1.00 | 52.24 | A |
| ATOM | 318 | N | SER | A | 46 | 35.911 | 22.613 | 16.883 | 1.00 | 51.11 | A |
| ATOM | 319 | CA | SER | A | 46 | 34.633 | 22.152 | 16.358 | 1.00 | 48.42 | A |
| ATOM | 320 | CB | SER | A | 46 | 34.175 | 20.912 | 17.122 | 1.00 | 48.98 | A |
| ATOM | 321 | OG | SER | A | 46 | 32.801 | 20.655 | 16.893 | 1.00 | 49.29 | A |
| ATOM | 322 | C | SER | A | 46 | 33.531 | 23.203 | 16.423 | 1.00 | 47.59 | A |
| ATOM | 323 | O | SER | A | 46 | 33.421 | 23.960 | 17.391 | 1.00 | 46.05 | A |
| ATOM | 324 | N | VAL | A | 47 | 32.711 | 23.243 | 15.380 | 1.00 | 45.49 | A |
| ATOM | 325 | CA | VAL | A | 47 | 31.605 | 24.181 | 15.326 | 1.00 | 42.26 | A |
| ATOM | 326 | CB | VAL | A | 47 | 31.764 | 25.186 | 14.164 | 1.00 | 41.88 | A |
| ATOM | 327 | CG1 | VAL | A | 47 | 30.602 | 26.174 | 14.167 | 1.00 | 41.99 | A |
| ATOM | 328 | CG2 | VAL | A | 47 | 33.079 | 25.937 | 14.295 | 1.00 | 41.85 | A |
| ATOM | 329 | C | VAL | A | 47 | 30.323 | 23.390 | 15.129 | 1.00 | 41.67 | A |
| ATOM | 330 | O | VAL | A | 47 | 30.199 | 22.631 | 14.171 | 1.00 | 42.19 | A |
| ATOM | 331 | N | VAL | A | 48 | 29.388 | 23.536 | 16.059 | 1.00 | 40.43 | A |
| ATOM | 332 | CA | VAL | A | 48 | 28.111 | 22.849 | 15.962 | 1.00 | 39.58 | A |
| ATOM | 333 | CB | VAL | A | 48 | 27.974 | 21.711 | 16.995 | 1.00 | 40.32 | A |
| ATOM | 334 | CG1 | VAL | A | 48 | 26.527 | 21.222 | 17.041 | 1.00 | 39.82 | A |
| ATOM | 335 | CG2 | VAL | A | 48 | 28.889 | 20.553 | 16.619 | 1.00 | 40.14 | A |
| ATOM | 336 | C | VAL | A | 48 | 27.012 | 23.869 | 16.197 | 1.00 | 39.83 | A |
| ATOM | 337 | O | VAL | A | 48 | 27.061 | 24.636 | 17.159 | 1.00 | 39.49 | A |
| ATOM | 338 | N | VAL | A | 49 | 26.023 | 23.874 | 15.308 | 1.00 | 39.22 | A |
| ATOM | 339 | CA | VAL | A | 49 | 24.914 | 24.808 | 15.393 | 1.00 | 38.77 | A |
| ATOM | 340 | CB | VAL | A | 49 | 24.974 | 25.838 | 14.235 | 1.00 | 38.65 | A |
| ATOM | 341 | CG1 | VAL | A | 49 | 24.027 | 26.994 | 14.514 | 1.00 | 39.77 | A |
| ATOM | 342 | CG2 | VAL | A | 49 | 26.394 | 26.331 | 14.047 | 1.00 | 37.33 | A |
| ATOM | 343 | C | VAL | A | 49 | 23.571 | 24.092 | 15.314 | 1.00 | 39.16 | A |
| ATOM | 344 | O | VAL | A | 49 | 23.427 | 23.091 | 14.611 | 1.00 | 39.92 | A |
| ATOM | 345 | N | PHE | A | 50 | 22.596 | 24.601 | 16.057 | 1.00 | 38.97 | A |
| ATOM | 346 | CA | PHE | A | 50 | 21.243 | 24.061 | 16.038 | 1.00 | 39.87 | A |
| ATOM | 347 | CB | PHE | A | 50 | 20.834 | 23.575 | 17.425 | 1.00 | 39.82 | A |
| ATOM | 348 | CG | PHE | A | 50 | 21.720 | 22.493 | 17.971 | 1.00 | 41.79 | A |
| ATOM | 349 | CD1 | PHE | A | 50 | 22.076 | 21.400 | 17.182 | 1.00 | 42.66 | A |
| ATOM | 350 | CD2 | PHE | A | 50 | 22.167 | 22.544 | 19.288 | 1.00 | 41.26 | A |
| ATOM | 351 | CE1 | PHE | A | 50 | 22.864 | 20.368 | 17.699 | 1.00 | 43.88 | A |
| ATOM | 352 | CE2 | PHE | A | 50 | 22.953 | 21.520 | 19.814 | 1.00 | 42.58 | A |
| ATOM | 353 | CZ | PHE | A | 50 | 23.302 | 20.429 | 19.019 | 1.00 | 41.73 | A |
| ATOM | 354 | C | PHE | A | 50 | 20.380 | 25.242 | 15.598 | 1.00 | 39.56 | A |
| ATOM | 355 | O | PHE | A | 50 | 20.261 | 26.227 | 16.320 | 1.00 | 38.63 | A |
| ATOM | 356 | N | SER | A | 51 | 19.772 | 25.139 | 14.419 | 1.00 | 39.59 | A |
| ATOM | 357 | CA | SER | A | 51 | 19.002 | 26.256 | 13.892 | 1.00 | 38.98 | A |
| ATOM | 358 | CB | SER | A | 51 | 19.631 | 26.692 | 12.571 | 1.00 | 39.41 | A |
| ATOM | 359 | OG | SER | A | 51 | 21.022 | 26.893 | 12.739 | 1.00 | 40.57 | A |
| ATOM | 360 | C | SER | A | 51 | 17.500 | 26.086 | 13.706 | 1.00 | 39.41 | A |
| ATOM | 361 | O | SER | A | 51 | 17.018 | 25.037 | 13.283 | 1.00 | 38.55 | A |
| ATOM | 362 | N | MET | A | 52 | 16.778 | 27.163 | 14.006 | 1.00 | 39.56 | A |
| ATOM | 363 | CA | MET | A | 52 | 15.326 | 27.203 | 13.904 | 1.00 | 41.09 | A |
| ATOM | 364 | CB | MET | A | 52 | 14.721 | 27.612 | 15.248 | 1.00 | 42.98 | A |
| ATOM | 365 | CG | MET | A | 52 | 14.952 | 29.080 | 15.553 | 1.00 | 44.79 | A |
| ATOM | 366 | SD | MET | A | 52 | 14.137 | 29.694 | 17.032 | 1.00 | 53.36 | A |
| ATOM | 367 | CE | MET | A | 52 | 12.461 | 29.878 | 16.420 | 1.00 | 50.19 | A |
| ATOM | 368 | C | MET | A | 52 | 14.948 | 28.254 | 12.867 | 1.00 | 39.86 | A |
| ATOM | 369 | O | MET | A | 52 | 15.736 | 29.144 | 12.577 | 1.00 | 37.96 | A |
| ATOM | 370 | N | ALA | A | 53 | 13.735 | 28.155 | 12.329 | 1.00 | 41.96 | A |
| ATOM | 371 | CA | ALA | A | 53 | 13.240 | 29.115 | 11.344 | 1.00 | 43.31 | A |
| ATOM | 372 | CB | ALA | A | 53 | 13.443 | 28.583 | 9.930 | 1.00 | 43.60 | A |
| ATOM | 373 | C | ALA | A | 53 | 11.757 | 29.373 | 11.605 | 1.00 | 44.82 | A |
| ATOM | 374 | O | ALA | A | 53 | 11.035 | 28.486 | 12.058 | 1.00 | 45.88 | A |
| ATOM | 375 | N | SER | A | 54 | 11.309 | 30.588 | 11.314 | 1.00 | 45.31 | A |
| ATOM | 376 | CA | SER | A | 54 | 9.920 | 30.975 | 11.536 | 1.00 | 46.31 | A |
| ATOM | 377 | CB | SER | A | 54 | 9.824 | 32.490 | 11.704 | 1.00 | 44.93 | A |
| ATOM | 378 | OG | SER | A | 54 | 9.947 | 33.126 | 10.439 | 1.00 | 42.54 | A |
| ATOM | 379 | C | SER | A | 54 | 8.992 | 30.569 | 10.402 | 1.00 | 47.54 | A |
| ATOM | 380 | O | SER | A | 54 | 9.417 | 30.002 | 9.398 | 1.00 | 47.54 | A |
| ATOM | 381 | N | GLY | A | 55 | 7.713 | 30.889 | 10.583 | 1.00 | 50.46 | A |
| ATOM | 382 | CA | GLY | A | 55 | 6.701 | 30.596 | 9.585 | 1.00 | 52.05 | A |

APPENDIX 1-continued

Atomic coordinates of aromatic prenyltransferase residues 3-302 of SEQ ID NO: 2.

| ATOM | 383 | C | GLY | A | 55 | 6.526 | 29.136 | 9.219 | 1.00 | 52.73 | A |
|---|---|---|---|---|---|---|---|---|---|---|---|
| ATOM | 384 | O | GLY | A | 55 | 6.502 | 28.256 | 10.081 | 1.00 | 52.54 | A |
| ATOM | 385 | N | ARG | A | 56 | 6.399 | 28.887 | 7.922 | 1.00 | 53.50 | A |
| ATOM | 386 | CA | ARG | A | 56 | 6.206 | 27.539 | 7.408 | 1.00 | 54.78 | A |
| ATOM | 387 | CB | ARG | A | 56 | 5.885 | 27.590 | 5.911 | 1.00 | 55.54 | A |
| ATOM | 388 | CG | ARG | A | 56 | 7.112 | 27.702 | 5.021 | 1.00 | 55.10 | A |
| ATOM | 389 | CD | ARG | A | 56 | 6.731 | 27.742 | 3.551 | 1.00 | 56.42 | A |
| ATOM | 390 | NE | ARG | A | 56 | 7.892 | 27.536 | 2.690 | 1.00 | 58.46 | A |
| ATOM | 391 | CZ | ARG | A | 56 | 7.858 | 27.590 | 1.363 | 1.00 | 59.31 | A |
| ATOM | 392 | NH1 | ARG | A | 56 | 6.718 | 27.849 | 0.737 | 1.00 | 59.88 | A |
| ATOM | 393 | NH2 | ARG | A | 56 | 8.961 | 27.375 | 0.658 | 1.00 | 59.39 | A |
| ATOM | 394 | C | ARG | A | 56 | 7.438 | 26.666 | 7.626 | 1.00 | 54.74 | A |
| ATOM | 395 | O | ARG | A | 56 | 7.404 | 25.464 | 7.359 | 1.00 | 54.18 | A |
| ATOM | 396 | N | HIS | A | 57 | 8.522 | 27.270 | 8.105 | 1.00 | 54.51 | A |
| ATOM | 397 | CA | HIS | A | 57 | 9.759 | 26.525 | 8.335 | 1.00 | 54.29 | A |
| ATOM | 398 | CB | HIS | A | 57 | 10.964 | 27.302 | 7.779 | 1.00 | 55.16 | A |
| ATOM | 399 | CG | HIS | A | 57 | 10.719 | 27.936 | 6.444 | 1.00 | 56.03 | A |
| ATOM | 400 | CD2 | HIS | A | 57 | 11.050 | 27.537 | 5.193 | 1.00 | 56.33 | A |
| ATOM | 401 | ND1 | HIS | A | 57 | 10.032 | 29.122 | 6.298 | 1.00 | 56.66 | A |
| ATOM | 402 | CE1 | HIS | A | 57 | 9.948 | 29.426 | 5.014 | 1.00 | 56.21 | A |
| ATOM | 403 | NE2 | HIS | A | 57 | 10.557 | 28.480 | 4.322 | 1.00 | 56.40 | A |
| ATOM | 404 | C | HIS | A | 57 | 9.986 | 26.266 | 9.822 | 1.00 | 53.88 | A |
| ATOM | 405 | O | HIS | A | 57 | 11.051 | 25.791 | 10.220 | 1.00 | 53.33 | A |
| ATOM | 406 | N | SER | A | 58 | 8.980 | 26.559 | 10.639 | 1.00 | 53.09 | A |
| ATOM | 407 | CA | SER | A | 58 | 9.108 | 26.402 | 12.085 | 1.00 | 52.87 | A |
| ATOM | 408 | CB | SER | A | 58 | 8.133 | 27.346 | 12.794 | 1.00 | 53.36 | A |
| ATOM | 409 | OG | SER | A | 58 | 6.792 | 27.058 | 12.437 | 1.00 | 54.09 | A |
| ATOM | 410 | C | SER | A | 58 | 8.967 | 25.009 | 12.689 | 1.00 | 51.52 | A |
| ATOM | 411 | O | SER | A | 58 | 9.114 | 24.859 | 13.901 | 1.00 | 52.42 | A |
| ATOM | 412 | N | THR | A | 59 | 8.696 | 23.995 | 11.874 | 1.00 | 49.99 | A |
| ATOM | 413 | CA | THR | A | 59 | 8.540 | 22.644 | 12.408 | 1.00 | 49.61 | A |
| ATOM | 414 | CB | THR | A | 59 | 7.321 | 21.926 | 11.805 | 1.00 | 50.26 | A |
| ATOM | 415 | OG1 | THR | A | 59 | 7.565 | 21.660 | 10.418 | 1.00 | 52.05 | A |
| ATOM | 416 | CG2 | THR | A | 59 | 6.070 | 22.778 | 11.955 | 1.00 | 49.84 | A |
| ATOM | 417 | C | THR | A | 59 | 9.750 | 21.755 | 12.168 | 1.00 | 48.80 | A |
| ATOM | 418 | O | THR | A | 59 | 9.627 | 20.534 | 12.141 | 1.00 | 50.12 | A |
| ATOM | 419 | N | GLU | A | 60 | 10.917 | 22.359 | 11.996 | 1.00 | 47.87 | A |
| ATOM | 420 | CA | GLU | A | 60 | 12.127 | 21.583 | 11.760 | 1.00 | 48.24 | A |
| ATOM | 421 | CB | GLU | A | 60 | 12.428 | 21.520 | 10.260 | 1.00 | 49.44 | A |
| ATOM | 422 | CG | GLU | A | 60 | 11.638 | 20.460 | 9.520 | 1.00 | 53.29 | A |
| ATOM | 423 | CD | GLU | A | 60 | 11.520 | 20.742 | 8.030 | 1.00 | 56.50 | A |
| ATOM | 424 | OE1 | GLU | A | 60 | 12.551 | 21.045 | 7.391 | 1.00 | 55.69 | A |
| ATOM | 425 | OE2 | GLU | A | 60 | 10.389 | 20.657 | 7.497 | 1.00 | 59.38 | A |
| ATOM | 426 | C | GLU | A | 60 | 13.328 | 22.148 | 12.498 | 1.00 | 46.12 | A |
| ATOM | 427 | O | GLU | A | 60 | 13.344 | 23.319 | 12.886 | 1.00 | 46.85 | A |
| ATOM | 428 | N | LEU | A | 61 | 14.328 | 21.301 | 12.708 | 1.00 | 43.44 | A |
| ATOM | 429 | CA | LEU | A | 61 | 15.544 | 21.737 | 13.374 | 1.00 | 41.98 | A |
| ATOM | 430 | CB | LEU | A | 61 | 15.603 | 21.245 | 14.822 | 1.00 | 41.96 | A |
| ATOM | 431 | CG | LEU | A | 61 | 16.830 | 21.736 | 15.603 | 1.00 | 40.28 | A |
| ATOM | 432 | CD1 | LEU | A | 61 | 16.748 | 23.234 | 15.798 | 1.00 | 41.49 | A |
| ATOM | 433 | CD2 | LEU | A | 61 | 16.899 | 21.043 | 16.957 | 1.00 | 43.82 | A |
| ATOM | 434 | C | LEU | A | 61 | 16.748 | 21.216 | 12.613 | 1.00 | 40.23 | A |
| ATOM | 435 | O | LEU | A | 61 | 16.951 | 20.005 | 12.487 | 1.00 | 38.93 | A |
| ATOM | 436 | N | ASP | A | 62 | 17.535 | 22.153 | 12.100 | 1.00 | 39.30 | A |
| ATOM | 437 | CA | ASP | A | 62 | 18.736 | 21.840 | 11.348 | 1.00 | 38.26 | A |
| ATOM | 438 | CB | ASP | A | 62 | 18.972 | 22.893 | 10.263 | 1.00 | 37.02 | A |
| ATOM | 439 | CG | ASP | A | 62 | 18.188 | 22.617 | 8.993 | 1.00 | 38.78 | A |
| ATOM | 440 | OD1 | ASP | A | 62 | 17.534 | 21.557 | 8.915 | 1.00 | 38.35 | A |
| ATOM | 441 | OD2 | ASP | A | 62 | 18.234 | 23.459 | 8.069 | 1.00 | 35.53 | A |
| ATOM | 442 | C | ASP | A | 62 | 19.948 | 21.817 | 12.261 | 1.00 | 37.32 | A |
| ATOM | 443 | O | ASP | A | 62 | 20.004 | 22.555 | 13.251 | 1.00 | 38.00 | A |
| ATOM | 444 | N | PHE | A | 63 | 20.905 | 20.956 | 11.938 | 1.00 | 36.34 | A |
| ATOM | 445 | CA | PHE | A | 63 | 22.142 | 20.894 | 12.692 | 1.00 | 36.73 | A |
| ATOM | 446 | CB | PHE | A | 63 | 22.235 | 19.624 | 13.552 | 1.00 | 38.45 | A |
| ATOM | 447 | CG | PHE | A | 63 | 22.102 | 18.336 | 12.790 | 1.00 | 40.09 | A |
| ATOM | 448 | CD1 | PHE | A | 63 | 20.849 | 17.814 | 12.491 | 1.00 | 41.21 | A |
| ATOM | 449 | CD2 | PHE | A | 63 | 23.230 | 17.620 | 12.413 | 1.00 | 38.85 | A |
| ATOM | 450 | CE1 | PHE | A | 63 | 20.722 | 16.596 | 11.830 | 1.00 | 41.80 | A |
| ATOM | 451 | CE2 | PHE | A | 63 | 23.117 | 16.405 | 11.753 | 1.00 | 40.48 | A |
| ATOM | 452 | CZ | PHE | A | 63 | 21.857 | 15.889 | 11.460 | 1.00 | 41.84 | A |
| ATOM | 453 | C | PHE | A | 63 | 23.297 | 20.961 | 11.709 | 1.00 | 36.67 | A |
| ATOM | 454 | O | PHE | A | 63 | 23.337 | 20.215 | 10.724 | 1.00 | 37.63 | A |
| ATOM | 455 | N | SER | A | 64 | 24.217 | 21.884 | 11.966 | 1.00 | 37.08 | A |
| ATOM | 456 | CA | SER | A | 64 | 25.389 | 22.078 | 11.123 | 1.00 | 37.11 | A |
| ATOM | 457 | CB | SER | A | 64 | 25.533 | 23.550 | 10.742 | 1.00 | 37.02 | A |
| ATOM | 458 | OG | SER | A | 64 | 24.347 | 24.054 | 10.156 | 1.00 | 37.59 | A |
| ATOM | 459 | C | SER | A | 64 | 26.617 | 21.641 | 11.908 | 1.00 | 37.78 | A |

APPENDIX 1-continued

Atomic coordinates of aromatic prenyltransferase residues 3-302 of SEQ ID NO: 2.

| ATOM | 460 | O | SER | A | 64 | 26.776 | 22.004 | 13.070 | 1.00 | 38.14 | A |
|---|---|---|---|---|---|---|---|---|---|---|---|
| ATOM | 461 | N | ILE | A | 65 | 27.486 | 20.869 | 11.269 | 1.00 | 37.84 | A |
| ATOM | 462 | CA | ILE | A | 65 | 28.687 | 20.375 | 11.931 | 1.00 | 38.20 | A |
| ATOM | 463 | CB | ILE | A | 65 | 28.517 | 18.881 | 12.298 | 1.00 | 38.18 | A |
| ATOM | 464 | CG2 | ILE | A | 65 | 29.813 | 18.319 | 12.870 | 1.00 | 39.41 | A |
| ATOM | 465 | CG1 | ILE | A | 65 | 27.372 | 18.732 | 13.306 | 1.00 | 37.70 | A |
| ATOM | 466 | CD1 | ILE | A | 65 | 26.947 | 17.304 | 13.552 | 1.00 | 38.47 | A |
| ATOM | 467 | C | ILE | A | 65 | 29.918 | 20.549 | 11.053 | 1.00 | 38.20 | A |
| ATOM | 468 | O | ILE | A | 65 | 29.936 | 20.120 | 9.903 | 1.00 | 38.89 | A |
| ATOM | 469 | N | SER | A | 66 | 30.947 | 21.184 | 11.598 | 1.00 | 38.03 | A |
| ATOM | 470 | CA | SER | A | 66 | 32.178 | 21.396 | 10.848 | 1.00 | 38.52 | A |
| ATOM | 471 | CB | SER | A | 66 | 33.091 | 22.367 | 11.599 | 1.00 | 37.05 | A |
| ATOM | 472 | OG | SER | A | 66 | 33.302 | 21.907 | 12.920 | 1.00 | 39.76 | A |
| ATOM | 473 | C | SER | A | 66 | 32.897 | 20.067 | 10.652 | 1.00 | 38.47 | A |
| ATOM | 474 | O | SER | A | 66 | 32.773 | 19.162 | 11.474 | 1.00 | 39.22 | A |
| ATOM | 475 | N | VAL | A | 67 | 33.635 | 19.954 | 9.553 | 1.00 | 37.19 | A |
| ATOM | 476 | CA | VAL | A | 67 | 34.393 | 18.745 | 9.242 | 1.00 | 36.16 | A |
| ATOM | 477 | CB | VAL | A | 67 | 33.639 | 17.821 | 8.251 | 1.00 | 36.78 | A |
| ATOM | 478 | CG1 | VAL | A | 67 | 34.466 | 16.561 | 7.977 | 1.00 | 34.33 | A |
| ATOM | 479 | CG2 | VAL | A | 67 | 32.277 | 17.439 | 8.816 | 1.00 | 33.97 | A |
| ATOM | 480 | C | VAL | A | 67 | 35.715 | 19.174 | 8.604 | 1.00 | 36.50 | A |
| ATOM | 481 | O | VAL | A | 67 | 35.739 | 19.707 | 7.496 | 1.00 | 34.41 | A |
| ATOM | 482 | N | PRO | A | 68 | 36.834 | 18.970 | 9.315 | 1.00 | 38.13 | A |
| ATOM | 483 | CD | PRO | A | 68 | 36.945 | 18.356 | 10.650 | 1.00 | 38.47 | A |
| ATOM | 484 | CA | PRO | A | 68 | 38.156 | 19.346 | 8.795 | 1.00 | 38.92 | A |
| ATOM | 485 | CB | PRO | A | 68 | 39.104 | 18.943 | 9.927 | 1.00 | 39.16 | A |
| ATOM | 486 | CG | PRO | A | 68 | 38.355 | 17.833 | 10.630 | 1.00 | 38.66 | A |
| ATOM | 487 | C | PRO | A | 68 | 38.469 | 18.638 | 7.482 | 1.00 | 38.57 | A |
| ATOM | 488 | O | PRO | A | 68 | 38.045 | 17.506 | 7.274 | 1.00 | 39.03 | A |
| ATOM | 489 | N | THR | A | 69 | 39.200 | 19.309 | 6.598 | 1.00 | 40.67 | A |
| ATOM | 490 | CA | THR | A | 69 | 39.542 | 18.736 | 5.297 | 1.00 | 41.89 | A |
| ATOM | 491 | CB | THR | A | 69 | 40.363 | 19.719 | 4.449 | 1.00 | 41.81 | A |
| ATOM | 492 | OG1 | THR | A | 69 | 41.533 | 20.109 | 5.174 | 1.00 | 45.53 | A |
| ATOM | 493 | CG2 | THR | A | 69 | 39.548 | 20.949 | 4.115 | 1.00 | 41.08 | A |
| ATOM | 494 | C | THR | A | 69 | 40.335 | 17.443 | 5.420 | 1.00 | 42.77 | A |
| ATOM | 495 | O | THR | A | 69 | 40.345 | 16.619 | 4.499 | 1.00 | 40.61 | A |
| ATOM | 496 | N | SER | A | 70 | 40.992 | 17.270 | 6.563 | 1.00 | 43.04 | A |
| ATOM | 497 | CA | SER | A | 70 | 41.802 | 16.083 | 6.810 | 1.00 | 44.22 | A |
| ATOM | 498 | CB | SER | A | 70 | 42.565 | 16.231 | 8.133 | 1.00 | 44.13 | A |
| ATOM | 499 | OG | SER | A | 70 | 41.679 | 16.254 | 9.239 | 1.00 | 42.16 | A |
| ATOM | 500 | C | SER | A | 70 | 40.934 | 14.833 | 6.854 | 1.00 | 44.81 | A |
| ATOM | 501 | O | SER | A | 70 | 41.387 | 13.734 | 6.531 | 1.00 | 45.00 | A |
| ATOM | 502 | N | HIS | A | 71 | 39.679 | 15.000 | 7.250 | 1.00 | 44.99 | A |
| ATOM | 503 | CA | HIS | A | 71 | 38.779 | 13.866 | 7.328 | 1.00 | 45.50 | A |
| ATOM | 504 | CB | HIS | A | 71 | 37.595 | 14.215 | 8.230 | 1.00 | 50.25 | A |
| ATOM | 505 | CG | HIS | A | 71 | 37.970 | 14.374 | 9.671 | 1.00 | 54.93 | A |
| ATOM | 506 | CD2 | HIS | A | 71 | 39.181 | 14.404 | 10.279 | 1.00 | 56.60 | A |
| ATOM | 507 | ND1 | HIS | A | 71 | 37.036 | 14.525 | 10.674 | 1.00 | 56.61 | A |
| ATOM | 508 | CE1 | HIS | A | 71 | 37.656 | 14.640 | 11.837 | 1.00 | 57.31 | A |
| ATOM | 509 | NE2 | HIS | A | 71 | 38.957 | 14.570 | 11.625 | 1.00 | 57.50 | A |
| ATOM | 510 | C | HIS | A | 71 | 38.313 | 13.397 | 5.948 | 1.00 | 44.27 | A |
| ATOM | 511 | O | HIS | A | 71 | 37.778 | 12.299 | 5.803 | 1.00 | 42.77 | A |
| ATOM | 512 | N | GLY | A | 72 | 38.539 | 14.226 | 4.935 | 1.00 | 42.93 | A |
| ATOM | 513 | CA | GLY | A | 72 | 38.151 | 13.868 | 3.582 | 1.00 | 42.01 | A |
| ATOM | 514 | C | GLY | A | 72 | 36.825 | 14.454 | 3.136 | 1.00 | 40.53 | A |
| ATOM | 515 | O | GLY | A | 72 | 36.046 | 14.934 | 3.954 | 1.00 | 40.70 | A |
| ATOM | 516 | N | ASP | A | 73 | 36.581 | 14.423 | 1.828 | 1.00 | 39.45 | A |
| ATOM | 517 | CA | ASP | A | 73 | 35.345 | 14.931 | 1.238 | 1.00 | 39.65 | A |
| ATOM | 518 | CB | ASP | A | 73 | 35.309 | 14.568 | −0.251 | 1.00 | 39.15 | A |
| ATOM | 519 | CG | ASP | A | 73 | 34.036 | 15.025 | −0.942 | 1.00 | 37.87 | A |
| ATOM | 520 | OD1 | ASP | A | 73 | 32.947 | 14.913 | −0.343 | 1.00 | 39.76 | A |
| ATOM | 521 | OD2 | ASP | A | 73 | 34.122 | 15.485 | −2.097 | 1.00 | 40.00 | A |
| ATOM | 522 | C | ASP | A | 73 | 34.162 | 14.280 | 1.957 | 1.00 | 37.48 | A |
| ATOM | 523 | O | ASP | A | 73 | 33.993 | 13.066 | 1.895 | 1.00 | 38.41 | A |
| ATOM | 524 | N | PRO | A | 74 | 33.335 | 15.079 | 2.652 | 1.00 | 36.55 | A |
| ATOM | 525 | CD | PRO | A | 74 | 33.529 | 16.507 | 2.958 | 1.00 | 37.15 | A |
| ATOM | 526 | CA | PRO | A | 74 | 32.175 | 14.544 | 3.378 | 1.00 | 34.86 | A |
| ATOM | 527 | CB | PRO | A | 74 | 31.752 | 15.714 | 4.268 | 1.00 | 34.11 | A |
| ATOM | 528 | CG | PRO | A | 74 | 32.170 | 16.906 | 3.466 | 1.00 | 36.59 | A |
| ATOM | 529 | C | PRO | A | 74 | 31.027 | 14.004 | 2.518 | 1.00 | 33.80 | A |
| ATOM | 530 | O | PRO | A | 74 | 30.274 | 13.156 | 2.982 | 1.00 | 33.04 | A |
| ATOM | 531 | N | TYR | A | 75 | 30.867 | 14.494 | 1.289 | 1.00 | 32.38 | A |
| ATOM | 532 | CA | TYR | A | 75 | 29.801 | 13.957 | 0.447 | 1.00 | 32.91 | A |
| ATOM | 533 | CD | TYR | A | 75 | 29.530 | 14.819 | −0.789 | 1.00 | 32.39 | A |
| ATOM | 534 | CG | TYR | A | 75 | 28.334 | 14.320 | −1.600 | 1.00 | 32.65 | A |
| ATOM | 535 | CD1 | TYR | A | 75 | 27.086 | 14.159 | −1.002 | 1.00 | 32.34 | A |
| ATOM | 536 | CE1 | TYR | A | 75 | 25.978 | 13.752 | −1.731 | 1.00 | 32.78 | A |

APPENDIX 1-continued

Atomic coordinates of aromatic prenyltransferase residues 3-302 of SEQ ID NO: 2.

| ATOM | 537 | CD2 | TYR | A | 75 | 28.442 | 14.047 | −2.966 | 1.00 | 35.34 | A |
|------|-----|-----|-----|---|----|--------|--------|--------|------|-------|---|
| ATOM | 538 | CE2 | TYR | A | 75 | 27.321 | 13.632 | −3.714 | 1.00 | 33.58 | A |
| ATOM | 539 | CZ | TYR | A | 75 | 26.098 | 13.494 | −3.084 | 1.00 | 33.86 | A |
| ATOM | 540 | OH | TYR | A | 75 | 24.972 | 13.132 | −3.797 | 1.00 | 33.63 | A |
| ATOM | 541 | C | TYR | A | 75 | 30.256 | 12.580 | −0.007 | 1.00 | 33.77 | A |
| ATOM | 542 | O | TYR | A | 75 | 29.464 | 11.641 | −0.055 | 1.00 | 33.18 | A |
| ATOM | 543 | N | ALA | A | 76 | 31.540 | 12.470 | −0.346 | 1.00 | 34.39 | A |
| ATOM | 544 | CA | ALA | A | 76 | 32.098 | 11.187 | −0.772 | 1.00 | 35.15 | A |
| ATOM | 545 | CB | ALA | A | 76 | 33.595 | 11.319 | −1.071 | 1.00 | 34.26 | A |
| ATOM | 546 | C | ALA | A | 76 | 31.885 | 10.199 | 0.362 | 1.00 | 34.76 | A |
| ATOM | 547 | O | ALA | A | 76 | 31.608 | 9.023 | 0.136 | 1.00 | 33.20 | A |
| ATOM | 548 | N | THR | A | 77 | 32.005 | 10.695 | 1.588 | 1.00 | 34.77 | A |
| ATOM | 549 | CA | THR | A | 77 | 31.824 | 9.858 | 2.767 | 1.00 | 36.06 | A |
| ATOM | 550 | CB | THR | A | 77 | 32.317 | 10.584 | 4.034 | 1.00 | 36.33 | A |
| ATOM | 551 | OG1 | THR | A | 77 | 33.740 | 10.719 | 3.968 | 1.00 | 37.57 | A |
| ATOM | 552 | CG2 | THR | A | 77 | 31.941 | 9.798 | 5.289 | 1.00 | 36.53 | A |
| ATOM | 553 | C | THR | A | 77 | 30.385 | 9.390 | 2.999 | 1.00 | 37.01 | A |
| ATOM | 554 | O | THR | A | 77 | 30.152 | 8.203 | 3.263 | 1.00 | 38.11 | A |
| ATOM | 555 | N | VAL | A | 78 | 29.420 | 10.303 | 2.911 | 1.00 | 36.63 | A |
| ATOM | 556 | CA | VAL | A | 78 | 28.027 | 9.923 | 3.138 | 1.00 | 36.66 | A |
| ATOM | 557 | CB | VAL | A | 78 | 27.087 | 11.164 | 3.268 | 1.00 | 36.95 | A |
| ATOM | 558 | CG1 | VAL | A | 78 | 27.499 | 11.998 | 4.468 | 1.00 | 36.05 | A |
| ATOM | 559 | CG2 | VAL | A | 78 | 27.124 | 12.002 | 1.999 | 1.00 | 36.59 | A |
| ATOM | 560 | C | VAL | A | 78 | 27.480 | 9.003 | 2.053 | 1.00 | 35.80 | A |
| ATOM | 561 | O | VAL | A | 78 | 26.614 | 8.176 | 2.325 | 1.00 | 35.84 | A |
| ATOM | 562 | N | VAL | A | 79 | 27.972 | 9.135 | 0.826 | 1.00 | 35.93 | A |
| ATOM | 563 | CA | VAL | A | 79 | 27.485 | 8.269 | −0.241 | 1.00 | 36.96 | A |
| ATOM | 564 | CB | VAL | A | 79 | 27.857 | 8.808 | −1.641 | 1.00 | 36.08 | A |
| ATOM | 565 | CG1 | VAL | A | 79 | 27.323 | 7.859 | −2.712 | 1.00 | 34.68 | A |
| ATOM | 566 | CG2 | VAL | A | 79 | 27.278 | 10.197 | −1.844 | 1.00 | 36.45 | A |
| ATOM | 567 | C | VAL | A | 79 | 28.091 | 6.872 | −0.064 | 1.00 | 37.92 | A |
| ATOM | 568 | O | VAL | A | 79 | 27.384 | 5.867 | −0.111 | 1.00 | 38.87 | A |
| ATOM | 569 | N | GLU | A | 80 | 29.402 | 6.823 | 0.155 | 1.00 | 38.87 | A |
| ATOM | 570 | CA | GLU | A | 80 | 30.106 | 5.562 | 0.345 | 1.00 | 40.08 | A |
| ATOM | 571 | CB | GLU | A | 80 | 31.589 | 5.809 | 0.592 | 1.00 | 42.04 | A |
| ATOM | 572 | CG | GLU | A | 80 | 32.435 | 5.911 | −0.653 | 1.00 | 47.22 | A |
| ATOM | 573 | CD | GLU | A | 80 | 33.913 | 5.949 | −0.316 | 1.00 | 50.49 | A |
| ATOM | 574 | OE1 | GLU | A | 80 | 34.379 | 5.027 | 0.396 | 1.00 | 51.53 | A |
| ATOM | 575 | OE2 | GLU | A | 80 | 34.603 | 6.895 | −0.760 | 1.00 | 52.54 | A |
| ATOM | 576 | C | GLU | A | 80 | 29.579 | 4.732 | 1.502 | 1.00 | 40.32 | A |
| ATOM | 577 | O | GLU | A | 80 | 29.569 | 3.504 | 1.436 | 1.00 | 39.33 | A |
| ATOM | 578 | N | LYS | A | 81 | 29.158 | 5.401 | 2.567 | 1.00 | 40.75 | A |
| ATOM | 579 | CA | LYS | A | 81 | 28.658 | 4.701 | 3.743 | 1.00 | 42.50 | A |
| ATOM | 580 | CB | LYS | A | 81 | 28.979 | 5.515 | 4.999 | 1.00 | 43.97 | A |
| ATOM | 581 | CG | LYS | A | 81 | 28.806 | 4.743 | 6.294 | 1.00 | 47.62 | A |
| ATOM | 582 | CD | LYS | A | 81 | 29.508 | 5.437 | 7.448 | 1.00 | 48.42 | A |
| ATOM | 583 | CE | LYS | A | 81 | 29.424 | 4.611 | 8.722 | 1.00 | 49.73 | A |
| ATOM | 584 | NZ | LYS | A | 81 | 30.230 | 5.215 | 9.816 | 1.00 | 50.46 | A |
| ATOM | 585 | C | LYS | A | 81 | 27.160 | 4.393 | 3.659 | 1.00 | 42.43 | A |
| ATOM | 586 | O | LYS | A | 81 | 26.583 | 3.794 | 4.569 | 1.00 | 43.82 | A |
| ATOM | 587 | N | GLY | A | 82 | 26.534 | 4.800 | 2.561 | 1.00 | 41.47 | A |
| ATOM | 588 | CA | GLY | A | 82 | 25.120 | 4.530 | 2.380 | 1.00 | 40.57 | A |
| ATOM | 589 | C | GLY | A | 82 | 24.167 | 5.412 | 3.165 | 1.00 | 39.41 | A |
| ATOM | 590 | O | GLY | A | 82 | 23.027 | 5.017 | 3.410 | 1.00 | 39.15 | A |
| ATOM | 591 | N | LEU | A | 83 | 24.617 | 6.606 | 3.551 | 1.00 | 38.67 | A |
| ATOM | 592 | CA | LEU | A | 83 | 23.776 | 7.530 | 4.310 | 1.00 | 36.40 | A |
| ATOM | 593 | CB | LEU | A | 83 | 24.625 | 8.331 | 5.296 | 1.00 | 37.66 | A |
| ATOM | 594 | CG | LEU | A | 83 | 25.301 | 7.524 | 6.409 | 1.00 | 39.03 | A |
| ATOM | 595 | CD1 | LEU | A | 83 | 26.040 | 8.469 | 7.328 | 1.00 | 39.46 | A |
| ATOM | 596 | CD2 | LEU | A | 83 | 24.260 | 6.734 | 7.203 | 1.00 | 38.72 | A |
| ATOM | 597 | C | LEU | A | 83 | 22.999 | 8.481 | 3.407 | 1.00 | 36.46 | A |
| ATOM | 598 | O | LEU | A | 83 | 22.058 | 9.144 | 3.845 | 1.00 | 38.34 | A |
| ATOM | 599 | N | PHE | A | 84 | 23.397 | 8.569 | 2.145 | 1.00 | 33.71 | A |
| ATOM | 600 | CA | PHE | A | 84 | 22.695 | 9.427 | 1.206 | 1.00 | 34.20 | A |
| ATOM | 601 | CB | PHE | A | 84 | 23.172 | 10.885 | 1.305 | 1.00 | 35.21 | A |
| ATOM | 602 | CG | PHE | A | 84 | 22.307 | 11.840 | 0.541 | 1.00 | 33.04 | A |
| ATOM | 603 | CD1 | PHE | A | 84 | 21.109 | 12.290 | 1.080 | 1.00 | 33.86 | A |
| ATOM | 604 | CD2 | PHE | A | 84 | 22.636 | 12.211 | −0.758 | 1.00 | 32.80 | A |
| ATOM | 605 | CE1 | PHE | A | 84 | 20.247 | 13.088 | 0.335 | 1.00 | 33.51 | A |
| ATOM | 606 | CE2 | PHE | A | 84 | 21.780 | 13.010 | −1.513 | 1.00 | 32.34 | A |
| ATOM | 607 | CZ | PHE | A | 84 | 20.583 | 13.449 | −0.970 | 1.00 | 33.64 | A |
| ATOM | 608 | C | PHE | A | 84 | 22.952 | 8.909 | −0.199 | 1.00 | 34.14 | A |
| ATOM | 609 | O | PHE | A | 84 | 24.055 | 8.456 | −0.502 | 1.00 | 32.87 | A |
| ATOM | 610 | N | PRO | A | 85 | 21.936 | 8.965 | −1.075 | 1.00 | 35.40 | A |
| ATOM | 611 | CD | PRO | A | 85 | 20.507 | 9.187 | −0.785 | 1.00 | 35.87 | A |
| ATOM | 612 | CA | PRO | A | 85 | 22.115 | 8.481 | −2.446 | 1.00 | 36.99 | A |
| ATOM | 613 | CB | PRO | A | 85 | 20.743 | 7.912 | −2.782 | 1.00 | 36.41 | A |

APPENDIX 1-continued

Atomic coordinates of aromatic prenyltransferase residues 3-302 of SEQ ID NO: 2.

| ATOM | 614 | CG | PRO | A | 85 | 19.836 | 8.885 | −2.131 | 1.00 | 36.37 | A |
|---|---|---|---|---|---|---|---|---|---|---|---|
| ATOM | 615 | C | PRO | A | 85 | 22.542 | 9.560 | −3.432 | 1.00 | 38.58 | A |
| ATOM | 616 | O | PRO | A | 85 | 22.088 | 10.697 | −3.343 | 1.00 | 37.08 | A |
| ATOM | 617 | N | ALA | A | 86 | 23.423 | 9.204 | −4.365 | 1.00 | 41.13 | A |
| ATOM | 618 | CA | ALA | A | 86 | 23.854 | 10.154 | −5.378 | 1.00 | 43.66 | A |
| ATOM | 619 | CB | ALA | A | 86 | 24.889 | 9.528 | −6.295 | 1.00 | 43.21 | A |
| ATOM | 620 | C | ALA | A | 86 | 22.605 | 10.524 | −6.171 | 1.00 | 45.42 | A |
| ATOM | 621 | O | ALA | A | 86 | 21.847 | 9.649 | −6.600 | 1.00 | 45.70 | A |
| ATOM | 622 | N | THR | A | 87 | 22.389 | 11.821 | −6.355 | 1.00 | 46.96 | A |
| ATOM | 623 | CA | THR | A | 87 | 21.222 | 12.308 | −7.076 | 1.00 | 47.91 | A |
| ATOM | 624 | CB | THR | A | 87 | 21.011 | 13.810 | −6.820 | 1.00 | 49.25 | A |
| ATOM | 625 | OG1 | THR | A | 87 | 22.142 | 14.537 | −7.318 | 1.00 | 50.27 | A |
| ATOM | 626 | CG2 | THR | A | 87 | 20.850 | 14.084 | −5.323 | 1.00 | 48.15 | A |
| ATOM | 627 | C | THR | A | 87 | 21.308 | 12.094 | −8.581 | 1.00 | 48.08 | A |
| ATOM | 628 | O | THR | A | 87 | 20.289 | 12.120 | −9.266 | 1.00 | 48.96 | A |
| ATOM | 629 | N | GLY | A | 88 | 22.515 | 11.868 | −9.088 | 1.00 | 47.81 | A |
| ATOM | 630 | CA | GLY | A | 88 | 22.701 | 11.692 | −10.520 | 1.00 | 47.20 | A |
| ATOM | 631 | C | GLY | A | 88 | 22.574 | 13.042 | −11.212 | 1.00 | 47.00 | A |
| ATOM | 632 | O | GLY | A | 88 | 22.365 | 13.131 | −12.424 | 1.00 | 47.22 | A |
| ATOM | 633 | N | HIS | A | 89 | 22.720 | 14.099 | −10.419 | 1.00 | 45.03 | A |
| ATOM | 634 | CA | HIS | A | 89 | 22.601 | 15.482 | −10.877 | 1.00 | 44.02 | A |
| ATOM | 635 | CB | HIS | A | 89 | 21.499 | 16.149 | −10.033 | 1.00 | 45.14 | A |
| ATOM | 636 | CG | HIS | A | 89 | 21.222 | 17.577 | −10.380 | 1.00 | 47.25 | A |
| ATOM | 637 | CD2 | HIS | A | 89 | 20.207 | 18.143 | −11.075 | 1.00 | 47.80 | A |
| ATOM | 638 | ND1 | HIS | A | 89 | 22.043 | 18.612 | −9.987 | 1.00 | 46.81 | A |
| ATOM | 639 | CE1 | HIS | A | 89 | 21.545 | 19.755 | −10.426 | 1.00 | 46.54 | A |
| ATOM | 640 | NE2 | HIS | A | 89 | 20.432 | 19.499 | −11.089 | 1.00 | 46.38 | A |
| ATOM | 641 | C | HIS | A | 89 | 23.962 | 16.183 | −10.701 | 1.00 | 42.11 | A |
| ATOM | 642 | O | HIS | A | 89 | 24.802 | 15.715 | −9.932 | 1.00 | 41.05 | A |
| ATOM | 643 | N | PRO | A | 90 | 24.208 | 17.292 | −11.425 | 1.00 | 40.53 | A |
| ATOM | 644 | CD | PRO | A | 90 | 23.425 | 17.878 | −12.529 | 1.00 | 41.84 | A |
| ATOM | 645 | CA | PRO | A | 90 | 25.492 | 17.990 | −11.285 | 1.00 | 39.95 | A |
| ATOM | 646 | CB | PRO | A | 90 | 25.282 | 19.254 | −12.103 | 1.00 | 39.62 | A |
| ATOM | 647 | CG | PRO | A | 90 | 24.447 | 18.759 | −13.224 | 1.00 | 42.14 | A |
| ATOM | 648 | C | PRO | A | 90 | 25.879 | 18.295 | −9.836 | 1.00 | 38.75 | A |
| ATOM | 649 | O | PRO | A | 90 | 27.062 | 18.400 | −9.508 | 1.00 | 36.43 | A |
| ATOM | 650 | N | VAL | A | 91 | 24.884 | 18.432 | −8.967 | 1.00 | 37.40 | A |
| ATOM | 651 | CA | VAL | A | 91 | 25.174 | 18.729 | −7.573 | 1.00 | 35.42 | A |
| ATOM | 652 | CB | VAL | A | 91 | 23.863 | 18.890 | −6.751 | 1.00 | 32.89 | A |
| ATOM | 653 | CG1 | VAL | A | 91 | 23.089 | 17.585 | −6.708 | 1.00 | 29.58 | A |
| ATOM | 654 | CG2 | VAL | A | 91 | 24.188 | 19.390 | −5.348 | 1.00 | 33.88 | A |
| ATOM | 655 | C | VAL | A | 91 | 26.070 | 17.647 | −6.973 | 1.00 | 36.43 | A |
| ATOM | 656 | O | VAL | A | 91 | 26.809 | 17.897 | −6.014 | 1.00 | 35.56 | A |
| ATOM | 657 | N | ASP | A | 92 | 26.041 | 16.453 | −7.562 | 1.00 | 36.81 | A |
| ATOM | 658 | CA | ASP | A | 92 | 26.862 | 15.352 | −7.064 | 1.00 | 37.47 | A |
| ATOM | 659 | CB | ASP | A | 92 | 26.513 | 14.033 | −7.764 | 1.00 | 39.17 | A |
| ATOM | 660 | CG | ASP | A | 92 | 25.111 | 13.547 | −7.441 | 1.00 | 42.34 | A |
| ATOM | 661 | OD1 | ASP | A | 92 | 24.703 | 13.605 | −6.257 | 1.00 | 42.11 | A |
| ATOM | 662 | OD2 | ASP | A | 92 | 24.426 | 13.094 | −8.379 | 1.00 | 41.11 | A |
| ATOM | 663 | C | ASP | A | 92 | 28.358 | 15.600 | −7.241 | 1.00 | 37.40 | A |
| ATOM | 664 | O | ASP | A | 92 | 29.176 | 15.030 | −6.522 | 1.00 | 36.00 | A |
| ATOM | 665 | N | ASP | A | 93 | 28.714 | 16.443 | −8.200 | 1.00 | 37.21 | A |
| ATOM | 666 | CA | ASP | A | 93 | 30.119 | 16.714 | −8.465 | 1.00 | 38.02 | A |
| ATOM | 667 | CB | ASP | A | 93 | 30.378 | 16.662 | −9.974 | 1.00 | 39.00 | A |
| ATOM | 668 | CG | ASP | A | 93 | 29.861 | 15.385 | −10.611 | 1.00 | 42.85 | A |
| ATOM | 669 | OD1 | ASP | A | 93 | 30.238 | 14.293 | −10.139 | 1.00 | 43.31 | A |
| ATOM | 670 | OD2 | ASP | A | 93 | 29.075 | 15.476 | −11.579 | 1.00 | 45.48 | A |
| ATOM | 671 | C | ASP | A | 93 | 30.625 | 18.044 | −7.932 | 1.00 | 37.00 | A |
| ATOM | 672 | O | ASP | A | 93 | 31.831 | 18.245 | −7.835 | 1.00 | 36.56 | A |
| ATOM | 673 | N | LEU | A | 94 | 29.710 | 18.938 | −7.568 | 1.00 | 35.71 | A |
| ATOM | 674 | CA | LEU | A | 94 | 30.104 | 20.268 | −7.120 | 1.00 | 34.14 | A |
| ATOM | 675 | CB | LEU | A | 94 | 28.867 | 21.131 | −6.853 | 1.00 | 34.32 | A |
| ATOM | 676 | CG | LEU | A | 94 | 29.151 | 22.629 | −6.678 | 1.00 | 33.22 | A |
| ATOM | 677 | CD1 | LEU | A | 94 | 30.004 | 23.160 | −7.823 | 1.00 | 33.67 | A |
| ATOM | 678 | CD2 | LEU | A | 94 | 27.839 | 23.368 | −6.627 | 1.00 | 34.83 | A |
| ATOM | 679 | C | LEU | A | 94 | 31.054 | 20.357 | −5.931 | 1.00 | 33.54 | A |
| ATOM | 680 | O | LEU | A | 94 | 32.010 | 21.132 | −5.971 | 1.00 | 32.88 | A |
| ATOM | 681 | N | LEU | A | 95 | 30.814 | 19.592 | −4.874 | 1.00 | 33.38 | A |
| ATOM | 682 | CA | LEU | A | 95 | 31.729 | 19.687 | −3.749 | 1.00 | 34.21 | A |
| ATOM | 683 | CB | LEU | A | 95 | 31.309 | 18.780 | −2.589 | 1.00 | 31.65 | A |
| ATOM | 684 | CG | LEU | A | 95 | 32.185 | 18.988 | −1.337 | 1.00 | 31.56 | A |
| ATOM | 685 | CD1 | LEU | A | 95 | 32.251 | 20.480 | −0.967 | 1.00 | 32.11 | A |
| ATOM | 686 | CD2 | LEU | A | 95 | 31.620 | 18.187 | −0.173 | 1.00 | 32.42 | A |
| ATOM | 687 | C | LEU | A | 95 | 33.111 | 19.300 | −4.249 | 1.00 | 34.32 | A |
| ATOM | 688 | O | LEU | A | 95 | 34.074 | 20.036 | −4.047 | 1.00 | 33.01 | A |
| ATOM | 689 | N | ALA | A | 96 | 33.197 | 18.158 | −4.933 | 1.00 | 34.56 | A |
| ATOM | 690 | CA | ALA | A | 96 | 34.473 | 17.675 | −5.457 | 1.00 | 35.45 | A |

APPENDIX 1-continued

Atomic coordinates of aromatic prenyltransferase residues 3-302 of SEQ ID NO: 2.

| ATOM | 691 | CB | ALA | A | 96 | 34.284 | 16.303 | −6.104 | 1.00 | 37.29 | A |
|---|---|---|---|---|---|---|---|---|---|---|---|
| ATOM | 692 | C | ALA | A | 96 | 35.132 | 18.641 | −6.447 | 1.00 | 34.95 | A |
| ATOM | 693 | O | ALA | A | 96 | 36.340 | 18.899 | −6.353 | 1.00 | 35.01 | A |
| ATOM | 694 | N | ASP | A | 97 | 34.358 | 19.175 | −7.392 | 1.00 | 34.87 | A |
| ATOM | 695 | CA | ASP | A | 97 | 34.915 | 20.110 | −8.377 | 1.00 | 34.02 | A |
| ATOM | 696 | CB | ASP | A | 97 | 33.874 | 20.486 | −9.439 | 1.00 | 35.17 | A |
| ATOM | 697 | CG | ASP | A | 97 | 33.636 | 19.385 | −10.457 | 1.00 | 36.22 | A |
| ATOM | 698 | OD1 | ASP | A | 97 | 34.319 | 18.338 | −10.405 | 1.00 | 37.31 | A |
| ATOM | 699 | OD2 | ASP | A | 97 | 32.752 | 19.580 | −11.318 | 1.00 | 35.57 | A |
| ATOM | 700 | C | ASP | A | 97 | 35.412 | 21.393 | −7.725 | 1.00 | 34.14 | A |
| ATOM | 701 | O | ASP | A | 97 | 36.325 | 22.052 | −8.232 | 1.00 | 33.33 | A |
| ATOM | 702 | N | THR | A | 98 | 34.791 | 21.757 | −6.609 | 1.00 | 34.23 | A |
| ATOM | 703 | CA | THR | A | 98 | 35.155 | 22.966 | −5.885 | 1.00 | 34.54 | A |
| ATOM | 704 | CB | THR | A | 98 | 34.095 | 23.286 | −4.795 | 1.00 | 33.81 | A |
| ATOM | 705 | OG1 | THR | A | 98 | 32.868 | 23.653 | −5.433 | 1.00 | 32.38 | A |
| ATOM | 706 | CG2 | THR | A | 98 | 34.551 | 24.430 | −3.889 | 1.00 | 32.67 | A |
| ATOM | 707 | C | THR | A | 98 | 36.528 | 22.809 | −5.242 | 1.00 | 35.23 | A |
| ATOM | 708 | O | THR | A | 98 | 37.356 | 23.722 | −5.282 | 1.00 | 36.85 | A |
| ATOM | 709 | N | GLN | A | 99 | 36.764 | 21.645 | −4.652 | 1.00 | 36.14 | A |
| ATOM | 710 | CA | GLN | A | 99 | 38.041 | 21.361 | −4.005 | 1.00 | 38.58 | A |
| ATOM | 711 | CB | GLN | A | 99 | 37.919 | 20.077 | −3.174 | 1.00 | 40.12 | A |
| ATOM | 712 | CG | GLN | A | 99 | 39.212 | 19.594 | −2.530 | 1.00 | 44.11 | A |
| ATOM | 713 | CD | GLN | A | 99 | 38.962 | 18.628 | −1.378 | 1.00 | 45.38 | A |
| ATOM | 714 | OE1 | GLN | A | 99 | 38.046 | 17.800 | −1.428 | 1.00 | 44.91 | A |
| ATOM | 715 | NE2 | GLN | A | 99 | 39.784 | 18.723 | −0.336 | 1.00 | 45.37 | A |
| ATOM | 716 | C | GLN | A | 99 | 39.121 | 21.224 | −5.079 | 1.00 | 39.44 | A |
| ATOM | 717 | O | GLN | A | 99 | 40.309 | 21.422 | −4.819 | 1.00 | 39.54 | A |
| ATOM | 718 | N | LYS | A | 100 | 38.693 | 20.899 | −6.294 | 1.00 | 39.83 | A |
| ATOM | 719 | CA | LYS | A | 100 | 39.603 | 20.754 | −7.423 | 1.00 | 41.72 | A |
| ATOM | 720 | CB | LYS | A | 100 | 38.913 | 19.961 | −8.541 | 1.00 | 43.31 | A |
| ATOM | 721 | CG | LYS | A | 100 | 39.711 | 19.870 | −9.841 | 1.00 | 47.29 | A |
| ATOM | 722 | CD | LYS | A | 100 | 38.870 | 19.299 | −10.986 | 1.00 | 49.04 | A |
| ATOM | 723 | CE | LYS | A | 100 | 39.606 | 19.396 | −12.327 | 1.00 | 50.86 | A |
| ATOM | 724 | NZ | LYS | A | 100 | 38.770 | 18.967 | −13.495 | 1.00 | 52.06 | A |
| ATOM | 725 | C | LYS | A | 100 | 40.085 | 22.113 | −7.970 | 1.00 | 41.64 | A |
| ATOM | 726 | O | LYS | A | 100 | 41.277 | 22.294 | −8.241 | 1.00 | 42.73 | A |
| ATOM | 727 | N | HIS | A | 101 | 39.163 | 23.062 | −8.126 | 1.00 | 40.66 | A |
| ATOM | 728 | CA | HIS | A | 101 | 39.494 | 24.378 | −8.667 | 1.00 | 40.67 | A |
| ATOM | 729 | CB | HIS | A | 101 | 38.349 | 24.901 | −9.546 | 1.00 | 41.87 | A |
| ATOM | 730 | CG | HIS | A | 101 | 38.153 | 24.138 | −10.817 | 1.00 | 41.74 | A |
| ATOM | 731 | CD2 | HIS | A | 101 | 38.455 | 24.453 | −12.100 | 1.00 | 42.24 | A |
| ATOM | 732 | ND1 | HIS | A | 101 | 37.587 | 22.882 | −10.854 | 1.00 | 43.06 | A |
| ATOM | 733 | CE1 | HIS | A | 101 | 37.547 | 22.456 | −12.104 | 1.00 | 42.69 | A |
| ATOM | 734 | NE2 | HIS | A | 101 | 38.069 | 23.390 | −12.880 | 1.00 | 42.38 | A |
| ATOM | 735 | C | HIS | A | 101 | 39.835 | 25.475 | −7.664 | 1.00 | 40.29 | A |
| ATOM | 736 | O | HIS | A | 101 | 40.307 | 26.537 | −8.065 | 1.00 | 41.90 | A |
| ATOM | 737 | N | LEU | A | 102 | 39.598 | 25.243 | −6.376 | 1.00 | 39.72 | A |
| ATOM | 738 | CA | LEU | A | 102 | 39.869 | 26.279 | −5.378 | 1.00 | 38.61 | A |
| ATOM | 739 | CB | LEU | A | 102 | 38.589 | 27.073 | −5.068 | 1.00 | 37.62 | A |
| ATOM | 740 | CG | LEU | A | 102 | 37.875 | 27.877 | −6.156 | 1.00 | 37.33 | A |
| ATOM | 741 | CD1 | LEU | A | 102 | 36.523 | 28.356 | −5.621 | 1.00 | 37.68 | A |
| ATOM | 742 | CD2 | LEU | A | 102 | 38.736 | 29.062 | −6.586 | 1.00 | 38.82 | A |
| ATOM | 743 | C | LEU | A | 102 | 40.412 | 25.735 | −4.069 | 1.00 | 37.71 | A |
| ATOM | 744 | O | LEU | A | 102 | 40.259 | 24.558 | −3.756 | 1.00 | 37.42 | A |
| ATOM | 745 | N | PRO | A | 103 | 41.055 | 26.603 | −3.279 | 1.00 | 38.28 | A |
| ATOM | 746 | CD | PRO | A | 103 | 41.519 | 27.947 | −3.660 | 1.00 | 38.45 | A |
| ATOM | 747 | CA | PRO | A | 103 | 41.620 | 26.209 | −1.988 | 1.00 | 38.75 | A |
| ATOM | 748 | CB | PRO | A | 103 | 42.559 | 27.367 | −1.647 | 1.00 | 39.03 | A |
| ATOM | 749 | CG | PRO | A | 103 | 42.849 | 28.006 | −2.977 | 1.00 | 39.90 | A |
| ATOM | 750 | C | PRO | A | 103 | 40.501 | 26.084 | −0.962 | 1.00 | 38.05 | A |
| ATOM | 751 | O | PRO | A | 103 | 39.871 | 27.079 | −0.608 | 1.00 | 39.88 | A |
| ATOM | 752 | N | VAL | A | 104 | 40.232 | 24.867 | −0.507 | 1.00 | 38.36 | A |
| ATOM | 753 | CA | VAL | A | 104 | 39.196 | 24.658 | 0.492 | 1.00 | 38.23 | A |
| ATOM | 754 | CB | VAL | A | 104 | 38.300 | 23.457 | 0.126 | 1.00 | 37.32 | A |
| ATOM | 755 | CG1 | VAL | A | 104 | 37.288 | 23.195 | 1.226 | 1.00 | 35.34 | A |
| ATOM | 756 | CG2 | VAL | A | 104 | 37.582 | 23.748 | −1.190 | 1.00 | 37.51 | A |
| ATOM | 757 | C | VAL | A | 104 | 39.902 | 24.426 | 1.819 | 1.00 | 39.33 | A |
| ATOM | 758 | O | VAL | A | 104 | 40.699 | 23.503 | 1.963 | 1.00 | 39.67 | A |
| ATOM | 759 | N | SER | A | 105 | 39.604 | 25.284 | 2.783 | 1.00 | 39.48 | A |
| ATOM | 760 | CA | SER | A | 105 | 40.228 | 25.230 | 4.098 | 1.00 | 38.55 | A |
| ATOM | 761 | CB | SER | A | 105 | 40.410 | 26.658 | 4.613 | 1.00 | 37.61 | A |
| ATOM | 762 | OG | SER | A | 105 | 39.157 | 27.324 | 4.641 | 1.00 | 38.92 | A |
| ATOM | 763 | C | SER | A | 105 | 39.452 | 24.421 | 5.127 | 1.00 | 37.52 | A |
| ATOM | 764 | O | SER | A | 105 | 39.991 | 24.060 | 6.176 | 1.00 | 36.61 | A |
| ATOM | 765 | N | MET | A | 106 | 38.188 | 24.132 | 4.836 | 1.00 | 36.90 | A |
| ATOM | 766 | CA | MET | A | 106 | 37.368 | 23.387 | 5.773 | 1.00 | 35.42 | A |
| ATOM | 767 | CB | MET | A | 106 | 37.114 | 24.245 | 7.013 | 1.00 | 39.45 | A |

APPENDIX 1-continued

Atomic coordinates of aromatic prenyltransferase residues 3-302 of SEQ ID NO: 2.

| ATOM | 768 | CG | MET | A | 106 | 36.289 | 23.574 | 8.088 | 1.00 | 44.17 | A |
|---|---|---|---|---|---|---|---|---|---|---|---|
| ATOM | 769 | SD | MET | A | 106 | 36.685 | 24.199 | 9.727 | 1.00 | 52.21 | A |
| ATOM | 770 | CE | MET | A | 106 | 35.296 | 25.277 | 10.026 | 1.00 | 49.49 | A |
| ATOM | 771 | C | MET | A | 106 | 36.036 | 23.000 | 5.147 | 1.00 | 34.14 | A |
| ATOM | 772 | O | MET | A | 106 | 35.596 | 23.624 | 4.187 | 1.00 | 31.92 | A |
| ATOM | 773 | N | PHE | A | 107 | 35.413 | 21.969 | 5.706 | 1.00 | 31.68 | A |
| ATOM | 774 | CA | PHE | A | 107 | 34.116 | 21.479 | 5.251 | 1.00 | 32.11 | A |
| ATOM | 775 | CB | PHE | A | 107 | 34.186 | 19.993 | 4.869 | 1.00 | 32.56 | A |
| ATOM | 776 | CG | PHE | A | 107 | 35.046 | 19.685 | 3.674 | 1.00 | 32.69 | A |
| ATOM | 777 | CD1 | PHE | A | 107 | 36.107 | 18.789 | 3.787 | 1.00 | 33.01 | A |
| ATOM | 778 | CD2 | PHE | A | 107 | 34.756 | 20.223 | 2.425 | 1.00 | 34.08 | A |
| ATOM | 779 | CE1 | PHE | A | 107 | 36.865 | 18.429 | 2.675 | 1.00 | 33.52 | A |
| ATOM | 780 | CE2 | PHE | A | 107 | 35.514 | 19.867 | 1.296 | 1.00 | 35.10 | A |
| ATOM | 781 | CZ | PHE | A | 107 | 36.565 | 18.969 | 1.426 | 1.00 | 34.67 | A |
| ATOM | 782 | C | PHE | A | 107 | 33.107 | 21.581 | 6.395 | 1.00 | 30.99 | A |
| ATOM | 783 | O | PHE | A | 107 | 33.445 | 21.943 | 7.525 | 1.00 | 30.91 | A |
| ATOM | 784 | N | ALA | A | 108 | 31.861 | 21.248 | 6.082 | 1.00 | 31.37 | A |
| ATOM | 785 | CA | ALA | A | 108 | 30.798 | 21.204 | 7.071 | 1.00 | 29.87 | A |
| ATOM | 786 | CB | ALA | A | 108 | 30.384 | 22.603 | 7.494 | 1.00 | 29.38 | A |
| ATOM | 787 | C | ALA | A | 108 | 29.629 | 20.457 | 6.441 | 1.00 | 30.97 | A |
| ATOM | 788 | O | ALA | A | 108 | 29.518 | 20.383 | 5.211 | 1.00 | 29.63 | A |
| ATOM | 789 | N | ILE | A | 109 | 28.790 | 19.855 | 7.274 | 1.00 | 31.61 | A |
| ATOM | 790 | CA | ILE | A | 109 | 27.624 | 19.156 | 6.763 | 1.00 | 33.76 | A |
| ATOM | 791 | CB | ILE | A | 109 | 27.718 | 17.627 | 6.925 | 1.00 | 35.00 | A |
| ATOM | 792 | CG2 | ILE | A | 109 | 28.841 | 17.086 | 6.047 | 1.00 | 34.55 | A |
| ATOM | 793 | CG1 | ILE | A | 109 | 27.911 | 17.261 | 8.398 | 1.00 | 35.82 | A |
| ATOM | 794 | CD1 | ILE | A | 109 | 27.901 | 15.782 | 8.661 | 1.00 | 39.05 | A |
| ATOM | 795 | C | ILE | A | 109 | 26.427 | 19.671 | 7.524 | 1.00 | 35.47 | A |
| ATOM | 796 | O | ILE | A | 109 | 26.553 | 20.197 | 8.634 | 1.00 | 34.00 | A |
| ATOM | 797 | N | ASP | A | 110 | 25.262 | 19.526 | 6.911 | 1.00 | 35.28 | A |
| ATOM | 798 | CA | ASP | A | 110 | 24.032 | 20.002 | 7.499 | 1.00 | 36.47 | A |
| ATOM | 799 | CB | ASP | A | 110 | 23.577 | 21.231 | 6.710 | 1.00 | 39.55 | A |
| ATOM | 800 | CG | ASP | A | 110 | 23.876 | 22.526 | 7.408 | 1.00 | 42.35 | A |
| ATOM | 801 | OD1 | ASP | A | 110 | 24.816 | 22.555 | 8.227 | 1.00 | 42.34 | A |
| ATOM | 802 | OD2 | ASP | A | 110 | 23.155 | 23.514 | 7.144 | 1.00 | 45.22 | A |
| ATOM | 803 | C | ASP | A | 110 | 22.997 | 18.886 | 7.419 | 1.00 | 34.76 | A |
| ATOM | 804 | O | ASP | A | 110 | 22.944 | 18.147 | 6.437 | 1.00 | 31.82 | A |
| ATOM | 805 | N | GLY | A | 111 | 22.195 | 18.762 | 8.470 | 1.00 | 33.94 | A |
| ATOM | 806 | CA | GLY | A | 111 | 21.156 | 17.755 | 8.509 | 1.00 | 35.79 | A |
| ATOM | 807 | C | GLY | A | 111 | 19.931 | 18.330 | 9.201 | 1.00 | 35.96 | A |
| ATOM | 808 | O | GLY | A | 111 | 19.957 | 19.465 | 9.672 | 1.00 | 35.30 | A |
| ATOM | 809 | N | GLU | A | 112 | 18.855 | 17.553 | 9.244 | 1.00 | 37.97 | A |
| ATOM | 810 | CA | GLU | A | 112 | 17.613 | 17.962 | 9.893 | 1.00 | 38.66 | A |
| ATOM | 811 | CB | GLU | A | 112 | 16.502 | 18.123 | 8.850 | 1.00 | 39.80 | A |
| ATOM | 812 | CG | GLU | A | 112 | 15.336 | 19.019 | 9.264 | 1.00 | 38.95 | A |
| ATOM | 813 | CD | GLU | A | 112 | 14.378 | 18.352 | 10.240 | 1.00 | 40.97 | A |
| ATOM | 814 | OE1 | GLU | A | 112 | 13.934 | 17.222 | 9.952 | 1.00 | 41.18 | A |
| ATOM | 815 | OE2 | GLU | A | 112 | 14.060 | 18.964 | 11.285 | 1.00 | 40.91 | A |
| ATOM | 816 | C | GLU | A | 112 | 17.311 | 16.810 | 10.845 | 1.00 | 39.79 | A |
| ATOM | 817 | O | GLU | A | 112 | 17.540 | 15.654 | 10.505 | 1.00 | 40.11 | A |
| ATOM | 818 | N | VAL | A | 113 | 16.808 | 17.118 | 12.034 | 1.00 | 41.22 | A |
| ATOM | 819 | CA | VAL | A | 113 | 16.536 | 16.082 | 13.027 | 1.00 | 42.17 | A |
| ATOM | 820 | CB | VAL | A | 113 | 16.051 | 16.700 | 14.363 | 1.00 | 41.43 | A |
| ATOM | 821 | CG1 | VAL | A | 113 | 17.131 | 17.595 | 14.931 | 1.00 | 40.29 | A |
| ATOM | 822 | CG2 | VAL | A | 113 | 14.762 | 17.478 | 14.153 | 1.00 | 39.96 | A |
| ATOM | 823 | C | VAL | A | 113 | 15.557 | 14.989 | 12.616 | 1.00 | 43.71 | A |
| ATOM | 824 | O | VAL | A | 113 | 15.492 | 13.939 | 13.251 | 1.00 | 45.17 | A |
| ATOM | 825 | N | THR | A | 114 | 14.802 | 15.222 | 11.553 | 1.00 | 45.21 | A |
| ATOM | 826 | CA | THR | A | 114 | 13.843 | 14.226 | 11.104 | 1.00 | 46.88 | A |
| ATOM | 827 | CB | THR | A | 114 | 12.410 | 14.782 | 11.146 | 1.00 | 48.04 | A |
| ATOM | 828 | CG1 | THR | A | 114 | 12.160 | 15.360 | 12.433 | 1.00 | 51.16 | A |
| ATOM | 829 | CG2 | THR | A | 114 | 11.405 | 13.675 | 10.900 | 1.00 | 50.04 | A |
| ATOM | 830 | C | THR | A | 114 | 14.126 | 13.764 | 9.681 | 1.00 | 46.51 | A |
| ATOM | 831 | O | THR | A | 114 | 13.642 | 12.715 | 9.256 | 1.00 | 47.78 | A |
| ATOM | 832 | N | GLY | A | 115 | 14.910 | 14.545 | 8.946 | 1.00 | 43.52 | A |
| ATOM | 833 | CA | GLY | A | 115 | 15.202 | 14.182 | 7.572 | 1.00 | 43.24 | A |
| ATOM | 834 | C | GLY | A | 115 | 16.606 | 13.680 | 7.324 | 1.00 | 41.33 | A |
| ATOM | 835 | O | GLY | A | 115 | 16.873 | 13.058 | 6.294 | 1.00 | 42.99 | A |
| ATOM | 836 | N | GLY | A | 116 | 17.507 | 13.954 | 8.259 | 1.00 | 40.18 | A |
| ATOM | 837 | CA | GLY | A | 116 | 18.881 | 13.509 | 8.102 | 1.00 | 38.86 | A |
| ATOM | 838 | C | GLY | A | 116 | 19.699 | 14.416 | 7.202 | 1.00 | 36.69 | A |
| ATOM | 839 | O | GLY | A | 116 | 19.308 | 15.543 | 6.940 | 1.00 | 36.36 | A |
| ATOM | 840 | N | PHE | A | 117 | 20.827 | 13.905 | 6.724 | 1.00 | 36.25 | A |
| ATOM | 841 | CA | PHE | A | 117 | 21.749 | 14.649 | 5.862 | 1.00 | 35.53 | A |
| ATOM | 842 | CB | PHE | A | 117 | 22.828 | 13.706 | 5.325 | 1.00 | 34.63 | A |
| ATOM | 843 | CG | PHE | A | 117 | 23.756 | 14.350 | 4.329 | 1.00 | 33.58 | A |
| ATOM | 844 | CD1 | PHE | A | 117 | 24.874 | 15.059 | 4.755 | 1.00 | 32.41 | A |

APPENDIX 1-continued

Atomic coordinates of aromatic prenyltransferase residues 3-302 of SEQ ID NO: 2.

| ATOM | 845 | CD2 | PHE | A | 117 | 23.502 | 14.255 | 2.961 | 1.00 | 32.56 | A |
|------|-----|-----|-----|---|-----|--------|--------|-------|------|-------|---|
| ATOM | 846 | CE1 | PHE | A | 117 | 25.737 | 15.666 | 3.836 | 1.00 | 31.07 | A |
| ATOM | 847 | CE2 | PHE | A | 117 | 24.357 | 14.859 | 2.032 | 1.00 | 31.84 | A |
| ATOM | 848 | CZ | PHE | A | 117 | 25.479 | 15.566 | 2.474 | 1.00 | 31.62 | A |
| ATOM | 849 | C | PHE | A | 117 | 21.081 | 15.337 | 4.675 | 1.00 | 35.92 | A |
| ATOM | 850 | O | PHE | A | 117 | 20.229 | 14.743 | 4.012 | 1.00 | 35.06 | A |
| ATOM | 851 | N | LYS | A | 118 | 21.491 | 16.576 | 4.395 | 1.00 | 34.72 | A |
| ATOM | 852 | CA | LYS | A | 118 | 20.937 | 17.315 | 3.265 | 1.00 | 34.75 | A |
| ATOM | 853 | CB | LYS | A | 118 | 19.691 | 18.098 | 3.698 | 1.00 | 36.47 | A |
| ATOM | 854 | CG | LYS | A | 118 | 19.918 | 19.142 | 4.783 | 1.00 | 37.72 | A |
| ATOM | 855 | CD | LYS | A | 118 | 18.714 | 20.079 | 4.867 | 1.00 | 40.72 | A |
| ATOM | 856 | CE | LYS | A | 118 | 18.968 | 21.253 | 5.807 | 1.00 | 39.89 | A |
| ATOM | 857 | NZ | LYS | A | 118 | 17.892 | 22.284 | 5.712 | 1.00 | 39.12 | A |
| ATOM | 858 | C | LYS | A | 118 | 21.920 | 18.251 | 2.546 | 1.00 | 32.27 | A |
| ATOM | 859 | O | LYS | A | 118 | 21.713 | 18.584 | 1.380 | 1.00 | 29.66 | A |
| ATOM | 860 | N | LYS | A | 119 | 22.992 | 18.672 | 3.218 | 1.00 | 31.59 | A |
| ATOM | 861 | CA | LYS | A | 119 | 23.955 | 19.551 | 2.564 | 1.00 | 30.61 | A |
| ATOM | 862 | CB | LYS | A | 119 | 23.400 | 20.985 | 2.489 | 1.00 | 34.11 | A |
| ATOM | 863 | CG | LYS | A | 119 | 22.923 | 21.579 | 3.783 | 1.00 | 34.64 | A |
| ATOM | 864 | CD | LYS | A | 119 | 22.230 | 22.956 | 3.600 | 1.00 | 33.28 | A |
| ATOM | 865 | CE | LYS | A | 119 | 23.155 | 23.995 | 2.982 | 1.00 | 32.16 | A |
| ATOM | 866 | NZ | LYS | A | 119 | 22.817 | 25.404 | 3.328 | 1.00 | 29.97 | A |
| ATOM | 867 | C | LYS | A | 119 | 25.381 | 19.578 | 3.110 | 1.00 | 30.58 | A |
| ATOM | 868 | O | LYS | A | 119 | 25.657 | 19.174 | 4.246 | 1.00 | 28.47 | A |
| ATOM | 869 | N | THR | A | 120 | 26.298 | 20.021 | 2.258 | 1.00 | 31.56 | A |
| ATOM | 870 | CA | THR | A | 120 | 27.702 | 20.156 | 2.637 | 1.00 | 30.27 | A |
| ATOM | 871 | CB | THR | A | 120 | 28.645 | 19.319 | 1.749 | 1.00 | 29.70 | A |
| ATOM | 872 | OG1 | THR | A | 120 | 28.467 | 19.710 | 0.381 | 1.00 | 28.77 | A |
| ATOM | 873 | CG2 | THR | A | 120 | 28.370 | 17.841 | 1.904 | 1.00 | 28.77 | A |
| ATOM | 874 | C | THR | A | 120 | 28.071 | 21.605 | 2.417 | 1.00 | 30.38 | A |
| ATOM | 875 | O | THR | A | 120 | 27.333 | 22.356 | 1.760 | 1.00 | 29.15 | A |
| ATOM | 876 | N | TYR | A | 121 | 29.226 | 21.984 | 2.952 | 1.00 | 28.30 | A |
| ATOM | 877 | CA | TYR | A | 121 | 29.740 | 23.332 | 2.817 | 1.00 | 29.10 | A |
| ATOM | 878 | CB | TYR | A | 121 | 29.632 | 24.107 | 4.136 | 1.00 | 30.57 | A |
| ATOM | 879 | CG | TYR | A | 121 | 28.233 | 24.402 | 4.611 | 1.00 | 31.61 | A |
| ATOM | 880 | CD1 | TYR | A | 121 | 27.450 | 23.416 | 5.208 | 1.00 | 32.95 | A |
| ATOM | 881 | CE1 | TYR | A | 121 | 26.160 | 23.692 | 5.650 | 1.00 | 33.00 | A |
| ATOM | 882 | CD2 | TYR | A | 121 | 27.692 | 25.674 | 4.468 | 1.00 | 33.43 | A |
| ATOM | 883 | CE2 | TYR | A | 121 | 26.406 | 25.959 | 4.903 | 1.00 | 35.44 | A |
| ATOM | 884 | CZ | TYR | A | 121 | 25.648 | 24.966 | 5.488 | 1.00 | 33.78 | A |
| ATOM | 885 | OH | TYR | A | 121 | 24.369 | 25.259 | 5.885 | 1.00 | 36.41 | A |
| ATOM | 886 | C | TYR | A | 121 | 31.215 | 23.250 | 2.461 | 1.00 | 28.23 | A |
| ATOM | 887 | O | TYR | A | 121 | 31.916 | 22.330 | 2.881 | 1.00 | 27.61 | A |
| ATOM | 888 | N | ALA | A | 122 | 31.675 | 24.212 | 1.679 | 1.00 | 29.43 | A |
| ATOM | 889 | CA | ALA | A | 122 | 33.079 | 24.284 | 1.324 | 1.00 | 30.31 | A |
| ATOM | 890 | CB | ALA | A | 122 | 33.258 | 24.126 | −0.168 | 1.00 | 29.87 | A |
| ATOM | 891 | C | ALA | A | 122 | 33.512 | 25.677 | 1.775 | 1.00 | 30.35 | A |
| ATOM | 892 | O | ALA | A | 122 | 32.971 | 26.675 | 1.305 | 1.00 | 30.95 | A |
| ATOM | 893 | N | PHE | A | 123 | 34.456 | 25.740 | 2.710 | 1.00 | 30.19 | A |
| ATOM | 894 | CA | PHE | A | 123 | 34.945 | 27.023 | 3.212 | 1.00 | 31.04 | A |
| ATOM | 895 | CB | PHE | A | 123 | 35.185 | 26.982 | 4.728 | 1.00 | 32.77 | A |
| ATOM | 896 | CG | PHE | A | 123 | 33.937 | 26.889 | 5.543 | 1.00 | 33.65 | A |
| ATOM | 897 | CD1 | PHE | A | 123 | 33.215 | 25.702 | 5.601 | 1.00 | 34.51 | A |
| ATOM | 898 | CD2 | PHE | A | 123 | 33.489 | 27.988 | 6.273 | 1.00 | 36.59 | A |
| ATOM | 899 | CE1 | PHE | A | 123 | 32.054 | 25.608 | 6.384 | 1.00 | 36.52 | A |
| ATOM | 900 | CE2 | PHE | A | 123 | 32.330 | 27.908 | 7.061 | 1.00 | 36.10 | A |
| ATOM | 901 | CZ | PHE | A | 123 | 31.616 | 26.719 | 7.115 | 1.00 | 34.21 | A |
| ATOM | 902 | C | PHE | A | 123 | 36.257 | 27.385 | 2.547 | 1.00 | 32.63 | A |
| ATOM | 903 | O | PHE | A | 123 | 37.079 | 26.507 | 2.265 | 1.00 | 34.75 | A |
| ATOM | 904 | N | PHE | A | 124 | 36.467 | 28.676 | 2.312 | 1.00 | 32.86 | A |
| ATOM | 905 | CA | PHE | A | 124 | 37.706 | 29.123 | 1.702 | 1.00 | 33.91 | A |
| ATOM | 906 | CB | PHE | A | 124 | 37.410 | 29.930 | 0.441 | 1.00 | 33.32 | A |
| ATOM | 907 | CG | PHE | A | 124 | 36.423 | 29.261 | −0.479 | 1.00 | 32.63 | A |
| ATOM | 908 | CD1 | PHE | A | 124 | 35.106 | 29.712 | −0.555 | 1.00 | 31.58 | A |
| ATOM | 909 | CD2 | PHE | A | 124 | 36.797 | 28.158 | −1.241 | 1.00 | 33.35 | A |
| ATOM | 910 | CE1 | PHE | A | 124 | 34.179 | 29.068 | −1.377 | 1.00 | 34.49 | A |
| ATOM | 911 | CE2 | PHE | A | 124 | 35.877 | 27.504 | −2.067 | 1.00 | 33.34 | A |
| ATOM | 912 | CZ | PHE | A | 124 | 34.569 | 27.957 | −2.135 | 1.00 | 33.17 | A |
| ATOM | 913 | C | PHE | A | 124 | 38.495 | 29.959 | 2.703 | 1.00 | 33.67 | A |
| ATOM | 914 | O | PHE | A | 124 | 37.940 | 30.463 | 3.681 | 1.00 | 33.97 | A |
| ATOM | 915 | N | PRO | A | 125 | 39.814 | 30.079 | 2.495 | 1.00 | 35.21 | A |
| ATOM | 916 | CD | PRO | A | 125 | 40.642 | 29.338 | 1.527 | 1.00 | 35.76 | A |
| ATOM | 917 | CA | PRO | A | 125 | 40.660 | 30.866 | 3.397 | 1.00 | 34.83 | A |
| ATOM | 918 | CB | PRO | A | 125 | 42.048 | 30.718 | 2.776 | 1.00 | 35.56 | A |
| ATOM | 919 | CG | PRO | A | 125 | 41.995 | 29.336 | 2.207 | 1.00 | 35.73 | A |
| ATOM | 920 | C | PRO | A | 125 | 40.192 | 32.310 | 3.439 | 1.00 | 34.10 | A |
| ATOM | 921 | O | PRO | A | 125 | 39.948 | 32.925 | 2.405 | 1.00 | 34.97 | A |

APPENDIX 1-continued

Atomic coordinates of aromatic prenyltransferase residues 3-302 of SEQ ID NO: 2.

| ATOM | 922 | N | THR | A | 126 | 40.056 | 32.846 | 4.645 | 1.00 | 36.61 | A |
|---|---|---|---|---|---|---|---|---|---|---|---|
| ATOM | 923 | CA | THR | A | 126 | 39.605 | 34.217 | 4.822 | 1.00 | 38.10 | A |
| ATOM | 924 | CB | THR | A | 126 | 39.556 | 34.572 | 6.319 | 1.00 | 37.99 | A |
| ATOM | 925 | OG1 | THR | A | 126 | 38.725 | 33.620 | 6.991 | 1.00 | 42.36 | A |
| ATOM | 926 | CG2 | THR | A | 126 | 38.977 | 35.966 | 6.535 | 1.00 | 41.12 | A |
| ATOM | 927 | C | THR | A | 126 | 40.492 | 35.218 | 4.085 | 1.00 | 37.53 | A |
| ATOM | 928 | O | THR | A | 126 | 40.014 | 36.258 | 3.635 | 1.00 | 37.06 | A |
| ATOM | 929 | N | ASP | A | 127 | 41.777 | 34.897 | 3.940 | 1.00 | 39.58 | A |
| ATOM | 930 | CA | ASP | A | 127 | 42.701 | 35.801 | 3.263 | 1.00 | 39.86 | A |
| ATOM | 931 | CB | ASP | A | 127 | 44.026 | 35.896 | 4.034 | 1.00 | 42.23 | A |
| ATOM | 932 | CG | ASP | A | 127 | 44.763 | 34.567 | 4.124 | 1.00 | 43.17 | A |
| ATOM | 933 | OD1 | ASP | A | 127 | 44.243 | 33.539 | 3.641 | 1.00 | 45.25 | A |
| ATOM | 934 | OD2 | ASP | A | 127 | 45.878 | 34.554 | 4.688 | 1.00 | 45.84 | A |
| ATOM | 935 | C | ASP | A | 127 | 42.973 | 35.435 | 1.810 | 1.00 | 39.84 | A |
| ATOM | 936 | O | ASP | A | 127 | 43.943 | 35.904 | 1.221 | 1.00 | 40.14 | A |
| ATOM | 937 | N | ASN | A | 128 | 42.109 | 34.600 | 1.238 | 1.00 | 39.79 | A |
| ATOM | 938 | CA | ASN | A | 128 | 42.238 | 34.182 | −0.153 | 1.00 | 39.11 | A |
| ATOM | 939 | CB | ASN | A | 128 | 43.332 | 33.121 | −0.305 | 1.00 | 40.96 | A |
| ATOM | 940 | CG | ASN | A | 128 | 43.608 | 32.772 | −1.763 | 1.00 | 42.76 | A |
| ATOM | 941 | OD1 | ASN | A | 128 | 44.327 | 31.816 | −2.058 | 1.00 | 45.02 | A |
| ATOM | 942 | ND2 | ASN | A | 128 | 43.044 | 33.548 | −2.679 | 1.00 | 43.31 | A |
| ATOM | 943 | C | ASN | A | 128 | 40.910 | 33.600 | −0.611 | 1.00 | 38.19 | A |
| ATOM | 944 | O | ASN | A | 128 | 40.834 | 32.444 | −1.027 | 1.00 | 36.34 | A |
| ATOM | 945 | N | MET | A | 129 | 39.860 | 34.407 | −0.532 | 1.00 | 37.03 | A |
| ATOM | 946 | CA | MET | A | 129 | 38.544 | 33.948 | −0.933 | 1.00 | 36.26 | A |
| ATOM | 947 | CB | MET | A | 129 | 37.462 | 34.742 | −0.205 | 1.00 | 35.19 | A |
| ATOM | 948 | CG | MET | A | 129 | 37.469 | 34.578 | 1.300 | 1.00 | 36.19 | A |
| ATOM | 949 | SD | MET | A | 129 | 36.104 | 35.498 | 2.022 | 1.00 | 35.06 | A |
| ATOM | 950 | CE | MET | A | 129 | 36.869 | 37.133 | 2.125 | 1.00 | 37.35 | A |
| ATOM | 951 | C | MET | A | 129 | 38.375 | 34.127 | −2.431 | 1.00 | 35.46 | A |
| ATOM | 952 | O | MET | A | 129 | 38.953 | 35.036 | −3.024 | 1.00 | 35.81 | A |
| ATOM | 953 | N | PRO | A | 130 | 37.587 | 33.252 | −3.067 | 1.00 | 35.15 | A |
| ATOM | 954 | CD | PRO | A | 130 | 37.024 | 31.988 | −2.558 | 1.00 | 33.45 | A |
| ATOM | 955 | CA | PRO | A | 130 | 37.375 | 33.374 | −4.510 | 1.00 | 34.52 | A |
| ATOM | 956 | CB | PRO | A | 130 | 36.935 | 31.968 | −4.907 | 1.00 | 34.77 | A |
| ATOM | 957 | CG | PRO | A | 130 | 36.155 | 31.528 | −3.713 | 1.00 | 33.09 | A |
| ATOM | 958 | C | PRO | A | 130 | 36.313 | 34.428 | −4.825 | 1.00 | 35.76 | A |
| ATOM | 959 | O | PRO | A | 130 | 35.502 | 34.785 | −3.966 | 1.00 | 34.18 | A |
| ATOM | 960 | N | GLY | A | 131 | 36.343 | 34.936 | −6.055 | 1.00 | 36.06 | A |
| ATOM | 961 | CA | GLY | A | 131 | 35.371 | 35.921 | −6.483 | 1.00 | 36.41 | A |
| ATOM | 962 | C | GLY | A | 131 | 34.313 | 35.190 | −7.282 | 1.00 | 37.83 | A |
| ATOM | 963 | O | GLY | A | 131 | 34.424 | 33.981 | −7.482 | 1.00 | 38.41 | A |
| ATOM | 964 | N | VAL | A | 132 | 33.288 | 35.900 | −7.739 | 1.00 | 37.75 | A |
| ATOM | 965 | CA | VAL | A | 132 | 32.229 | 35.269 | −8.515 | 1.00 | 39.80 | A |
| ATOM | 966 | CB | VAL | A | 132 | 31.106 | 36.277 | −8.848 | 1.00 | 39.90 | A |
| ATOM | 967 | CG1 | VAL | A | 132 | 30.089 | 35.649 | −9.792 | 1.00 | 39.29 | A |
| ATOM | 968 | CG2 | VAL | A | 132 | 30.420 | 36.711 | −7.569 | 1.00 | 39.79 | A |
| ATOM | 969 | C | VAL | A | 132 | 32.795 | 34.688 | −9.804 | 1.00 | 40.83 | A |
| ATOM | 970 | O | VAL | A | 132 | 32.388 | 33.615 | −10.245 | 1.00 | 41.10 | A |
| ATOM | 971 | N | ALA | A | 133 | 33.747 | 35.397 | −10.398 | 1.00 | 42.28 | A |
| ATOM | 972 | CA | ALA | A | 133 | 34.378 | 34.949 | −11.632 | 1.00 | 43.17 | A |
| ATOM | 973 | CB | ALA | A | 133 | 35.482 | 35.923 | −12.036 | 1.00 | 44.08 | A |
| ATOM | 974 | C | ALA | A | 133 | 34.955 | 33.548 | −11.462 | 1.00 | 43.96 | A |
| ATOM | 975 | O | ALA | A | 133 | 34.636 | 32.651 | −12.235 | 1.00 | 43.99 | A |
| ATOM | 976 | N | GLU | A | 134 | 35.799 | 33.366 | −10.446 | 1.00 | 44.05 | A |
| ATOM | 977 | CA | GLU | A | 134 | 36.421 | 32.067 | −10.173 | 1.00 | 44.20 | A |
| ATOM | 978 | CB | GLU | A | 134 | 37.366 | 32.159 | −8.969 | 1.00 | 45.02 | A |
| ATOM | 979 | CG | GLU | A | 134 | 38.507 | 33.150 | −9.119 | 1.00 | 48.35 | A |
| ATOM | 980 | CD | GLU | A | 134 | 38.168 | 34.527 | −8.579 | 1.00 | 50.23 | A |
| ATOM | 981 | OE1 | GLU | A | 134 | 37.190 | 35.148 | −9.057 | 1.00 | 51.33 | A |
| ATOM | 982 | OE2 | GLU | A | 134 | 38.889 | 34.991 | −7.670 | 1.00 | 52.57 | A |
| ATOM | 983 | C | GLU | A | 134 | 35.406 | 30.954 | −9.905 | 1.00 | 42.84 | A |
| ATOM | 984 | O | GLU | A | 134 | 35.587 | 29.821 | −10.348 | 1.00 | 44.08 | A |
| ATOM | 985 | N | LEU | A | 135 | 34.343 | 31.272 | −9.175 | 1.00 | 41.08 | A |
| ATOM | 986 | CA | LEU | A | 135 | 33.325 | 30.276 | −8.859 | 1.00 | 40.14 | A |
| ATOM | 987 | CB | LEU | A | 135 | 32.349 | 30.827 | −7.808 | 1.00 | 38.00 | A |
| ATOM | 988 | CG | LEU | A | 135 | 32.858 | 30.961 | −6.363 | 1.00 | 35.55 | A |
| ATOM | 989 | CD1 | LEU | A | 135 | 31.813 | 31.634 | −5.501 | 1.00 | 37.80 | A |
| ATOM | 990 | CD2 | LEU | A | 135 | 33.180 | 29.589 | −5.807 | 1.00 | 32.97 | A |
| ATOM | 991 | C | LEU | A | 135 | 32.544 | 29.786 | −10.079 | 1.00 | 41.44 | A |
| ATOM | 992 | O | LEU | A | 135 | 32.419 | 28.583 | −10.294 | 1.00 | 41.03 | A |
| ATOM | 993 | N | SER | A | 136 | 32.018 | 30.710 | −10.877 | 1.00 | 43.65 | A |
| ATOM | 994 | CA | SER | A | 136 | 31.234 | 30.341 | −12.064 | 1.00 | 45.88 | A |
| ATOM | 995 | CB | SER | A | 136 | 30.756 | 31.599 | −12.798 | 1.00 | 47.35 | A |
| ATOM | 996 | OG | SER | A | 136 | 31.851 | 32.390 | −13.227 | 1.00 | 49.44 | A |
| ATOM | 997 | C | SER | A | 136 | 31.995 | 29.448 | −13.041 | 1.00 | 45.67 | A |
| ATOM | 998 | O | SER | A | 136 | 31.395 | 28.799 | −13.903 | 1.00 | 46.58 | A |

APPENDIX 1-continued

Atomic coordinates of aromatic prenyltransferase residues 3-302 of SEQ ID NO: 2.

| ATOM | 999 | N | ALA | A | 137 | 33.316 | 29.416 | −12.892 | 1.00 | 45.23 | A |
| ATOM | 1000 | CA | ALA | A | 137 | 34.185 | 28.618 | −13.746 | 1.00 | 44.09 | A |
| ATOM | 1001 | CB | ALA | A | 137 | 35.618 | 29.123 | −13.627 | 1.00 | 45.40 | A |
| ATOM | 1002 | C | ALA | A | 137 | 34.128 | 27.127 | −13.413 | 1.00 | 43.23 | A |
| ATOM | 1003 | O | ALA | A | 137 | 34.433 | 26.284 | −14.258 | 1.00 | 42.56 | A |
| ATOM | 1004 | N | ILE | A | 138 | 33.758 | 26.799 | −12.179 | 1.00 | 41.63 | A |
| ATOM | 1005 | CA | ILE | A | 138 | 33.664 | 25.398 | −11.775 | 1.00 | 40.86 | A |
| ATOM | 1006 | CB | ILE | A | 138 | 33.260 | 25.275 | −10.280 | 1.00 | 39.46 | A |
| ATOM | 1007 | CG2 | ILE | A | 138 | 33.120 | 23.812 | −9.893 | 1.00 | 39.81 | A |
| ATOM | 1008 | CG1 | ILE | A | 138 | 34.319 | 25.955 | −9.403 | 1.00 | 40.37 | A |
| ATOM | 1009 | CD1 | ILE | A | 138 | 33.990 | 25.985 | −7.921 | 1.00 | 38.95 | A |
| ATOM | 1010 | C | ILE | A | 138 | 32.600 | 24.771 | −12.677 | 1.00 | 40.15 | A |
| ATOM | 1011 | O | ILE | A | 138 | 31.481 | 25.261 | −12.745 | 1.00 | 39.48 | A |
| ATOM | 1012 | N | PRO | A | 139 | 32.949 | 23.688 | −13.391 | 1.00 | 42.04 | A |
| ATOM | 1013 | CD | PRO | A | 139 | 34.277 | 23.056 | −13.319 | 1.00 | 42.63 | A |
| ATOM | 1014 | CA | PRO | A | 139 | 32.080 | 22.950 | −14.325 | 1.00 | 42.17 | A |
| ATOM | 1015 | CB | PRO | A | 139 | 32.913 | 21.716 | −14.668 | 1.00 | 43.33 | A |
| ATOM | 1016 | CG | PRO | A | 139 | 34.308 | 22.234 | −14.591 | 1.00 | 44.53 | A |
| ATOM | 1017 | C | PRO | A | 139 | 30.672 | 22.568 | −13.873 | 1.00 | 41.62 | A |
| ATOM | 1018 | O | PRO | A | 139 | 29.717 | 22.686 | −14.646 | 1.00 | 41.11 | A |
| ATOM | 1019 | N | SER | A | 140 | 30.548 | 22.103 | −12.634 | 1.00 | 40.71 | A |
| ATOM | 1020 | CA | SER | A | 140 | 29.262 | 21.677 | −12.095 | 1.00 | 40.02 | A |
| ATOM | 1021 | CB | SER | A | 140 | 29.458 | 20.440 | −11.207 | 1.00 | 38.55 | A |
| ATOM | 1022 | OG | SER | A | 140 | 30.473 | 20.655 | −10.239 | 1.00 | 37.26 | A |
| ATOM | 1023 | C | SER | A | 140 | 28.510 | 22.765 | −11.329 | 1.00 | 40.37 | A |
| ATOM | 1024 | O | SER | A | 140 | 27.460 | 22.507 | −10.735 | 1.00 | 40.00 | A |
| ATOM | 1025 | N | MET | A | 141 | 29.044 | 23.981 | −11.351 | 1.00 | 39.35 | A |
| ATOM | 1026 | CA | MET | A | 141 | 28.409 | 25.107 | −10.671 | 1.00 | 38.79 | A |
| ATOM | 1027 | CB | MET | A | 141 | 29.383 | 26.292 | −10.608 | 1.00 | 38.90 | A |
| ATOM | 1028 | CG | MET | A | 141 | 28.904 | 27.492 | −9.790 | 1.00 | 39.10 | A |
| ATOM | 1029 | SD | MET | A | 141 | 28.779 | 27.156 | −8.006 | 1.00 | 38.89 | A |
| ATOM | 1030 | CE | MET | A | 141 | 30.511 | 27.219 | −7.524 | 1.00 | 39.82 | A |
| ATOM | 1031 | C | MET | A | 141 | 27.167 | 25.500 | −11.474 | 1.00 | 38.43 | A |
| ATOM | 1032 | O | MET | A | 141 | 27.168 | 25.418 | −12.704 | 1.00 | 38.34 | A |
| ATOM | 1033 | N | PRO | A | 142 | 26.088 | 25.924 | −10.794 | 1.00 | 38.99 | A |
| ATOM | 1034 | CD | PRO | A | 142 | 25.876 | 26.042 | −9.340 | 1.00 | 37.35 | A |
| ATOM | 1035 | CA | PRO | A | 142 | 24.882 | 26.314 | −11.535 | 1.00 | 37.96 | A |
| ATOM | 1036 | CB | PRO | A | 142 | 23.949 | 26.823 | −10.439 | 1.00 | 38.94 | A |
| ATOM | 1037 | CG | PRO | A | 142 | 24.372 | 26.043 | −9.235 | 1.00 | 37.01 | A |
| ATOM | 1038 | C | PRO | A | 142 | 25.210 | 27.413 | −12.545 | 1.00 | 39.39 | A |
| ATOM | 1039 | O | PRO | A | 142 | 25.983 | 28.329 | −12.248 | 1.00 | 38.95 | A |
| ATOM | 1040 | N | PRO | A | 143 | 24.644 | 27.328 | −13.758 | 1.00 | 37.81 | A |
| ATOM | 1041 | CD | PRO | A | 143 | 23.843 | 26.222 | −14.307 | 1.00 | 39.42 | A |
| ATOM | 1042 | CA | PRO | A | 143 | 24.903 | 28.344 | −14.780 | 1.00 | 38.06 | A |
| ATOM | 1043 | CB | PRO | A | 143 | 24.060 | 27.863 | −15.964 | 1.00 | 38.66 | A |
| ATOM | 1044 | CG | PRO | A | 143 | 24.053 | 26.383 | −15.793 | 1.00 | 39.51 | A |
| ATOM | 1045 | C | PRO | A | 143 | 24.439 | 29.708 | −14.266 | 1.00 | 38.30 | A |
| ATOM | 1046 | O | PRO | A | 143 | 24.955 | 30.755 | −14.665 | 1.00 | 37.08 | A |
| ATOM | 1047 | N | ALA | A | 144 | 23.462 | 29.670 | −13.364 | 1.00 | 37.27 | A |
| ATOM | 1048 | CA | ALA | A | 144 | 22.887 | 30.871 | −12.773 | 1.00 | 37.43 | A |
| ATOM | 1049 | CB | ALA | A | 144 | 21.813 | 30.485 | −11.767 | 1.00 | 35.79 | A |
| ATOM | 1050 | C | ALA | A | 144 | 23.910 | 31.793 | −12.115 | 1.00 | 36.34 | A |
| ATOM | 1051 | O | ALA | A | 144 | 23.700 | 33.002 | −12.047 | 1.00 | 37.01 | A |
| ATOM | 1052 | N | VAL | A | 145 | 25.018 | 31.241 | −11.636 | 1.00 | 35.52 | A |
| ATOM | 1053 | CA | VAL | A | 145 | 26.020 | 32.087 | −10.993 | 1.00 | 36.56 | A |
| ATOM | 1054 | CB | VAL | A | 145 | 27.105 | 31.231 | −10.292 | 1.00 | 33.87 | A |
| ATOM | 1055 | CG1 | VAL | A | 145 | 28.206 | 32.118 | −9.755 | 1.00 | 32.14 | A |
| ATOM | 1056 | CG2 | VAL | A | 145 | 26.475 | 30.421 | −9.164 | 1.00 | 33.34 | A |
| ATOM | 1057 | C | VAL | A | 145 | 26.674 | 33.047 | −12.000 | 1.00 | 37.24 | A |
| ATOM | 1058 | O | VAL | A | 145 | 26.787 | 34.246 | −11.746 | 1.00 | 35.40 | A |
| ATOM | 1059 | N | ALA | A | 146 | 27.093 | 32.524 | −13.146 | 1.00 | 38.95 | A |
| ATOM | 1060 | CA | ALA | A | 146 | 27.713 | 33.365 | −14.165 | 1.00 | 40.89 | A |
| ATOM | 1061 | CB | ALA | A | 146 | 28.233 | 32.505 | −15.323 | 1.00 | 41.08 | A |
| ATOM | 1062 | C | ALA | A | 146 | 26.695 | 34.374 | −14.679 | 1.00 | 41.46 | A |
| ATOM | 1063 | O | ALA | A | 146 | 27.013 | 35.543 | −14.889 | 1.00 | 41.33 | A |
| ATOM | 1064 | N | GLU | A | 147 | 25.464 | 33.917 | −14.866 | 1.00 | 42.76 | A |
| ATOM | 1065 | CA | GLU | A | 147 | 24.405 | 34.777 | −15.367 | 1.00 | 44.04 | A |
| ATOM | 1066 | CB | GLU | A | 147 | 23.161 | 33.938 | −15.657 | 1.00 | 46.32 | A |
| ATOM | 1067 | CG | GLU | A | 147 | 23.296 | 33.089 | −16.924 | 1.00 | 51.66 | A |
| ATOM | 1068 | CD | GLU | A | 147 | 22.729 | 31.687 | −16.774 | 1.00 | 53.70 | A |
| ATOM | 1069 | OE1 | GLU | A | 147 | 21.566 | 31.555 | −16.334 | 1.00 | 55.88 | A |
| ATOM | 1070 | OE2 | GLU | A | 147 | 23.449 | 30.717 | −17.104 | 1.00 | 56.34 | A |
| ATOM | 1071 | C | GLU | A | 147 | 24.066 | 35.923 | −14.421 | 1.00 | 43.26 | A |
| ATOM | 1072 | O | GLU | A | 147 | 23.458 | 36.910 | −14.833 | 1.00 | 41.77 | A |
| ATOM | 1073 | N | ASN | A | 148 | 24.474 | 35.797 | −13.162 | 1.00 | 42.18 | A |
| ATOM | 1074 | CA | ASN | A | 148 | 24.200 | 36.827 | −12.165 | 1.00 | 41.99 | A |
| ATOM | 1075 | CB | ASN | A | 148 | 23.588 | 36.193 | −10.911 | 1.00 | 42.15 | A |

APPENDIX 1-continued

Atomic coordinates of aromatic prenyltransferase residues 3-302 of SEQ ID NO: 2.

| ATOM | 1076 | CG  | ASN | A | 148 | 22.104 | 35.918 | -11.059 | 1.00 | 40.63 | A |
|------|------|-----|-----|---|-----|--------|--------|---------|------|-------|---|
| ATOM | 1077 | OD1 | ASN | A | 148 | 21.301 | 36.841 | -11.145 | 1.00 | 42.33 | A |
| ATOM | 1078 | ND2 | ASN | A | 148 | 21.735 | 34.649 | -11.093 | 1.00 | 41.13 | A |
| ATOM | 1079 | C   | ASN | A | 148 | 25.435 | 37.630 | -11.774 | 1.00 | 41.70 | A |
| ATOM | 1080 | O   | ASN | A | 148 | 25.361 | 38.492 | -10.904 | 1.00 | 41.52 | A |
| ATOM | 1081 | N   | ALA | A | 149 | 26.560 | 37.350 | -12.427 | 1.00 | 42.05 | A |
| ATOM | 1082 | CA  | ALA | A | 149 | 27.825 | 38.027 | -12.150 | 1.00 | 42.82 | A |
| ATOM | 1083 | CB  | ALA | A | 149 | 28.898 | 37.556 | -13.143 | 1.00 | 41.85 | A |
| ATOM | 1084 | C   | ALA | A | 149 | 27.743 | 39.553 | -12.169 | 1.00 | 43.54 | A |
| ATOM | 1085 | O   | ALA | A | 149 | 28.236 | 40.217 | -11.257 | 1.00 | 44.06 | A |
| ATOM | 1086 | N   | GLU | A | 150 | 27.132 | 40.103 | -13.215 | 1.00 | 44.98 | A |
| ATOM | 1087 | CA  | GLU | A | 150 | 26.997 | 41.549 | -13.355 | 1.00 | 45.33 | A |
| ATOM | 1088 | CB  | GLU | A | 150 | 26.373 | 41.891 | -14.708 | 1.00 | 47.44 | A |
| ATOM | 1089 | CG  | GLU | A | 150 | 27.297 | 41.639 | -15.876 | 1.00 | 52.19 | A |
| ATOM | 1090 | CD  | GLU | A | 150 | 26.605 | 41.834 | -17.206 | 1.00 | 54.21 | A |
| ATOM | 1091 | OE1 | GLU | A | 150 | 25.720 | 41.018 | -17.540 | 1.00 | 56.56 | A |
| ATOM | 1092 | OE2 | GLU | A | 150 | 26.936 | 42.808 | -17.912 | 1.00 | 54.57 | A |
| ATOM | 1093 | C   | GLU | A | 150 | 26.156 | 42.145 | -12.241 | 1.00 | 43.75 | A |
| ATOM | 1094 | O   | GLU | A | 150 | 26.485 | 43.200 | -11.695 | 1.00 | 43.51 | A |
| ATOM | 1095 | N   | LEU | A | 151 | 25.063 | 41.468 | -11.915 | 1.00 | 42.63 | A |
| ATOM | 1096 | CA  | LEU | A | 151 | 24.181 | 41.922 | -10.853 | 1.00 | 41.40 | A |
| ATOM | 1097 | CB  | LEU | A | 151 | 22.963 | 40.995 | -10.777 | 1.00 | 42.33 | A |
| ATOM | 1098 | CG  | LEU | A | 151 | 21.804 | 41.368 | -9.850  | 1.00 | 42.54 | A |
| ATOM | 1099 | CD1 | LEU | A | 151 | 20.538 | 40.668 | -10.323 | 1.00 | 43.25 | A |
| ATOM | 1100 | CD2 | LEU | A | 151 | 22.139 | 40.989 | -8.414  | 1.00 | 41.89 | A |
| ATOM | 1101 | C   | LEU | A | 151 | 24.954 | 41.941 | -9.522  | 1.00 | 40.27 | A |
| ATOM | 1102 | O   | LEU | A | 151 | 24.973 | 42.956 | -8.822  | 1.00 | 41.45 | A |
| ATOM | 1103 | N   | PHE | A | 152 | 25.597 | 40.826 | -9.181  | 1.00 | 38.34 | A |
| ATOM | 1104 | CA  | PHE | A | 152 | 26.372 | 40.745 | -7.946  | 1.00 | 36.94 | A |
| ATOM | 1105 | CB  | PHE | A | 152 | 27.129 | 39.417 | -7.870  | 1.00 | 34.62 | A |
| ATOM | 1106 | CG  | PHE | A | 152 | 26.249 | 38.217 | -7.670  | 1.00 | 33.59 | A |
| ATOM | 1107 | CD1 | PHE | A | 152 | 26.625 | 36.981 | -8.183  | 1.00 | 32.62 | A |
| ATOM | 1108 | CD2 | PHE | A | 152 | 25.071 | 38.307 | -6.936  | 1.00 | 31.47 | A |
| ATOM | 1109 | CE1 | PHE | A | 152 | 25.842 | 35.844 | -7.969  | 1.00 | 32.66 | A |
| ATOM | 1110 | CE2 | PHE | A | 152 | 24.281 | 37.177 | -6.714  | 1.00 | 31.36 | A |
| ATOM | 1111 | CZ  | PHE | A | 152 | 24.670 | 35.941 | -7.232  | 1.00 | 32.67 | A |
| ATOM | 1112 | C   | PHE | A | 152 | 27.379 | 41.891 | -7.889  | 1.00 | 38.16 | A |
| ATOM | 1113 | O   | PHE | A | 152 | 27.499 | 42.575 | -6.874  | 1.00 | 38.05 | A |
| ATOM | 1114 | N   | ALA | A | 153 | 28.098 | 42.094 | -8.989  | 1.00 | 38.70 | A |
| ATOM | 1115 | CA  | ALA | A | 153 | 29.106 | 43.145 | -9.066  | 1.00 | 39.88 | A |
| ATOM | 1116 | CB  | ALA | A | 153 | 29.783 | 43.117 | -10.433 | 1.00 | 41.69 | A |
| ATOM | 1117 | C   | ALA | A | 153 | 28.523 | 44.526 | -8.805  | 1.00 | 40.13 | A |
| ATOM | 1118 | O   | ALA | A | 153 | 29.120 | 45.342 | -8.101  | 1.00 | 40.16 | A |
| ATOM | 1119 | N   | ARG | A | 154 | 27.350 | 44.777 | -9.374  | 1.00 | 40.05 | A |
| ATOM | 1120 | CA  | ARG | A | 154 | 26.682 | 46.055 | -9.217  | 1.00 | 40.63 | A |
| ATOM | 1121 | CB  | ARG | A | 154 | 25.394 | 46.057 | -10.044 | 1.00 | 42.51 | A |
| ATOM | 1122 | CG  | ARG | A | 154 | 24.770 | 47.425 | -10.221 | 1.00 | 47.49 | A |
| ATOM | 1123 | CD  | ARG | A | 154 | 24.025 | 47.541 | -11.555 | 1.00 | 48.14 | A |
| ATOM | 1124 | NE  | ARG | A | 154 | 23.060 | 46.463 | -11.764 | 1.00 | 48.78 | A |
| ATOM | 1125 | CZ  | ARG | A | 154 | 23.298 | 45.368 | -12.482 | 1.00 | 46.90 | A |
| ATOM | 1126 | NH1 | ARG | A | 154 | 24.473 | 45.197 | -13.069 | 1.00 | 48.01 | A |
| ATOM | 1127 | NH2 | ARG | A | 154 | 22.359 | 44.443 | -12.617 | 1.00 | 46.15 | A |
| ATOM | 1128 | C   | ARG | A | 154 | 26.387 | 46.397 | -7.750  | 1.00 | 40.64 | A |
| ATOM | 1129 | O   | ARG | A | 154 | 26.297 | 47.574 | -7.387  | 1.00 | 40.09 | A |
| ATOM | 1130 | N   | TYR | A | 155 | 26.256 | 45.383 | -6.897  | 1.00 | 40.35 | A |
| ATOM | 1131 | CA  | TYR | A | 155 | 25.975 | 45.652 | -5.493  | 1.00 | 38.19 | A |
| ATOM | 1132 | CB  | TYR | A | 155 | 24.720 | 44.901 | -5.052  | 1.00 | 38.67 | A |
| ATOM | 1133 | CG  | TYR | A | 155 | 23.503 | 45.381 | -5.790  | 1.00 | 38.24 | A |
| ATOM | 1134 | CD1 | TYR | A | 155 | 23.171 | 44.855 | -7.035  | 1.00 | 38.78 | A |
| ATOM | 1135 | CE1 | TYR | A | 155 | 22.099 | 45.357 | -7.766  | 1.00 | 39.06 | A |
| ATOM | 1136 | CD2 | TYR | A | 155 | 22.725 | 46.424 | -5.284  | 1.00 | 38.96 | A |
| ATOM | 1137 | CE2 | TYR | A | 155 | 21.651 | 46.935 | -6.006  | 1.00 | 40.27 | A |
| ATOM | 1138 | CZ  | TYR | A | 155 | 21.346 | 46.398 | -7.249  | 1.00 | 40.64 | A |
| ATOM | 1139 | OH  | TYR | A | 155 | 20.301 | 46.910 | -7.983  | 1.00 | 42.74 | A |
| ATOM | 1140 | C   | TYR | A | 155 | 27.129 | 45.367 | -4.545  | 1.00 | 38.20 | A |
| ATOM | 1141 | O   | TYR | A | 155 | 26.957 | 45.356 | -3.325  | 1.00 | 38.12 | A |
| ATOM | 1142 | N   | GLY | A | 156 | 28.311 | 45.147 | -5.105  | 1.00 | 37.37 | A |
| ATOM | 1143 | CA  | GLY | A | 156 | 29.471 | 44.904 | -4.270  | 1.00 | 37.64 | A |
| ATOM | 1144 | C   | GLY | A | 156 | 29.602 | 43.510 | -3.700  | 1.00 | 37.28 | A |
| ATOM | 1145 | O   | GLY | A | 156 | 30.449 | 43.274 | -2.835  | 1.00 | 37.51 | A |
| ATOM | 1146 | N   | LEU | A | 157 | 28.765 | 42.586 | -4.157  | 1.00 | 36.82 | A |
| ATOM | 1147 | CA  | LEU | A | 157 | 28.846 | 41.210 | -3.682  | 1.00 | 36.96 | A |
| ATOM | 1148 | CB  | LEU | A | 157 | 27.531 | 40.480 | -3.947  | 1.00 | 35.41 | A |
| ATOM | 1149 | CG  | LEU | A | 157 | 26.314 | 41.101 | -3.245  | 1.00 | 35.60 | A |
| ATOM | 1150 | CD1 | LEU | A | 157 | 25.045 | 40.359 | -3.646  | 1.00 | 33.80 | A |
| ATOM | 1151 | CD2 | LEU | A | 157 | 26.508 | 41.048 | -1.741  | 1.00 | 34.21 | A |
| ATOM | 1152 | C   | LEU | A | 157 | 29.984 | 40.588 | -4.479  | 1.00 | 37.62 | A |

APPENDIX 1-continued

Atomic coordinates of aromatic prenyltransferase residues 3-302 of SEQ ID NO: 2.

| ATOM | 1153 | O | LEU | A | 157 | 29.814 | 40.233 | −5.641 | 1.00 | 38.02 | A |
|------|------|------|-----|---|-----|--------|--------|--------|------|-------|---|
| ATOM | 1154 | N | ASP | A | 158 | 31.147 | 40.466 | −3.847 | 1.00 | 37.12 | A |
| ATOM | 1155 | CA | ASP | A | 158 | 32.323 | 39.942 | −4.526 | 1.00 | 37.41 | A |
| ATOM | 1156 | CB | ASP | A | 158 | 33.355 | 41.083 | −4.669 | 1.00 | 38.84 | A |
| ATOM | 1157 | CG | ASP | A | 158 | 34.737 | 40.598 | −5.106 | 1.00 | 39.06 | A |
| ATOM | 1158 | OD1 | ASP | A | 158 | 34.823 | 39.688 | −5.952 | 1.00 | 40.99 | A |
| ATOM | 1159 | OD2 | ASP | A | 158 | 35.743 | 41.150 | −4.610 | 1.00 | 42.10 | A |
| ATOM | 1160 | C | ASP | A | 158 | 32.948 | 38.713 | −3.871 | 1.00 | 37.01 | A |
| ATOM | 1161 | O | ASP | A | 158 | 32.820 | 37.600 | −4.386 | 1.00 | 37.39 | A |
| ATOM | 1162 | N | LYS | A | 159 | 33.608 | 38.902 | −2.734 | 1.00 | 35.40 | A |
| ATOM | 1163 | CA | LYS | A | 159 | 34.258 | 37.790 | −2.061 | 1.00 | 34.29 | A |
| ATOM | 1164 | CB | LYS | A | 159 | 35.313 | 38.316 | −1.083 | 1.00 | 35.64 | A |
| ATOM | 1165 | CG | LYS | A | 159 | 36.464 | 39.047 | −1.782 | 1.00 | 35.48 | A |
| ATOM | 1166 | CD | LYS | A | 159 | 37.021 | 38.202 | −2.931 | 1.00 | 39.05 | A |
| ATOM | 1167 | CE | LYS | A | 159 | 38.115 | 38.924 | −3.701 | 1.00 | 42.30 | A |
| ATOM | 1168 | NZ | LYS | A | 159 | 37.950 | 38.741 | −5.171 | 1.00 | 44.17 | A |
| ATOM | 1169 | C | LYS | A | 159 | 33.312 | 36.824 | −1.362 | 1.00 | 33.08 | A |
| ATOM | 1170 | O | LYS | A | 159 | 32.411 | 37.218 | −0.615 | 1.00 | 32.50 | A |
| ATOM | 1171 | N | VAL | A | 160 | 33.555 | 35.546 | −1.615 | 1.00 | 33.33 | A |
| ATOM | 1172 | CA | VAL | A | 160 | 32.764 | 34.453 | −1.071 | 1.00 | 33.25 | A |
| ATOM | 1173 | CB | VAL | A | 160 | 32.317 | 33.542 | −2.223 | 1.00 | 32.90 | A |
| ATOM | 1174 | CG1 | VAL | A | 160 | 31.591 | 32.306 | −1.698 | 1.00 | 33.69 | A |
| ATOM | 1175 | CG2 | VAL | A | 160 | 31.429 | 34.344 | −3.162 | 1.00 | 30.05 | A |
| ATOM | 1176 | C | VAL | A | 160 | 33.574 | 33.668 | −0.045 | 1.00 | 33.60 | A |
| ATOM | 1177 | O | VAL | A | 160 | 34.608 | 33.086 | −0.375 | 1.00 | 33.21 | A |
| ATOM | 1178 | N | GLN | A | 161 | 33.105 | 33.681 | 1.204 | 1.00 | 33.10 | A |
| ATOM | 1179 | CA | GLN | A | 161 | 33.760 | 32.981 | 2.308 | 1.00 | 34.17 | A |
| ATOM | 1180 | CB | GLN | A | 161 | 33.308 | 33.587 | 3.645 | 1.00 | 33.46 | A |
| ATOM | 1181 | CG | GLN | A | 161 | 33.870 | 32.894 | 4.882 | 1.00 | 38.50 | A |
| ATOM | 1182 | CD | GLN | A | 161 | 35.384 | 33.046 | 5.024 | 1.00 | 38.34 | A |
| ATOM | 1183 | OE1 | GLN | A | 161 | 35.883 | 34.116 | 5.365 | 1.00 | 42.77 | A |
| ATOM | 1184 | NE2 | GLN | A | 161 | 36.115 | 31.972 | 4.753 | 1.00 | 40.54 | A |
| ATOM | 1185 | C | GLN | A | 161 | 33.479 | 31.470 | 2.297 | 1.00 | 33.79 | A |
| ATOM | 1186 | O | GLN | A | 161 | 34.224 | 30.684 | 2.893 | 1.00 | 33.36 | A |
| ATOM | 1187 | N | MET | A | 162 | 32.401 | 31.065 | 1.629 | 1.00 | 31.86 | A |
| ATOM | 1188 | CA | MET | A | 162 | 32.056 | 29.649 | 1.536 | 1.00 | 30.83 | A |
| ATOM | 1189 | CB | MET | A | 162 | 31.812 | 29.048 | 2.925 | 1.00 | 34.42 | A |
| ATOM | 1190 | CG | MET | A | 162 | 30.424 | 29.337 | 3.461 | 1.00 | 36.50 | A |
| ATOM | 1191 | SD | MET | A | 162 | 30.433 | 30.247 | 5.003 | 1.00 | 43.69 | A |
| ATOM | 1192 | CE | MET | A | 162 | 29.357 | 29.180 | 5.978 | 1.00 | 40.85 | A |
| ATOM | 1193 | C | MET | A | 162 | 30.804 | 29.439 | 0.694 | 1.00 | 28.08 | A |
| ATOM | 1194 | O | MET | A | 162 | 30.068 | 30.373 | 0.416 | 1.00 | 29.84 | A |
| ATOM | 1195 | N | THR | A | 163 | 30.585 | 28.200 | 0.278 | 1.00 | 27.90 | A |
| ATOM | 1196 | CA | THR | A | 163 | 29.404 | 27.862 | −0.501 | 1.00 | 28.23 | A |
| ATOM | 1197 | CB | THR | A | 163 | 29.753 | 27.471 | −1.969 | 1.00 | 28.07 | A |
| ATOM | 1198 | OG1 | THR | A | 163 | 30.534 | 26.268 | −1.981 | 1.00 | 28.96 | A |
| ATOM | 1199 | CG2 | THR | A | 163 | 30.515 | 28.579 | −2.640 | 1.00 | 28.00 | A |
| ATOM | 1200 | C | THR | A | 163 | 28.781 | 26.657 | 0.160 | 1.00 | 28.16 | A |
| ATOM | 1201 | O | THR | A | 163 | 29.440 | 25.960 | 0.938 | 1.00 | 27.88 | A |
| ATOM | 1202 | N | SER | A | 164 | 27.500 | 26.426 | −0.117 | 1.00 | 27.41 | A |
| ATOM | 1203 | CA | SER | A | 164 | 26.840 | 25.255 | 0.412 | 1.00 | 28.60 | A |
| ATOM | 1204 | CB | SER | A | 164 | 25.893 | 25.594 | 1.574 | 1.00 | 27.04 | A |
| ATOM | 1205 | OG | SER | A | 164 | 24.747 | 26.310 | 1.159 | 1.00 | 26.10 | A |
| ATOM | 1206 | C | SER | A | 164 | 26.078 | 24.620 | −0.735 | 1.00 | 28.66 | A |
| ATOM | 1207 | O | SER | A | 164 | 25.693 | 25.301 | −1.693 | 1.00 | 27.23 | A |
| ATOM | 1208 | N | MET | A | 165 | 25.909 | 23.306 | −0.630 | 1.00 | 29.00 | A |
| ATOM | 1209 | CA | MET | A | 165 | 25.199 | 22.495 | −1.606 | 1.00 | 31.67 | A |
| ATOM | 1210 | CB | MET | A | 165 | 26.157 | 21.497 | −2.263 | 1.00 | 31.92 | A |
| ATOM | 1211 | CG | MET | A | 165 | 26.990 | 22.068 | −3.396 | 1.00 | 35.54 | A |
| ATOM | 1212 | SD | MET | A | 165 | 28.324 | 23.135 | −2.843 | 1.00 | 41.52 | A |
| ATOM | 1213 | CE | MET | A | 165 | 29.438 | 21.940 | −2.325 | 1.00 | 31.41 | A |
| ATOM | 1214 | C | MET | A | 165 | 24.075 | 21.727 | −0.920 | 1.00 | 29.72 | A |
| ATOM | 1215 | O | MET | A | 165 | 24.315 | 20.961 | 0.013 | 1.00 | 27.76 | A |
| ATOM | 1216 | N | ASP | A | 166 | 22.844 | 21.947 | −1.375 | 1.00 | 30.14 | A |
| ATOM | 1217 | CA | ASP | A | 166 | 21.698 | 21.252 | −0.814 | 1.00 | 29.25 | A |
| ATOM | 1218 | CB | ASP | A | 166 | 20.522 | 22.221 | −0.637 | 1.00 | 31.09 | A |
| ATOM | 1219 | CG | ASP | A | 166 | 19.320 | 21.570 | 0.030 | 1.00 | 28.72 | A |
| ATOM | 1220 | OD1 | ASP | A | 166 | 19.106 | 20.354 | −0.163 | 1.00 | 28.28 | A |
| ATOM | 1221 | OD2 | ASP | A | 166 | 18.580 | 22.284 | 0.733 | 1.00 | 30.52 | A |
| ATOM | 1222 | C | ASP | A | 166 | 21.359 | 20.167 | −1.826 | 1.00 | 28.71 | A |
| ATOM | 1223 | O | ASP | A | 166 | 20.857 | 20.458 | −2.918 | 1.00 | 27.49 | A |
| ATOM | 1224 | N | TYR | A | 167 | 21.650 | 18.923 | −1.457 | 1.00 | 29.03 | A |
| ATOM | 1225 | CA | TYR | A | 167 | 21.433 | 17.766 | −2.319 | 1.00 | 30.30 | A |
| ATOM | 1226 | CB | TYR | A | 167 | 22.224 | 16.577 | −1.777 | 1.00 | 30.78 | A |
| ATOM | 1227 | CG | TYR | A | 167 | 23.710 | 16.837 | −1.744 | 1.00 | 30.91 | A |
| ATOM | 1228 | CD1 | TYR | A | 167 | 24.500 | 16.645 | −2.889 | 1.00 | 29.35 | A |
| ATOM | 1229 | CE1 | TYR | A | 167 | 25.854 | 16.960 | −2.888 | 1.00 | 30.22 | A |

APPENDIX 1-continued

Atomic coordinates of aromatic prenyltransferase residues 3-302 of SEQ ID NO: 2.

| ATOM | 1230 | CD2 | TYR | A | 167 | 24.320 | 17.351 | −0.597 | 1.00 | 28.48 | A |
|------|------|-----|-----|---|-----|--------|--------|--------|------|-------|---|
| ATOM | 1231 | CE2 | TYR | A | 167 | 25.676 | 17.672 | −0.591 | 1.00 | 29.07 | A |
| ATOM | 1232 | CZ | TYR | A | 167 | 26.436 | 17.475 | −1.735 | 1.00 | 28.34 | A |
| ATOM | 1233 | OH | TYR | A | 167 | 27.774 | 17.779 | −1.732 | 1.00 | 28.84 | A |
| ATOM | 1234 | C | TYR | A | 167 | 19.974 | 17.371 | −2.530 | 1.00 | 32.95 | A |
| ATOM | 1235 | O | TYR | A | 167 | 19.651 | 16.750 | −3.531 | 1.00 | 31.97 | A |
| ATOM | 1236 | N | LYS | A | 168 | 19.096 | 17.730 | −1.596 | 1.00 | 32.49 | A |
| ATOM | 1237 | CA | LYS | A | 168 | 17.678 | 17.408 | −1.731 | 1.00 | 34.77 | A |
| ATOM | 1238 | CB | LYS | A | 168 | 17.017 | 17.311 | −0.355 | 1.00 | 34.50 | A |
| ATOM | 1239 | CG | LYS | A | 168 | 17.505 | 16.127 | 0.448 | 1.00 | 35.07 | A |
| ATOM | 1240 | CD | LYS | A | 168 | 16.738 | 15.999 | 1.750 | 1.00 | 38.33 | A |
| ATOM | 1241 | CE | LYS | A | 168 | 17.052 | 14.688 | 2.438 | 1.00 | 39.81 | A |
| ATOM | 1242 | NZ | LYS | A | 168 | 16.297 | 14.561 | 3.714 | 1.00 | 41.97 | A |
| ATOM | 1243 | C | LYS | A | 168 | 16.937 | 18.427 | −2.588 | 1.00 | 33.66 | A |
| ATOM | 1244 | O | LYS | A | 168 | 16.064 | 18.070 | −3.368 | 1.00 | 35.97 | A |
| ATOM | 1245 | N | LYS | A | 169 | 17.285 | 19.696 | −2.451 | 1.00 | 33.56 | A |
| ATOM | 1246 | CA | LYS | A | 169 | 16.623 | 20.720 | −3.231 | 1.00 | 33.68 | A |
| ATOM | 1247 | CB | LYS | A | 169 | 16.364 | 21.946 | −2.357 | 1.00 | 34.85 | A |
| ATOM | 1248 | CG | LYS | A | 169 | 15.481 | 21.625 | −1.168 | 1.00 | 39.08 | A |
| ATOM | 1249 | CD | LYS | A | 169 | 15.060 | 22.866 | −0.415 | 1.00 | 42.71 | A |
| ATOM | 1250 | CE | LYS | A | 169 | 14.149 | 22.503 | 0.749 | 1.00 | 44.29 | A |
| ATOM | 1251 | NZ | LYS | A | 169 | 13.666 | 23.718 | 1.473 | 1.00 | 47.87 | A |
| ATOM | 1252 | C | LYS | A | 169 | 17.424 | 21.113 | −4.459 | 1.00 | 32.16 | A |
| ATOM | 1253 | O | LYS | A | 169 | 16.948 | 21.880 | −5.291 | 1.00 | 32.91 | A |
| ATOM | 1254 | N | ARG | A | 170 | 18.635 | 20.573 | −4.573 | 1.00 | 30.70 | A |
| ATOM | 1255 | CA | ARG | A | 170 | 19.519 | 20.889 | −5.691 | 1.00 | 31.30 | A |
| ATOM | 1256 | CB | ARG | A | 170 | 18.959 | 20.322 | −6.999 | 1.00 | 34.37 | A |
| ATOM | 1257 | CG | ARG | A | 170 | 18.911 | 18.794 | −7.048 | 1.00 | 40.86 | A |
| ATOM | 1258 | CD | ARG | A | 170 | 18.230 | 18.309 | −8.329 | 1.00 | 45.92 | A |
| ATOM | 1259 | NE | ARG | A | 170 | 18.162 | 16.848 | −8.360 | 1.00 | 51.57 | A |
| ATOM | 1260 | CZ | ARG | A | 170 | 18.496 | 16.048 | −7.350 | 1.00 | 53.83 | A |
| ATOM | 1261 | NH1 | ARG | A | 170 | 18.930 | 16.558 | −6.207 | 1.00 | 55.24 | A |
| ATOM | 1262 | NH2 | ARG | A | 170 | 18.394 | 14.733 | −7.489 | 1.00 | 55.41 | A |
| ATOM | 1263 | C | ARG | A | 170 | 19.684 | 22.403 | −5.793 | 1.00 | 30.20 | A |
| ATOM | 1264 | O | ARG | A | 170 | 19.392 | 23.012 | −6.827 | 1.00 | 27.37 | A |
| ATOM | 1265 | N | GLN | A | 171 | 20.157 | 23.006 | −4.702 | 1.00 | 27.02 | A |
| ATOM | 1266 | CA | GLN | A | 171 | 20.361 | 24.446 | −4.634 | 1.00 | 27.26 | A |
| ATOM | 1267 | CB | GLN | A | 171 | 19.271 | 25.112 | −3.784 | 1.00 | 27.34 | A |
| ATOM | 1268 | CG | GLN | A | 171 | 17.861 | 24.995 | −4.373 | 1.00 | 29.77 | A |
| ATOM | 1269 | CD | GLN | A | 171 | 16.795 | 25.663 | −3.519 | 1.00 | 31.84 | A |
| ATOM | 1270 | OE1 | GLN | A | 171 | 16.885 | 25.688 | −2.293 | 1.00 | 30.82 | A |
| ATOM | 1271 | NE2 | GLN | A | 171 | 15.762 | 26.192 | −4.171 | 1.00 | 33.68 | A |
| ATOM | 1272 | C | GLN | A | 171 | 21.731 | 24.751 | −4.044 | 1.00 | 26.95 | A |
| ATOM | 1273 | O | GLN | A | 171 | 22.286 | 23.940 | −3.303 | 1.00 | 24.99 | A |
| ATOM | 1274 | N | VAL | A | 172 | 22.264 | 25.918 | −4.397 | 1.00 | 26.41 | A |
| ATOM | 1275 | CA | VAL | A | 172 | 23.573 | 26.369 | −3.936 | 1.00 | 29.58 | A |
| ATOM | 1276 | CB | VAL | A | 172 | 24.593 | 26.436 | −5.114 | 1.00 | 27.24 | A |
| ATOM | 1277 | CG1 | VAL | A | 172 | 25.931 | 26.995 | −4.627 | 1.00 | 28.16 | A |
| ATOM | 1278 | CG2 | VAL | A | 172 | 24.802 | 25.061 | −5.703 | 1.00 | 27.97 | A |
| ATOM | 1279 | C | VAL | A | 172 | 23.476 | 27.761 | −3.309 | 1.00 | 30.14 | A |
| ATOM | 1280 | O | VAL | A | 172 | 22.788 | 28.645 | −3.836 | 1.00 | 32.05 | A |
| ATOM | 1281 | N | ASN | A | 173 | 24.153 | 27.941 | −2.176 | 1.00 | 29.48 | A |
| ATOM | 1282 | CA | ASN | A | 173 | 24.182 | 29.228 | −1.490 | 1.00 | 27.27 | A |
| ATOM | 1283 | CB | ASN | A | 173 | 23.887 | 29.074 | 0.014 | 1.00 | 29.16 | A |
| ATOM | 1284 | CG | ASN | A | 173 | 22.423 | 28.831 | 0.308 | 1.00 | 28.68 | A |
| ATOM | 1285 | OD1 | ASN | A | 173 | 21.594 | 28.860 | −0.595 | 1.00 | 27.97 | A |
| ATOM | 1286 | ND2 | ASN | A | 173 | 22.094 | 28.599 | 1.591 | 1.00 | 26.44 | A |
| ATOM | 1287 | C | ASN | A | 173 | 25.588 | 29.809 | −1.639 | 1.00 | 27.49 | A |
| ATOM | 1288 | O | ASN | A | 173 | 26.572 | 29.080 | −1.523 | 1.00 | 27.57 | A |
| ATOM | 1289 | N | LEU | A | 174 | 25.672 | 31.109 | −1.907 | 1.00 | 26.38 | A |
| ATOM | 1290 | CA | LEU | A | 174 | 26.961 | 31.793 | −2.011 | 1.00 | 27.88 | A |
| ATOM | 1291 | CB | LEU | A | 174 | 27.047 | 32.605 | −3.308 | 1.00 | 29.77 | A |
| ATOM | 1292 | CG | LEU | A | 174 | 26.831 | 31.854 | −4.631 | 1.00 | 29.34 | A |
| ATOM | 1293 | CD1 | LEU | A | 174 | 27.115 | 32.800 | −5.784 | 1.00 | 30.72 | A |
| ATOM | 1294 | CD2 | LEU | A | 174 | 27.750 | 30.647 | −4.718 | 1.00 | 29.99 | A |
| ATOM | 1295 | C | LEU | A | 174 | 27.041 | 32.735 | −0.810 | 1.00 | 27.33 | A |
| ATOM | 1296 | O | LEU | A | 174 | 26.324 | 33.737 | −0.749 | 1.00 | 24.91 | A |
| ATOM | 1297 | N | TYR | A | 175 | 27.906 | 32.420 | 0.151 | 1.00 | 27.35 | A |
| ATOM | 1298 | CA | TYR | A | 175 | 28.023 | 33.266 | 1.330 | 1.00 | 28.53 | A |
| ATOM | 1299 | CB | TYR | A | 175 | 28.377 | 32.420 | 2.565 | 1.00 | 26.66 | A |
| ATOM | 1300 | CG | TYR | A | 175 | 27.343 | 31.347 | 2.890 | 1.00 | 28.27 | A |
| ATOM | 1301 | CD1 | TYR | A | 175 | 27.339 | 30.115 | 2.229 | 1.00 | 28.80 | A |
| ATOM | 1302 | CE1 | TYR | A | 175 | 26.352 | 29.150 | 2.496 | 1.00 | 29.04 | A |
| ATOM | 1303 | CD2 | TYR | A | 175 | 26.340 | 31.588 | 3.826 | 1.00 | 29.47 | A |
| ATOM | 1304 | CE2 | TYR | A | 175 | 25.355 | 30.642 | 4.094 | 1.00 | 29.90 | A |
| ATOM | 1305 | CZ | TYR | A | 175 | 25.360 | 29.432 | 3.433 | 1.00 | 30.82 | A |
| ATOM | 1306 | OH | TYR | A | 175 | 24.358 | 28.522 | 3.702 | 1.00 | 28.60 | A |

APPENDIX 1-continued

Atomic coordinates of aromatic prenyltransferase residues 3-302 of SEQ ID NO: 2.

| ATOM | 1307 | C | TYR | A | 175 | 29.043 | 34.380 | 1.109 | 1.00 | 28.09 | A |
|------|------|------|-----|---|-----|--------|--------|--------|------|-------|---|
| ATOM | 1308 | O | TYR | A | 175 | 30.239 | 34.182 | 1.298 | 1.00 | 31.10 | A |
| ATOM | 1309 | N | PHE | A | 176 | 28.550 | 35.551 | 0.704 | 1.00 | 27.31 | A |
| ATOM | 1310 | CA | PHE | A | 176 | 29.393 | 36.714 | 0.444 | 1.00 | 28.26 | A |
| ATOM | 1311 | CB | PHE | A | 176 | 28.622 | 37.774 | −0.341 | 1.00 | 27.28 | A |
| ATOM | 1312 | CG | PHE | A | 176 | 28.354 | 37.387 | −1.772 | 1.00 | 27.93 | A |
| ATOM | 1313 | CD1 | PHE | A | 176 | 27.081 | 36.992 | −2.173 | 1.00 | 28.47 | A |
| ATOM | 1314 | CD2 | PHE | A | 176 | 29.373 | 37.435 | −2.719 | 1.00 | 28.88 | A |
| ATOM | 1315 | CE1 | PHE | A | 176 | 26.822 | 36.650 | −3.511 | 1.00 | 29.48 | A |
| ATOM | 1316 | CE2 | PHE | A | 176 | 29.126 | 37.096 | −4.062 | 1.00 | 28.83 | A |
| ATOM | 1317 | CZ | PHE | A | 176 | 27.848 | 36.704 | −4.452 | 1.00 | 28.88 | A |
| ATOM | 1318 | C | PHE | A | 176 | 29.916 | 37.315 | 1.744 | 1.00 | 29.45 | A |
| ATOM | 1319 | O | PHE | A | 176 | 29.180 | 37.418 | 2.734 | 1.00 | 27.17 | A |
| ATOM | 1320 | N | SER | A | 177 | 31.184 | 37.726 | 1.722 | 1.00 | 30.00 | A |
| ATOM | 1321 | CA | SER | A | 177 | 31.841 | 38.281 | 2.910 | 1.00 | 31.18 | A |
| ATOM | 1322 | CB | SER | A | 177 | 32.876 | 37.270 | 3.419 | 1.00 | 30.63 | A |
| ATOM | 1323 | OG | SER | A | 177 | 33.179 | 37.472 | 4.786 | 1.00 | 31.80 | A |
| ATOM | 1324 | C | SER | A | 177 | 32.516 | 39.631 | 2.637 | 1.00 | 32.16 | A |
| ATOM | 1325 | O | SER | A | 177 | 32.466 | 40.149 | 1.513 | 1.00 | 31.15 | A |
| ATOM | 1326 | N | GLU | A | 178 | 33.161 | 40.188 | 3.663 | 1.00 | 32.64 | A |
| ATOM | 1327 | CA | GLU | A | 178 | 33.822 | 41.485 | 3.542 | 1.00 | 33.04 | A |
| ATOM | 1328 | CB | GLU | A | 178 | 35.134 | 41.352 | 2.743 | 1.00 | 35.78 | A |
| ATOM | 1329 | CG | GLU | A | 178 | 36.116 | 40.349 | 3.361 | 1.00 | 36.71 | A |
| ATOM | 1330 | CD | GLU | A | 178 | 37.519 | 40.402 | 2.759 | 1.00 | 37.67 | A |
| ATOM | 1331 | OE1 | GLU | A | 178 | 37.654 | 40.565 | 1.521 | 1.00 | 36.25 | A |
| ATOM | 1332 | OE2 | GLU | A | 178 | 38.490 | 40.259 | 3.535 | 1.00 | 37.28 | A |
| ATOM | 1333 | C | GLU | A | 178 | 32.866 | 42.458 | 2.856 | 1.00 | 33.20 | A |
| ATOM | 1334 | O | GLU | A | 178 | 33.208 | 43.106 | 1.860 | 1.00 | 35.37 | A |
| ATOM | 1335 | N | LEU | A | 179 | 31.653 | 42.548 | 3.395 | 1.00 | 32.06 | A |
| ATOM | 1336 | CA | LEU | A | 179 | 30.623 | 43.422 | 2.843 | 1.00 | 32.29 | A |
| ATOM | 1337 | CB | LEU | A | 179 | 29.261 | 43.035 | 3.417 | 1.00 | 31.59 | A |
| ATOM | 1338 | CG | LEU | A | 179 | 28.898 | 41.550 | 3.303 | 1.00 | 32.74 | A |
| ATOM | 1339 | CD1 | LEU | A | 179 | 27.623 | 41.288 | 4.080 | 1.00 | 34.49 | A |
| ATOM | 1340 | CD2 | LEU | A | 179 | 28.736 | 41.160 | 1.826 | 1.00 | 32.26 | A |
| ATOM | 1341 | C | LEU | A | 179 | 30.889 | 44.900 | 3.128 | 1.00 | 33.85 | A |
| ATOM | 1342 | O | LEU | A | 179 | 31.072 | 45.295 | 4.282 | 1.00 | 33.79 | A |
| ATOM | 1343 | N | SER | A | 180 | 30.905 | 45.717 | 2.078 | 1.00 | 34.71 | A |
| ATOM | 1344 | CA | SER | A | 180 | 31.132 | 47.149 | 2.240 | 1.00 | 36.87 | A |
| ATOM | 1345 | CB | SER | A | 180 | 31.390 | 47.821 | 0.890 | 1.00 | 38.51 | A |
| ATOM | 1346 | OG | SER | A | 180 | 30.177 | 48.062 | 0.205 | 1.00 | 41.84 | A |
| ATOM | 1347 | C | SER | A | 180 | 29.888 | 47.770 | 2.864 | 1.00 | 38.21 | A |
| ATOM | 1348 | O | SER | A | 180 | 28.784 | 47.236 | 2.723 | 1.00 | 35.22 | A |
| ATOM | 1349 | N | ALA | A | 181 | 30.073 | 48.898 | 3.544 | 1.00 | 37.72 | A |
| ATOM | 1350 | CA | ALA | A | 181 | 28.969 | 49.597 | 4.188 | 1.00 | 39.03 | A |
| ATOM | 1351 | CB | ALA | A | 181 | 29.487 | 50.855 | 4.886 | 1.00 | 37.87 | A |
| ATOM | 1352 | C | ALA | A | 181 | 27.901 | 49.968 | 3.166 | 1.00 | 39.40 | A |
| ATOM | 1353 | O | ALA | A | 181 | 26.701 | 49.909 | 3.449 | 1.00 | 39.97 | A |
| ATOM | 1354 | N | GLN | A | 182 | 28.342 | 50.337 | 1.971 | 1.00 | 38.70 | A |
| ATOM | 1355 | CA | GLN | A | 182 | 27.419 | 50.733 | 0.918 | 1.00 | 39.60 | A |
| ATOM | 1356 | CB | GLN | A | 182 | 28.192 | 51.136 | −0.336 | 1.00 | 40.99 | A |
| ATOM | 1357 | CG | GLN | A | 182 | 27.303 | 51.450 | −1.522 | 1.00 | 45.59 | A |
| ATOM | 1358 | CD | GLN | A | 182 | 27.915 | 52.474 | −2.455 | 1.00 | 46.88 | A |
| ATOM | 1359 | OE1 | GLN | A | 182 | 29.124 | 52.485 | −2.683 | 1.00 | 51.04 | A |
| ATOM | 1360 | NE2 | GLN | A | 182 | 27.075 | 53.336 | −3.013 | 1.00 | 49.22 | A |
| ATOM | 1361 | C | GLN | A | 182 | 26.430 | 49.634 | 0.580 | 1.00 | 39.40 | A |
| ATOM | 1362 | O | GLN | A | 182 | 25.218 | 49.869 | 0.548 | 1.00 | 40.56 | A |
| ATOM | 1363 | N | THR | A | 183 | 26.951 | 48.435 | 0.330 | 1.00 | 38.08 | A |
| ATOM | 1364 | CA | THR | A | 183 | 26.125 | 47.284 | −0.006 | 1.00 | 36.74 | A |
| ATOM | 1365 | CB | THR | A | 183 | 26.980 | 45.990 | −0.097 | 1.00 | 36.40 | A |
| ATOM | 1366 | OG1 | THR | A | 183 | 27.950 | 46.122 | −1.146 | 1.00 | 36.47 | A |
| ATOM | 1367 | CG2 | THR | A | 183 | 26.098 | 44.789 | −0.378 | 1.00 | 34.06 | A |
| ATOM | 1368 | C | THR | A | 183 | 25.003 | 47.045 | 1.005 | 1.00 | 36.17 | A |
| ATOM | 1369 | O | THR | A | 183 | 23.900 | 46.661 | 0.627 | 1.00 | 35.97 | A |
| ATOM | 1370 | N | LEU | A | 184 | 25.282 | 47.278 | 2.284 | 1.00 | 35.23 | A |
| ATOM | 1371 | CA | LEU | A | 184 | 24.287 | 47.051 | 3.327 | 1.00 | 35.08 | A |
| ATOM | 1372 | CB | LEU | A | 184 | 24.969 | 46.532 | 4.598 | 1.00 | 34.37 | A |
| ATOM | 1373 | CG | LEU | A | 184 | 25.642 | 45.161 | 4.475 | 1.00 | 32.38 | A |
| ATOM | 1374 | CD1 | LEU | A | 184 | 26.367 | 44.840 | 5.767 | 1.00 | 34.20 | A |
| ATOM | 1375 | CD2 | LEU | A | 184 | 24.609 | 44.089 | 4.153 | 1.00 | 31.86 | A |
| ATOM | 1376 | C | LEU | A | 184 | 23.397 | 48.241 | 3.681 | 1.00 | 37.71 | A |
| ATOM | 1377 | O | LEU | A | 184 | 22.552 | 48.128 | 4.574 | 1.00 | 36.83 | A |
| ATOM | 1378 | N | GLU | A | 185 | 23.577 | 49.375 | 3.007 | 1.00 | 37.02 | A |
| ATOM | 1379 | CA | GLU | A | 185 | 22.726 | 50.525 | 3.296 | 1.00 | 39.60 | A |
| ATOM | 1380 | CB | GLU | A | 185 | 23.325 | 51.831 | 2.771 | 1.00 | 42.09 | A |
| ATOM | 1381 | CG | GLU | A | 185 | 24.105 | 52.608 | 3.819 | 1.00 | 47.09 | A |
| ATOM | 1382 | CD | GLU | A | 185 | 23.375 | 52.699 | 5.158 | 1.00 | 49.21 | A |
| ATOM | 1383 | OE1 | GLU | A | 185 | 22.140 | 52.931 | 5.168 | 1.00 | 50.57 | A |

APPENDIX 1-continued

Atomic coordinates of aromatic prenyltransferase residues 3-302 of SEQ ID NO: 2.

| ATOM | 1384 | OE2 | GLU | A | 185 | 24.040 | 52.546 | 6.206 | 1.00 | 48.86 | A |
|---|---|---|---|---|---|---|---|---|---|---|---|
| ATOM | 1385 | C | GLU | A | 185 | 21.369 | 50.296 | 2.660 | 1.00 | 37.48 | A |
| ATOM | 1386 | O | GLU | A | 185 | 21.261 | 49.592 | 1.656 | 1.00 | 35.55 | A |
| ATOM | 1387 | N | ALA | A | 186 | 20.342 | 50.898 | 3.257 | 1.00 | 37.32 | A |
| ATOM | 1388 | CA | ALA | A | 186 | 18.965 | 50.754 | 2.795 | 1.00 | 35.80 | A |
| ATOM | 1389 | CB | ALA | A | 186 | 18.073 | 51.738 | 3.535 | 1.00 | 35.92 | A |
| ATOM | 1390 | C | ALA | A | 186 | 18.777 | 50.915 | 1.290 | 1.00 | 36.43 | A |
| ATOM | 1391 | O | ALA | A | 186 | 18.143 | 50.080 | 0.645 | 1.00 | 34.72 | A |
| ATOM | 1392 | N | GLU | A | 187 | 19.316 | 51.995 | 0.734 | 1.00 | 37.69 | A |
| ATOM | 1393 | CA | GLU | A | 187 | 19.183 | 52.254 | −0.690 | 1.00 | 38.57 | A |
| ATOM | 1394 | CB | GLU | A | 187 | 19.920 | 53.549 | −1.042 | 1.00 | 42.29 | A |
| ATOM | 1395 | CG | GLU | A | 187 | 20.121 | 53.794 | −2.529 | 1.00 | 46.35 | A |
| ATOM | 1396 | CD | GLU | A | 187 | 20.874 | 55.089 | −2.798 | 1.00 | 48.77 | A |
| ATOM | 1397 | OE1 | GLU | A | 187 | 20.265 | 56.173 | −2.642 | 1.00 | 51.07 | A |
| ATOM | 1398 | OE2 | GLU | A | 187 | 22.075 | 55.019 | −3.149 | 1.00 | 49.51 | A |
| ATOM | 1399 | C | GLU | A | 187 | 19.697 | 51.092 | −1.536 | 1.00 | 37.10 | A |
| ATOM | 1400 | O | GLU | A | 187 | 19.036 | 50.672 | −2.482 | 1.00 | 36.07 | A |
| ATOM | 1401 | N | SER | A | 188 | 20.874 | 50.580 | −1.195 | 1.00 | 36.10 | A |
| ATOM | 1402 | CA | SER | A | 188 | 21.476 | 49.461 | −1.914 | 1.00 | 34.79 | A |
| ATOM | 1403 | CB | SER | A | 188 | 22.916 | 49.240 | −1.439 | 1.00 | 35.13 | A |
| ATOM | 1404 | OG | SER | A | 188 | 23.412 | 47.986 | −1.888 | 1.00 | 42.19 | A |
| ATOM | 1405 | C | SER | A | 188 | 20.685 | 48.161 | −1.749 | 1.00 | 33.67 | A |
| ATOM | 1406 | O | SER | A | 188 | 20.430 | 47.450 | −2.725 | 1.00 | 32.43 | A |
| ATOM | 1407 | N | VAL | A | 189 | 20.308 | 47.846 | −0.512 | 1.00 | 32.53 | A |
| ATOM | 1408 | CA | VAL | A | 189 | 19.548 | 46.633 | −0.241 | 1.00 | 33.25 | A |
| ATOM | 1409 | CB | VAL | A | 189 | 19.229 | 46.498 | 1.269 | 1.00 | 34.36 | A |
| ATOM | 1410 | CG1 | VAL | A | 189 | 18.267 | 45.345 | 1.500 | 1.00 | 32.73 | A |
| ATOM | 1411 | CG2 | VAL | A | 189 | 20.512 | 46.259 | 2.052 | 1.00 | 35.61 | A |
| ATOM | 1412 | C | VAL | A | 189 | 18.240 | 46.610 | −1.032 | 1.00 | 32.13 | A |
| ATOM | 1413 | O | VAL | A | 189 | 17.916 | 45.611 | −1.660 | 1.00 | 31.84 | A |
| ATOM | 1414 | N | LEU | A | 190 | 17.495 | 47.714 | −1.005 | 1.00 | 32.08 | A |
| ATOM | 1415 | CA | LEU | A | 190 | 16.220 | 47.798 | −1.718 | 1.00 | 32.32 | A |
| ATOM | 1416 | CB | LEU | A | 190 | 15.539 | 49.139 | −1.426 | 1.00 | 33.11 | A |
| ATOM | 1417 | CG | LEU | A | 190 | 14.876 | 49.287 | −0.052 | 1.00 | 32.87 | A |
| ATOM | 1418 | CD1 | LEU | A | 190 | 14.378 | 50.724 | 0.120 | 1.00 | 33.09 | A |
| ATOM | 1419 | CD2 | LEU | A | 190 | 13.713 | 48.304 | 0.071 | 1.00 | 31.45 | A |
| ATOM | 1420 | C | LEU | A | 190 | 16.362 | 47.618 | −3.229 | 1.00 | 33.42 | A |
| ATOM | 1421 | O | LEU | A | 190 | 15.555 | 46.936 | −3.855 | 1.00 | 33.09 | A |
| ATOM | 1422 | N | ALA | A | 191 | 17.379 | 48.238 | −3.816 | 1.00 | 33.70 | A |
| ATOM | 1423 | CA | ALA | A | 191 | 17.600 | 48.113 | −5.251 | 1.00 | 34.39 | A |
| ATOM | 1424 | CB | ALA | A | 191 | 18.766 | 48.987 | −5.681 | 1.00 | 36.16 | A |
| ATOM | 1425 | C | ALA | A | 191 | 17.886 | 46.656 | −5.576 | 1.00 | 35.14 | A |
| ATOM | 1426 | O | ALA | A | 191 | 17.399 | 46.122 | −6.572 | 1.00 | 36.27 | A |
| ATOM | 1427 | N | LEU | A | 192 | 18.674 | 46.012 | −4.718 | 1.00 | 36.49 | A |
| ATOM | 1428 | CA | LEU | A | 192 | 19.023 | 44.612 | −4.902 | 1.00 | 34.74 | A |
| ATOM | 1429 | CB | LEU | A | 192 | 20.024 | 44.165 | −3.830 | 1.00 | 34.60 | A |
| ATOM | 1430 | CG | LEU | A | 192 | 20.375 | 42.671 | −3.754 | 1.00 | 34.43 | A |
| ATOM | 1431 | CD1 | LEU | A | 192 | 20.924 | 42.176 | −5.084 | 1.00 | 33.47 | A |
| ATOM | 1432 | CD2 | LEU | A | 192 | 21.394 | 42.451 | −2.645 | 1.00 | 34.05 | A |
| ATOM | 1433 | C | LEU | A | 192 | 17.782 | 43.727 | −4.858 | 1.00 | 35.29 | A |
| ATOM | 1434 | O | LEU | A | 192 | 17.570 | 42.927 | −5.767 | 1.00 | 33.59 | A |
| ATOM | 1435 | N | VAL | A | 193 | 16.962 | 43.865 | −3.816 | 1.00 | 35.74 | A |
| ATOM | 1436 | CA | VAL | A | 193 | 15.763 | 43.039 | −3.717 | 1.00 | 38.00 | A |
| ATOM | 1437 | CB | VAL | A | 193 | 14.985 | 43.274 | −2.395 | 1.00 | 37.63 | A |
| ATOM | 1438 | CG1 | VAL | A | 193 | 15.920 | 43.105 | −1.201 | 1.00 | 39.87 | A |
| ATOM | 1439 | CG2 | VAL | A | 193 | 14.351 | 44.634 | −2.389 | 1.00 | 37.77 | A |
| ATOM | 1440 | C | VAL | A | 193 | 14.837 | 43.327 | −4.887 | 1.00 | 38.50 | A |
| ATOM | 1441 | O | VAL | A | 193 | 14.280 | 42.413 | −5.483 | 1.00 | 38.16 | A |
| ATOM | 1442 | N | ARG | A | 194 | 14.677 | 44.604 | −5.207 | 1.00 | 40.37 | A |
| ATOM | 1443 | CA | ARG | A | 194 | 13.830 | 45.019 | −6.314 | 1.00 | 43.28 | A |
| ATOM | 1444 | CB | ARG | A | 194 | 13.899 | 46.549 | −6.461 | 1.00 | 45.33 | A |
| ATOM | 1445 | CG | ARG | A | 194 | 12.637 | 47.237 | −6.974 | 1.00 | 50.72 | A |
| ATOM | 1446 | CD | ARG | A | 194 | 12.881 | 48.130 | −8.183 | 1.00 | 54.41 | A |
| ATOM | 1447 | NE | ARG | A | 194 | 11.661 | 48.393 | −8.942 | 1.00 | 57.37 | A |
| ATOM | 1448 | CZ | ARG | A | 194 | 10.458 | 48.505 | −8.389 | 1.00 | 59.05 | A |
| ATOM | 1449 | NH1 | ARG | A | 194 | 10.317 | 48.368 | −7.079 | 1.00 | 61.10 | A |
| ATOM | 1450 | NH2 | ARG | A | 194 | 9.398 | 48.773 | −9.140 | 1.00 | 61.23 | A |
| ATOM | 1451 | C | ARG | A | 194 | 14.283 | 44.305 | −7.588 | 1.00 | 41.65 | A |
| ATOM | 1452 | O | ARG | A | 194 | 13.481 | 43.683 | −8.280 | 1.00 | 41.71 | A |
| ATOM | 1453 | N | GLU | A | 195 | 15.576 | 44.360 | −7.877 | 1.00 | 41.34 | A |
| ATOM | 1454 | CA | GLU | A | 195 | 16.094 | 43.713 | −9.070 | 1.00 | 41.44 | A |
| ATOM | 1455 | CB | GLU | A | 195 | 17.565 | 44.071 | −9.264 | 1.00 | 43.69 | A |
| ATOM | 1456 | CG | GLU | A | 195 | 17.882 | 44.479 | −10.693 | 1.00 | 46.31 | A |
| ATOM | 1457 | CD | GLU | A | 195 | 19.346 | 44.778 | −10.911 | 1.00 | 45.36 | A |
| ATOM | 1458 | OE1 | GLU | A | 195 | 19.879 | 45.680 | −10.233 | 1.00 | 45.90 | A |
| ATOM | 1459 | OE2 | GLU | A | 195 | 19.960 | 44.107 | −11.765 | 1.00 | 46.65 | A |
| ATOM | 1460 | C | GLU | A | 195 | 15.925 | 42.189 | −9.052 | 1.00 | 41.97 | A |

APPENDIX 1-continued

Atomic coordinates of aromatic prenyltransferase residues 3-302 of SEQ ID NO: 2.

| ATOM | 1461 | O | GLU | A | 195 | 15.700 | 41.577 | −10.097 | 1.00 | 41.48 | A |
|---|---|---|---|---|---|---|---|---|---|---|---|
| ATOM | 1462 | N | LEU | A | 196 | 16.032 | 41.576 | −7.874 | 1.00 | 40.20 | A |
| ATOM | 1463 | CA | LEU | A | 196 | 15.878 | 40.126 | −7.762 | 1.00 | 38.53 | A |
| ATOM | 1464 | CB | LEU | A | 196 | 16.686 | 39.590 | −6.570 | 1.00 | 36.27 | A |
| ATOM | 1465 | CG | LEU | A | 196 | 18.212 | 39.731 | −6.649 | 1.00 | 37.41 | A |
| ATOM | 1466 | CD1 | LEU | A | 196 | 18.852 | 39.207 | −5.371 | 1.00 | 36.85 | A |
| ATOM | 1467 | CD2 | LEU | A | 196 | 18.740 | 38.969 | −7.855 | 1.00 | 37.56 | A |
| ATOM | 1468 | C | LEU | A | 196 | 14.399 | 39.753 | −7.608 | 1.00 | 38.13 | A |
| ATOM | 1469 | O | LEU | A | 196 | 14.047 | 38.576 | −7.509 | 1.00 | 38.58 | A |
| ATOM | 1470 | N | GLY | A | 197 | 13.541 | 40.768 | −7.590 | 1.00 | 38.66 | A |
| ATOM | 1471 | CA | GLY | A | 197 | 12.112 | 40.537 | −7.458 | 1.00 | 38.24 | A |
| ATOM | 1472 | C | GLY | A | 197 | 11.712 | 39.891 | −6.149 | 1.00 | 38.25 | A |
| ATOM | 1473 | O | GLY | A | 197 | 10.833 | 39.028 | −6.121 | 1.00 | 38.47 | A |
| ATOM | 1474 | N | LEU | A | 198 | 12.334 | 40.318 | −5.055 | 1.00 | 37.09 | A |
| ATOM | 1475 | CA | LEU | A | 198 | 12.031 | 39.733 | −3.756 | 1.00 | 36.88 | A |
| ATOM | 1476 | CB | LEU | A | 198 | 13.340 | 39.324 | −3.065 | 1.00 | 35.42 | A |
| ATOM | 1477 | CG | LEU | A | 198 | 14.267 | 38.410 | −3.874 | 1.00 | 36.31 | A |
| ATOM | 1478 | CD1 | LEU | A | 198 | 15.612 | 38.284 | −3.170 | 1.00 | 37.54 | A |
| ATOM | 1479 | CD2 | LEU | A | 198 | 13.631 | 37.037 | −4.050 | 1.00 | 36.41 | A |
| ATOM | 1480 | C | LEU | A | 198 | 11.211 | 40.629 | −2.827 | 1.00 | 36.62 | A |
| ATOM | 1481 | O | LEU | A | 198 | 11.042 | 41.829 | −3.064 | 1.00 | 33.54 | A |
| ATOM | 1482 | N | HIS | A | 199 | 10.707 | 40.025 | −1.759 | 1.00 | 36.58 | A |
| ATOM | 1483 | CA | HIS | A | 199 | 9.918 | 40.738 | −0.763 | 1.00 | 37.83 | A |
| ATOM | 1484 | CB | HIS | A | 199 | 9.667 | 39.833 | 0.440 | 1.00 | 39.68 | A |
| ATOM | 1485 | CG | HIS | A | 199 | 8.795 | 40.447 | 1.487 | 1.00 | 39.54 | A |
| ATOM | 1486 | CD2 | HIS | A | 199 | 9.094 | 40.986 | 2.692 | 1.00 | 41.01 | A |
| ATOM | 1487 | ND1 | HIS | A | 199 | 7.429 | 40.549 | 1.348 | 1.00 | 42.14 | A |
| ATOM | 1488 | CE1 | HIS | A | 199 | 6.921 | 41.121 | 2.426 | 1.00 | 42.34 | A |
| ATOM | 1489 | NE2 | HIS | A | 199 | 7.911 | 41.396 | 3.257 | 1.00 | 43.77 | A |
| ATOM | 1490 | C | HIS | A | 199 | 10.650 | 41.992 | −0.296 | 1.00 | 38.39 | A |
| ATOM | 1491 | O | HIS | A | 199 | 11.845 | 41.950 | 0.012 | 1.00 | 38.41 | A |
| ATOM | 1492 | N | VAL | A | 200 | 9.928 | 43.107 | −0.246 | 1.00 | 37.60 | A |
| ATOM | 1493 | CA | VAL | A | 200 | 10.506 | 44.367 | 0.188 | 1.00 | 37.98 | A |
| ATOM | 1494 | CB | VAL | A | 200 | 9.689 | 45.569 | −0.348 | 1.00 | 38.84 | A |
| ATOM | 1495 | CG1 | VAL | A | 200 | 10.254 | 46.869 | 0.201 | 1.00 | 39.30 | A |
| ATOM | 1496 | CG2 | VAL | A | 200 | 9.709 | 45.578 | −1.878 | 1.00 | 39.44 | A |
| ATOM | 1497 | C | VAL | A | 200 | 10.537 | 44.447 | 1.714 | 1.00 | 38.23 | A |
| ATOM | 1498 | O | VAL | A | 200 | 9.506 | 44.353 | 2.369 | 1.00 | 37.38 | A |
| ATOM | 1499 | N | PRO | A | 201 | 11.734 | 44.604 | 2.302 | 1.00 | 38.40 | A |
| ATOM | 1500 | CD | PRO | A | 201 | 13.070 | 44.490 | 1.687 | 1.00 | 36.88 | A |
| ATOM | 1501 | CA | PRO | A | 201 | 11.835 | 44.694 | 3.761 | 1.00 | 38.03 | A |
| ATOM | 1502 | CB | PRO | A | 201 | 13.306 | 44.377 | 4.012 | 1.00 | 39.05 | A |
| ATOM | 1503 | CG | PRO | A | 201 | 13.971 | 44.949 | 2.792 | 1.00 | 37.38 | A |
| ATOM | 1504 | C | PRO | A | 201 | 11.436 | 46.091 | 4.252 | 1.00 | 39.00 | A |
| ATOM | 1505 | O | PRO | A | 201 | 11.552 | 47.068 | 3.516 | 1.00 | 38.29 | A |
| ATOM | 1506 | N | ASN | A | 202 | 10.947 | 46.191 | 5.483 | 1.00 | 38.73 | A |
| ATOM | 1507 | CA | ASN | A | 202 | 10.564 | 47.492 | 6.007 | 1.00 | 38.53 | A |
| ATOM | 1508 | CB | ASN | A | 202 | 9.273 | 47.393 | 6.827 | 1.00 | 37.55 | A |
| ATOM | 1509 | CG | ASN | A | 202 | 9.323 | 46.302 | 7.861 | 1.00 | 36.97 | A |
| ATOM | 1510 | OD1 | ASN | A | 202 | 10.368 | 46.051 | 8.463 | 1.00 | 34.21 | A |
| ATOM | 1511 | ND2 | ASN | A | 202 | 8.183 | 45.650 | 8.090 | 1.00 | 35.55 | A |
| ATOM | 1512 | C | ASN | A | 202 | 11.687 | 48.072 | 6.857 | 1.00 | 39.15 | A |
| ATOM | 1513 | O | ASN | A | 202 | 12.798 | 47.539 | 6.877 | 1.00 | 38.30 | A |
| ATOM | 1514 | N | GLU | A | 203 | 11.392 | 49.161 | 7.561 | 1.00 | 38.76 | A |
| ATOM | 1515 | CA | GLU | A | 203 | 12.386 | 49.835 | 8.391 | 1.00 | 41.10 | A |
| ATOM | 1516 | CB | GLU | A | 203 | 11.727 | 50.944 | 9.212 | 1.00 | 44.04 | A |
| ATOM | 1517 | CG | GLU | A | 203 | 12.689 | 52.040 | 9.638 | 1.00 | 49.57 | A |
| ATOM | 1518 | CD | GLU | A | 203 | 12.048 | 53.040 | 10.584 | 1.00 | 52.76 | A |
| ATOM | 1519 | OE1 | GLU | A | 203 | 10.873 | 53.402 | 10.362 | 1.00 | 54.28 | A |
| ATOM | 1520 | OE2 | GLU | A | 203 | 12.722 | 53.470 | 11.543 | 1.00 | 54.88 | A |
| ATOM | 1521 | C | GLU | A | 203 | 13.128 | 48.889 | 9.328 | 1.00 | 39.75 | A |
| ATOM | 1522 | O | GLU | A | 203 | 14.353 | 48.941 | 9.434 | 1.00 | 38.21 | A |
| ATOM | 1523 | N | LEU | A | 204 | 12.383 | 48.028 | 10.006 | 1.00 | 38.08 | A |
| ATOM | 1524 | CA | LEU | A | 204 | 12.984 | 47.081 | 10.932 | 1.00 | 37.43 | A |
| ATOM | 1525 | CB | LEU | A | 204 | 11.884 | 46.297 | 11.649 | 1.00 | 39.35 | A |
| ATOM | 1526 | CG | LEU | A | 204 | 12.342 | 45.230 | 12.644 | 1.00 | 41.12 | A |
| ATOM | 1527 | CD1 | LEU | A | 204 | 13.153 | 45.882 | 13.753 | 1.00 | 41.94 | A |
| ATOM | 1528 | CD2 | LEU | A | 204 | 11.131 | 44.512 | 13.218 | 1.00 | 43.55 | A |
| ATOM | 1529 | C | LEU | A | 204 | 13.922 | 46.121 | 10.195 | 1.00 | 37.20 | A |
| ATOM | 1530 | O | LEU | A | 204 | 15.060 | 45.897 | 10.624 | 1.00 | 36.41 | A |
| ATOM | 1531 | N | GLY | A | 205 | 13.438 | 45.561 | 9.086 | 1.00 | 34.65 | A |
| ATOM | 1532 | CA | GLY | A | 205 | 14.240 | 44.634 | 8.303 | 1.00 | 35.07 | A |
| ATOM | 1533 | C | GLY | A | 205 | 15.512 | 45.257 | 7.756 | 1.00 | 34.00 | A |
| ATOM | 1534 | O | GLY | A | 205 | 16.577 | 44.628 | 7.753 | 1.00 | 33.65 | A |
| ATOM | 1535 | N | LEU | A | 206 | 15.408 | 46.500 | 7.297 | 1.00 | 34.66 | A |
| ATOM | 1536 | CA | LEU | A | 206 | 16.559 | 47.201 | 6.734 | 1.00 | 35.09 | A |
| ATOM | 1537 | CB | LEU | A | 206 | 16.095 | 48.464 | 6.012 | 1.00 | 36.03 | A |

APPENDIX 1-continued

Atomic coordinates of aromatic prenyltransferase residues 3-302 of SEQ ID NO: 2.

| ATOM | 1538 | CG | LEU | A | 206 | 15.387 | 48.179 | 4.679 | 1.00 | 33.49 | A |
|------|------|-----|-----|---|-----|--------|--------|--------|------|-------|---|
| ATOM | 1539 | CD1 | LEU | A | 206 | 14.670 | 49.426 | 4.182 | 1.00 | 33.05 | A |
| ATOM | 1540 | CD2 | LEU | A | 206 | 16.404 | 47.701 | 3.662 | 1.00 | 32.40 | A |
| ATOM | 1541 | C | LEU | A | 206 | 17.616 | 47.532 | 7.782 | 1.00 | 36.87 | A |
| ATOM | 1542 | O | LEU | A | 206 | 18.821 | 47.468 | 7.505 | 1.00 | 36.00 | A |
| ATOM | 1543 | N | LYS | A | 207 | 17.168 | 47.878 | 8.987 | 1.00 | 36.83 | A |
| ATOM | 1544 | CA | LYS | A | 207 | 18.091 | 48.177 | 10.074 | 1.00 | 37.90 | A |
| ATOM | 1545 | CB | LYS | A | 207 | 17.320 | 48.600 | 11.326 | 1.00 | 39.99 | A |
| ATOM | 1546 | CG | LYS | A | 207 | 18.216 | 49.007 | 12.495 | 1.00 | 45.04 | A |
| ATOM | 1547 | CD | LYS | A | 207 | 17.400 | 49.347 | 13.740 | 1.00 | 50.01 | A |
| ATOM | 1548 | CE | LYS | A | 207 | 18.268 | 49.988 | 14.828 | 1.00 | 52.95 | A |
| ATOM | 1549 | NZ | LYS | A | 207 | 19.403 | 49.110 | 15.254 | 1.00 | 55.35 | A |
| ATOM | 1550 | C | LYS | A | 207 | 18.891 | 46.903 | 10.362 | 1.00 | 37.50 | A |
| ATOM | 1551 | O | LYS | A | 207 | 20.095 | 46.951 | 10.611 | 1.00 | 38.54 | A |
| ATOM | 1552 | N | PHE | A | 208 | 18.208 | 45.762 | 10.312 | 1.00 | 35.87 | A |
| ATOM | 1553 | CA | PHE | A | 208 | 18.831 | 44.468 | 10.552 | 1.00 | 35.98 | A |
| ATOM | 1554 | CB | PHE | A | 208 | 17.746 | 43.376 | 10.613 | 1.00 | 34.44 | A |
| ATOM | 1555 | CG | PHE | A | 208 | 18.288 | 41.966 | 10.743 | 1.00 | 36.93 | A |
| ATOM | 1556 | CD1 | PHE | A | 208 | 18.732 | 41.264 | 9.621 | 1.00 | 35.75 | A |
| ATOM | 1557 | CD2 | PHE | A | 208 | 18.328 | 41.332 | 11.987 | 1.00 | 36.14 | A |
| ATOM | 1558 | CE1 | PHE | A | 208 | 19.201 | 39.955 | 9.734 | 1.00 | 36.55 | A |
| ATOM | 1559 | CE2 | PHE | A | 208 | 18.798 | 40.020 | 12.110 | 1.00 | 37.86 | A |
| ATOM | 1560 | CZ | PHE | A | 208 | 19.234 | 39.330 | 10.977 | 1.00 | 37.36 | A |
| ATOM | 1561 | C | PHE | A | 208 | 19.866 | 44.149 | 9.464 | 1.00 | 35.26 | A |
| ATOM | 1562 | O | PHE | A | 208 | 20.976 | 43.700 | 9.758 | 1.00 | 34.23 | A |
| ATOM | 1563 | N | CYS | A | 209 | 19.508 | 44.389 | 8.208 | 1.00 | 35.13 | A |
| ATOM | 1564 | CA | CYS | A | 209 | 20.424 | 44.115 | 7.106 | 1.00 | 35.37 | A |
| ATOM | 1565 | CB | CYS | A | 209 | 19.756 | 44.438 | 5.762 | 1.00 | 33.36 | A |
| ATOM | 1566 | SG | CYS | A | 209 | 18.357 | 43.364 | 5.322 | 1.00 | 33.51 | A |
| ATOM | 1567 | C | CYS | A | 209 | 21.720 | 44.920 | 7.244 | 1.00 | 35.58 | A |
| ATOM | 1568 | O | CYS | A | 209 | 22.805 | 44.416 | 6.961 | 1.00 | 36.94 | A |
| ATOM | 1569 | N | LYS | A | 210 | 21.592 | 46.172 | 7.669 | 1.00 | 35.97 | A |
| ATOM | 1570 | CA | LYS | A | 210 | 22.736 | 47.067 | 7.844 | 1.00 | 36.87 | A |
| ATOM | 1571 | CB | LYS | A | 210 | 22.239 | 48.429 | 8.341 | 1.00 | 37.10 | A |
| ATOM | 1572 | CG | LYS | A | 210 | 23.296 | 49.330 | 8.973 | 1.00 | 42.31 | A |
| ATOM | 1573 | CD | LYS | A | 210 | 22.677 | 50.663 | 9.409 | 1.00 | 44.14 | A |
| ATOM | 1574 | CE | LYS | A | 210 | 23.705 | 51.801 | 9.307 | 1.00 | 47.02 | A |
| ATOM | 1575 | NZ | LYS | A | 210 | 23.114 | 53.178 | 9.361 | 1.00 | 48.89 | A |
| ATOM | 1576 | C | LYS | A | 210 | 23.761 | 46.497 | 8.824 | 1.00 | 36.21 | A |
| ATOM | 1577 | O | LYS | A | 210 | 24.949 | 46.793 | 8.739 | 1.00 | 37.65 | A |
| ATOM | 1578 | N | ARG | A | 211 | 23.285 | 45.669 | 9.743 | 1.00 | 35.86 | A |
| ATOM | 1579 | CA | ARG | A | 211 | 24.123 | 45.053 | 10.765 | 1.00 | 36.74 | A |
| ATOM | 1580 | CB | ARG | A | 211 | 23.273 | 44.863 | 12.023 | 1.00 | 37.38 | A |
| ATOM | 1581 | CG | ARG | A | 211 | 23.965 | 44.280 | 13.223 | 1.00 | 40.40 | A |
| ATOM | 1582 | CD | ARG | A | 211 | 23.039 | 44.393 | 14.423 | 1.00 | 43.85 | A |
| ATOM | 1583 | NE | ARG | A | 211 | 23.632 | 43.875 | 15.651 | 1.00 | 46.63 | A |
| ATOM | 1584 | CZ | ARG | A | 211 | 23.104 | 44.050 | 16.857 | 1.00 | 48.65 | A |
| ATOM | 1585 | NH1 | ARG | A | 211 | 21.973 | 44.734 | 16.992 | 1.00 | 49.90 | A |
| ATOM | 1586 | NH2 | ARG | A | 211 | 23.697 | 43.535 | 17.929 | 1.00 | 48.82 | A |
| ATOM | 1587 | C | ARG | A | 211 | 24.735 | 43.715 | 10.325 | 1.00 | 35.55 | A |
| ATOM | 1588 | O | ARG | A | 211 | 25.559 | 43.141 | 11.038 | 1.00 | 35.83 | A |
| ATOM | 1589 | N | SER | A | 212 | 24.345 | 43.238 | 9.144 | 1.00 | 33.22 | A |
| ATOM | 1590 | CA | SER | A | 212 | 24.818 | 41.954 | 8.607 | 1.00 | 33.87 | A |
| ATOM | 1591 | CB | SER | A | 212 | 24.125 | 41.652 | 7.269 | 1.00 | 31.55 | A |
| ATOM | 1592 | OG | SER | A | 212 | 22.738 | 41.403 | 7.448 | 1.00 | 33.21 | A |
| ATOM | 1593 | C | SER | A | 212 | 26.319 | 41.789 | 8.401 | 1.00 | 32.15 | A |
| ATOM | 1594 | O | SER | A | 212 | 27.009 | 42.714 | 8.009 | 1.00 | 35.39 | A |
| ATOM | 1595 | N | PHE | A | 213 | 26.818 | 40.585 | 8.657 | 1.00 | 33.61 | A |
| ATOM | 1596 | CA | PHE | A | 213 | 28.236 | 40.295 | 8.447 | 1.00 | 34.25 | A |
| ATOM | 1597 | CB | PHE | A | 213 | 28.862 | 39.641 | 9.695 | 1.00 | 33.84 | A |
| ATOM | 1598 | CG | PHE | A | 213 | 28.500 | 38.192 | 9.887 | 1.00 | 34.55 | A |
| ATOM | 1599 | CD1 | PHE | A | 213 | 29.384 | 37.186 | 9.509 | 1.00 | 34.18 | A |
| ATOM | 1600 | CD2 | PHE | A | 213 | 27.291 | 37.834 | 10.471 | 1.00 | 34.89 | A |
| ATOM | 1601 | CE1 | PHE | A | 213 | 29.071 | 35.846 | 9.717 | 1.00 | 37.02 | A |
| ATOM | 1602 | CE2 | PHE | A | 213 | 26.965 | 36.501 | 10.683 | 1.00 | 36.59 | A |
| ATOM | 1603 | CZ | PHE | A | 213 | 27.858 | 35.500 | 10.306 | 1.00 | 35.85 | A |
| ATOM | 1604 | C | PHE | A | 213 | 28.349 | 39.363 | 7.242 | 1.00 | 33.28 | A |
| ATOM | 1605 | O | PHE | A | 213 | 29.422 | 39.178 | 6.685 | 1.00 | 32.96 | A |
| ATOM | 1606 | N | SER | A | 214 | 27.222 | 38.786 | 6.838 | 1.00 | 34.50 | A |
| ATOM | 1607 | CA | SER | A | 214 | 27.192 | 37.874 | 5.698 | 1.00 | 31.86 | A |
| ATOM | 1608 | CB | SER | A | 214 | 27.375 | 36.434 | 6.170 | 1.00 | 33.79 | A |
| ATOM | 1609 | OG | SER | A | 214 | 27.224 | 35.521 | 5.093 | 1.00 | 37.93 | A |
| ATOM | 1610 | C | SER | A | 214 | 25.860 | 37.988 | 4.974 | 1.00 | 31.77 | A |
| ATOM | 1611 | O | SER | A | 214 | 24.833 | 38.202 | 5.610 | 1.00 | 28.63 | A |
| ATOM | 1612 | N | VAL | A | 215 | 25.892 | 37.856 | 3.648 | 1.00 | 30.90 | A |
| ATOM | 1613 | CA | VAL | A | 215 | 24.685 | 37.908 | 2.818 | 1.00 | 29.86 | A |
| ATOM | 1614 | CB | VAL | A | 215 | 24.618 | 39.187 | 1.947 | 1.00 | 30.29 | A |

APPENDIX 1-continued

Atomic coordinates of aromatic prenyltransferase residues 3-302 of SEQ ID NO: 2.

| ATOM | 1615 | CG1 | VAL | A | 215 | 23.443 | 39.103 | 0.993 | 1.00 | 32.52 | A |
|---|---|---|---|---|---|---|---|---|---|---|---|
| ATOM | 1616 | CG2 | VAL | A | 215 | 24.460 | 40.412 | 2.817 | 1.00 | 33.53 | A |
| ATOM | 1617 | C | VAL | A | 215 | 24.759 | 36.725 | 1.866 | 1.00 | 28.93 | A |
| ATOM | 1618 | O | VAL | A | 215 | 25.802 | 36.513 | 1.238 | 1.00 | 28.44 | A |
| ATOM | 1619 | N | TYR | A | 216 | 23.679 | 35.952 | 1.749 | 1.00 | 27.25 | A |
| ATOM | 1620 | CA | TYR | A | 216 | 23.703 | 34.817 | 0.824 | 1.00 | 27.51 | A |
| ATOM | 1621 | CB | TYR | A | 216 | 24.119 | 33.499 | 1.522 | 1.00 | 26.91 | A |
| ATOM | 1622 | CG | TYR | A | 216 | 23.361 | 33.072 | 2.774 | 1.00 | 27.45 | A |
| ATOM | 1623 | CD1 | TYR | A | 216 | 22.508 | 31.959 | 2.769 | 1.00 | 26.55 | A |
| ATOM | 1624 | CE1 | TYR | A | 216 | 21.913 | 31.487 | 3.967 | 1.00 | 29.46 | A |
| ATOM | 1625 | CD2 | TYR | A | 216 | 23.593 | 33.710 | 3.992 | 1.00 | 30.60 | A |
| ATOM | 1626 | CE2 | TYR | A | 216 | 23.016 | 33.258 | 5.178 | 1.00 | 29.33 | A |
| ATOM | 1627 | CZ | TYR | A | 216 | 22.186 | 32.156 | 5.165 | 1.00 | 29.32 | A |
| ATOM | 1628 | OH | TYR | A | 216 | 21.654 | 31.734 | 6.360 | 1.00 | 31.96 | A |
| ATOM | 1629 | C | TYR | A | 216 | 22.477 | 34.534 | −0.019 | 1.00 | 27.43 | A |
| ATOM | 1630 | O | TYR | A | 216 | 21.383 | 34.337 | 0.492 | 1.00 | 25.60 | A |
| ATOM | 1631 | N | PRO | A | 217 | 22.658 | 34.519 | −1.349 | 1.00 | 28.06 | A |
| ATOM | 1632 | CD | PRO | A | 217 | 23.839 | 35.061 | −2.054 | 1.00 | 28.05 | A |
| ATOM | 1633 | CA | PRO | A | 217 | 21.576 | 34.241 | −2.293 | 1.00 | 27.27 | A |
| ATOM | 1634 | CB | PRO | A | 217 | 22.008 | 35.008 | −3.534 | 1.00 | 28.73 | A |
| ATOM | 1635 | CG | PRO | A | 217 | 23.512 | 34.790 | −3.521 | 1.00 | 27.12 | A |
| ATOM | 1636 | C | PRO | A | 217 | 21.558 | 32.736 | −2.550 | 1.00 | 27.30 | A |
| ATOM | 1637 | O | PRO | A | 217 | 22.596 | 32.066 | −2.432 | 1.00 | 26.63 | A |
| ATOM | 1638 | N | THR | A | 218 | 20.393 | 32.204 | −2.890 | 1.00 | 25.62 | A |
| ATOM | 1639 | CA | THR | A | 218 | 20.258 | 30.784 | −3.204 | 1.00 | 26.97 | A |
| ATOM | 1640 | CB | THR | A | 218 | 19.073 | 30.132 | −2.452 | 1.00 | 27.35 | A |
| ATOM | 1641 | OG1 | THR | A | 218 | 19.274 | 30.242 | −1.035 | 1.00 | 28.53 | A |
| ATOM | 1642 | CG2 | THR | A | 218 | 18.962 | 28.645 | −2.818 | 1.00 | 26.30 | A |
| ATOM | 1643 | C | THR | A | 218 | 19.991 | 30.674 | −4.707 | 1.00 | 28.41 | A |
| ATOM | 1644 | O | THR | A | 218 | 19.115 | 31.364 | −5.231 | 1.00 | 29.31 | A |
| ATOM | 1645 | N | LEU | A | 219 | 20.755 | 29.823 | −5.388 | 1.00 | 29.45 | A |
| ATOM | 1646 | CA | LEU | A | 219 | 20.608 | 29.619 | −6.826 | 1.00 | 31.35 | A |
| ATOM | 1647 | CB | LEU | A | 219 | 21.884 | 30.066 | −7.562 | 1.00 | 32.22 | A |
| ATOM | 1648 | CG | LEU | A | 219 | 22.337 | 31.509 | −7.312 | 1.00 | 32.16 | A |
| ATOM | 1649 | CD1 | LEU | A | 219 | 23.346 | 31.516 | −6.160 | 1.00 | 31.96 | A |
| ATOM | 1650 | CD2 | LEU | A | 219 | 22.961 | 32.105 | −8.584 | 1.00 | 29.71 | A |
| ATOM | 1651 | C | LEU | A | 219 | 20.315 | 28.149 | −7.148 | 1.00 | 32.09 | A |
| ATOM | 1652 | O | LEU | A | 219 | 20.540 | 27.255 | −6.329 | 1.00 | 31.23 | A |
| ATOM | 1653 | N | ASN | A | 220 | 19.812 | 27.898 | −8.349 | 1.00 | 33.47 | A |
| ATOM | 1654 | CA | ASN | A | 220 | 19.498 | 26.537 | −8.767 | 1.00 | 34.71 | A |
| ATOM | 1655 | CB | ASN | A | 220 | 17.990 | 26.289 | −8.648 | 1.00 | 36.03 | A |
| ATOM | 1656 | CG | ASN | A | 220 | 17.186 | 27.115 | −9.629 | 1.00 | 39.61 | A |
| ATOM | 1657 | OD1 | ASN | A | 220 | 17.141 | 26.809 | −10.819 | 1.00 | 40.74 | A |
| ATOM | 1658 | ND2 | ASN | A | 220 | 16.558 | 28.177 | −9.138 | 1.00 | 38.72 | A |
| ATOM | 1659 | C | ASN | A | 220 | 19.965 | 26.294 | −10.205 | 1.00 | 35.49 | A |
| ATOM | 1660 | O | ASN | A | 220 | 20.354 | 27.228 | −10.906 | 1.00 | 33.83 | A |
| ATOM | 1661 | N | TRP | A | 221 | 19.927 | 25.033 | −10.623 | 1.00 | 36.36 | A |
| ATOM | 1662 | CA | TRP | A | 221 | 20.354 | 24.615 | −11.956 | 1.00 | 38.77 | A |
| ATOM | 1663 | CB | TRP | A | 221 | 20.845 | 23.162 | −11.906 | 1.00 | 37.13 | A |
| ATOM | 1664 | CG | TRP | A | 221 | 22.255 | 22.982 | −11.415 | 1.00 | 35.49 | A |
| ATOM | 1665 | CD2 | TRP | A | 221 | 22.679 | 22.785 | −10.056 | 1.00 | 34.23 | A |
| ATOM | 1666 | CE2 | TRP | A | 221 | 24.084 | 22.613 | −10.078 | 1.00 | 34.61 | A |
| ATOM | 1667 | CE3 | TRP | A | 221 | 22.009 | 22.733 | −8.826 | 1.00 | 33.47 | A |
| ATOM | 1668 | CD1 | TRP | A | 221 | 23.388 | 22.932 | −12.180 | 1.00 | 36.61 | A |
| ATOM | 1669 | NE1 | TRP | A | 221 | 24.490 | 22.707 | −11.384 | 1.00 | 36.62 | A |
| ATOM | 1670 | CZ2 | TRP | A | 221 | 24.832 | 22.391 | −8.916 | 1.00 | 31.63 | A |
| ATOM | 1671 | CZ3 | TRP | A | 221 | 22.752 | 22.511 | −7.665 | 1.00 | 31.82 | A |
| ATOM | 1672 | CH2 | TRP | A | 221 | 24.153 | 22.343 | −7.722 | 1.00 | 33.18 | A |
| ATOM | 1673 | C | TRP | A | 221 | 19.261 | 24.736 | −13.020 | 1.00 | 41.28 | A |
| ATOM | 1674 | O | TRP | A | 221 | 19.546 | 24.642 | −14.214 | 1.00 | 41.24 | A |
| ATOM | 1675 | N | GLU | A | 222 | 18.017 | 24.943 | −12.594 | 1.00 | 42.94 | A |
| ATOM | 1676 | CA | GLU | A | 222 | 16.905 | 25.058 | −13.534 | 1.00 | 46.16 | A |
| ATOM | 1677 | CB | GLU | A | 222 | 15.587 | 24.689 | −12.848 | 1.00 | 46.48 | A |
| ATOM | 1678 | CG | GLU | A | 222 | 15.530 | 23.273 | −12.303 | 1.00 | 49.88 | A |
| ATOM | 1679 | CD | GLU | A | 222 | 15.994 | 22.238 | −13.307 | 1.00 | 52.45 | A |
| ATOM | 1680 | OE1 | GLU | A | 222 | 15.705 | 22.404 | −14.512 | 1.00 | 55.71 | A |
| ATOM | 1681 | OE2 | GLU | A | 222 | 16.640 | 21.251 | −12.894 | 1.00 | 53.80 | A |
| ATOM | 1682 | C | GLU | A | 222 | 16.748 | 26.425 | −14.203 | 1.00 | 46.68 | A |
| ATOM | 1683 | O | GLU | A | 222 | 16.463 | 26.501 | −15.398 | 1.00 | 47.48 | A |
| ATOM | 1684 | N | THR | A | 223 | 16.920 | 27.500 | −13.439 | 1.00 | 46.30 | A |
| ATOM | 1685 | CA | THR | A | 223 | 16.777 | 28.848 | −13.985 | 1.00 | 46.13 | A |
| ATOM | 1686 | CB | THR | A | 223 | 15.407 | 29.462 | −13.613 | 1.00 | 47.72 | A |
| ATOM | 1687 | OG1 | THR | A | 223 | 15.332 | 29.646 | −12.194 | 1.00 | 49.52 | A |
| ATOM | 1688 | CG2 | THR | A | 223 | 14.270 | 28.546 | −14.051 | 1.00 | 49.10 | A |
| ATOM | 1689 | C | THR | A | 223 | 17.867 | 29.791 | −13.477 | 1.00 | 46.02 | A |
| ATOM | 1690 | O | THR | A | 223 | 18.643 | 29.437 | −12.591 | 1.00 | 44.84 | A |
| ATOM | 1691 | N | GLY | A | 224 | 17.915 | 30.994 | −14.044 | 1.00 | 44.46 | A |

APPENDIX 1-continued

Atomic coordinates of aromatic prenyltransferase residues 3-302 of SEQ ID NO: 2.

| ATOM | 1692 | CA | GLY | A | 224 | 18.906 | 31.971 | −13.626 | 1.00 | 43.49 | A |
|---|---|---|---|---|---|---|---|---|---|---|---|
| ATOM | 1693 | C | GLY | A | 224 | 18.341 | 32.872 | −12.545 | 1.00 | 42.65 | A |
| ATOM | 1694 | O | GLY | A | 224 | 19.014 | 33.777 | −12.057 | 1.00 | 43.27 | A |
| ATOM | 1695 | N | LYS | A | 225 | 17.093 | 32.618 | −12.167 | 1.00 | 41.43 | A |
| ATOM | 1696 | CA | LYS | A | 225 | 16.426 | 33.415 | −11.150 | 1.00 | 41.27 | A |
| ATOM | 1697 | CB | LYS | A | 225 | 14.908 | 33.310 | −11.320 | 1.00 | 43.63 | A |
| ATOM | 1698 | CG | LYS | A | 225 | 14.111 | 34.119 | −10.308 | 1.00 | 47.97 | A |
| ATOM | 1699 | CD | LYS | A | 225 | 12.604 | 33.860 | −10.427 | 1.00 | 52.08 | A |
| ATOM | 1700 | CE | LYS | A | 225 | 12.243 | 32.430 | −10.017 | 1.00 | 53.90 | A |
| ATOM | 1701 | NZ | LYS | A | 225 | 10.779 | 32.155 | −10.145 | 1.00 | 56.20 | A |
| ATOM | 1702 | C | LYS | A | 225 | 16.816 | 32.981 | −9.734 | 1.00 | 38.89 | A |
| ATOM | 1703 | O | LYS | A | 225 | 16.693 | 31.812 | −9.376 | 1.00 | 36.62 | A |
| ATOM | 1704 | N | ILE | A | 226 | 17.290 | 33.934 | −8.939 | 1.00 | 37.52 | A |
| ATOM | 1705 | CA | ILE | A | 226 | 17.676 | 33.648 | −7.565 | 1.00 | 35.91 | A |
| ATOM | 1706 | CB | ILE | A | 226 | 18.415 | 34.860 | −6.939 | 1.00 | 34.66 | A |
| ATOM | 1707 | CG2 | ILE | A | 226 | 18.474 | 34.725 | −5.412 | 1.00 | 32.77 | A |
| ATOM | 1708 | CG1 | ILE | A | 226 | 19.831 | 34.932 | −7.526 | 1.00 | 35.67 | A |
| ATOM | 1709 | CD1 | ILE | A | 226 | 20.616 | 36.173 | −7.142 | 1.00 | 35.94 | A |
| ATOM | 1710 | C | ILE | A | 226 | 16.419 | 33.297 | −6.775 | 1.00 | 35.16 | A |
| ATOM | 1711 | O | ILE | A | 226 | 15.420 | 34.010 | −6.838 | 1.00 | 36.27 | A |
| ATOM | 1712 | N | ASP | A | 227 | 16.472 | 32.183 | −6.048 | 1.00 | 34.90 | A |
| ATOM | 1713 | CA | ASP | A | 227 | 15.337 | 31.700 | −5.260 | 1.00 | 35.04 | A |
| ATOM | 1714 | CB | ASP | A | 227 | 15.589 | 30.250 | −4.845 | 1.00 | 37.48 | A |
| ATOM | 1715 | CG | ASP | A | 227 | 15.768 | 29.329 | −6.041 | 1.00 | 40.26 | A |
| ATOM | 1716 | OD1 | ASP | A | 227 | 14.795 | 29.161 | −6.811 | 1.00 | 40.93 | A |
| ATOM | 1717 | OD2 | ASP | A | 227 | 16.881 | 28.784 | −6.213 | 1.00 | 40.47 | A |
| ATOM | 1718 | C | ASP | A | 227 | 15.009 | 32.536 | −4.024 | 1.00 | 35.52 | A |
| ATOM | 1719 | O | ASP | A | 227 | 13.836 | 32.772 | −3.710 | 1.00 | 33.67 | A |
| ATOM | 1720 | N | ARG | A | 228 | 16.045 | 32.966 | −3.311 | 1.00 | 33.10 | A |
| ATOM | 1721 | CA | ARG | A | 228 | 15.859 | 33.774 | −2.117 | 1.00 | 31.73 | A |
| ATOM | 1722 | CB | ARG | A | 228 | 15.297 | 32.910 | −0.974 | 1.00 | 31.32 | A |
| ATOM | 1723 | CG | ARG | A | 228 | 16.153 | 31.704 | −0.621 | 1.00 | 29.51 | A |
| ATOM | 1724 | CD | ARG | A | 228 | 15.468 | 30.793 | 0.405 | 1.00 | 32.46 | A |
| ATOM | 1725 | NE | ARG | A | 228 | 16.370 | 29.723 | 0.826 | 1.00 | 31.71 | A |
| ATOM | 1726 | CZ | ARG | A | 228 | 16.486 | 28.550 | 0.215 | 1.00 | 33.70 | A |
| ATOM | 1727 | NH1 | ARG | A | 228 | 15.741 | 28.266 | −0.848 | 1.00 | 35.15 | A |
| ATOM | 1728 | NH2 | ARG | A | 228 | 17.382 | 27.675 | 0.646 | 1.00 | 35.72 | A |
| ATOM | 1729 | C | ARG | A | 228 | 17.189 | 34.408 | −1.723 | 1.00 | 30.83 | A |
| ATOM | 1730 | O | ARG | A | 228 | 18.239 | 34.052 | −2.264 | 1.00 | 32.29 | A |
| ATOM | 1731 | N | LEU | A | 229 | 17.134 | 35.353 | −0.793 | 1.00 | 31.06 | A |
| ATOM | 1732 | CA | LEU | A | 229 | 18.327 | 36.066 | −0.330 | 1.00 | 29.02 | A |
| ATOM | 1733 | CB | LEU | A | 229 | 18.365 | 37.451 | −0.964 | 1.00 | 27.74 | A |
| ATOM | 1734 | CG | LEU | A | 229 | 19.548 | 38.344 | −0.595 | 1.00 | 26.58 | A |
| ATOM | 1735 | CD1 | LEU | A | 229 | 20.822 | 37.775 | −1.210 | 1.00 | 24.82 | A |
| ATOM | 1736 | CD2 | LEU | A | 229 | 19.266 | 39.765 | −1.083 | 1.00 | 26.37 | A |
| ATOM | 1737 | C | LEU | A | 229 | 18.293 | 36.211 | 1.187 | 1.00 | 27.73 | A |
| ATOM | 1738 | O | LEU | A | 229 | 17.310 | 36.701 | 1.743 | 1.00 | 28.78 | A |
| ATOM | 1739 | N | CYS | A | 230 | 19.367 | 35.808 | 1.855 | 1.00 | 28.33 | A |
| ATOM | 1740 | CA | CYS | A | 230 | 19.404 | 35.894 | 3.313 | 1.00 | 29.29 | A |
| ATOM | 1741 | CB | CYS | A | 230 | 19.510 | 34.485 | 3.909 | 1.00 | 29.74 | A |
| ATOM | 1742 | SG | CYS | A | 230 | 19.579 | 34.453 | 5.743 | 1.00 | 31.41 | A |
| ATOM | 1743 | C | CYS | A | 230 | 20.523 | 36.777 | 3.878 | 1.00 | 28.54 | A |
| ATOM | 1744 | O | CYS | A | 230 | 21.661 | 36.749 | 3.406 | 1.00 | 28.22 | A |
| ATOM | 1745 | N | PHE | A | 231 | 20.172 | 37.574 | 4.882 | 1.00 | 28.82 | A |
| ATOM | 1746 | CA | PHE | A | 231 | 21.114 | 38.451 | 5.564 | 1.00 | 29.99 | A |
| ATOM | 1747 | CB | PHE | A | 231 | 20.539 | 39.867 | 5.695 | 1.00 | 28.76 | A |
| ATOM | 1748 | CG | PHE | A | 231 | 20.349 | 40.570 | 4.371 | 1.00 | 31.79 | A |
| ATOM | 1749 | CD1 | PHE | A | 231 | 19.261 | 40.265 | 3.550 | 1.00 | 31.62 | A |
| ATOM | 1750 | CD2 | PHE | A | 231 | 21.279 | 41.515 | 3.930 | 1.00 | 31.11 | A |
| ATOM | 1751 | CE1 | PHE | A | 231 | 19.103 | 40.891 | 2.305 | 1.00 | 30.59 | A |
| ATOM | 1752 | CE2 | PHE | A | 231 | 21.130 | 42.147 | 2.683 | 1.00 | 31.97 | A |
| ATOM | 1753 | CZ | PHE | A | 231 | 20.038 | 41.830 | 1.873 | 1.00 | 29.20 | A |
| ATOM | 1754 | C | PHE | A | 231 | 21.339 | 37.846 | 6.946 | 1.00 | 30.94 | A |
| ATOM | 1755 | O | PHE | A | 231 | 20.380 | 37.553 | 7.660 | 1.00 | 30.10 | A |
| ATOM | 1756 | N | ALA | A | 232 | 22.600 | 37.645 | 7.319 | 1.00 | 30.85 | A |
| ATOM | 1757 | CA | ALA | A | 232 | 22.916 | 37.051 | 8.617 | 1.00 | 31.42 | A |
| ATOM | 1758 | CB | ALA | A | 232 | 23.814 | 35.825 | 8.420 | 1.00 | 30.46 | A |
| ATOM | 1759 | C | ALA | A | 232 | 23.584 | 38.039 | 9.580 | 1.00 | 30.98 | A |
| ATOM | 1760 | O | ALA | A | 232 | 24.402 | 38.857 | 9.175 | 1.00 | 31.61 | A |
| ATOM | 1761 | N | VAL | A | 233 | 23.227 | 37.933 | 10.856 | 1.00 | 32.02 | A |
| ATOM | 1762 | CA | VAL | A | 233 | 23.757 | 38.794 | 11.911 | 1.00 | 33.05 | A |
| ATOM | 1763 | CB | VAL | A | 233 | 22.651 | 39.748 | 12.449 | 1.00 | 34.08 | A |
| ATOM | 1764 | CG1 | VAL | A | 233 | 23.109 | 40.432 | 13.753 | 1.00 | 35.86 | A |
| ATOM | 1765 | CG2 | VAL | A | 233 | 22.325 | 40.800 | 11.396 | 1.00 | 31.79 | A |
| ATOM | 1766 | C | VAL | A | 233 | 24.271 | 37.931 | 13.065 | 1.00 | 33.07 | A |
| ATOM | 1767 | O | VAL | A | 233 | 23.580 | 37.024 | 13.524 | 1.00 | 34.33 | A |
| ATOM | 1768 | N | ILE | A | 234 | 25.485 | 38.211 | 13.526 | 1.00 | 34.06 | A |

APPENDIX 1-continued

Atomic coordinates of aromatic prenyltransferase residues 3-302 of SEQ ID NO: 2.

| ATOM | 1769 | CA  | ILE | A | 234 | 26.073 | 37.449 | 14.623 | 1.00 | 36.42 | A |
|------|------|-----|-----|---|-----|--------|--------|--------|------|-------|---|
| ATOM | 1770 | CB  | ILE | A | 234 | 27.519 | 37.004 | 14.260 | 1.00 | 34.49 | A |
| ATOM | 1771 | CG2 | ILE | A | 234 | 28.420 | 38.209 | 14.104 | 1.00 | 35.27 | A |
| ATOM | 1772 | CG1 | ILE | A | 234 | 28.051 | 36.032 | 15.316 | 1.00 | 35.08 | A |
| ATOM | 1773 | CD1 | ILE | A | 234 | 29.314 | 35.277 | 14.888 | 1.00 | 32.27 | A |
| ATOM | 1774 | C   | ILE | A | 234 | 26.053 | 38.313 | 15.888 | 1.00 | 35.82 | A |
| ATOM | 1775 | O   | ILE | A | 234 | 26.473 | 39.461 | 15.863 | 1.00 | 36.21 | A |
| ATOM | 1776 | N   | SER | A | 235 | 25.549 | 37.772 | 16.989 | 1.00 | 38.61 | A |
| ATOM | 1777 | CA  | SER | A | 235 | 25.471 | 38.561 | 18.219 | 1.00 | 40.77 | A |
| ATOM | 1778 | CB  | SER | A | 235 | 24.385 | 39.633 | 18.065 | 1.00 | 41.97 | A |
| ATOM | 1779 | OG  | SER | A | 235 | 24.220 | 40.392 | 19.248 | 1.00 | 43.56 | A |
| ATOM | 1780 | C   | SER | A | 235 | 25.175 | 37.742 | 19.467 | 1.00 | 42.35 | A |
| ATOM | 1781 | O   | SER | A | 235 | 24.793 | 36.574 | 19.384 | 1.00 | 41.79 | A |
| ATOM | 1782 | N   | ASN | A | 236 | 25.356 | 38.372 | 20.626 | 1.00 | 44.38 | A |
| ATOM | 1783 | CA  | ASN | A | 236 | 25.081 | 37.731 | 21.906 | 1.00 | 45.74 | A |
| ATOM | 1784 | CB  | ASN | A | 236 | 26.115 | 38.151 | 22.958 | 1.00 | 47.60 | A |
| ATOM | 1785 | CG  | ASN | A | 236 | 27.488 | 37.569 | 22.694 | 1.00 | 48.75 | A |
| ATOM | 1786 | OD1 | ASN | A | 236 | 27.661 | 36.350 | 22.680 | 1.00 | 51.03 | A |
| ATOM | 1787 | ND2 | ASN | A | 236 | 28.472 | 38.436 | 22.479 | 1.00 | 49.64 | A |
| ATOM | 1788 | C   | ASN | A | 236 | 23.692 | 38.172 | 22.350 | 1.00 | 46.12 | A |
| ATOM | 1789 | O   | ASN | A | 236 | 23.088 | 37.568 | 23.236 | 1.00 | 47.30 | A |
| ATOM | 1790 | N   | ASP | A | 237 | 23.201 | 39.230 | 21.713 | 1.00 | 46.49 | A |
| ATOM | 1791 | CA  | ASP | A | 237 | 21.889 | 39.806 | 21.993 | 1.00 | 46.83 | A |
| ATOM | 1792 | CB  | ASP | A | 237 | 21.746 | 41.105 | 21.198 | 1.00 | 47.75 | A |
| ATOM | 1793 | CG  | ASP | A | 237 | 20.662 | 42.013 | 21.736 | 1.00 | 47.79 | A |
| ATOM | 1794 | OD1 | ASP | A | 237 | 19.513 | 41.560 | 21.923 | 1.00 | 47.65 | A |
| ATOM | 1795 | OD2 | ASP | A | 237 | 20.970 | 43.198 | 21.957 | 1.00 | 48.75 | A |
| ATOM | 1796 | C   | ASP | A | 237 | 20.786 | 38.825 | 21.591 | 1.00 | 47.10 | A |
| ATOM | 1797 | O   | ASP | A | 237 | 20.665 | 38.463 | 20.422 | 1.00 | 47.73 | A |
| ATOM | 1798 | N   | PRO | A | 238 | 19.965 | 38.383 | 22.557 | 1.00 | 46.57 | A |
| ATOM | 1799 | CD  | PRO | A | 238 | 20.211 | 38.488 | 24.009 | 1.00 | 47.58 | A |
| ATOM | 1800 | CA  | PRO | A | 238 | 18.878 | 37.439 | 22.281 | 1.00 | 45.52 | A |
| ATOM | 1801 | CB  | PRO | A | 238 | 18.796 | 36.641 | 23.576 | 1.00 | 47.17 | A |
| ATOM | 1802 | CG  | PRO | A | 238 | 19.055 | 37.703 | 24.605 | 1.00 | 47.42 | A |
| ATOM | 1803 | C   | PRO | A | 238 | 17.530 | 38.049 | 21.893 | 1.00 | 45.24 | A |
| ATOM | 1804 | O   | PRO | A | 238 | 16.509 | 37.361 | 21.900 | 1.00 | 45.57 | A |
| ATOM | 1805 | N   | THR | A | 239 | 17.521 | 39.331 | 21.545 | 1.00 | 45.54 | A |
| ATOM | 1806 | CA  | THR | A | 239 | 16.280 | 40.001 | 21.153 | 1.00 | 45.56 | A |
| ATOM | 1807 | CB  | THR | A | 239 | 15.920 | 41.117 | 22.162 | 1.00 | 45.90 | A |
| ATOM | 1808 | OG1 | THR | A | 239 | 16.886 | 42.173 | 22.067 | 1.00 | 46.13 | A |
| ATOM | 1809 | CG2 | THR | A | 239 | 15.921 | 40.574 | 23.588 | 1.00 | 46.71 | A |
| ATOM | 1810 | C   | THR | A | 239 | 16.372 | 40.642 | 19.761 | 1.00 | 44.94 | A |
| ATOM | 1811 | O   | THR | A | 239 | 15.657 | 41.600 | 19.473 | 1.00 | 44.48 | A |
| ATOM | 1812 | N   | LEU | A | 240 | 17.226 | 40.106 | 18.892 | 1.00 | 45.21 | A |
| ATOM | 1813 | CA  | LEU | A | 240 | 17.412 | 40.689 | 17.563 | 1.00 | 44.68 | A |
| ATOM | 1814 | CB  | LEU | A | 240 | 18.887 | 40.606 | 17.167 | 1.00 | 44.71 | A |
| ATOM | 1815 | CG  | LEU | A | 240 | 19.890 | 41.396 | 18.008 | 1.00 | 45.86 | A |
| ATOM | 1816 | CD1 | LEU | A | 240 | 21.292 | 41.136 | 17.488 | 1.00 | 46.25 | A |
| ATOM | 1817 | CD2 | LEU | A | 240 | 19.566 | 42.885 | 17.952 | 1.00 | 45.57 | A |
| ATOM | 1818 | C   | LEU | A | 240 | 16.573 | 40.190 | 16.387 | 1.00 | 44.93 | A |
| ATOM | 1819 | O   | LEU | A | 240 | 16.801 | 40.625 | 15.258 | 1.00 | 44.99 | A |
| ATOM | 1820 | N   | VAL | A | 241 | 15.614 | 39.298 | 16.617 | 1.00 | 44.69 | A |
| ATOM | 1821 | CA  | VAL | A | 241 | 14.809 | 38.806 | 15.504 | 1.00 | 44.20 | A |
| ATOM | 1822 | CB  | VAL | A | 241 | 13.775 | 37.744 | 15.976 | 1.00 | 44.62 | A |
| ATOM | 1823 | CG1 | VAL | A | 241 | 12.661 | 38.393 | 16.781 | 1.00 | 45.74 | A |
| ATOM | 1824 | CG2 | VAL | A | 241 | 13.219 | 36.998 | 14.778 | 1.00 | 43.96 | A |
| ATOM | 1825 | C   | VAL | A | 241 | 14.114 | 40.004 | 14.839 | 1.00 | 44.51 | A |
| ATOM | 1826 | O   | VAL | A | 241 | 13.424 | 40.780 | 15.498 | 1.00 | 44.10 | A |
| ATOM | 1827 | N   | PRO | A | 242 | 14.302 | 40.175 | 13.520 | 1.00 | 42.66 | A |
| ATOM | 1828 | CD  | PRO | A | 242 | 15.176 | 39.385 | 12.635 | 1.00 | 41.53 | A |
| ATOM | 1829 | CA  | PRO | A | 242 | 13.696 | 41.293 | 12.787 | 1.00 | 41.75 | A |
| ATOM | 1830 | CB  | PRO | A | 242 | 14.584 | 41.403 | 11.557 | 1.00 | 41.67 | A |
| ATOM | 1831 | CG  | PRO | A | 242 | 14.865 | 39.966 | 11.257 | 1.00 | 41.45 | A |
| ATOM | 1832 | C   | PRO | A | 242 | 12.229 | 41.111 | 12.419 | 1.00 | 42.06 | A |
| ATOM | 1833 | O   | PRO | A | 242 | 11.849 | 41.287 | 11.265 | 1.00 | 39.87 | A |
| ATOM | 1834 | N   | SER | A | 243 | 11.409 | 40.772 | 13.407 | 1.00 | 42.14 | A |
| ATOM | 1835 | CA  | SER | A | 243 | 9.987  | 40.566 | 13.181 | 1.00 | 43.50 | A |
| ATOM | 1836 | CB  | SER | A | 243 | 9.629  | 39.096 | 13.421 | 1.00 | 42.47 | A |
| ATOM | 1837 | OG  | SER | A | 243 | 8.237  | 38.875 | 13.288 | 1.00 | 41.75 | A |
| ATOM | 1838 | C   | SER | A | 243 | 9.170  | 41.460 | 14.109 | 1.00 | 45.15 | A |
| ATOM | 1839 | O   | SER | A | 243 | 9.611  | 41.799 | 15.208 | 1.00 | 42.95 | A |
| ATOM | 1840 | N   | SER | A | 244 | 7.981  | 41.844 | 13.657 | 1.00 | 47.40 | A |
| ATOM | 1841 | CA  | SER | A | 244 | 7.102  | 42.697 | 14.450 | 1.00 | 49.90 | A |
| ATOM | 1842 | CB  | SER | A | 244 | 6.520  | 43.813 | 13.579 | 1.00 | 49.67 | A |
| ATOM | 1843 | OG  | SER | A | 244 | 5.769  | 43.277 | 12.500 | 1.00 | 48.66 | A |
| ATOM | 1844 | C   | SER | A | 244 | 5.971  | 41.865 | 15.033 | 1.00 | 51.74 | A |
| ATOM | 1845 | O   | SER | A | 244 | 5.122  | 42.375 | 15.765 | 1.00 | 53.20 | A |

APPENDIX 1-continued

Atomic coordinates of aromatic prenyltransferase residues 3-302 of SEQ ID NO: 2.

| ATOM | 1846 | N | ASP | A | 245 | 5.964 | 40.580 | 14.693 | 1.00 | 53.53 | A |
| ATOM | 1847 | CA | ASP | A | 245 | 4.946 | 39.653 | 15.171 | 1.00 | 55.50 | A |
| ATOM | 1848 | CB | ASP | A | 245 | 4.823 | 38.470 | 14.207 | 1.00 | 56.42 | A |
| ATOM | 1849 | CG | ASP | A | 245 | 3.803 | 37.450 | 14.665 | 1.00 | 57.31 | A |
| ATOM | 1850 | OD1 | ASP | A | 245 | 2.631 | 37.830 | 14.862 | 1.00 | 59.97 | A |
| ATOM | 1851 | OD2 | ASP | A | 245 | 4.170 | 36.269 | 14.827 | 1.00 | 57.82 | A |
| ATOM | 1852 | C | ASP | A | 245 | 5.283 | 39.149 | 16.571 | 1.00 | 55.95 | A |
| ATOM | 1853 | O | ASP | A | 245 | 6.250 | 38.411 | 16.758 | 1.00 | 55.39 | A |
| ATOM | 1854 | N | GLU | A | 246 | 4.479 | 39.562 | 17.549 | 1.00 | 57.53 | A |
| ATOM | 1855 | CA | GLU | A | 246 | 4.673 | 39.162 | 18.941 | 1.00 | 58.27 | A |
| ATOM | 1856 | CB | GLU | A | 246 | 3.443 | 39.537 | 19.776 | 1.00 | 60.44 | A |
| ATOM | 1857 | CG | GLU | A | 246 | 3.265 | 41.033 | 19.999 | 1.00 | 63.33 | A |
| ATOM | 1858 | CD | GLU | A | 246 | 2.015 | 41.367 | 20.806 | 1.00 | 65.68 | A |
| ATOM | 1859 | OE1 | GLU | A | 246 | 0.893 | 41.126 | 20.306 | 1.00 | 65.94 | A |
| ATOM | 1860 | OE2 | GLU | A | 246 | 2.156 | 41.868 | 21.944 | 1.00 | 67.06 | A |
| ATOM | 1861 | C | GLU | A | 246 | 4.949 | 37.666 | 19.072 | 1.00 | 57.75 | A |
| ATOM | 1862 | O | GLU | A | 246 | 5.645 | 37.236 | 19.989 | 1.00 | 57.64 | A |
| ATOM | 1863 | N | GLY | A | 247 | 4.400 | 36.876 | 18.155 | 1.00 | 57.63 | A |
| ATOM | 1864 | CA | GLY | A | 247 | 4.625 | 35.440 | 18.196 | 1.00 | 57.31 | A |
| ATOM | 1865 | C | GLY | A | 247 | 6.097 | 35.098 | 18.032 | 1.00 | 56.48 | A |
| ATOM | 1866 | O | GLY | A | 247 | 6.657 | 34.325 | 18.814 | 1.00 | 56.42 | A |
| ATOM | 1867 | N | ASP | A | 248 | 6.731 | 35.677 | 17.016 | 1.00 | 55.47 | A |
| ATOM | 1868 | CA | ASP | A | 248 | 8.146 | 35.430 | 16.760 | 1.00 | 54.34 | A |
| ATOM | 1869 | CB | ASP | A | 248 | 8.576 | 36.044 | 15.426 | 1.00 | 52.59 | A |
| ATOM | 1870 | CG | ASP | A | 248 | 7.876 | 35.427 | 14.246 | 1.00 | 51.48 | A |
| ATOM | 1871 | OD1 | ASP | A | 248 | 7.731 | 34.188 | 14.225 | 1.00 | 51.37 | A |
| ATOM | 1872 | OD2 | ASP | A | 248 | 7.485 | 36.180 | 13.328 | 1.00 | 51.45 | A |
| ATOM | 1873 | C | ASP | A | 248 | 9.018 | 36.022 | 17.855 | 1.00 | 54.31 | A |
| ATOM | 1874 | O | ASP | A | 248 | 9.865 | 35.339 | 18.428 | 1.00 | 54.40 | A |
| ATOM | 1875 | N | ILE | A | 249 | 8.813 | 37.306 | 18.123 | 1.00 | 55.01 | A |
| ATOM | 1876 | CA | ILE | A | 249 | 9.578 | 38.028 | 19.131 | 1.00 | 55.17 | A |
| ATOM | 1877 | CB | ILE | A | 249 | 8.906 | 39.378 | 19.454 | 1.00 | 55.80 | A |
| ATOM | 1878 | CG2 | ILE | A | 249 | 9.831 | 40.234 | 20.307 | 1.00 | 55.95 | A |
| ATOM | 1879 | CG1 | ILE | A | 249 | 8.575 | 40.109 | 18.151 | 1.00 | 56.11 | A |
| ATOM | 1880 | CD1 | ILE | A | 249 | 7.749 | 41.366 | 18.338 | 1.00 | 57.14 | A |
| ATOM | 1881 | C | ILE | A | 249 | 9.682 | 37.201 | 20.404 | 1.00 | 55.78 | A |
| ATOM | 1882 | O | ILE | A | 249 | 10.697 | 37.234 | 21.102 | 1.00 | 55.95 | A |
| ATOM | 1883 | N | GLU | A | 250 | 8.626 | 36.450 | 20.690 | 1.00 | 55.60 | A |
| ATOM | 1884 | CA | GLU | A | 250 | 8.577 | 35.611 | 21.875 | 1.00 | 55.90 | A |
| ATOM | 1885 | CB | GLU | A | 250 | 7.126 | 35.267 | 22.214 | 1.00 | 57.52 | A |
| ATOM | 1886 | CG | GLU | A | 250 | 6.987 | 34.358 | 23.416 | 1.00 | 60.65 | A |
| ATOM | 1887 | CD | GLU | A | 250 | 7.686 | 34.919 | 24.634 | 1.00 | 62.45 | A |
| ATOM | 1888 | OE1 | GLU | A | 250 | 7.352 | 36.054 | 25.038 | 1.00 | 63.26 | A |
| ATOM | 1889 | OE2 | GLU | A | 250 | 8.572 | 34.229 | 25.182 | 1.00 | 63.88 | A |
| ATOM | 1890 | C | GLU | A | 250 | 9.368 | 34.323 | 21.698 | 1.00 | 54.72 | A |
| ATOM | 1891 | O | GLU | A | 250 | 10.349 | 34.080 | 22.405 | 1.00 | 53.29 | A |
| ATOM | 1892 | N | LYS | A | 251 | 8.928 | 33.506 | 20.745 | 1.00 | 54.03 | A |
| ATOM | 1893 | CA | LYS | A | 251 | 9.555 | 32.221 | 20.461 | 1.00 | 53.48 | A |
| ATOM | 1894 | CB | LYS | A | 251 | 8.880 | 31.573 | 19.251 | 1.00 | 54.33 | A |
| ATOM | 1895 | CG | LYS | A | 251 | 9.268 | 30.122 | 19.033 | 1.00 | 55.38 | A |
| ATOM | 1896 | CD | LYS | A | 251 | 8.414 | 29.489 | 17.953 | 1.00 | 57.26 | A |
| ATOM | 1897 | CE | LYS | A | 251 | 8.646 | 27.989 | 17.873 | 1.00 | 58.08 | A |
| ATOM | 1898 | NZ | LYS | A | 251 | 7.790 | 27.348 | 16.833 | 1.00 | 58.69 | A |
| ATOM | 1899 | C | LYS | A | 251 | 11.067 | 32.292 | 20.235 | 1.00 | 52.15 | A |
| ATOM | 1900 | O | LYS | A | 251 | 11.812 | 31.441 | 20.731 | 1.00 | 51.69 | A |
| ATOM | 1901 | N | PHE | A | 252 | 11.523 | 33.300 | 19.497 | 1.00 | 50.10 | A |
| ATOM | 1902 | CA | PHE | A | 252 | 12.951 | 33.434 | 19.232 | 1.00 | 48.89 | A |
| ATOM | 1903 | CB | PHE | A | 252 | 13.197 | 34.435 | 18.099 | 1.00 | 45.87 | A |
| ATOM | 1904 | CG | PHE | A | 252 | 12.915 | 33.875 | 16.733 | 1.00 | 43.99 | A |
| ATOM | 1905 | CD1 | PHE | A | 252 | 11.616 | 33.564 | 16.349 | 1.00 | 41.90 | A |
| ATOM | 1906 | CD2 | PHE | A | 252 | 13.957 | 33.623 | 15.841 | 1.00 | 42.23 | A |
| ATOM | 1907 | CE1 | PHE | A | 252 | 11.356 | 33.009 | 15.097 | 1.00 | 41.89 | A |
| ATOM | 1908 | CE2 | PHE | A | 252 | 13.708 | 33.069 | 14.587 | 1.00 | 41.06 | A |
| ATOM | 1909 | CZ | PHE | A | 252 | 12.409 | 32.762 | 14.214 | 1.00 | 41.75 | A |
| ATOM | 1910 | C | PHE | A | 252 | 13.744 | 33.837 | 20.466 | 1.00 | 48.68 | A |
| ATOM | 1911 | O | PHE | A | 252 | 14.855 | 33.355 | 20.680 | 1.00 | 49.06 | A |
| ATOM | 1912 | N | HIS | A | 253 | 13.181 | 34.722 | 21.279 | 1.00 | 48.76 | A |
| ATOM | 1913 | CA | HIS | A | 253 | 13.870 | 35.145 | 22.490 | 1.00 | 49.30 | A |
| ATOM | 1914 | CB | HIS | A | 253 | 13.079 | 36.237 | 23.215 | 1.00 | 49.55 | A |
| ATOM | 1915 | CG | HIS | A | 253 | 13.576 | 36.513 | 24.599 | 1.00 | 50.62 | A |
| ATOM | 1916 | CD2 | HIS | A | 253 | 14.564 | 37.324 | 25.045 | 1.00 | 50.93 | A |
| ATOM | 1917 | ND1 | HIS | A | 253 | 13.084 | 35.861 | 25.709 | 1.00 | 51.60 | A |
| ATOM | 1918 | CE1 | HIS | A | 253 | 13.749 | 36.258 | 26.779 | 1.00 | 52.53 | A |
| ATOM | 1919 | NE2 | HIS | A | 253 | 14.653 | 37.144 | 26.404 | 1.00 | 52.16 | A |
| ATOM | 1920 | C | HIS | A | 253 | 14.033 | 33.937 | 23.403 | 1.00 | 48.72 | A |
| ATOM | 1921 | O | HIS | A | 253 | 15.067 | 33.765 | 24.052 | 1.00 | 47.39 | A |
| ATOM | 1922 | N | ASN | A | 254 | 12.995 | 33.108 | 23.437 | 1.00 | 48.76 | A |

APPENDIX 1-continued

Atomic coordinates of aromatic prenyltransferase residues 3-302 of SEQ ID NO: 2.

| ATOM | 1923 | CA  | ASN | A | 254 | 12.986 | 31.900 | 24.246 | 1.00 | 50.80 | A |
| ATOM | 1924 | CB  | ASN | A | 254 | 11.657 | 31.165 | 24.060 | 1.00 | 52.29 | A |
| ATOM | 1925 | CG  | ASN | A | 254 | 11.531 | 29.948 | 24.955 | 1.00 | 55.40 | A |
| ATOM | 1926 | OD1 | ASN | A | 254 | 11.461 | 30.066 | 26.181 | 1.00 | 57.62 | A |
| ATOM | 1927 | ND2 | ASN | A | 254 | 11.503 | 28.768 | 24.345 | 1.00 | 55.81 | A |
| ATOM | 1928 | C   | ASN | A | 254 | 14.137 | 30.998 | 23.817 | 1.00 | 50.81 | A |
| ATOM | 1929 | O   | ASN | A | 254 | 15.008 | 30.646 | 24.623 | 1.00 | 50.82 | A |
| ATOM | 1930 | N   | TYR | A | 255 | 14.138 | 30.637 | 22.537 | 1.00 | 50.64 | A |
| ATOM | 1931 | CA  | TYR | A | 255 | 15.171 | 29.773 | 21.977 | 1.00 | 49.68 | A |
| ATOM | 1932 | CB  | TYR | A | 255 | 14.963 | 29.601 | 20.471 | 1.00 | 50.04 | A |
| ATOM | 1933 | CG  | TYR | A | 255 | 15.905 | 28.596 | 19.842 | 1.00 | 50.36 | A |
| ATOM | 1934 | CD1 | TYR | A | 255 | 15.670 | 27.228 | 19.959 | 1.00 | 49.51 | A |
| ATOM | 1935 | CE1 | TYR | A | 255 | 16.550 | 26.296 | 19.415 | 1.00 | 49.32 | A |
| ATOM | 1936 | CD2 | TYR | A | 255 | 17.047 | 29.012 | 19.162 | 1.00 | 49.32 | A |
| ATOM | 1937 | CE2 | TYR | A | 255 | 17.936 | 28.088 | 18.614 | 1.00 | 49.59 | A |
| ATOM | 1938 | CZ  | TYR | A | 255 | 17.680 | 26.732 | 18.746 | 1.00 | 48.94 | A |
| ATOM | 1939 | OH  | TYR | A | 255 | 18.557 | 25.811 | 18.223 | 1.00 | 48.35 | A |
| ATOM | 1940 | C   | TYR | A | 255 | 16.545 | 30.365 | 22.217 | 1.00 | 48.91 | A |
| ATOM | 1941 | O   | TYR | A | 255 | 17.471 | 29.660 | 22.607 | 1.00 | 49.09 | A |
| ATOM | 1942 | N   | ALA | A | 256 | 16.659 | 31.670 | 21.989 | 1.00 | 48.96 | A |
| ATOM | 1943 | CA  | ALA | A | 256 | 17.918 | 32.392 | 22.145 | 1.00 | 49.88 | A |
| ATOM | 1944 | CB  | ALA | A | 256 | 17.756 | 33.820 | 21.618 | 1.00 | 48.87 | A |
| ATOM | 1945 | C   | ALA | A | 256 | 18.500 | 32.422 | 23.564 | 1.00 | 50.82 | A |
| ATOM | 1946 | O   | ALA | A | 256 | 19.716 | 32.536 | 23.735 | 1.00 | 50.22 | A |
| ATOM | 1947 | N   | THR | A | 257 | 17.651 | 32.328 | 24.582 | 1.00 | 52.17 | A |
| ATOM | 1948 | CA  | THR | A | 257 | 18.152 | 32.352 | 25.954 | 1.00 | 53.69 | A |
| ATOM | 1949 | CB  | THR | A | 257 | 17.347 | 33.334 | 26.837 | 1.00 | 52.46 | A |
| ATOM | 1950 | OG1 | THR | A | 257 | 15.945 | 33.092 | 26.677 | 1.00 | 51.52 | A |
| ATOM | 1951 | CG2 | THR | A | 257 | 17.667 | 34.771 | 26.462 | 1.00 | 52.76 | A |
| ATOM | 1952 | C   | THR | A | 257 | 18.145 | 30.977 | 26.615 | 1.00 | 55.15 | A |
| ATOM | 1953 | O   | THR | A | 257 | 18.703 | 30.804 | 27.699 | 1.00 | 55.75 | A |
| ATOM | 1954 | N   | LYS | A | 258 | 17.528 | 29.997 | 25.959 | 1.00 | 56.37 | A |
| ATOM | 1955 | CA  | LYS | A | 258 | 17.461 | 28.648 | 26.514 | 1.00 | 56.73 | A |
| ATOM | 1956 | CB  | LYS | A | 258 | 16.001 | 28.247 | 26.728 | 1.00 | 58.42 | A |
| ATOM | 1957 | CG  | LYS | A | 258 | 15.285 | 29.088 | 27.773 | 1.00 | 59.53 | A |
| ATOM | 1958 | CD  | LYS | A | 258 | 13.861 | 28.613 | 27.997 | 1.00 | 60.71 | A |
| ATOM | 1959 | CE  | LYS | A | 258 | 13.205 | 29.387 | 29.127 | 1.00 | 61.23 | A |
| ATOM | 1960 | NZ  | LYS | A | 258 | 11.785 | 28.986 | 29.313 | 1.00 | 62.40 | A |
| ATOM | 1961 | C   | LYS | A | 258 | 18.160 | 27.590 | 25.666 | 1.00 | 57.04 | A |
| ATOM | 1962 | O   | LYS | A | 258 | 18.072 | 26.398 | 25.963 | 1.00 | 56.70 | A |
| ATOM | 1963 | N   | ALA | A | 259 | 18.860 | 28.020 | 24.621 | 1.00 | 55.90 | A |
| ATOM | 1964 | CA  | ALA | A | 259 | 19.557 | 27.082 | 23.743 | 1.00 | 55.40 | A |
| ATOM | 1965 | CB  | ALA | A | 259 | 19.969 | 27.781 | 22.450 | 1.00 | 54.73 | A |
| ATOM | 1966 | C   | ALA | A | 259 | 20.780 | 26.456 | 24.409 | 1.00 | 55.07 | A |
| ATOM | 1967 | O   | ALA | A | 259 | 21.536 | 27.126 | 25.110 | 1.00 | 54.82 | A |
| ATOM | 1968 | N   | PRO | A | 260 | 20.988 | 25.150 | 24.196 | 1.00 | 55.21 | A |
| ATOM | 1969 | CD  | PRO | A | 260 | 20.123 | 24.180 | 23.501 | 1.00 | 54.90 | A |
| ATOM | 1970 | CA  | PRO | A | 260 | 22.139 | 24.480 | 24.799 | 1.00 | 55.01 | A |
| ATOM | 1971 | CB  | PRO | A | 260 | 21.806 | 23.003 | 24.615 | 1.00 | 55.58 | A |
| ATOM | 1972 | CG  | PRO | A | 260 | 21.050 | 22.999 | 23.328 | 1.00 | 55.22 | A |
| ATOM | 1973 | C   | PRO | A | 260 | 23.455 | 24.860 | 24.138 | 1.00 | 54.81 | A |
| ATOM | 1974 | O   | PRO | A | 260 | 23.525 | 25.030 | 22.923 | 1.00 | 55.25 | A |
| ATOM | 1975 | N   | TYR | A | 261 | 24.493 | 25.011 | 24.952 | 1.00 | 54.39 | A |
| ATOM | 1976 | CA  | TYR | A | 261 | 25.818 | 25.337 | 24.452 | 1.00 | 55.68 | A |
| ATOM | 1977 | CB  | TYR | A | 261 | 25.992 | 26.853 | 24.287 | 1.00 | 55.85 | A |
| ATOM | 1978 | CG  | TYR | A | 261 | 25.843 | 27.685 | 25.542 | 1.00 | 55.90 | A |
| ATOM | 1979 | CD1 | TYR | A | 261 | 26.945 | 28.326 | 26.108 | 1.00 | 55.27 | A |
| ATOM | 1980 | CE1 | TYR | A | 261 | 26.809 | 29.139 | 27.232 | 1.00 | 55.94 | A |
| ATOM | 1981 | CD2 | TYR | A | 261 | 24.594 | 27.873 | 26.136 | 1.00 | 55.74 | A |
| ATOM | 1982 | CE2 | TYR | A | 261 | 24.446 | 28.682 | 27.261 | 1.00 | 56.36 | A |
| ATOM | 1983 | CZ  | TYR | A | 261 | 25.558 | 29.313 | 27.803 | 1.00 | 56.36 | A |
| ATOM | 1984 | OH  | TYR | A | 261 | 25.416 | 30.118 | 28.911 | 1.00 | 57.53 | A |
| ATOM | 1985 | C   | TYR | A | 261 | 26.851 | 24.761 | 25.408 | 1.00 | 57.21 | A |
| ATOM | 1986 | O   | TYR | A | 261 | 26.639 | 24.738 | 26.623 | 1.00 | 57.77 | A |
| ATOM | 1987 | N   | ALA | A | 262 | 27.958 | 24.279 | 24.855 | 1.00 | 57.89 | A |
| ATOM | 1988 | CA  | ALA | A | 262 | 29.010 | 23.668 | 25.655 | 1.00 | 58.96 | A |
| ATOM | 1989 | CB  | ALA | A | 262 | 29.794 | 22.674 | 24.800 | 1.00 | 58.74 | A |
| ATOM | 1990 | C   | ALA | A | 262 | 29.963 | 24.668 | 26.296 | 1.00 | 59.61 | A |
| ATOM | 1991 | O   | ALA | A | 262 | 30.337 | 24.515 | 27.460 | 1.00 | 60.65 | A |
| ATOM | 1992 | N   | TYR | A | 263 | 30.352 | 25.687 | 25.539 | 1.00 | 59.26 | A |
| ATOM | 1993 | CA  | TYR | A | 263 | 31.276 | 26.705 | 26.027 | 1.00 | 58.56 | A |
| ATOM | 1994 | CB  | TYR | A | 263 | 31.688 | 27.627 | 24.872 | 1.00 | 57.62 | A |
| ATOM | 1995 | CG  | TYR | A | 263 | 30.532 | 28.126 | 24.031 | 1.00 | 55.64 | A |
| ATOM | 1996 | CD1 | TYR | A | 263 | 29.825 | 27.261 | 23.193 | 1.00 | 55.16 | A |
| ATOM | 1997 | CE1 | TYR | A | 263 | 28.753 | 27.712 | 22.431 | 1.00 | 53.62 | A |
| ATOM | 1998 | CD2 | TYR | A | 263 | 30.134 | 29.460 | 24.082 | 1.00 | 55.16 | A |
| ATOM | 1999 | CE2 | TYR | A | 263 | 29.061 | 29.922 | 23.323 | 1.00 | 53.97 | A |

APPENDIX 1-continued

Atomic coordinates of aromatic prenyltransferase residues 3-302 of SEQ ID NO: 2.

| ATOM | 2000 | CZ | TYR | A | 263 | 28.375 | 29.044 | 22.503 | 1.00 | 53.51 | A |
|---|---|---|---|---|---|---|---|---|---|---|---|
| ATOM | 2001 | OH | TYR | A | 263 | 27.296 | 29.494 | 21.778 | 1.00 | 51.12 | A |
| ATOM | 2002 | C | TYR | A | 263 | 30.762 | 27.547 | 27.202 | 1.00 | 58.82 | A |
| ATOM | 2003 | O | TYR | A | 263 | 30.686 | 28.773 | 27.109 | 1.00 | 58.03 | A |
| ATOM | 2004 | N | VAL | A | 264 | 30.419 | 26.889 | 28.307 | 1.00 | 59.23 | A |
| ATOM | 2005 | CA | VAL | A | 264 | 29.941 | 27.593 | 29.496 | 1.00 | 59.65 | A |
| ATOM | 2006 | CB | VAL | A | 264 | 29.576 | 26.607 | 30.634 | 1.00 | 60.55 | A |
| ATOM | 2007 | CG1 | VAL | A | 264 | 29.253 | 27.377 | 31.911 | 1.00 | 61.12 | A |
| ATOM | 2008 | CG2 | VAL | A | 264 | 28.384 | 25.754 | 30.220 | 1.00 | 60.60 | A |
| ATOM | 2009 | C | VAL | A | 264 | 31.034 | 28.539 | 29.990 | 1.00 | 59.17 | A |
| ATOM | 2010 | O | VAL | A | 264 | 32.211 | 28.175 | 30.033 | 1.00 | 58.78 | A |
| ATOM | 2011 | N | GLY | A | 265 | 30.636 | 29.751 | 30.359 | 1.00 | 58.41 | A |
| ATOM | 2012 | CA | GLY | A | 265 | 31.591 | 30.739 | 30.824 | 1.00 | 57.69 | A |
| ATOM | 2013 | C | GLY | A | 265 | 31.473 | 31.966 | 29.945 | 1.00 | 57.54 | A |
| ATOM | 2014 | O | GLY | A | 265 | 31.800 | 33.086 | 30.341 | 1.00 | 56.90 | A |
| ATOM | 2015 | N | GLU | A | 266 | 31.009 | 31.740 | 28.724 | 1.00 | 57.93 | A |
| ATOM | 2016 | CA | GLU | A | 266 | 30.811 | 32.820 | 27.777 | 1.00 | 58.46 | A |
| ATOM | 2017 | CB | GLU | A | 266 | 31.588 | 32.567 | 26.490 | 1.00 | 58.78 | A |
| ATOM | 2018 | CG | GLU | A | 266 | 33.066 | 32.327 | 26.702 | 1.00 | 59.25 | A |
| ATOM | 2019 | CD | GLU | A | 266 | 33.790 | 32.041 | 25.405 | 1.00 | 59.38 | A |
| ATOM | 2020 | OE1 | GLU | A | 266 | 34.004 | 32.986 | 24.616 | 1.00 | 59.35 | A |
| ATOM | 2021 | OE2 | GLU | A | 266 | 34.135 | 30.865 | 25.171 | 1.00 | 60.57 | A |
| ATOM | 2022 | C | GLU | A | 266 | 29.326 | 32.844 | 27.480 | 1.00 | 58.93 | A |
| ATOM | 2023 | O | GLU | A | 266 | 28.578 | 31.961 | 27.913 | 1.00 | 59.06 | A |
| ATOM | 2024 | N | LYS | A | 267 | 28.893 | 33.855 | 26.743 | 1.00 | 58.87 | A |
| ATOM | 2025 | CA | LYS | A | 267 | 27.489 | 33.963 | 26.403 | 1.00 | 58.23 | A |
| ATOM | 2026 | CB | LYS | A | 267 | 27.080 | 35.438 | 26.338 | 1.00 | 59.85 | A |
| ATOM | 2027 | CG | LYS | A | 267 | 27.061 | 36.127 | 27.703 | 1.00 | 61.48 | A |
| ATOM | 2028 | CD | LYS | A | 267 | 28.411 | 36.008 | 28.406 | 1.00 | 62.59 | A |
| ATOM | 2029 | CE | LYS | A | 267 | 28.296 | 36.229 | 29.907 | 1.00 | 62.62 | A |
| ATOM | 2030 | NZ | LYS | A | 267 | 29.556 | 35.847 | 30.602 | 1.00 | 60.90 | A |
| ATOM | 2031 | C | LYS | A | 267 | 27.256 | 33.268 | 25.073 | 1.00 | 56.21 | A |
| ATOM | 2032 | O | LYS | A | 267 | 28.154 | 33.213 | 24.230 | 1.00 | 55.89 | A |
| ATOM | 2033 | N | ARG | A | 268 | 26.057 | 32.717 | 24.903 | 1.00 | 54.39 | A |
| ATOM | 2034 | CA | ARG | A | 268 | 25.698 | 32.023 | 23.674 | 1.00 | 52.55 | A |
| ATOM | 2035 | CB | ARG | A | 268 | 24.194 | 31.750 | 23.605 | 1.00 | 51.64 | A |
| ATOM | 2036 | CG | ARG | A | 268 | 23.639 | 30.751 | 24.585 | 1.00 | 52.17 | A |
| ATOM | 2037 | CD | ARG | A | 268 | 22.164 | 30.533 | 24.291 | 1.00 | 53.30 | A |
| ATOM | 2038 | NE | ARG | A | 268 | 21.522 | 29.641 | 25.251 | 1.00 | 55.82 | A |
| ATOM | 2039 | CZ | ARG | A | 268 | 21.311 | 29.938 | 26.530 | 1.00 | 56.60 | A |
| ATOM | 2040 | NH1 | ARG | A | 268 | 21.689 | 31.114 | 27.014 | 1.00 | 57.37 | A |
| ATOM | 2041 | NH2 | ARG | A | 268 | 20.722 | 29.055 | 27.325 | 1.00 | 57.84 | A |
| ATOM | 2042 | C | ARG | A | 268 | 26.053 | 32.847 | 22.454 | 1.00 | 50.70 | A |
| ATOM | 2043 | O | ARG | A | 268 | 25.856 | 34.065 | 22.435 | 1.00 | 51.42 | A |
| ATOM | 2044 | N | THR | A | 269 | 26.585 | 32.176 | 21.441 | 1.00 | 50.18 | A |
| ATOM | 2045 | CA | THR | A | 269 | 26.902 | 32.828 | 20.183 | 1.00 | 47.44 | A |
| ATOM | 2046 | CB | THR | A | 269 | 28.116 | 32.200 | 19.498 | 1.00 | 48.13 | A |
| ATOM | 2047 | OG1 | THR | A | 269 | 29.289 | 32.466 | 20.277 | 1.00 | 48.94 | A |
| ATOM | 2048 | CG2 | THR | A | 269 | 28.297 | 32.784 | 18.096 | 1.00 | 47.82 | A |
| ATOM | 2049 | C | THR | A | 269 | 25.656 | 32.572 | 19.343 | 1.00 | 46.15 | A |
| ATOM | 2050 | O | THR | A | 269 | 25.227 | 31.430 | 19.188 | 1.00 | 46.11 | A |
| ATOM | 2051 | N | LEU | A | 270 | 25.063 | 33.641 | 18.830 | 1.00 | 44.47 | A |
| ATOM | 2052 | CA | LEU | A | 270 | 23.853 | 33.532 | 18.031 | 1.00 | 43.06 | A |
| ATOM | 2053 | CB | LEU | A | 270 | 22.713 | 34.265 | 18.740 | 1.00 | 43.60 | A |
| ATOM | 2054 | CG | LEU | A | 270 | 22.468 | 33.872 | 20.200 | 1.00 | 44.62 | A |
| ATOM | 2055 | CD1 | LEU | A | 270 | 21.764 | 35.002 | 20.927 | 1.00 | 44.69 | A |
| ATOM | 2056 | CD2 | LEU | A | 270 | 21.646 | 32.597 | 20.261 | 1.00 | 44.54 | A |
| ATOM | 2057 | C | LEU | A | 270 | 24.054 | 34.133 | 16.642 | 1.00 | 40.92 | A |
| ATOM | 2058 | O | LEU | A | 270 | 24.858 | 35.046 | 16.462 | 1.00 | 42.68 | A |
| ATOM | 2059 | N | VAL | A | 271 | 23.332 | 33.603 | 15.663 | 1.00 | 39.89 | A |
| ATOM | 2060 | CA | VAL | A | 271 | 23.394 | 34.120 | 14.298 | 1.00 | 38.73 | A |
| ATOM | 2061 | CB | VAL | A | 271 | 24.243 | 33.236 | 13.371 | 1.00 | 39.03 | A |
| ATOM | 2062 | CG1 | VAL | A | 271 | 24.009 | 33.628 | 11.911 | 1.00 | 37.91 | A |
| ATOM | 2063 | CG2 | VAL | A | 271 | 25.703 | 33.419 | 13.699 | 1.00 | 37.99 | A |
| ATOM | 2064 | C | VAL | A | 271 | 21.972 | 34.181 | 13.775 | 1.00 | 37.49 | A |
| ATOM | 2065 | O | VAL | A | 271 | 21.330 | 33.154 | 13.568 | 1.00 | 36.59 | A |
| ATOM | 2066 | N | TYR | A | 272 | 21.475 | 35.398 | 13.602 | 1.00 | 37.97 | A |
| ATOM | 2067 | CA | TYR | A | 272 | 20.121 | 35.605 | 13.113 | 1.00 | 36.60 | A |
| ATOM | 2068 | CB | TYR | A | 272 | 19.528 | 36.903 | 13.659 | 1.00 | 37.13 | A |
| ATOM | 2069 | CG | TYR | A | 272 | 19.312 | 36.932 | 15.152 | 1.00 | 40.37 | A |
| ATOM | 2070 | CD1 | TYR | A | 272 | 20.387 | 37.056 | 16.033 | 1.00 | 40.17 | A |
| ATOM | 2071 | CE1 | TYR | A | 272 | 20.178 | 37.136 | 17.413 | 1.00 | 42.29 | A |
| ATOM | 2072 | CD2 | TYR | A | 272 | 18.021 | 36.879 | 15.685 | 1.00 | 41.07 | A |
| ATOM | 2073 | CE2 | TYR | A | 272 | 17.805 | 36.956 | 17.056 | 1.00 | 41.54 | A |
| ATOM | 2074 | CZ | TYR | A | 272 | 18.883 | 37.086 | 17.913 | 1.00 | 41.60 | A |
| ATOM | 2075 | OH | TYR | A | 272 | 18.657 | 37.172 | 19.266 | 1.00 | 43.79 | A |
| ATOM | 2076 | C | TYR | A | 272 | 20.109 | 35.686 | 11.603 | 1.00 | 35.69 | A |

APPENDIX 1-continued

Atomic coordinates of aromatic prenyltransferase residues 3-302 of SEQ ID NO: 2.

| ATOM | 2077 | O | TYR | A | 272 | 21.119 | 35.983 | 10.977 | 1.00 | 34.57 | A |
|---|---|---|---|---|---|---|---|---|---|---|---|
| ATOM | 2078 | N | GLY | A | 273 | 18.940 | 35.444 | 11.031 | 1.00 | 34.52 | A |
| ATOM | 2079 | CA | GLY | A | 273 | 18.815 | 35.508 | 9.596 | 1.00 | 34.19 | A |
| ATOM | 2080 | C | GLY | A | 273 | 17.487 | 36.075 | 9.159 | 1.00 | 32.96 | A |
| ATOM | 2081 | O | GLY | A | 273 | 16.435 | 35.786 | 9.747 | 1.00 | 33.22 | A |
| ATOM | 2082 | N | LEU | A | 274 | 17.548 | 36.915 | 8.136 | 1.00 | 31.58 | A |
| ATOM | 2083 | CA | LEU | A | 274 | 16.360 | 37.508 | 7.557 | 1.00 | 30.07 | A |
| ATOM | 2084 | CB | LEU | A | 274 | 16.417 | 39.029 | 7.606 | 1.00 | 30.58 | A |
| ATOM | 2085 | CG | LEU | A | 274 | 15.329 | 39.712 | 6.766 | 1.00 | 32.48 | A |
| ATOM | 2086 | CD1 | LEU | A | 274 | 13.961 | 39.283 | 7.256 | 1.00 | 32.49 | A |
| ATOM | 2087 | CD2 | LEU | A | 274 | 15.470 | 41.216 | 6.855 | 1.00 | 31.20 | A |
| ATOM | 2088 | C | LEU | A | 274 | 16.403 | 37.044 | 6.119 | 1.00 | 29.70 | A |
| ATOM | 2089 | O | LEU | A | 274 | 17.318 | 37.399 | 5.377 | 1.00 | 27.86 | A |
| ATOM | 2090 | N | THR | A | 275 | 15.429 | 36.231 | 5.737 | 1.00 | 28.56 | A |
| ATOM | 2091 | CA | THR | A | 275 | 15.384 | 35.704 | 4.390 | 1.00 | 30.21 | A |
| ATOM | 2092 | CB | THR | A | 275 | 15.249 | 34.174 | 4.397 | 1.00 | 30.89 | A |
| ATOM | 2093 | OG1 | THR | A | 275 | 16.243 | 33.611 | 5.263 | 1.00 | 31.27 | A |
| ATOM | 2094 | CG2 | THR | A | 275 | 15.466 | 33.617 | 2.985 | 1.00 | 32.12 | A |
| ATOM | 2095 | C | THR | A | 275 | 14.228 | 36.296 | 3.613 | 1.00 | 31.45 | A |
| ATOM | 2096 | O | THR | A | 275 | 13.095 | 36.367 | 4.106 | 1.00 | 30.04 | A |
| ATOM | 2097 | N | LEU | A | 276 | 14.534 | 36.707 | 2.389 | 1.00 | 30.98 | A |
| ATOM | 2098 | CA | LEU | A | 276 | 13.560 | 37.306 | 1.502 | 1.00 | 32.05 | A |
| ATOM | 2099 | CB | LEU | A | 276 | 14.029 | 38.692 | 1.063 | 1.00 | 32.02 | A |
| ATOM | 2100 | CG | LEU | A | 276 | 14.463 | 39.658 | 2.161 | 1.00 | 31.99 | A |
| ATOM | 2101 | CD1 | LEU | A | 276 | 15.012 | 40.926 | 1.528 | 1.00 | 33.02 | A |
| ATOM | 2102 | CD2 | LEU | A | 276 | 13.287 | 39.968 | 3.067 | 1.00 | 31.46 | A |
| ATOM | 2103 | C | LEU | A | 276 | 13.377 | 36.442 | 0.269 | 1.00 | 32.27 | A |
| ATOM | 2104 | O | LEU | A | 276 | 14.331 | 36.202 | −0.471 | 1.00 | 31.75 | A |
| ATOM | 2105 | N | SER | A | 277 | 12.151 | 35.967 | 0.065 | 1.00 | 33.88 | A |
| ATOM | 2106 | CA | SER | A | 277 | 11.830 | 35.164 | −1.101 | 1.00 | 34.99 | A |
| ATOM | 2107 | CB | SER | A | 277 | 11.166 | 33.848 | −0.689 | 1.00 | 35.49 | A |
| ATOM | 2108 | OG | SER | A | 277 | 9.833 | 34.061 | −0.264 | 1.00 | 37.40 | A |
| ATOM | 2109 | C | SER | A | 277 | 10.873 | 36.020 | −1.931 | 1.00 | 36.36 | A |
| ATOM | 2110 | O | SER | A | 277 | 10.451 | 37.090 | −1.493 | 1.00 | 34.72 | A |
| ATOM | 2111 | N | PRO | A | 278 | 10.514 | 35.563 | −3.139 | 1.00 | 39.44 | A |
| ATOM | 2112 | CD | PRO | A | 278 | 10.974 | 34.375 | −3.875 | 1.00 | 39.05 | A |
| ATOM | 2113 | CA | PRO | A | 278 | 9.606 | 36.369 | −3.957 | 1.00 | 40.64 | A |
| ATOM | 2114 | CB | PRO | A | 278 | 9.433 | 35.521 | −5.214 | 1.00 | 40.18 | A |
| ATOM | 2115 | CG | PRO | A | 278 | 10.752 | 34.792 | −5.306 | 1.00 | 40.69 | A |
| ATOM | 2116 | C | PRO | A | 278 | 8.272 | 36.695 | −3.300 | 1.00 | 42.09 | A |
| ATOM | 2117 | O | PRO | A | 278 | 7.765 | 37.807 | −3.428 | 1.00 | 43.87 | A |
| ATOM | 2118 | N | LYS | A | 279 | 7.715 | 35.740 | −2.570 | 1.00 | 44.32 | A |
| ATOM | 2119 | CA | LYS | A | 279 | 6.414 | 35.959 | −1.964 | 1.00 | 45.01 | A |
| ATOM | 2120 | CB | LYS | A | 279 | 5.533 | 34.738 | −2.224 | 1.00 | 46.55 | A |
| ATOM | 2121 | CG | LYS | A | 279 | 5.493 | 34.307 | −3.693 | 1.00 | 48.65 | A |
| ATOM | 2122 | CD | LYS | A | 279 | 4.868 | 35.368 | −4.594 | 1.00 | 49.82 | A |
| ATOM | 2123 | CE | LYS | A | 279 | 4.878 | 34.913 | −6.054 | 1.00 | 50.84 | A |
| ATOM | 2124 | NZ | LYS | A | 279 | 4.280 | 35.916 | −6.979 | 1.00 | 51.34 | A |
| ATOM | 2125 | C | LYS | A | 279 | 6.380 | 36.303 | −0.483 | 1.00 | 44.70 | A |
| ATOM | 2126 | O | LYS | A | 279 | 5.385 | 36.834 | 0.001 | 1.00 | 45.30 | A |
| ATOM | 2127 | N | GLU | A | 280 | 7.457 | 36.029 | 0.240 | 1.00 | 43.74 | A |
| ATOM | 2128 | CA | GLU | A | 280 | 7.464 | 36.308 | 1.670 | 1.00 | 42.41 | A |
| ATOM | 2129 | CB | GLU | A | 280 | 6.956 | 35.086 | 2.439 | 1.00 | 45.17 | A |
| ATOM | 2130 | CG | GLU | A | 280 | 7.607 | 33.770 | 1.997 | 1.00 | 48.54 | A |
| ATOM | 2131 | CD | GLU | A | 280 | 7.531 | 32.665 | 3.051 | 1.00 | 51.12 | A |
| ATOM | 2132 | OE1 | GLU | A | 280 | 6.653 | 32.737 | 3.940 | 1.00 | 53.02 | A |
| ATOM | 2133 | OE2 | GLU | A | 280 | 8.346 | 31.717 | 2.982 | 1.00 | 50.28 | A |
| ATOM | 2134 | C | GLU | A | 280 | 8.816 | 36.688 | 2.244 | 1.00 | 40.99 | A |
| ATOM | 2135 | O | GLU | A | 280 | 9.796 | 36.885 | 1.527 | 1.00 | 37.74 | A |
| ATOM | 2136 | N | GLU | A | 281 | 8.828 | 36.773 | 3.569 | 1.00 | 40.26 | A |
| ATOM | 2137 | CA | GLU | A | 281 | 10.003 | 37.079 | 4.363 | 1.00 | 39.86 | A |
| ATOM | 2138 | CB | GLU | A | 281 | 10.008 | 38.562 | 4.754 | 1.00 | 40.81 | A |
| ATOM | 2139 | CG | GLU | A | 281 | 10.698 | 38.866 | 6.077 | 1.00 | 41.06 | A |
| ATOM | 2140 | CD | GLU | A | 281 | 10.540 | 40.316 | 6.517 | 1.00 | 43.02 | A |
| ATOM | 2141 | OE1 | GLU | A | 281 | 10.990 | 41.219 | 5.784 | 1.00 | 42.38 | A |
| ATOM | 2142 | OE2 | GLU | A | 281 | 9.967 | 40.558 | 7.603 | 1.00 | 42.59 | A |
| ATOM | 2143 | C | GLU | A | 281 | 9.874 | 36.224 | 5.621 | 1.00 | 39.25 | A |
| ATOM | 2144 | O | GLU | A | 281 | 8.813 | 36.204 | 6.242 | 1.00 | 39.38 | A |
| ATOM | 2145 | N | TYR | A | 282 | 10.929 | 35.501 | 5.984 | 1.00 | 36.51 | A |
| ATOM | 2146 | CA | TYR | A | 282 | 10.895 | 34.703 | 7.200 | 1.00 | 35.17 | A |
| ATOM | 2147 | CB | TYR | A | 282 | 10.575 | 33.231 | 6.909 | 1.00 | 34.96 | A |
| ATOM | 2148 | CG | TYR | A | 282 | 11.546 | 32.493 | 6.022 | 1.00 | 35.52 | A |
| ATOM | 2149 | CD1 | TYR | A | 282 | 12.574 | 31.728 | 6.569 | 1.00 | 35.03 | A |
| ATOM | 2150 | CE1 | TYR | A | 282 | 13.446 | 31.001 | 5.758 | 1.00 | 36.48 | A |
| ATOM | 2151 | CD2 | TYR | A | 282 | 11.411 | 32.521 | 4.631 | 1.00 | 34.37 | A |
| ATOM | 2152 | CE2 | TYR | A | 282 | 12.279 | 31.796 | 3.809 | 1.00 | 34.23 | A |
| ATOM | 2153 | CZ | TYR | A | 282 | 13.291 | 31.040 | 4.380 | 1.00 | 34.88 | A |

APPENDIX 1-continued

Atomic coordinates of aromatic prenyltransferase residues 3-302 of SEQ ID NO: 2.

| ATOM | 2154 | OH | TYR | A | 282 | 14.143 | 30.310 | 3.584 | 1.00 | 37.85 | A |
|---|---|---|---|---|---|---|---|---|---|---|---|
| ATOM | 2155 | C | TYR | A | 282 | 12.205 | 34.871 | 7.956 | 1.00 | 34.80 | A |
| ATOM | 2156 | O | TYR | A | 282 | 13.182 | 35.398 | 7.415 | 1.00 | 32.60 | A |
| ATOM | 2157 | N | TYR | A | 283 | 12.216 | 34.423 | 9.206 | 1.00 | 34.19 | A |
| ATOM | 2158 | CA | TYR | A | 283 | 13.369 | 34.598 | 10.080 | 1.00 | 33.80 | A |
| ATOM | 2159 | CB | TYR | A | 283 | 12.910 | 35.412 | 11.288 | 1.00 | 35.23 | A |
| ATOM | 2160 | CG | TYR | A | 283 | 11.860 | 36.424 | 10.889 | 1.00 | 36.91 | A |
| ATOM | 2161 | CD1 | TYR | A | 283 | 12.193 | 37.541 | 10.117 | 1.00 | 37.31 | A |
| ATOM | 2162 | CE1 | TYR | A | 283 | 11.206 | 38.407 | 9.629 | 1.00 | 37.64 | A |
| ATOM | 2163 | CD2 | TYR | A | 283 | 10.512 | 36.203 | 11.175 | 1.00 | 38.08 | A |
| ATOM | 2164 | CE2 | TYR | A | 283 | 9.521 | 37.059 | 10.695 | 1.00 | 38.79 | A |
| ATOM | 2165 | CZ | TYR | A | 283 | 9.875 | 38.154 | 9.923 | 1.00 | 39.16 | A |
| ATOM | 2166 | OH | TYR | A | 283 | 8.890 | 38.986 | 9.446 | 1.00 | 39.66 | A |
| ATOM | 2167 | C | TYR | A | 283 | 14.041 | 33.302 | 10.519 | 1.00 | 33.97 | A |
| ATOM | 2168 | O | TYR | A | 283 | 13.404 | 32.258 | 10.627 | 1.00 | 34.03 | A |
| ATOM | 2169 | N | LYS | A | 284 | 15.342 | 33.375 | 10.768 | 1.00 | 32.82 | A |
| ATOM | 2170 | CA | LYS | A | 284 | 16.086 | 32.191 | 11.170 | 1.00 | 33.38 | A |
| ATOM | 2171 | CB | LYS | A | 284 | 16.893 | 31.668 | 9.974 | 1.00 | 34.19 | A |
| ATOM | 2172 | CG | LYS | A | 284 | 15.989 | 31.260 | 8.809 | 1.00 | 36.80 | A |
| ATOM | 2173 | CD | LYS | A | 284 | 16.733 | 30.629 | 7.633 | 1.00 | 39.12 | A |
| ATOM | 2174 | CE | LYS | A | 284 | 17.536 | 31.643 | 6.843 | 1.00 | 40.11 | A |
| ATOM | 2175 | NZ | LYS | A | 284 | 18.047 | 31.069 | 5.548 | 1.00 | 34.37 | A |
| ATOM | 2176 | C | LYS | A | 284 | 16.988 | 32.481 | 12.362 | 1.00 | 32.66 | A |
| ATOM | 2177 | O | LYS | A | 284 | 17.392 | 33.624 | 12.583 | 1.00 | 33.84 | A |
| ATOM | 2178 | N | LEU | A | 285 | 17.283 | 31.448 | 13.143 | 1.00 | 33.01 | A |
| ATOM | 2179 | CA | LEU | A | 285 | 18.141 | 31.621 | 14.308 | 1.00 | 33.94 | A |
| ATOM | 2180 | CB | LEU | A | 285 | 17.309 | 32.021 | 15.531 | 1.00 | 34.70 | A |
| ATOM | 2181 | CG | LEU | A | 285 | 18.063 | 32.102 | 16.862 | 1.00 | 36.10 | A |
| ATOM | 2182 | CD1 | LEU | A | 285 | 19.214 | 33.085 | 16.752 | 1.00 | 35.16 | A |
| ATOM | 2183 | CD2 | LEU | A | 285 | 17.097 | 32.525 | 17.965 | 1.00 | 36.19 | A |
| ATOM | 2184 | C | LEU | A | 285 | 18.950 | 30.377 | 14.633 | 1.00 | 33.22 | A |
| ATOM | 2185 | O | LEU | A | 285 | 18.401 | 29.311 | 14.918 | 1.00 | 34.61 | A |
| ATOM | 2186 | N | GLY | A | 286 | 20.265 | 30.527 | 14.582 | 1.00 | 33.99 | A |
| ATOM | 2187 | CA | GLY | A | 286 | 21.142 | 29.422 | 14.893 | 1.00 | 34.28 | A |
| ATOM | 2188 | C | GLY | A | 286 | 21.824 | 29.682 | 16.218 | 1.00 | 34.79 | A |
| ATOM | 2189 | O | GLY | A | 286 | 22.402 | 30.745 | 16.418 | 1.00 | 35.42 | A |
| ATOM | 2190 | N | ALA | A | 287 | 21.728 | 28.726 | 17.135 | 1.00 | 36.63 | A |
| ATOM | 2191 | CA | ALA | A | 287 | 22.369 | 28.848 | 18.439 | 1.00 | 37.80 | A |
| ATOM | 2192 | CB | ALA | A | 287 | 21.384 | 28.517 | 19.546 | 1.00 | 37.09 | A |
| ATOM | 2193 | C | ALA | A | 287 | 23.530 | 27.865 | 18.454 | 1.00 | 38.30 | A |
| ATOM | 2194 | O | ALA | A | 287 | 23.326 | 26.648 | 18.412 | 1.00 | 38.88 | A |
| ATOM | 2195 | N | TYR | A | 288 | 24.746 | 28.397 | 18.497 | 1.00 | 40.30 | A |
| ATOM | 2196 | CA | TYR | A | 288 | 25.936 | 27.569 | 18.505 | 1.00 | 42.62 | A |
| ATOM | 2197 | CB | TYR | A | 288 | 27.189 | 28.434 | 18.343 | 1.00 | 43.09 | A |
| ATOM | 2198 | CG | TYR | A | 288 | 27.362 | 29.009 | 16.955 | 1.00 | 43.83 | A |
| ATOM | 2199 | CD1 | TYR | A | 288 | 26.405 | 29.865 | 16.409 | 1.00 | 45.17 | A |
| ATOM | 2200 | CE1 | TYR | A | 288 | 26.545 | 30.373 | 15.119 | 1.00 | 44.97 | A |
| ATOM | 2201 | CD2 | TYR | A | 288 | 28.469 | 28.679 | 16.175 | 1.00 | 43.95 | A |
| ATOM | 2202 | CE2 | TYR | A | 288 | 28.621 | 29.182 | 14.885 | 1.00 | 43.70 | A |
| ATOM | 2203 | CZ | TYR | A | 288 | 27.654 | 30.027 | 14.365 | 1.00 | 45.56 | A |
| ATOM | 2204 | OH | TYR | A | 288 | 27.789 | 30.525 | 13.090 | 1.00 | 46.87 | A |
| ATOM | 2205 | C | TYR | A | 288 | 26.059 | 26.734 | 19.768 | 1.00 | 45.18 | A |
| ATOM | 2206 | O | TYR | A | 288 | 25.919 | 27.240 | 20.882 | 1.00 | 44.32 | A |
| ATOM | 2207 | N | TYR | A | 289 | 26.305 | 25.443 | 19.573 | 1.00 | 46.25 | A |
| ATOM | 2208 | CA | TYR | A | 289 | 26.496 | 24.519 | 20.674 | 1.00 | 47.59 | A |
| ATOM | 2209 | CB | TYR | A | 289 | 25.997 | 23.126 | 20.305 | 1.00 | 48.44 | A |
| ATOM | 2210 | CG | TYR | A | 289 | 26.224 | 22.105 | 21.393 | 1.00 | 51.30 | A |
| ATOM | 2211 | CD1 | TYR | A | 289 | 25.700 | 22.294 | 22.674 | 1.00 | 51.82 | A |
| ATOM | 2212 | CE1 | TYR | A | 289 | 25.937 | 21.378 | 23.688 | 1.00 | 53.60 | A |
| ATOM | 2213 | CD2 | TYR | A | 289 | 26.988 | 20.965 | 21.155 | 1.00 | 50.81 | A |
| ATOM | 2214 | CE2 | TYR | A | 289 | 27.230 | 20.041 | 22.162 | 1.00 | 53.45 | A |
| ATOM | 2215 | CZ | TYR | A | 289 | 26.702 | 20.255 | 23.426 | 1.00 | 53.78 | A |
| ATOM | 2216 | OH | TYR | A | 289 | 26.946 | 19.346 | 24.428 | 1.00 | 55.63 | A |
| ATOM | 2217 | C | TYR | A | 289 | 27.998 | 24.496 | 20.912 | 1.00 | 47.53 | A |
| ATOM | 2218 | O | TYR | A | 289 | 28.458 | 24.476 | 22.053 | 1.00 | 48.27 | A |
| ATOM | 2219 | N | HIS | A | 290 | 28.755 | 24.505 | 19.819 | 1.00 | 46.65 | A |
| ATOM | 2220 | CA | HIS | A | 290 | 30.214 | 24.524 | 19.871 | 1.00 | 45.99 | A |
| ATOM | 2221 | CB | HIS | A | 290 | 30.824 | 23.263 | 19.246 | 1.00 | 47.09 | A |
| ATOM | 2222 | CG | HIS | A | 290 | 30.663 | 22.026 | 20.070 | 1.00 | 47.66 | A |
| ATOM | 2223 | CD2 | HIS | A | 290 | 30.004 | 21.803 | 21.231 | 1.00 | 48.23 | A |
| ATOM | 2224 | ND1 | HIS | A | 290 | 31.203 | 20.815 | 19.697 | 1.00 | 48.48 | A |
| ATOM | 2225 | CE1 | HIS | A | 290 | 30.880 | 19.897 | 20.592 | 1.00 | 48.01 | A |
| ATOM | 2226 | NE2 | HIS | A | 290 | 30.152 | 20.471 | 21.532 | 1.00 | 47.65 | A |
| ATOM | 2227 | C | HIS | A | 290 | 30.695 | 25.715 | 19.061 | 1.00 | 46.29 | A |
| ATOM | 2228 | O | HIS | A | 290 | 30.152 | 26.000 | 17.986 | 1.00 | 45.19 | A |
| ATOM | 2229 | N | ILE | A | 291 | 31.708 | 26.407 | 19.573 | 1.00 | 44.93 | A |
| ATOM | 2230 | CA | ILE | A | 291 | 32.282 | 27.548 | 18.875 | 1.00 | 45.16 | A |

APPENDIX 1-continued

Atomic coordinates of aromatic prenyltransferase residues 3-302 of SEQ ID NO: 2.

| ATOM | 2231 | CB | ILE | A | 291 | 31.889 | 28.907 | 19.524 | 1.00 | 45.11 | A |
|------|------|-----|-----|---|-----|--------|--------|--------|------|-------|---|
| ATOM | 2232 | CG2 | ILE | A | 291 | 30.417 | 29.188 | 19.301 | 1.00 | 43.33 | A |
| ATOM | 2233 | CG1 | ILE | A | 291 | 32.243 | 28.899 | 21.019 | 1.00 | 45.59 | A |
| ATOM | 2234 | CD1 | ILE | A | 291 | 32.186 | 30.259 | 21.675 | 1.00 | 45.30 | A |
| ATOM | 2235 | C | ILE | A | 291 | 33.798 | 27.454 | 18.879 | 1.00 | 45.61 | A |
| ATOM | 2236 | O | ILE | A | 291 | 34.387 | 26.651 | 19.602 | 1.00 | 47.34 | A |
| ATOM | 2237 | N | THR | A | 292 | 34.424 | 28.291 | 18.065 | 1.00 | 47.17 | A |
| ATOM | 2238 | CA | THR | A | 292 | 35.875 | 28.341 | 17.967 | 1.00 | 47.28 | A |
| ATOM | 2239 | CB | THR | A | 292 | 36.371 | 27.755 | 16.639 | 1.00 | 47.48 | A |
| ATOM | 2240 | OG1 | THR | A | 292 | 35.993 | 28.617 | 15.555 | 1.00 | 44.68 | A |
| ATOM | 2241 | CG2 | THR | A | 292 | 35.775 | 26.374 | 16.426 | 1.00 | 46.70 | A |
| ATOM | 2242 | C | THR | A | 292 | 36.212 | 29.814 | 18.001 | 1.00 | 47.83 | A |
| ATOM | 2243 | O | THR | A | 292 | 35.307 | 30.644 | 18.064 | 1.00 | 48.07 | A |
| ATOM | 2244 | N | ASP | A | 293 | 37.497 | 30.149 | 17.954 | 1.00 | 48.59 | A |
| ATOM | 2245 | CA | ASP | A | 293 | 37.883 | 31.551 | 17.982 | 1.00 | 48.64 | A |
| ATOM | 2246 | CB | ASP | A | 293 | 39.408 | 31.705 | 17.988 | 1.00 | 49.60 | A |
| ATOM | 2247 | CG | ASP | A | 293 | 40.045 | 31.150 | 19.249 | 1.00 | 50.84 | A |
| ATOM | 2248 | OD1 | ASP | A | 293 | 39.394 | 31.201 | 20.317 | 1.00 | 52.13 | A |
| ATOM | 2249 | OD2 | ASP | A | 293 | 41.200 | 30.673 | 19.176 | 1.00 | 51.40 | A |
| ATOM | 2250 | C | ASP | A | 293 | 37.299 | 32.284 | 16.784 | 1.00 | 48.56 | A |
| ATOM | 2251 | O | ASP | A | 293 | 37.058 | 33.488 | 16.851 | 1.00 | 49.15 | A |
| ATOM | 2252 | N | VAL | A | 294 | 37.070 | 31.561 | 15.689 | 1.00 | 47.81 | A |
| ATOM | 2253 | CA | VAL | A | 294 | 36.512 | 32.179 | 14.487 | 1.00 | 46.87 | A |
| ATOM | 2254 | CB | VAL | A | 294 | 36.140 | 31.120 | 13.418 | 1.00 | 47.55 | A |
| ATOM | 2255 | CG1 | VAL | A | 294 | 35.346 | 31.772 | 12.291 | 1.00 | 47.30 | A |
| ATOM | 2256 | CG2 | VAL | A | 294 | 37.409 | 30.490 | 12.847 | 1.00 | 47.74 | A |
| ATOM | 2257 | C | VAL | A | 294 | 35.272 | 32.985 | 14.843 | 1.00 | 45.87 | A |
| ATOM | 2258 | O | VAL | A | 294 | 35.123 | 34.130 | 14.416 | 1.00 | 46.94 | A |
| ATOM | 2259 | N | GLN | A | 295 | 34.389 | 32.380 | 15.629 | 1.00 | 45.48 | A |
| ATOM | 2260 | CA | GLN | A | 295 | 33.162 | 33.035 | 16.061 | 1.00 | 45.44 | A |
| ATOM | 2261 | CB | GLN | A | 295 | 32.190 | 32.002 | 16.647 | 1.00 | 45.04 | A |
| ATOM | 2262 | CG | GLN | A | 295 | 31.550 | 31.080 | 15.603 | 1.00 | 44.79 | A |
| ATOM | 2263 | CD | GLN | A | 295 | 32.555 | 30.174 | 14.906 | 1.00 | 45.62 | A |
| ATOM | 2264 | OE1 | GLN | A | 295 | 32.408 | 29.860 | 13.720 | 1.00 | 44.71 | A |
| ATOM | 2265 | NE2 | GLN | A | 295 | 33.576 | 29.741 | 15.642 | 1.00 | 42.80 | A |
| ATOM | 2266 | C | GLN | A | 295 | 33.472 | 34.118 | 17.096 | 1.00 | 45.66 | A |
| ATOM | 2267 | O | GLN | A | 295 | 32.840 | 35.178 | 17.109 | 1.00 | 44.55 | A |
| ATOM | 2268 | N | ARG | A | 296 | 34.449 | 33.850 | 17.960 | 1.00 | 45.23 | A |
| ATOM | 2269 | CA | ARG | A | 296 | 34.842 | 34.819 | 18.982 | 1.00 | 45.03 | A |
| ATOM | 2270 | CB | ARG | A | 296 | 35.964 | 34.255 | 19.862 | 1.00 | 44.33 | A |
| ATOM | 2271 | CG | ARG | A | 296 | 35.592 | 32.952 | 20.540 | 1.00 | 44.26 | A |
| ATOM | 2272 | CD | ARG | A | 296 | 36.126 | 32.857 | 21.970 | 1.00 | 45.12 | A |
| ATOM | 2273 | NE | ARG | A | 296 | 35.665 | 31.624 | 22.597 | 1.00 | 44.32 | A |
| ATOM | 2274 | CZ | ARG | A | 296 | 36.124 | 30.419 | 22.280 | 1.00 | 44.21 | A |
| ATOM | 2275 | NH1 | ARG | A | 296 | 37.069 | 30.292 | 21.357 | 1.00 | 44.51 | A |
| ATOM | 2276 | NH2 | ARG | A | 296 | 35.613 | 29.341 | 22.860 | 1.00 | 45.05 | A |
| ATOM | 2277 | C | ARG | A | 296 | 35.317 | 36.091 | 18.297 | 1.00 | 44.39 | A |
| ATOM | 2278 | O | ARG | A | 296 | 35.067 | 37.202 | 18.766 | 1.00 | 44.29 | A |
| ATOM | 2279 | N | GLY | A | 297 | 36.004 | 35.917 | 17.175 | 1.00 | 43.83 | A |
| ATOM | 2280 | CA | GLY | A | 297 | 36.494 | 37.061 | 16.436 | 1.00 | 44.22 | A |
| ATOM | 2281 | C | GLY | A | 297 | 35.372 | 37.832 | 15.766 | 1.00 | 45.50 | A |
| ATOM | 2282 | O | GLY | A | 297 | 35.370 | 39.064 | 15.771 | 1.00 | 46.22 | A |
| ATOM | 2283 | N | LEU | A | 298 | 34.417 | 37.108 | 15.188 | 1.00 | 45.75 | A |
| ATOM | 2284 | CA | LEU | A | 298 | 33.292 | 37.732 | 14.498 | 1.00 | 46.53 | A |
| ATOM | 2285 | CB | LEU | A | 298 | 32.402 | 36.663 | 13.848 | 1.00 | 45.17 | A |
| ATOM | 2286 | CG | LEU | A | 298 | 33.021 | 35.931 | 12.650 | 1.00 | 45.06 | A |
| ATOM | 2287 | CD1 | LEU | A | 298 | 32.084 | 34.824 | 12.164 | 1.00 | 44.48 | A |
| ATOM | 2288 | CD2 | LEU | A | 298 | 33.307 | 36.932 | 11.537 | 1.00 | 45.31 | A |
| ATOM | 2289 | C | LEU | A | 298 | 32.462 | 38.602 | 15.433 | 1.00 | 47.62 | A |
| ATOM | 2290 | O | LEU | A | 298 | 31.945 | 39.646 | 15.028 | 1.00 | 47.53 | A |
| ATOM | 2291 | N | LEU | A | 299 | 32.340 | 38.171 | 16.685 | 1.00 | 48.72 | A |
| ATOM | 2292 | CA | LEU | A | 299 | 31.580 | 38.924 | 17.667 | 1.00 | 50.18 | A |
| ATOM | 2293 | CB | LEU | A | 299 | 31.390 | 38.090 | 18.930 | 1.00 | 49.60 | A |
| ATOM | 2294 | CG | LEU | A | 299 | 30.350 | 36.975 | 18.807 | 1.00 | 48.08 | A |
| ATOM | 2295 | CD1 | LEU | A | 299 | 30.486 | 36.019 | 19.974 | 1.00 | 47.37 | A |
| ATOM | 2296 | CD2 | LEU | A | 299 | 28.953 | 37.573 | 18.765 | 1.00 | 48.29 | A |
| ATOM | 2297 | C | LEU | A | 299 | 32.240 | 40.260 | 18.004 | 1.00 | 51.67 | A |
| ATOM | 2298 | O | LEU | A | 299 | 31.550 | 41.240 | 18.282 | 1.00 | 51.55 | A |
| ATOM | 2299 | N | LYS | A | 300 | 33.572 | 40.303 | 17.970 | 1.00 | 53.35 | A |
| ATOM | 2300 | CA | LYS | A | 300 | 34.304 | 41.537 | 18.263 | 1.00 | 53.76 | A |
| ATOM | 2301 | CB | LYS | A | 300 | 35.794 | 41.265 | 18.493 | 1.00 | 54.63 | A |
| ATOM | 2302 | CG | LYS | A | 300 | 36.147 | 40.439 | 19.703 | 1.00 | 56.78 | A |
| ATOM | 2303 | CD | LYS | A | 300 | 37.663 | 40.361 | 19.835 | 1.00 | 58.59 | A |
| ATOM | 2304 | CE | LYS | A | 300 | 38.091 | 39.473 | 20.991 | 1.00 | 60.33 | A |
| ATOM | 2305 | NZ | LYS | A | 300 | 39.558 | 39.580 | 21.244 | 1.00 | 61.89 | A |
| ATOM | 2306 | C | LYS | A | 300 | 34.192 | 42.492 | 17.086 | 1.00 | 53.47 | A |
| ATOM | 2307 | O | LYS | A | 300 | 34.072 | 43.705 | 17.259 | 1.00 | 54.79 | A |

APPENDIX 1-continued

Atomic coordinates of aromatic prenyltransferase residues 3-302 of SEQ ID NO: 2.

| ATOM | 2308 | N | ALA | A | 301 | 34.241 | 41.933 | 15.885 | 1.00 | 51.85 | A |
|------|------|------|------|---|-----|--------|--------|--------|------|-------|---|
| ATOM | 2309 | CA | ALA | A | 301 | 34.172 | 42.729 | 14.669 | 1.00 | 50.07 | A |
| ATOM | 2310 | CB | ALA | A | 301 | 34.698 | 41.913 | 13.495 | 1.00 | 50.60 | A |
| ATOM | 2311 | C | ALA | A | 301 | 32.791 | 43.272 | 14.332 | 1.00 | 49.04 | A |
| ATOM | 2312 | O | ALA | A | 301 | 32.672 | 44.404 | 13.855 | 1.00 | 48.99 | A |
| ATOM | 2313 | N | PHE | A | 302 | 31.750 | 42.479 | 14.583 | 1.00 | 47.91 | A |
| ATOM | 2314 | CA | PHE | A | 302 | 30.391 | 42.895 | 14.244 | 1.00 | 46.87 | A |
| ATOM | 2315 | CB | PHE | A | 302 | 29.775 | 41.920 | 13.229 | 1.00 | 45.69 | A |
| ATOM | 2316 | CG | PHE | A | 302 | 30.542 | 41.819 | 11.943 | 1.00 | 41.83 | A |
| ATOM | 2317 | CD1 | PHE | A | 302 | 31.567 | 40.890 | 11.801 | 1.00 | 41.69 | A |
| ATOM | 2318 | CD2 | PHE | A | 302 | 30.256 | 42.672 | 10.881 | 1.00 | 42.51 | A |
| ATOM | 2319 | CE1 | PHE | A | 302 | 32.298 | 40.813 | 10.620 | 1.00 | 40.43 | A |
| ATOM | 2320 | CE2 | PHE | A | 302 | 30.982 | 42.603 | 9.693 | 1.00 | 40.70 | A |
| ATOM | 2321 | CZ | PHE | A | 302 | 32.004 | 41.675 | 9.562 | 1.00 | 41.10 | A |
| ATOM | 2322 | C | PHE | A | 302 | 29.418 | 43.061 | 15.398 | 1.00 | 47.58 | A |
| ATOM | 2323 | O | PHE | A | 302 | 28.303 | 43.536 | 15.198 | 1.00 | 47.34 | A |
| ATOM | 2324 | N | ASP | A | 303 | 29.817 | 42.668 | 16.600 | 1.00 | 48.39 | A |
| ATOM | 2325 | CA | ASP | A | 303 | 28.919 | 42.807 | 17.738 | 1.00 | 49.75 | A |
| ATOM | 2326 | CB | ASP | A | 303 | 28.481 | 41.423 | 18.224 | 1.00 | 48.37 | A |
| ATOM | 2327 | CG | ASP | A | 303 | 27.185 | 41.462 | 18.998 | 1.00 | 47.54 | A |
| ATOM | 2328 | OD1 | ASP | A | 303 | 26.215 | 42.066 | 18.497 | 1.00 | 47.88 | A |
| ATOM | 2329 | OD2 | ASP | A | 303 | 27.126 | 40.879 | 20.100 | 1.00 | 49.46 | A |
| ATOM | 2330 | C | ASP | A | 303 | 29.581 | 43.589 | 18.874 | 1.00 | 50.31 | A |
| ATOM | 2331 | O | ASP | A | 303 | 29.661 | 43.050 | 19.995 | 1.00 | 51.55 | A |
| ATOM | 2332 | OXT | ASP | A | 303 | 30.012 | 44.737 | 18.627 | 1.00 | 51.61 | A |
| ATOM | 2333 | MG+2 | MG2 | A | 1 | 19.221 | 25.308 | 7.555 | 1.00 | 43.67 | M |
| ATOM | 2334 | PA | GSP | A | 1 | 19.534 | 27.534 | 3.619 | 1.00 | 40.67 | G |
| ATOM | 2335 | O1A | GSP | A | 1 | 19.609 | 28.204 | 2.288 | 1.00 | 39.03 | G |
| ATOM | 2336 | O2A | GSP | A | 1 | 20.362 | 26.298 | 3.674 | 1.00 | 39.43 | G |
| ATOM | 2337 | O3A | GSP | A | 1 | 18.121 | 27.257 | 4.002 | 1.00 | 42.12 | G |
| ATOM | 2338 | O1B | GSP | A | 1 | 20.124 | 28.585 | 4.679 | 1.00 | 40.27 | G |
| ATOM | 2339 | PB | GSP | A | 1 | 20.529 | 28.366 | 6.198 | 1.00 | 40.45 | G |
| ATOM | 2340 | O2B | GSP | A | 1 | 20.225 | 29.576 | 7.030 | 1.00 | 40.45 | G |
| ATOM | 2341 | O3B | GSP | A | 1 | 19.816 | 27.203 | 6.821 | 1.00 | 40.17 | G |
| ATOM | 2342 | S1 | GSP | A | 1 | 22.118 | 28.106 | 6.368 | 1.00 | 46.86 | G |
| ATOM | 2343 | C1 | GSP | A | 1 | 22.785 | 28.278 | 7.611 | 1.00 | 48.16 | G |
| ATOM | 2344 | C2 | GSP | A | 1 | 23.948 | 27.320 | 7.744 | 1.00 | 48.30 | G |
| ATOM | 2345 | C3 | GSP | A | 1 | 25.237 | 27.674 | 7.899 | 1.00 | 48.85 | G |
| ATOM | 2346 | C10 | GSP | A | 1 | 25.862 | 28.840 | 7.172 | 1.00 | 48.34 | G |
| ATOM | 2347 | C4 | GSP | A | 1 | 26.165 | 26.878 | 8.794 | 1.00 | 49.42 | G |
| ATOM | 2348 | C5 | GSP | A | 1 | 27.559 | 27.525 | 8.868 | 1.00 | 51.23 | G |
| ATOM | 2349 | C6 | GSP | A | 1 | 28.644 | 26.503 | 9.103 | 1.00 | 53.24 | G |
| ATOM | 2350 | C7 | GSP | A | 1 | 29.414 | 26.374 | 10.200 | 1.00 | 53.60 | G |
| ATOM | 2351 | C9 | GSP | A | 1 | 30.505 | 27.374 | 10.507 | 1.00 | 54.65 | G |
| ATOM | 2352 | C8 | GSP | A | 1 | 29.296 | 25.257 | 11.211 | 1.00 | 55.35 | G |
| ATOM | 2353 | C1 | DH2 | A | 1 | 26.153 | 31.881 | 8.710 | 1.00 | 65.18 | D |
| ATOM | 2354 | C2 | DH2 | A | 1 | 24.959 | 31.390 | 9.301 | 1.00 | 65.39 | D |
| ATOM | 2355 | C3 | DH2 | A | 1 | 25.028 | 30.627 | 10.451 | 1.00 | 66.41 | D |
| ATOM | 2356 | C4 | DH2 | A | 1 | 26.279 | 30.324 | 11.055 | 1.00 | 66.26 | D |
| ATOM | 2357 | C5 | DH2 | A | 1 | 27.435 | 30.796 | 10.488 | 1.00 | 66.06 | D |
| ATOM | 2358 | C6 | DH2 | A | 1 | 28.585 | 32.099 | 8.675 | 1.00 | 64.51 | D |
| ATOM | 2359 | C7 | DH2 | A | 1 | 27.251 | 33.138 | 6.948 | 1.00 | 63.33 | D |
| ATOM | 2360 | C8 | DH2 | A | 1 | 26.099 | 32.663 | 7.525 | 1.00 | 63.43 | D |
| ATOM | 2361 | O1 | DH2 | A | 1 | 29.857 | 31.880 | 9.155 | 1.00 | 65.00 | D |
| ATOM | 2362 | O2 | DH2 | A | 1 | 23.839 | 30.179 | 10.983 | 1.00 | 66.99 | D |
| ATOM | 2363 | C9 | DH2 | A | 1 | 28.509 | 32.861 | 7.519 | 1.00 | 64.14 | D |
| ATOM | 2364 | C10 | DH2 | A | 1 | 27.409 | 31.584 | 9.306 | 1.00 | 65.41 | D |
| ATOM | 2365 | N | NO3 | A | 1 | 42.060 | 34.777 | −5.122 | 1.00 | 69.01 | N |
| ATOM | 2366 | O1 | NO3 | A | 1 | 41.197 | 34.277 | −5.872 | 1.00 | 69.03 | N |
| ATOM | 2367 | O2 | NO3 | A | 1 | 41.725 | 35.701 | −4.452 | 1.00 | 68.04 | N |
| ATOM | 2368 | O3 | NO3 | A | 1 | 43.135 | 34.230 | −5.061 | 1.00 | 68.81 | N |
| ATOM | 2369 | OH2 | TIP | A | 1 | 30.490 | 35.181 | 26.300 | 1.00 | 65.42 | W |
| ATOM | 2370 | OH2 | TIP | A | 2 | 36.852 | 21.356 | 11.220 | 1.00 | 62.71 | W |
| ATOM | 2371 | OH2 | TIP | A | 3 | 13.275 | 6.277 | 5.899 | 1.00 | 52.03 | W |
| ATOM | 2372 | OH2 | TIP | A | 4 | 39.421 | 26.056 | 19.137 | 1.00 | 55.68 | W |
| ATOM | 2373 | OH2 | TIP | A | 5 | 29.221 | 47.052 | 19.171 | 1.00 | 51.85 | W |
| ATOM | 2374 | OH2 | TIP | A | 6 | 25.560 | 30.322 | 10.756 | 1.00 | 97.83 | W |
| ATOM | 2375 | OH2 | TIP | A | 7 | 23.552 | 52.697 | −2.797 | 1.00 | 48.74 | W |
| ATOM | 2376 | OH2 | TIP | A | 8 | 15.783 | 28.067 | 4.579 | 1.00 | 42.75 | W |
| ATOM | 2377 | OH2 | TIP | A | 9 | 35.855 | 25.568 | −13.555 | 1.00 | 79.37 | W |
| ATOM | 2378 | OH2 | TIP | A | 10 | 36.538 | 42.420 | −0.112 | 1.00 | 49.25 | W |
| ATOM | 2379 | OH2 | TIP | A | 11 | 23.745 | 35.145 | 24.150 | 1.00 | 53.80 | W |
| ATOM | 2380 | OH2 | TIP | A | 12 | 19.673 | 51.064 | 6.990 | 1.00 | 47.69 | W |
| ATOM | 2381 | OH2 | TIP | A | 13 | 27.368 | 30.522 | 28.673 | 1.00 | 65.03 | W |
| ATOM | 2382 | OH2 | TIP | A | 14 | 32.186 | 14.701 | −3.539 | 1.00 | 56.64 | W |
| ATOM | 2383 | OH2 | TIP | A | 15 | 24.460 | 14.475 | −13.361 | 1.00 | 59.07 | W |
| ATOM | 2384 | OH2 | TIP | A | 16 | 40.585 | 17.057 | 1.471 | 1.00 | 59.15 | W |

APPENDIX 1-continued

Atomic coordinates of aromatic prenyltransferase residues 3-302 of SEQ ID NO: 2.

| ATOM | 2385 | OH2 | TIP | A | 17 | 17.913 | 13.365 | −5.351 | 1.00 | 45.07 | W |
|------|------|-----|-----|---|----|--------|--------|--------|------|-------|---|
| ATOM | 2386 | OH2 | TIP | A | 18 | 15.723 | 27.642 | 7.214 | 1.00 | 47.54 | W |
| ATOM | 2387 | OH2 | TIP | A | 19 | 22.263 | 7.047 | −6.225 | 1.00 | 59.29 | W |
| ATOM | 2388 | OH2 | TIP | A | 20 | 19.969 | 29.141 | −17.580 | 1.00 | 67.73 | W |
| ATOM | 2389 | OH2 | TIP | A | 21 | 21.634 | 48.493 | 12.171 | 1.00 | 47.20 | W |
| ATOM | 2390 | OH2 | TIP | A | 22 | 18.106 | 22.881 | −16.847 | 1.00 | 50.83 | W |
| ATOM | 2391 | OH2 | TIP | A | 23 | 29.495 | 40.536 | 21.854 | 1.00 | 60.58 | W |
| ATOM | 2392 | OH2 | TIP | A | 24 | 36.302 | 27.268 | 13.132 | 1.00 | 55.92 | W |
| ATOM | 2393 | OH2 | TIP | A | 25 | 29.732 | 35.121 | 4.882 | 1.00 | 50.52 | W |
| ATOM | 2394 | OH2 | TIP | A | 26 | 45.475 | 29.946 | 0.240 | 1.00 | 44.34 | W |
| ATOM | 2395 | OH2 | TIP | A | 27 | 15.795 | 10.968 | 19.889 | 1.00 | 77.54 | W |
| ATOM | 2396 | OH2 | TIP | A | 28 | 14.431 | 30.709 | −8.734 | 1.00 | 39.58 | W |
| ATOM | 2397 | OH2 | TIP | A | 29 | 13.313 | 28.671 | −1.901 | 1.00 | 44.66 | W |
| ATOM | 2398 | OH2 | TIP | A | 30 | 27.440 | 52.388 | 8.029 | 1.00 | 60.67 | W |
| ATOM | 2399 | OH2 | TIP | A | 31 | 42.559 | 22.415 | 4.064 | 1.00 | 53.62 | W |
| ATOM | 2400 | OH2 | TIP | A | 32 | 20.941 | 43.226 | 24.809 | 1.00 | 55.10 | W |
| ATOM | 2401 | OH2 | TIP | A | 33 | 33.359 | 44.497 | −2.388 | 1.00 | 58.45 | W |
| ATOM | 2402 | OH2 | TIP | A | 34 | 31.147 | 53.165 | −0.332 | 1.00 | 46.23 | W |
| ATOM | 2403 | OH2 | TIP | A | 35 | 12.356 | 25.536 | 1.697 | 1.00 | 64.15 | W |
| ATOM | 2404 | OH2 | TIP | A | 36 | 35.138 | 10.636 | 12.652 | 1.00 | 61.46 | W |
| ATOM | 2405 | OH2 | TIP | A | 37 | 15.020 | 50.521 | −4.580 | 1.00 | 40.30 | W |
| ATOM | 2406 | OH2 | TIP | A | 38 | 9.781 | 27.922 | 21.238 | 1.00 | 68.26 | W |
| ATOM | 2407 | OH2 | TIP | A | 39 | 41.691 | 22.533 | −2.565 | 1.00 | 54.13 | W |
| ATOM | 2408 | OH2 | TIP | A | 40 | 20.666 | 45.859 | 15.289 | 1.00 | 70.16 | W |
| ATOM | 2409 | OH2 | TIP | A | 41 | 34.363 | 37.353 | 21.374 | 1.00 | 53.19 | W |
| ATOM | 2410 | OH2 | TIP | A | 42 | 26.734 | 5.871 | −6.191 | 1.00 | 45.50 | W |
| ATOM | 2411 | OH2 | TIP | A | 43 | 10.365 | 49.794 | 12.437 | 1.00 | 50.70 | W |
| ATOM | 2412 | OH2 | TIP | A | 44 | 34.543 | 29.704 | 9.768 | 1.00 | 55.92 | W |
| ATOM | 2413 | OH2 | TIP | A | 45 | 40.376 | 31.076 | 6.686 | 1.00 | 58.22 | W |
| ATOM | 2414 | OH2 | TIP | A | 46 | 34.553 | 5.913 | 23.858 | 1.00 | 71.52 | W |
| ATOM | 2415 | OH2 | TIP | A | 47 | 14.200 | 27.005 | 5.946 | 1.00 | 53.11 | W |
| ATOM | 2416 | OH2 | TIP | A | 48 | 42.976 | 30.424 | −5.522 | 1.00 | 44.67 | W |
| ATOM | 2417 | OH2 | TIP | A | 49 | 31.686 | 41.102 | 21.600 | 1.00 | 49.60 | W |
| ATOM | 2418 | OH2 | TIP | A | 50 | 37.985 | 29.637 | 6.203 | 1.00 | 60.32 | W |
| ATOM | 2419 | OH2 | TIP | A | 51 | 16.521 | 36.553 | −8.898 | 1.00 | 49.77 | W |
| ATOM | 2420 | OH2 | TIP | A | 52 | 31.859 | 17.997 | −13.734 | 1.00 | 53.29 | W |
| ATOM | 2421 | OH2 | TIP | A | 53 | 27.801 | 29.505 | 30.891 | 1.00 | 49.38 | W |
| ATOM | 2422 | OH2 | TIP | A | 54 | 4.648 | 43.961 | 2.873 | 1.00 | 57.90 | W |
| ATOM | 2423 | OH2 | TIP | A | 55 | 18.093 | 43.972 | 14.582 | 1.00 | 66.29 | W |
| ATOM | 2424 | OH2 | TIP | A | 56 | 32.762 | 25.967 | 29.911 | 1.00 | 57.94 | W |
| ATOM | 2425 | OH2 | TIP | A | 57 | 6.942 | 34.079 | 7.083 | 1.00 | 48.37 | W |
| ATOM | 2426 | OH2 | TIP | A | 58 | 43.391 | 12.772 | 6.133 | 1.00 | 61.46 | W |
| ATOM | 2427 | OH2 | TIP | A | 59 | 8.265 | 49.640 | −10.664 | 1.00 | 59.37 | W |
| ATOM | 2428 | OH2 | TIP | A | 60 | 6.971 | 18.923 | 10.395 | 1.00 | 62.11 | W |
| ATOM | 2429 | OH2 | TIP | A | 61 | 12.616 | 28.504 | 1.451 | 1.00 | 57.01 | W |
| ATOM | 2430 | OH2 | TIP | A | 62 | 25.673 | 48.908 | −3.608 | 1.00 | 48.26 | W |
| ATOM | 2431 | OH2 | TIP | A | 63 | 11.864 | 30.819 | −2.529 | 1.00 | 57.25 | W |
| ATOM | 2432 | OH2 | TIP | A | 64 | 23.756 | 43.583 | −16.811 | 1.00 | 53.58 | W |
| ATOM | 2433 | OH2 | TIP | A | 65 | 14.207 | 19.466 | 0.982 | 1.00 | 52.77 | W |
| ATOM | 2434 | OH2 | TIP | A | 66 | 2.064 | 35.531 | −8.984 | 1.00 | 67.76 | W |
| ATOM | 2435 | OH2 | TIP | A | 67 | 27.154 | 45.880 | 16.535 | 1.00 | 61.40 | W |
| ATOM | 2436 | OH2 | TIP | A | 68 | 29.710 | 31.367 | 12.036 | 1.00 | 54.10 | W |
| ATOM | 2437 | OH2 | TIP | A | 69 | 37.562 | 26.637 | 4.885 | 1.00 | 84.16 | W |
| ATOM | 2438 | OH2 | TIP | A | 70 | 16.121 | 18.617 | −9.991 | 1.00 | 46.09 | W |
| ATOM | 2439 | OH2 | TIP | A | 1 | 28.748 | 17.651 | −3.973 | 1.00 | 43.52 | SS |
| ATOM | 2440 | OH2 | TIP | A | 2 | 40.158 | 21.998 | 7.668 | 1.00 | 43.52 | SS |
| ATOM | 2441 | OH2 | TIP | A | 3 | 20.062 | 48.816 | 5.351 | 1.00 | 43.52 | SS |
| ATOM | 2442 | OH2 | TIP | A | 4 | 24.944 | 5.885 | −0.742 | 1.00 | 43.52 | SS |
| ATOM | 2443 | OH2 | TIP | A | 5 | 30.688 | 25.005 | −4.289 | 1.00 | 43.52 | SS |
| ATOM | 2444 | OH2 | TIP | A | 6 | 19.073 | 30.215 | −9.776 | 1.00 | 43.52 | SS |
| ATOM | 2445 | OH2 | TIP | A | 7 | 18.367 | 30.661 | 2.655 | 1.00 | 43.52 | SS |
| ATOM | 2446 | OH2 | TIP | A | 8 | 19.367 | 32.272 | 0.565 | 1.00 | 43.52 | SS |
| ATOM | 2447 | OH2 | TIP | A | 9 | 29.275 | 23.177 | −0.801 | 1.00 | 43.52 | SS |
| ATOM | 2448 | OH2 | TIP | A | 10 | 30.926 | 16.038 | −5.142 | 1.00 | 43.52 | SS |
| ATOM | 2449 | OH2 | TIP | A | 11 | 34.325 | 28.514 | 11.449 | 1.00 | 43.52 | SS |
| ATOM | 2450 | OH2 | TIP | A | 12 | 21.383 | 27.492 | −13.294 | 1.00 | 43.52 | SS |
| ATOM | 2451 | OH2 | TIP | A | 13 | 22.108 | 28.693 | 11.655 | 1.00 | 43.52 | SS |
| ATOM | 2452 | OH2 | TIP | A | 14 | 18.252 | 23.094 | −9.262 | 1.00 | 43.52 | SS |
| ATOM | 2453 | OH2 | TIP | A | 15 | 18.047 | 20.583 | −11.156 | 1.00 | 43.52 | SS |
| ATOM | 2454 | OH2 | TIP | A | 16 | 17.057 | 52.115 | −4.118 | 1.00 | 43.52 | SS |
| ATOM | 2455 | OH2 | TIP | A | 17 | 22.954 | 25.044 | −0.471 | 1.00 | 43.52 | SS |
| ATOM | 2456 | OH2 | TIP | A | 18 | 30.914 | 51.700 | 1.620 | 1.00 | 43.52 | SS |
| ATOM | 2457 | OH2 | TIP | A | 19 | 18.868 | 45.761 | 14.958 | 1.00 | 43.52 | SS |
| ATOM | 2458 | OH2 | TIP | A | 20 | 11.192 | 43.417 | 6.627 | 1.00 | 43.52 | SS |
| ATOM | 2459 | OH2 | TIP | A | 21 | 21.395 | 33.255 | 9.085 | 1.00 | 43.52 | SS |
| ATOM | 2460 | OH2 | TIP | A | 22 | 31.566 | 40.059 | −1.449 | 1.00 | 43.52 | SS |
| ATOM | 2461 | OH2 | TIP | A | 23 | 26.608 | 40.843 | 12.469 | 1.00 | 43.52 | SS |

APPENDIX 1-continued

Atomic coordinates of aromatic prenyltransferase residues 3-302 of SEQ ID NO: 2.

| ATOM | 2462 | OH2 | TIP | A | 24 | 10.882 | 49.731 | 3.097 | 1.00 | 43.52 | SS |
|---|---|---|---|---|---|---|---|---|---|---|---|
| ATOM | 2463 | OH2 | TIP | A | 25 | 24.112 | 6.394 | −4.916 | 1.00 | 43.52 | SS |
| ATOM | 2464 | OH2 | TIP | A | 26 | 20.065 | 29.530 | 9.976 | 1.00 | 43.52 | SS |
| ATOM | 2465 | OH2 | TIP | A | 27 | 26.915 | 45.385 | 9.401 | 1.00 | 43.52 | SS |
| ATOM | 2466 | OH2 | TIP | A | 28 | 16.232 | 36.475 | 12.662 | 1.00 | 43.52 | SS |
| ATOM | 2467 | OH2 | TIP | A | 29 | 17.678 | 25.766 | 6.317 | 1.00 | 43.52 | SS |
| ATOM | 2468 | OH2 | TIP | A | 30 | 20.570 | 25.957 | 0.315 | 1.00 | 43.52 | SS |
| ATOM | 2469 | OH2 | TIP | A | 31 | 8.561 | 24.058 | 9.246 | 1.00 | 43.52 | SS |
| ATOM | 2470 | OH2 | TIP | A | 32 | 20.329 | 24.123 | 6.075 | 1.00 | 43.52 | SS |
| ATOM | 2471 | OH2 | TIP | A | 33 | 25.927 | 42.053 | 15.359 | 1.00 | 43.52 | SS |
| ATOM | 2472 | OH2 | TIP | A | 34 | 33.530 | 38.867 | −7.089 | 1.00 | 43.52 | SS |
| ATOM | 2473 | OH2 | TIP | A | 35 | 35.591 | 12.620 | 10.017 | 1.00 | 43.52 | SS |
| ATOM | 2474 | OH2 | TIP | A | 36 | 31.225 | 41.351 | 6.010 | 1.00 | 43.52 | SS |
| ATOM | 2475 | OH2 | TIP | A | 37 | 22.123 | 24.472 | 11.325 | 1.00 | 43.52 | SS |
| ATOM | 2476 | OH2 | TIP | A | 38 | 28.087 | 29.403 | −13.302 | 1.00 | 43.52 | SS |
| ATOM | 2477 | OH2 | TIP | A | 39 | 34.560 | 12.999 | 5.277 | 1.00 | 43.52 | SS |
| ATOM | 2478 | OH2 | TIP | A | 40 | 9.465 | 48.542 | 10.702 | 1.00 | 43.52 | SS |
| ATOM | 2479 | OH2 | TIP | A | 41 | 12.503 | 38.149 | 20.364 | 1.00 | 43.52 | SS |
| ATOM | 2480 | OH2 | TIP | A | 42 | 7.420 | 41.639 | 10.909 | 1.00 | 43.52 | SS |
| ATOM | 2481 | OH2 | TIP | A | 43 | 35.680 | 12.866 | 7.902 | 1.00 | 43.52 | SS |
| ATOM | 2482 | OH2 | TIP | A | 44 | 39.502 | 27.931 | 18.775 | 1.00 | 43.52 | SS |
| ATOM | 2483 | OH2 | TIP | A | 45 | 21.146 | 25.021 | 8.714 | 1.00 | 43.52 | SS |
| ATOM | 2484 | OH2 | TIP | A | 46 | 30.337 | 39.275 | −10.268 | 1.00 | 43.52 | SS |
| ATOM | 2485 | OH2 | TIP | A | 47 | 18.733 | 12.572 | 4.205 | 1.00 | 43.52 | SS |
| ATOM | 2486 | OH2 | TIP | A | 48 | 8.456 | 43.720 | 10.493 | 1.00 | 43.52 | SS |
| ATOM | 2487 | OH2 | TIP | A | 49 | 21.738 | 21.295 | 7.389 | 1.00 | 43.52 | SS |
| ATOM | 2488 | OH2 | TIP | A | 50 | 20.445 | 28.671 | −16.154 | 1.00 | 43.52 | SS |
| ATOM | 2489 | OH2 | TIP | A | 51 | 22.600 | 12.989 | −4.498 | 1.00 | 43.52 | SS |
| ATOM | 2490 | OH2 | TIP | A | 52 | 36.376 | 34.961 | 13.547 | 1.00 | 43.52 | SS |
| ATOM | 2491 | OH2 | TIP | A | 53 | 42.964 | 28.274 | −7.367 | 1.00 | 43.52 | SS |
| ATOM | 2492 | OH2 | TIP | A | 54 | 17.026 | 16.386 | 5.402 | 1.00 | 43.52 | SS |
| ATOM | 2493 | OH2 | TIP | A | 55 | 20.135 | 54.487 | 2.295 | 1.00 | 43.52 | SS |
| ATOM | 2494 | OH2 | TIP | A | 56 | 30.869 | 37.274 | 6.313 | 1.00 | 43.52 | SS |
| ATOM | 2495 | OH2 | TIP | A | 57 | 33.853 | 40.105 | 6.671 | 1.00 | 43.52 | SS |
| ATOM | 2496 | OH2 | TIP | A | 58 | 16.349 | 43.334 | 14.737 | 1.00 | 43.52 | SS |
| ATOM | 2497 | OH2 | TIP | A | 59 | 18.622 | 23.529 | 3.183 | 1.00 | 43.52 | SS |
| ATOM | 2498 | OH2 | TIP | A | 60 | 26.630 | 48.674 | 7.609 | 1.00 | 43.52 | SS |
| ATOM | 2499 | OH2 | TIP | A | 61 | 16.555 | 47.864 | −8.705 | 1.00 | 43.52 | SS |
| ATOM | 2500 | OH2 | TIP | A | 62 | 23.193 | 10.211 | −8.266 | 1.00 | 43.52 | SS |
| ATOM | 2501 | OH2 | TIP | A | 63 | 6.761 | 33.422 | 13.017 | 1.00 | 43.52 | SS |
| ATOM | 2502 | OH2 | TIP | A | 64 | 31.235 | 43.998 | 6.574 | 1.00 | 43.52 | SS |
| ATOM | 2503 | OH2 | TIP | A | 65 | 12.837 | 27.261 | −2.851 | 1.00 | 43.52 | SS |
| ATOM | 2504 | OH2 | TIP | A | 66 | 7.112 | 44.502 | 1.340 | 1.00 | 43.52 | SS |
| ATOM | 2505 | OH2 | TIP | A | 67 | 41.572 | 21.679 | −0.685 | 1.00 | 43.52 | SS |
| ATOM | 2506 | OH2 | TIP | A | 68 | 22.680 | 39.284 | 19.173 | 1.00 | 43.52 | SS |
| ATOM | 2507 | OH2 | TIP | A | 69 | 39.463 | 37.601 | −3.326 | 1.00 | 43.52 | SS |
| ATOM | 2508 | OH2 | TIP | A | 70 | 27.198 | 44.213 | 12.911 | 1.00 | 43.52 | SS |
| ATOM | 2509 | OH2 | TIP | A | 71 | 20.278 | 32.081 | 11.495 | 1.00 | 43.52 | SS |
| ATOM | 2510 | OH2 | TIP | A | 72 | 18.798 | 23.783 | 14.243 | 1.00 | 43.52 | SS |
| ATOM | 2511 | OH2 | TIP | A | 73 | 29.802 | 13.025 | 4.755 | 1.00 | 43.52 | SS |
| ATOM | 2512 | OH2 | TIP | A | 74 | 10.477 | 43.339 | −5.465 | 1.00 | 43.52 | SS |
| ATOM | 2513 | OH2 | TIP | A | 75 | 36.280 | 13.938 | −3.506 | 1.00 | 43.52 | SS |
| ATOM | 2514 | OH2 | TIP | A | 76 | 17.052 | 11.701 | −7.565 | 1.00 | 43.52 | SS |
| ATOM | 2515 | OH2 | TIP | A | 77 | 18.133 | 24.995 | −0.393 | 1.00 | 43.52 | SS |
| ATOM | 2516 | OH2 | TIP | A | 78 | 38.072 | 39.296 | 5.240 | 1.00 | 43.52 | SS |
| ATOM | 2517 | OH2 | TIP | A | 79 | 25.945 | 15.534 | −14.313 | 1.00 | 43.52 | SS |
| ATOM | 2518 | OH2 | TIP | A | 80 | 15.465 | 37.437 | 19.549 | 1.00 | 43.52 | SS |
| ATOM | 2519 | OH2 | TIP | A | 81 | 16.620 | 20.634 | 1.922 | 1.00 | 43.52 | SS |
| ATOM | 2520 | OH2 | TIP | A | 82 | 23.545 | 39.853 | −13.805 | 1.00 | 43.52 | SS |
| ATOM | 2521 | OH2 | TIP | A | 83 | 20.253 | 35.091 | −10.327 | 1.00 | 43.52 | SS |
| ATOM | 2522 | OH2 | TIP | A | 84 | 36.698 | 24.059 | 13.386 | 1.00 | 43.52 | SS |
| ATOM | 2523 | OH2 | TIP | A | 85 | 13.944 | 26.765 | 1.654 | 1.00 | 43.52 | SS |
| ATOM | 2524 | OH2 | TIP | A | 86 | 3.518 | 41.699 | 1.425 | 1.00 | 43.52 | SS |
| ATOM | 2525 | OH2 | TIP | A | 87 | 23.552 | 46.329 | −1.900 | 1.00 | 43.52 | SS |
| ATOM | 2526 | OH2 | TIP | A | 88 | 21.467 | 19.279 | −8.361 | 1.00 | 43.52 | SS |
| ATOM | 2527 | OH2 | TIP | A | 89 | 11.984 | 27.072 | 27.543 | 1.00 | 43.52 | SS |
| ATOM | 2528 | OH2 | TIP | A | 90 | 23.521 | 11.079 | 23.940 | 1.00 | 43.52 | SS |
| ATOM | 2529 | OH2 | TIP | A | 91 | 28.454 | 48.510 | −3.162 | 1.00 | 43.52 | SS |
| ATOM | 2530 | OH2 | TIP | A | 92 | 13.904 | 43.690 | 16.624 | 1.00 | 43.52 | SS |
| ATOM | 2531 | OH2 | TIP | A | 93 | 7.949 | 31.840 | 5.015 | 1.00 | 43.52 | SS |
| ATOM | 2532 | OH2 | TIP | A | 94 | 32.500 | 19.725 | 14.392 | 1.00 | 43.52 | SS |
| ATOM | 2533 | OH2 | TIP | A | 95 | 38.390 | 28.352 | −11.079 | 1.00 | 43.52 | SS |
| ATOM | 2534 | OH2 | TIP | A | 96 | 33.535 | 30.231 | 18.680 | 1.00 | 43.52 | SS |
| ATOM | 2535 | OH2 | TIP | A | 97 | 42.143 | 19.333 | 8.275 | 1.00 | 43.52 | SS |
| ATOM | 2536 | OH2 | TIP | A | 98 | 14.934 | 50.010 | −7.142 | 1.00 | 43.52 | SS |
| ATOM | 2537 | OH2 | TIP | A | 99 | 30.152 | 44.543 | −0.015 | 1.00 | 43.52 | SS |
| ATOM | 2538 | OH2 | TIP | A | 100 | 8.844 | 47.803 | −7.596 | 1.00 | 43.52 | SS |

APPENDIX 1-continued

Atomic coordinates of aromatic prenyltransferase residues 3-302 of SEQ ID NO: 2.

| ATOM | 2539 | OH2 | TIP | A | 101 | 27.103 | 37.051 | 19.604 | 1.00 | 43.52 | SS |
|------|------|-----|-----|---|-----|--------|--------|--------|------|-------|----|
| ATOM | 2540 | OH2 | TIP | A | 102 | 17.787 | 15.577 | −9.801 | 1.00 | 43.52 | SS |
| ATOM | 2541 | OH2 | TIP | A | 104 | 16.591 | 25.543 | 2.635 | 1.00 | 43.52 | SS |
| ATOM | 2542 | OH2 | TIP | A | 105 | 27.295 | 22.133 | −0.598 | 1.00 | 43.52 | SS |
| ATOM | 2543 | OH2 | TIP | A | 106 | 8.558 | 49.822 | −12.353 | 1.00 | 43.52 | SS |
| ATOM | 2544 | OH2 | TIP | A | 107 | 6.922 | 43.138 | −1.316 | 1.00 | 43.52 | SS |
| ATOM | 2545 | OH2 | TIP | A | 108 | 42.011 | 13.562 | 11.695 | 1.00 | 43.52 | SS |
| ATOM | 2546 | OH2 | TIP | A | 109 | 20.749 | 53.219 | 5.773 | 1.00 | 43.52 | SS |
| ATOM | 2547 | OH2 | TIP | A | 110 | 32.142 | 24.552 | 22.465 | 1.00 | 43.52 | SS |
| ATOM | 2548 | OH2 | TIP | A | 111 | 13.126 | 28.687 | 14.559 | 1.00 | 43.52 | SS |
| ATOM | 2549 | OH2 | TIP | A | 112 | 36.222 | 10.792 | 2.017 | 1.00 | 43.52 | SS |
| ATOM | 2550 | OH2 | TIP | A | 113 | 20.573 | 36.856 | 1.414 | 1.00 | 43.52 | SS |
| ATOM | 2551 | OH2 | TIP | A | 115 | 27.421 | 10.974 | 25.524 | 1.00 | 43.52 | SS |
| ATOM | 2552 | OH2 | TIP | A | 116 | 42.751 | 19.151 | 10.460 | 1.00 | 43.52 | SS |
| ATOM | 2553 | OH2 | TIP | A | 117 | 35.543 | 36.745 | 5.730 | 1.00 | 43.52 | SS |
| ATOM | 2554 | OH2 | TIP | A | 118 | 11.440 | 28.831 | 21.618 | 1.00 | 43.52 | SS |
| ATOM | 2555 | OH2 | TIP | A | 119 | 7.319 | 34.101 | 9.399 | 1.00 | 43.52 | SS |
| ATOM | 2556 | OH2 | TIP | A | 121 | 36.857 | 26.359 | 21.626 | 1.00 | 43.52 | SS |
| ATOM | 2557 | OH2 | TIP | A | 123 | 36.523 | 30.443 | 7.429 | 1.00 | 43.52 | SS |
| ATOM | 2558 | OH2 | TIP | A | 124 | 26.132 | 50.469 | 5.525 | 1.00 | 43.52 | SS |
| ATOM | 2559 | OH2 | TIP | A | 126 | 34.329 | 44.402 | −4.548 | 1.00 | 43.52 | SS |
| ATOM | 2560 | OH2 | TIP | A | 127 | 26.999 | 33.484 | −9.280 | 1.00 | 43.52 | SS |
| ATOM | 2561 | OH2 | TIP | A | 128 | 18.443 | 27.124 | 21.387 | 1.00 | 43.52 | SS |
| ATOM | 2562 | OH2 | TIP | A | 129 | 17.596 | 28.119 | 10.054 | 1.00 | 43.52 | SS |
| ATOM | 2563 | OH2 | TIP | A | 131 | 14.334 | 35.901 | 18.626 | 1.00 | 43.52 | SS |
| ATOM | 2564 | OH2 | TIP | A | 132 | 31.030 | 32.454 | 7.688 | 1.00 | 43.52 | SS |
| ATOM | 2565 | OH2 | TIP | A | 133 | 2.973 | 33.533 | 13.781 | 1.00 | 43.52 | SS |
| ATOM | 2566 | OH2 | TIP | A | 137 | 25.307 | 9.302 | −4.123 | 1.00 | 43.52 | SS |
| ATOM | 2567 | OH2 | TIP | A | 138 | 22.308 | 8.017 | 22.539 | 1.00 | 43.52 | SS |
| ATOM | 2568 | OH2 | TIP | A | 140 | 21.574 | 38.666 | 3.205 | 1.00 | 43.52 | SS |
| ATOM | 2569 | OH2 | TIP | A | 146 | 31.586 | 31.424 | 10.186 | 1.00 | 43.52 | SS |
| ATOM | 2570 | OH2 | TIP | A | 154 | 6.490 | 36.861 | 3.474 | 1.00 | 43.52 | SS |
| ATOM | 2571 | OH2 | TIP | A | 156 | 12.899 | 47.499 | −10.970 | 1.00 | 43.52 | SS |
| ATOM | 2572 | OH2 | TIP | A | 160 | 38.133 | 32.578 | 21.040 | 1.00 | 43.52 | SS |
| ATOM | 2573 | OH2 | TIP | A | 185 | 16.312 | 28.123 | 22.475 | 1.00 | 43.52 | SS |
| ATOM | 2574 | OH2 | TIP | A | 191 | 34.865 | 30.182 | −7.396 | 1.00 | 43.52 | SS |
| ATOM | 2575 | OH2 | TIP | A | 198 | 38.682 | 29.942 | 21.401 | 1.00 | 43.52 | SS |
| ATOM | 2576 | OH2 | TIP | A | 221 | 20.664 | 28.062 | −4.027 | 1.00 | 43.52 | SS |
| ATOM | 2577 | OH2 | TIP | A | 227 | 38.426 | 34.659 | 9.615 | 1.00 | 43.52 | SS |
| TER |
| END |

That which is claimed is:

1. An isolated and purified non-crystalline aromatic prenyltransferase having a beta/alpha barrel structure and at least 95% sequence identity with the amino acid sequence set forth in SEQ ID NO:2.

2. An aromatic prenyltransferase according to claim 1, wherein said aromatic prenyltransferase has the amino acid sequence set forth in SEQ ID NO:2.

3. A method of identifying a potential inhibitor of the activity of an aromatic prenyltransferase according to claim 1, said method comprising:
   contacting said aromatic prenyltransferase with a potential compound; and
   determining the ability of said compound to inhibit the activity of said aromatic prenyltransferase, whereby those compounds which inhibit the activity of said aromatic prenyltransferase are identified as inhibitors of the activity of said aromatic prenyltransferase.

4. A composition comprising an aromatic prenyltransferase consisting of the amino acid seguence of SEQ ID NO:2 in crystalline form, wherein the crystalline form of said aromatic prenyltransferase has space group $P2_12_12$, with average unit cell dimensions of a=71 Å, b=92 Å, c=48 Å, $\alpha=\beta=\gamma=90°$.

5. A composition according to claim 4, wherein the crystalline form of said aromatic prenyltransferase contains one monomer per asymmetric unit and a solvent content of 45%.

6. A composition according to claim 4, wherein said prenyltransferase having the structural coordinates set forth in Appendix 1.

7. A composition according to claim 5 having the structural coordinates set forth in Appendix 1.

* * * * *

SEQUENCE LISTING

<160> NUMBER OF SEQ ID NOS: 7

<210> SEQ ID NO 1
<211> LENGTH: 924
<212> TYPE: DNA
<213> ORGANISM: Streptomyces sp.

<400> SEQUENCE: 1

```
atgtccgaag ccgctgatgt cgagcgcgtg tacgcggcca tggaggaagc ggctggactg      60
ctgggtgtgg cctgcgcacg cgacaagatc tatccgctgc tgagcacgtt ccaggacacg     120
ctcgtcgagg gcggcagcgt cgtcgtcttc ccatggcga gcgggcgtca ttccacggaa      180
ctggacttca gcatctcggt gccgaccagc cacggcgacc gtacgccac cgtcgtggaa      240 aaggggctgt ccccggcgac cggccacccc gtggacgacc tgctcgcgga cacccagaag     300
caccttccgg tctccatgtt cgccatcgac ggcgaggtca ccggcggctt caagaagacg     360
tacgccttct tccccaccga caacatgccc ggcgtcgccg agctgagcgc catcccctcc     420
atgccgccgg ccgtcgccga gaacgcggag ctgttcgccc gctacggtct ggacaaggtc     480
cagatgacgt cgatggacta caagaagcgg caggtcaacc tctacttcag cgagctgagc     540
```

```
gcgcagaccc tggaggcgga atccgtcctc gccctggtgc gcgagctggg cctgcacgtg    600
ccgaacgagc tgggcctgaa gttctgcaag cgctccttct cggtctaccc caccctcaac    660
tgggagaccg gcaagatcga ccggctgtgt ttcgccgtca tctccaacga ccccaccctg    720
gtgccgtcct cggacgaggg cgacatcgag aagttccaca actacgcgac caaggcgccg    780
tacgcgtacg tcggcgagaa gcgcaccctc gtctatgggc tcacgctgtc gcccaaggag    840
gagtactaca agctgggcgc gtactaccac atcaccgatg ccagcgcgg actgctgaag    900 gcgttcgact cgctggagga ctga                                           924
```

<210> SEQ ID NO 2
<211> LENGTH: 307
<212> TYPE: PRT
<213> ORGANISM: Streptomyces sp.

<400> SEQUENCE: 2

```
Met Ser Glu Ala Ala Asp Val Glu Arg Val Tyr Ala Ala Met Glu Glu
 1               5                  10                  15

Ala Ala Gly Leu Leu Gly Val Ala Cys Ala Arg Asp Lys Ile Tyr Pro
             20                  25                  30

Leu Leu Ser Thr Phe Gln Asp Thr Leu Val Glu Gly Gly Ser Val Val
         35                  40                  45

Val Phe Ser Met Ala Ser Gly Arg His Ser Thr Glu Leu Asp Phe Ser
     50                  55                  60

Ile Ser Val Pro Thr Ser His Gly Asp Pro Tyr Ala Thr Val Val Glu
 65                  70                  75                  80

Lys Gly Leu Phe Pro Ala Thr Gly His Pro Val Asp Asp Leu Leu Ala
                 85                  90                  95

Asp Thr Gln Lys His Leu Pro Val Ser Met Phe Ala Ile Asp Gly Glu
            100                 105                 110

Val Thr Gly Gly Phe Lys Lys Thr Tyr Ala Phe Phe Pro Thr Asp Asn
        115                 120                 125

Met Pro Gly Val Ala Glu Leu Ser Ala Ile Pro Ser Met Pro Pro Ala
    130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
            180                 185                 190

Val Arg Glu Leu Gly Leu His Val Pro Asn Glu Leu Gly Leu Lys Phe
        195                 200                 205

Cys Lys Arg Ser Phe Ser Val Tyr Pro Thr Leu Asn Trp Glu Thr Gly
    210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
            260                 265                 270

Gly Leu Thr Leu Ser Pro Lys Glu Glu Tyr Tyr Lys Leu Gly Ala Tyr
        275                 280                 285
```

Tyr His Ile Thr Asp Val Gln Arg Gly Leu Leu Lys Ala Phe Asp Ser
290                 295                 300

Leu Glu Asp
305

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggggggggat cctccgaagc cgctgatgtc g                                 31

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggggggaat tctcagtcct ccagcgagtc g                                 31

<210> SEQ ID NO 5
<211> LENGTH: 295
<212> TYPE: PRT
<213> ORGANISM: Streptomyces coelicolor

<400> SEQUENCE: 5

Met Pro Thr Gly Arg Thr Thr Asp Leu Ala Leu Phe Leu Ser Asp Leu
 1               5                  10                  15

Glu Ala Tyr Ala Lys Leu Ala Glu Val Thr Phe Asp Lys Arg Ala Val
             20                  25                  30

Glu Gln Val Val Asp Val Phe Ala Glu Gln Phe Ala Thr Gly Thr Ile
         35                  40                  45

Thr Val Arg Thr Thr Thr His Glu Ala Ala Asn Arg Ser Val Asn Phe
     50                  55                  60

Arg Tyr Met Tyr Pro Asp Ser Pro His Asp Pro Val Glu Ile Ala Arg
 65                  70                  75                  80

Ala His Gly Leu Leu Pro Asp Ala Asp Pro Ala Val Met Ser Leu Leu
                 85                  90                  95

Ala Glu Val Thr Glu Lys Ile Pro Leu Trp Trp Gly Leu Asp Ala Ser
            100                 105                 110

Val Gly His Gly Val Gln Lys Val Trp Ala Phe Phe Glu Gln Pro Leu
        115                 120                 125

Glu Phe Gly Glu Ile Ala Ser Leu Glu Asn Thr Pro His Ser Leu Arg
    130                 135                 140

Asp His Arg Glu Arg Phe Gly Glu Ala Arg Ile Asp Arg Phe Ala Ile
145                 150                 155                 160

Met Gly Phe Asp Phe Arg Asp Asn Thr Thr Asn Leu Tyr Ser Glu Met
                165                 170                 175

Val Ser Pro Gly Tyr Phe Glu Gln Glu Val Ala Arg Met Ile Arg
            180                 185                 190

Asp Val Gly Ser Leu Pro Pro Asp Asn Glu Glu Ile Glu Arg Cys Arg
        195                 200                 205

```
Gly Ala Ile Asn Val Tyr Tyr Thr Phe Asp Trp Asn Ser Pro Gln Ala
    210                 215                 220

Arg Arg Leu Cys Phe Ala Val Pro Ser Arg Asp Gly Glu Phe Pro Ser
225                 230                 235                 240

His Leu His Pro Leu Ala Ala Arg Phe Ala Ala Glu Ala Pro Val Gln
                245                 250                 255

Ala Glu Arg Arg Glu Leu Ile Phe Asn Pro Thr Phe Gly Ala Arg Gly
            260                 265                 270

Ser Tyr Leu Lys Met Glu Ala Asp Tyr Thr Gly Asp Ala Ala Ser Arg
        275                 280                 285

Val Phe Gly Tyr Trp Asn Arg
    290                 295

<210> SEQ ID NO 6
<211> LENGTH: 323
<212> TYPE: PRT
<213> ORGANISM: Streptomyces spheroides

<400> SEQUENCE: 6

Met Pro Ala Leu Pro Met Asn Gln Glu Phe Asp Arg Glu Arg Phe Arg
1               5                   10                  15

Val Asp Leu Arg Ala Thr Ala Ala Ile Gly Ala Pro Val Thr Pro
            20                  25                  30

Arg Val Thr Asp Thr Val Leu Glu Thr Phe Arg Asp Asn Phe Ala Gln
        35                  40                  45

Gly Ala Thr Leu Trp Lys Thr Thr Ser Gln Pro Gly Asp Gln Leu Ser
    50                  55                  60

Tyr Arg Phe Phe Ser Arg Leu Lys Met Asp Thr Val Gly Arg Ala Val
65                  70                  75                  80

Asp Ala Gly Leu Leu Asp Gly Thr His Pro Thr Val Pro Ile Val Glu
                85                  90                  95

Asp Trp Ser Asp Leu Tyr Gly Gly Thr Pro Val Gln Ser Ala Asp Phe
            100                 105                 110

Asp Ala Gly Arg Gly Met Ala Lys Thr Trp Leu Tyr Phe Gly Gly Leu
        115                 120                 125

Arg Pro Ala Glu Asp Ile Leu Ser Val Pro Ala Leu Pro Ala Pro Val
    130                 135                 140

Gln Ala Arg Leu Lys Asp Phe Leu Gly Leu Gly Leu Ala His Val Arg
145                 150                 155                 160

Phe Ala Ala Val Asp Trp Arg His Arg Ser Ala Asn Val Tyr Phe Arg
                165                 170                 175

Gly Gln Gly Pro Leu Asp Thr Ala Gln Phe Ala Arg Val His Ala Leu
            180                 185                 190

Ser Gly Gly Thr Pro Pro Ala Ala Asp Val Val Ala Glu Val Leu Ala
        195                 200                 205

Tyr Val Pro Glu Asp Tyr Cys Val Ala Ile Thr Leu Asp Leu His Thr
    210                 215                 220

Gly Ala Ile Asp Arg Val Cys Phe Tyr Ala Leu Lys Val Pro Lys Asp
225                 230                 235                 240

Ala Arg Pro Arg Val Pro Ala Arg Ile Ala Thr Phe Leu Glu Val Ala
                245                 250                 255

Pro Ser His Asp Pro Glu Glu Cys Asn Val Ile Gly Trp Ser Phe Gly
            260                 265                 270

Arg Ser Gly Asp Tyr Val Lys Ala Glu Arg Ser Tyr Thr Gly Asn Met
        275                 280                 285
```

```
Thr Glu Ile Leu Ser Gly Trp Asn Cys Phe Phe His Gly Glu Glu Gly
    290                 295                 300

Arg Asp His Asp Leu Arg Ala Leu Gln Asp Thr Gly Ser Ile Thr Gly
305                 310                 315                 320

Gly Ala Arg

<210> SEQ ID NO 7
<211> LENGTH: 324
<212> TYPE: PRT
<213> ORGANISM: Streptomyces roseochromogenes

<400> SEQUENCE: 7

Met Pro Ala Leu Pro Ile Asp Gln Glu Phe Asp Cys Glu Arg Phe Arg
  1               5                  10                  15

Ala Asp Ile Arg Ala Thr Ala Ala Ile Gly Ala Pro Ile Ala His
             20                  25                  30

Arg Leu Thr Asp Thr Val Leu Glu Ala Phe Arg Asp Asn Phe Ala Gln
             35                  40                  45

Gly Ala Thr Leu Trp Lys Thr Thr Ser Gln Pro Gly Asp Gln Leu Ser
 50                  55                  60

Tyr Arg Phe Phe Ser Arg Leu Lys Met Asp Thr Val Ser Arg Ala Ile
 65                  70                  75                  80

Asp Ala Gly Leu Leu Asp Ala Ala His Pro Thr Leu Ala Val Val Asp
                 85                  90                  95

Ala Trp Ser Ser Leu Tyr Gly Gly Ala Pro Val Gln Ser Gly Asp Phe
                100                 105                 110

Asp Ala Gly Arg Gly Met Ala Lys Thr Trp Leu Tyr Phe Gly Gly Leu
                115                 120                 125

Arg Pro Ala Glu Asp Ile Leu Thr Val Pro Ala Leu Pro Ala Ser Val
130                 135                 140

Gln Ala Arg Leu Lys Asp Phe Leu Ala Leu Gly Leu Ala His Val Arg
145                 150                 155                 160

Phe Ala Ala Val Asp Trp Arg His His Ser Ala Asn Val Tyr Phe Arg
                165                 170                 175

Gly Lys Gly Pro Leu Asp Thr Val Gln Phe Ala Arg Ile His Ala Leu
                180                 185                 190

Ser Gly Ser Thr Pro Pro Ala Ala His Val Val Glu Glu Val Leu Ala
                195                 200                 205

Tyr Met Pro Glu Asp Tyr Cys Val Ala Ile Thr Leu Asp Leu His Ser
210                 215                 220

Gly Asp Ile Glu Arg Val Cys Phe Tyr Ala Leu Lys Val Pro Lys Asn
225                 230                 235                 240

Ala Leu Pro Arg Ile Pro Thr Arg Ile Ala Arg Phe Leu Glu Val Ala
                245                 250                 255

Pro Ser His Asp Val Glu Glu Cys Asn Val Ile Gly Trp Ser Phe Gly
                260                 265                 270

Arg Ser Gly Asp Tyr Val Lys Ala Glu Arg Ser Tyr Thr Gly Asn Met
            275                 280                 285

Ala Glu Ile Leu Ala Gly Trp Asn Cys Phe Phe His Gly Glu Glu Gly
    290                 295                 300

Arg Asp His Asp Leu Arg Ala Leu His Gln His Thr Glu Ser Thr Met
305                 310                 315                 320

Gly Gly Ala Arg
```